US008617554B2

(12) United States Patent
Roberts et al.

(10) Patent No.: US 8,617,554 B2
(45) Date of Patent: Dec. 31, 2013

(54) ANTI-HUMAN CD52 IMMUNOGLOBULINS

(75) Inventors: Bruce L Roberts, Southborough, MA (US); Srinivas Shankara, Shrewsbury, MA (US); William Harold Brondyk, Mansfield, MA (US); William M Siders, Franklin, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 13/320,019

(22) PCT Filed: May 13, 2010

(86) PCT No.: PCT/US2010/034704
§ 371 (c)(1),
(2), (4) Date: Nov. 10, 2011

(87) PCT Pub. No.: WO2010/132659
PCT Pub. Date: Nov. 18, 2010

(65) Prior Publication Data
US 2012/0100152 A1  Apr. 26, 2012

Related U.S. Application Data

(60) Provisional application No. 61/177,837, filed on May 13, 2009.

(51) Int. Cl.
*A61K 39/395* (2006.01)
*C07K 16/28* (2006.01)
*C12N 5/10* (2006.01)
*C12N 15/13* (2006.01)
*C12P 21/08* (2006.01)

(52) U.S. Cl.
USPC ............... 424/154.1; 424/130.1; 424/133.1; 424/141.1; 424/153.1; 424/173.1; 530/387.1; 530/387.3; 530/388.1; 530/388.7; 530/388.73; 530/388.75; 536/23.1; 536/23.5; 536/23.53; 435/69.6; 435/326; 435/343.1; 435/343.2

(58) Field of Classification Search
None
See application file for complete search history.

(56) References Cited

U.S. PATENT DOCUMENTS

| 6,054,561 | A  | 4/2000  | Ring        |
|-----------|----|---------|-------------|
| 2002/0132983 | A1 | 9/2002 | Junghans    |
| 2006/0204496 | A1 | 9/2006 | Kojima et al. |
| 2007/0178098 | A1 | 8/2007 | Way et al.  |
| 2007/0253948 | A1 | 11/2007 | Chan et al. |

FOREIGN PATENT DOCUMENTS

| EP | 0 120 694 B1 | 10/1984 |
|----|--------------|---------|
| EP | 0 125 023 B1 | 11/1984 |
| EP | 0 239 400 B1 | 9/1987 |
| EP | 0 519 596 B1 | 12/1992 |
| EP | 0 194 276 B1 | 8/1993 |
| EP | 0 616 537 B1 | 3/1999 |
| WO | WO 86/01533 | 3/1986 |
| WO | WO 88/07089 | 9/1988 |
| WO | WO 89/07142 | 8/1989 |
| WO | WO 92/03918 | 3/1992 |
| WO | WO 93/10423 | 5/1993 |
| WO | WO 94/04679 | 3/1994 |
| WO | WO 94/26087 | 11/1994 |
| WO | WO 94/29351 | 12/1994 |
| WO | WO 98/06248 | 2/1998 |
| WO | WO 98/52976 | 11/1998 |
| WO | WO 00/34317 | 6/2000 |
| WO | WO 01/38318 | 5/2001 |
| WO | WO 2008/031626 | 3/2008 |

OTHER PUBLICATIONS

Agarwal et al., "The role of alemtuzumab in facilitating maintenance immunosuppression minimization following solid organ transplantation," Transplant Immunol., 20:6-11 (2008).
Alexander et al., "Development of high potency universal DR-restricted helper epitopes by modification of high affinity DR-blocking peptides," Immunity, 1:751-761 (1994).
Bach et al., "Regulatory T cells under scrutiny," Nat. Rev. Immunol. 3:189-98 (2003).
Barrat et al., "In vitro generation of interleukin 10-producing regulatory CD4(+) T cells is induced by immunosuppressive drugs and inhibited by T helper type 1 (Th1)- and Th2-inducing cytokines," J. Exp. Med., 195:603-616 (2002).
Battaglia et al., "Rapamycin promotes expansion of functional CD4+CD25+FOXP3+ regulatory T cells of both healthy subjects and type 1 diabetic patients," J. Immunol., 177:8338-8347 (2006).
Battaglia et al., "Rapamycin selectively expands CD4+CD25+FoxP3+ regulatory T cells," Blood, 105:4743-4748 (2005).
Coles et al. "Alemtuzumab vs. interferon Beta-1a in early multiple sclerosis," The CAMMS223 Trial Investigators, New England Journal of Medicine, 359:1786-1801 (2008).
Dick et al., "Campath-1H therapy in refractory ocular inflammatory disease," Br. J. Ophthalmol., 84:107-109 (2000).
Elsner et al., "Surface and mRNA expression of the CD52 antigen by human eosinophils but not by neutrophils," Blood, 88:4684-4693 (1996).
Gilleece et al., "Effect of Campath-1H antibody on human hematopoietic progenitors in vitro," Blood, 82:807-812 (1993).
Gilliland et al., "Elimination of the immunogenicity of therapeutic antibodies," Journal of Immunology, 162:3663-3671 (1999).

(Continued)

*Primary Examiner* — Phillip Gambel
(74) *Attorney, Agent, or Firm* — Ropes & Gray LLP

(57) ABSTRACT

The present invention relates to humanized immunoglobulins, mouse monoclonal antibodies and chimeric antibodies that have binding specificity for human CD52. The present invention further relates to a humanized immunoglobulin light chain and a humanized immunoglobulin heavy chain. The invention also relates to isolated nucleic acids, recombinant vectors and host cells that comprise a sequence which encodes a humanized immunoglobulin or immunoglobulin light chain or heavy chain, and to a method of preparing a humanized immunoglobulin. The humanized immunoglobulins can be used in therapeutic applications to treat, for example, autoimmune disease, cancer, non-Hodgkin's lymphoma, multiple sclerosis and chronic lymphocytic leukemia.

44 Claims, 194 Drawing Sheets

(56) References Cited

OTHER PUBLICATIONS

Ginaldi et al., "Levels of expression of CD52 in normal and leukemic B and T cells: correlation with in vivo therapeutic responses to Campath-1H," Leuk. Res., 22:185-191 (1998).

Gregori et al., "Regulatory T cells induced by 1 alpha,25-dihydroxyvitamin D3 and mycophenolate mofetil treatment mediate transplantation tolerance ," J. Immunol. 167:1945-1953 (2001).

Gribben et al., "Rediscovering alemtuzumab: current and emerging therapeutic roles," British Journal of Haematology, 144:818-831 (2009).

Hale et al., "CD52 (CAMPATH1)," J. Biol. Regul. Homeost. Agents, 15:386-391 (2001).

Hale, "Synthetic peptide mimotype of the CAMPATH-1 (CD52) antigen, a small glycosylphosphatidylinositol-anchored glycoprotein," Immunotechnology, 1:175-187 (1995).

Hederer et al., "The CD45 tyrosine phosphatase regulates Campath-1H (CD52)-induced TCR-dependent signal transduction in human T cells," Int'l. Immunology, 12:505-516 (2000).

Hirst et al., "Campath 1-H treatment in patients with aggressive relapsing remitting multiple sclerosis" J. Neurology, 255:231-238 (2008).

Hu et al., "Investigation of the mechanism of action of alemtuzumab in a human CD52 transgenic mouse model," Immunology, 128:260-270 (2009).

Isaacs et al., "Humanized monoclonal antibody therapy for rheumatoid arthritis" Lancet, 340:748-752 (1992).

Jia et al., "A novel method of Multiplexed Competitive Antibody Binning for the characterization of monoclonal antibodies," Journal of Immunological Methods, 288:91-98 (2004).

Kenanova et al., "Tailoring the Pharmacokinetics and Positron Emission Tomography Imaging Properties of Anti-Carcinoembryonic Antigen Single-Chain Fv-Fc Antibody Fragments," Cancer Research, 65:622-631 (2005).

Lim et al., "Effect of anti-CD52 antibody alemtuzumab on ex-vivo culture of umbilical cord blood stem cells," J. Hematology & Oncology 1:19 (2008).

Lundin et al., "Phase 2 study of alemtuzumab (anti-CD52 monoclonal antibody) in patients with advanced mycosis fungoides/Sezary syndrome," Blood, 101:4267-4272 (2003).

Nguyen et al., "Campath-1H activates multiple pathways and transcription factors (CREB, ATF-1, Egr1&2 and Stat3) upon binding to CD52 on B-cells," Abstract #4431.

Pulaski et al., "Identifying alemtuzumab as an anti-myeloid cell antiangiogenic therapy for the treatment of ovarian cancer,"J. Translational Med., 7:49 (2009).

Rawstron et al., The PHN phenotype cells that emerge in most patients after CAMPATH-1H therapy are present prior to treatment, British Journal of Haematology, 107:148-153 (1999).

Reiff, "A review of Campath in autoimmune disease: biologic therapy in the gray zone between immunosuppression and immunoablation," Hematology, 10:79-93 (2005).

Rodig et al., "Heterogeneous CD52 expression among hematologic neoplasms: implications for the use of alemtuzumab (CAMPATH-1H)," Clinical Cancer Research, 12:7174-7179 (2006).

Rowan et al., "Cross-linking of the CAMPATH-1 antigen (CD52) triggers activation of normal human T lymphocytes," Int. Immunol., 7:69-77 (1995).

Sato et al., "Reshaping a human antibody to inhibit the interleukin 6-dependent tumor cell growth," Cancer Research, 53:851-856 (1993).

Siders et al., "Involvement of neutrophils and natural killer cells in the anti-tumor activity of alemtuzumab in xenograft tumor models," Leukemia & Lymphoma, 51(7):1293-1304 (2010).

Sportes et al., "Perspective on potential clinical applications of recombinant human interleukin-7," Cytokine Therapies: Ann. N.Y. Acad. Sci. 1182:28-38 (2009).

Treumann et al., "Primary structure of CD52," J. Biol. Chem. 270:6088-6099 (1995).

Vivas et al., "Alemtuzumab for refractory celiac disease in a patient at risk for enteropathy-associated T-cell lymphoma," New England Journal of Medicine, 354:2514-2515 (2006).

Walsh et al., "Long-term follow-up of relapsing/refractory anti-neutrophil cytoplasm antibody associated vasculitis treated with the lymphocyte depleting antibody alemtuzumab (CAMPATH-1H)," Ann. Rheum. Dis., 67:1322-1327 (2008).

Watanabe et al., "CD52 is a novel costimulatory molecule for induction of CD4+ regulatory T cells," Clin. Immunol., 120:247-259 (2006).

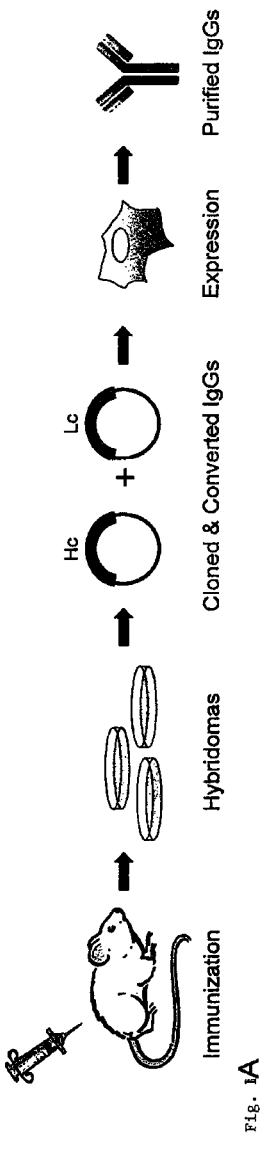

Light Chain Sequences of Mouse Anti-Human CD52 Antibodies

Light Chain (Kappa) sequence

1) Campath 1G Kappa (rat)
2) CF1D12 Kappa
3) Mouse BG3.25.3.5 kappa
4) Mouse GMA 4G7.F3 kappa
5) Mouse GMA 9D9.A2 kappa
6) Mouse GMA 11C11.C5 kappa
7) Mouse GMA 3G7.E9 kappa
8) Mouse 5F7.1.1.4 kappa
9) Mouse 12G6.15.1.2 kappa
10) Mouse 23E6.2.2.1 kappa
11) Mouse 2C3.3.8.1 kappa
12) Mouse 7F11.1.9.7 kappa
13) Mouse 4B10I.2.4 kappa

```
      [------FR1--------][---CDR1-----][----FR2----][CDR2-][-------FR3-------][--CDR3--][JREGION-]
 1) DIKMTQSPSFLSASVGDRVTLNCKASQNIDK.....YLNWYQQKLGESPKLLIYNTNNLQTGIPSRFSGSGSGTDFTLTISSLQPEDVATYFCLQHISRP.RTFGTGTKLELK  (SEQ ID NO:1)
 2) DVVMTQTPLALSVTIGHPASISCKSSQSLLDSDGKTYLNWLFQRPGQSPKRLIYLVSNLDSGVPDRFTGSGSGTDFTLKISRVEAEDLGVYYCWQGTHFP.WTFGGGTKLEIK  (SEQ ID NO:2)
 3) DIVLTQSTLSLSVTIGQPASISCKSSQSLLDSDGKTYLNWMLQRPGQSPKRLIYLVSKLDSGVPDRFTGSGSGTDFTLKISRVEAEDLGVYYCWQGTHFP.WTFGGGTKLEIK  (SEQ ID NO:3)
 4) DIVMTQTPLTLSVTIGQPASISCKSSQSLLDSDGKTYLNWLLQRPGQSPKRLIYLVSNLGSGVPDRFTGSGSGTDFTLKISRVEAEDLGVYYCWQGTHFP.WTFGGGTKLEII  (SEQ ID NO:4)
 5) DIVMTQTPLTLSVTIGQPASIPCKSSQSLLDSDGKTYLNWLLQREGQSPKRLYLVSALDSGVPDRFTGSGSGTDFTLKISRVEAEDLGIYYCWQGTHFP.WTFGGGTKLEIK  (SEQ ID NO:5)
 6) DIVMTQTPLTLSVTIGQPASISCKSSQSLLDSDGKTYLNWLLSQRPGQSPKRLIYLVSKLDSGVPDRFTGSGSGTDFTLKISRVEAEDLGVYYCWQGTHFP.WTFGGGTKLEIK  (SEQ ID NO:6)
 7) DIVMTQSPLTLSVTIGQPASISCKSSQSLLDSDGKTYLNWLLQRPGQSPKRLIYLVSNLNSGLPDRFIGSGSGTDFTLKISRVEAEDLGVYYCWQGTHFP.WTFGGGTKLEIK  (SEQ ID NO:7)
 8) DIVLTQTTLTLSVTIGQPASISCKSSQSLLDSDGKTYLNWLFLVSHLDSGVPDRFTGSGSGTDFTLKISRVEAEDLGVYYCWQGTHFP.WTFGGGTKLEIK  (SEQ ID NO:8)
 9) DIVMTQTFLTLSVTIGQPASIACKSSQSILLYSNGKTYLNWLLQRPGQSPKRLIYLVSKLDSGVPDRFTGSGSGTDFTLK:SRVEAEDLGVYYCVQGSHFH..TFGAGTKLELK  (SEQ ID NO:9)
10) DIVLTQTPRTLSVTIGQPASISCKSSQSILLYSNGKTYLSNGKTYLMFLLQRPGQSPKRLYLVSKLDSGVPDRFAGSGSGTDFTLKISRVEAEDLGVYYCVQGTRFH..TFGAGTKLELK  (SEQ ID NO:10)
11) DIVITQCPLTLSVTIGQPVSISCKSSQSILZSNGKTYLNWLLQRPGQSPKRLIYLVSKLDSGVPDRFTGSGSGTDFTLKISRVEAEDLGVYCVQGTHLH..TFGAGTKLEAK  (SEQ ID NO:11)
12) DIVMTQTPLSLPVSLGDQASISCRSSQSIVHTNGNSYLHWYLQKPGQSPRLLIYWVSNRFSGVPDRFSGIGSGTDFTLKISRVEAEDLGVYFCSDSTHVF.FTFGSGTKLEIK  (SEQ ID NO:12)
13) DIVMTQSFLSLTVSLGDQASISCRSSQSIVHTNGNTYLHHYLQKPGQSPKLLIYMWSNRFSGVDRFSGSGSGTDFTLKISRVEAEDLGIYFCSQSAHVPPLIFGAGTKLELK  (SEQ ID NO:13)
```

FIG 2

Heavy Chain Sequences of Mouse Anti-Human CD52 Antibodies

Heavy Chain Sequence

1) Campath 1G heavy (rat)         (SEQ ID NO:14)
2) CF1D12 IgG3 heavy              (SEQ ID NO:15)
3) Mouse 8G3.25.3.5 IgG3 heavy    (SEQ ID NO:16)
4) Mouse 4G7.F3 IgG3 heavy        (SEQ ID NO:17)
5) Mouse 9D9.A2 IgG3 heavy        (SEQ ID NO:18)
6) Mouse 11C11.C5 IgG3 heavy      (SEQ ID NO:19)
7) Mouse 3G7.E9 IgG2b heavy       (SEQ ID NO:20)
8) Mouse 5F7.1.1.4 IgG3 heavy     (SEQ ID NO:21)
9) Mouse 12G6.15.1.2 IgG3 heavy   (SEQ ID NO:22)
10) Mouse 23E6.2.2.1 IgG3 heavy   (SEQ ID NO:23)
11) Mouse 2C3.3.8.1 IgG3 heavy    (SEQ ID NO:24)
12) Mouse 7F11.1.9.7 IgG1 heavy   (SEQ ID NO:25)
13) Mouse 4B10.1.2.4 IgG2a heavy  (SEQ ID NO:26)

[-------FR1---------][--CDR1--][---FR2----][----CDR2-----][--------FR3---------][---CDR3--][--JREGION-]
1)  EVKLLEESGGGLVQPGGSMRLSCAGSGFTFTDFYMNWVIRQPAGKAPEWLGFIRDKAKGYTTEYNPSVKGRFTISRDNTQNMLYLQMNTLRAEDTATYYCAREGHTAAPFDYWGQGVMVTVSS
2)  EVKLEESGGGLVQPGGSMKLSCAASGFTFSDAWMDWVRQSPEKGLEWIAEIRNKAINHVAYYAESVKGRFTISRDDSKSSVYLQMNNLRAEDTGIYYC..TTL.....DSWGQGTALITVSS
3)  EVKLEESGGGLVQPGGSMKLSCAVSGFTFSDAWMDWVRQSPEKGLEWIAEIRNKAINHATYYAESVKGRFTISRDDSKSRVFLQMNNLRPEDTGIYYC..TSL.....DYWGQGTALTVSS
4)  EVKLEESGGGLVQPGGSMKLSCAVSGFTFSDAWMDWVRQSPEKGLEWIAEIRNKAINHVKYYAESVKGRFTISRDDSKSSVYLQMNNLRTEDTGIYYC..TSL.....DYWGQGTSVTVSS
5)  EVKLEESGGGLVQPGGSMKLSCAASGFTFSDAWMDWVRQSPEKGLELITAEIRNKAINHATYYAESVKGRFTISRDDSKSRVYLQMNNLRTEDTGIYYC..TTL.....DSWGQGTSVTVSS
6)  EVKLEESGGGLVQPGGSMKLSCAVSGFTFSDAWMDWVRQSPEKGLEWVAEIRNKAINHATYYAESVKGRFTISRDDSKSSVYLQMNRLRAEDTGIYYC..TSL.....DYWGQGTLITVSS
7)  EVKLEESGGGLVQPGGSMKLSCTASGFTFSDAWMDWVRQSPEKGLEWVAEIRKKVNNHATYYAESVKGRFTISRDDSKSSVYLQMNNLRAEDTGIYYC..TSL.....DYWGQGTLTVSS
8)  EVKLEESGGGLVQPGGSMKLSCAVSGLTFSDAWMDWVRQSPEKGLEWIAEIRNKAINHATYYAESVKGRFTISRDDSKSGVYLQMNNLRAEDTGIYYC..TGL.....DYWGHGTSVTVSS
9)  EVQLEESGGGLVQPGGSMKLSCVASGFPFSNYWMNWVRQSPEKGLEWVAQIRLKSNNYATHYAESVKGRFTIARDDSKSSVYLQMNNLRAEDTGIYYC..TPI.....DYWGQGTLTVSS
10) EVKLEESGGGLVQPGGSMKLSCVASGFTFDNKYWMNWVRQSPDKGLECIAQIRLKSDNYATHYAESVKGRFTISRDDSKNSVYLQMNNLRAEDTGIYYC..TPI.....DYWGQGTLITVSS
11) EVKLEESGGGLVQPGGSMKLSCVASGFTFTNYWMNWVRQSPEKGLEWVAQIRLKSNNYATHYAESVKGRFTISRDDSKSSVYLQMNNLRAEDTGIYYC..TPV....DFWGQGTLITVSS
12) EVKLEESGGGLVQPGGSLSLSCAASGFTFTDYMSWVRQPPGKALEWMLGFIRNKANGYTTEYSASVKGRFTISRDDSKSGVYLQMNALRAEDSATYYC..TRYIFF..DYWGQGTLITVSS
13) EVQLEESGGGLVQPGGSGALSLSCAGSGFTFTDYMSWVRQPPGKALEWMLGFIRNKANGYTTEYSASVKGRFTISRDDSQSILYLQMNALRAEDSATYYC..TRYIWF..DYWGQGTLITVSS

FIG 3

Point Mutations within the CD52 Protein

| | |
|---|---|
| WT | GQNDTSQTSSPS |
| MUT 1 | AQNDTSQTSSPS |
| MUT 2 | GANDTSQTSSPS |
| MUT 3 | GQADTSQTSSPS |
| MUT 4 | GQNATSQTSSPS |
| MUT 5 | GQNDASQTSSPS |
| MUT 6 | GQNDTAQTSSPS |
| MUT 7 | GQNDTSATSSPS |
| MUT 8 | GQNDTSQASSPS |
| MUT 9 | GQNDTSQTASPS |
| MUT 10 | GQNDTSQTSAPS |

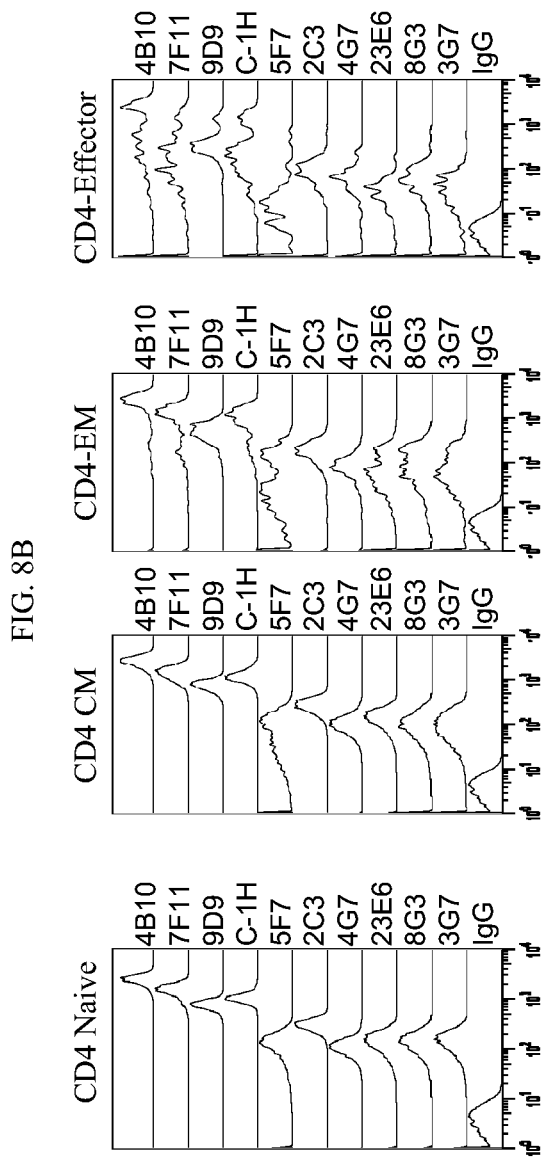

Alignment of anti human CD52 mouse(m) antibody V region with human germline(h) and humanized anti-CD52 V region sequences

4B10 Heavy Chain V region

```
4B10 Heavy chain(m)  1 EVQLEESGGGLVQPGGALSLSCAGSGFTFTDYMSWVRQPPGKALEWLGF  50  (SEQ ID NO:96)
VH3-72 germline (h)  1 EVQLVESGGGLVQPGGSLRLSCAASGFTFSDHYMDWVRQAPGKGLEWVGR  50  (SEQ ID NO:97)
4B10 humanized HC    1 EVQLVESGGGLVQPGGSLRLSCAASGFTFSDYMSWVRQAPGKGLEWVGF    50  (SEQ ID NO:98)
                       ****.************.*.**** ******.* *.**** *** ***.*

4B10 Heavy chain(m)  51 IRNKANGYTTEYSASVKGRFTISRDDSQSILYLQMNALRAEDSATYYCTR 100
VH3-72 germline (h)  51 TRNKANSYTTEYAASVKGRFTISRDDSKNSLYLQMNSLKTEDTAVYYCAR 100
4B10 humanized HC    51 IRNKANGYTTEYSASVKGRFTISRDDSKNSLYLQMNSLKTEDTAVYYCAR 100
                        ***** *****.***********.  ****** *..**.* *** .*
```

4B10 Light chain V region

```
4B10 Light chain(m)  1 DIVMTQSPLSLTVSLGDQASISCRSSQSLVHTNGNTYLHWYLQKPGQSPK  50  (SEQ ID NO:99)
VK2-A18b germline(h) 1 DIVMTQTPLSLSVTPGQPASISCKSSQSLLHSDGKTYLYWYLQKPGQSPQ  50  (SEQ ID NO:100)
4B10 Humanized LC    1 DIVMTQTPLSLSVTPGQPASISCRSSQSLVHTNGNTYLHWYLQKPGQSPQ  50  (SEQ ID NO:101)
                       ******.****.*.* * *****.*****.*.* * *** **********.

4B10 light chain(m)  51 LLIYMVSNRFSGVPDRFSGSGSGTDFTLKISRVEAEDLGIYFCSQSAHVP 100
VK2-A18b germline(h) 51 LLIYEVSSRFSGVPDRFSGSGSGTDFTLKISRVEAEDVGVYYCMQGIHLP 100
4B10 Humanized LC    51 LLIYMVSNRFSGVPDRFSGSGSGTDFTLKISRVEAEDVGVYYCSQSAHVP 100
                        ****  ** ********************************.*.** * *
```

FIG 16

Humanized 4B10 kappa (light chain) variable region

DIVMTQTPLSLSVTPGQPASISCRSSQSLVHTNGNTYLHWYLQKPGQSPQLLIYMVSNRFSGVPDRFSGSGSGTDFTLKISRVEAEDVGVYYC
SQSAHVPPLTFGQGTRLEIK
(SEQ ID NO:102)

Humanized 4B10 heavy chain variable region

EVQLVESGGGLVQPGGSLRLSCAASGFTFSDYYMSWVRQAPGKGLEWVGFIRNKANGYTTEYSASVKGRFTISRDDSKNSLYLQMNSLKTEDT
AVYYCARYIWFDYWGQGTTVTVSS
(SEQ ID NO:103)

FIG 17

Humanized 7F11 clone heavy chain variable region sequences

7F11-SFD1
EVQLVESGGGLVQPGGSLRLSCAASGFTFTDYYMSWVRQAPGKGLEWVG**FIRNK
ANGYTTEYNASVKGRFTISRDDSKNSLYLQMNSLKTEDTAVYYC<u>T</u>RYIFFDY**WG
QGTTVTVSS  (SEQ ID NO: 136)

7F11-SFD2
EVQLVESGGGLVQPGGSLRLSCAASGFTFTDYYMSWVRQAPGKGLEWVG**FIRNK
ANGYTTEYNASVKGRFTISRDDSKNSLYLQMNSLKTEDTAVYYC<u>A</u>RYIFFDY**WG
QGTTVTVSS  (SEQ ID NO: 137)

Humanized 7F11 clone light (kappa) chain variable region sequence

7F11-VK2
DIVMTQTPLSLSVTPGQPASISCRSSQSLVHTNGNSYLHWYLQKPGQSPQLLIY**MV
SNRFSGVPDRFSGSGSGTDFTLKISRVEAEDVGVYYCSQSTHVPFT**FGQGTKLEIK
(SEQ ID NO: 138)

FIG. 24

Humanized 2C3 clone heavy chain variable region sequences

2C3-SFD1
EVQLVESGGGLVQPGGSLRLSCAASGFTFNTYWMNWVRQAPGKGLEWVGQIRLKSNNYATHYAESVKGRFTISRDDSKNSLYLQM
NSLKTEDTAVYYCTPVDFWGQGTTVTVSS (SEQ ID NO: 139)

2C3-VH12
EVQLVESGGGLVQPGGSLRLSCAASGFTFNTYWMNWVRQAPGKGLEWVGQIRLKSNNYATHYAESVKGRFTISRDDSKNSVYLQ
MNSLKTEDTAVYYCTPVDFWGQGTTVTVSS (SEQ ID NO: 140)

2C3-VH15
EVQLVESGGGLVQPGGSLRLSCAASGFTFNTYWMNWVRQAPGKGLEWVAQIRLKSNNYATHYAESVKGRFTISRDDSKNSLYLQM
NSLKTEDTAVYYCTPVDFWGQGTTVTVSS (SEQ ID NO: 141)

2C3-VH16
EVQLVESGGGLVQPGGSLRLSCAASGFTFNTYWMNWVRQAPGKGLEWVAQIRLKSNNYATHYAESVKGRFTISRDDSKNSVYLQ
MNSLKTEDTAVYYCTPVDFWGQGTTVTVSS (SEQ ID NO: 142)

2C3-VH17
EVQLVESGGGLVQPGGSMRLSCAASGFTFNTYWMNWVRQAPGKGLEWVAQIRLKSNNYATHYAESVKGRFTISRDDSKNSVYLQ
MNSLKTEDTAVYYCTPVDFWGQGTTVTVSS (SEQ ID NO: 143)

2C3-VH19
EVQLVESGGGLVQPGGSMRLSCAASGFTFNTYWMNWVRQAPEKGLEWVAQIRLKSNNYATHYAESVKGRFTISRDDSKNSVYLQ
MNSLKTEDTAVYYCTPVDFWGQGTTVTVSS (SEQ ID NO: 144)

FIG. 26A

Humanized 2C3 clone light (kappa) chain variable region sequences

2C3-VK1
DIVMTQTPLSLSVTPGQPASISCKSSQSLLYSNGKTYLNWYLQKPGQSPQLLIYLVSKLDSGVPDRFSGSGSGTDFTLKISRVEAE
DVGVYYCVQGTHLHTFGQGTRLEIK   (SEQ ID NO: 145)

2C3-VK11
DIVMTQTPLSLSVTPGQPASISCKSSQSLLYSNGKTYLNWYLQKPGQSPQRLIYLVSKLDSGVPDRFSGSGSGTDFTLKISRVEAE
DVGVYYCVQGTHLHTFGQGTRLEIK   (SEQ ID NO: 146)

2C3-VK12
DIVMTQTPLSLSVTPGQPASISCKSSQSLLYSNGKTYLNWLLQKPGQSPQRLIYLVSKLDSGVPDRFSGSGSGTDFTLKISRVEAE
DVGVYYCVQGTHLHTFGQGTRLEIK   (SEQ ID NO: 147)

2C3-VK13
DIVTQTPLSLSVTPGQPVSICKSSQSLLYSNGKTYLNWLLQKPGQSPKRLYLVSKLDSGVPDRFSGSGSGTDFTLKISRVEAE
DVGVYYCVQGTHLHTFGQGTRLEIK   (SEQ ID NO: 148)

FIG. 26B

Humanized 12G6 clone heavy chain variable region sequences

12G6-SFD1
EVQLVESGGGLVQPGGSLRLSCAASGFPFSNYWMNWVRQAPGKGLEWVG**QIRLK
SNNYATHYAESVKGRFTISRDDSKNSLYLQMNSLKTEDTAVYYCTPIDY**WGQGTT
VTVSS (SEQ ID NO: 149)

12G6-VH 10
EVQLVESGGGLVQPGGSLRLSCAASGFPFSNYWMNWVRQAPGKGLEWVG**QIRLK
SNNYATHYAESVKGRFTISRDDSKNS<u>V</u>YLQMNSLKTEDTAVYYCTPIDY**WGQGTT
VTVSS (SEQ ID NO: 150)

12G6-VH 11
EVQLVESGGGLRLSCAASGFPFSNYWMNWVRQAPGKGLEWV<u>A</u>**QIRLK
SNNYATHYAESVKGRFTISRDDSKNSLYLQMNSLKTEDTAVYYCTPIDY**WGQGTT
VTVSS (SEQ ID NO: 151)

12G6-VH12
EVQLVESGGGLVQPGGSLRLSCAASGFPFSNYWMNWVRQAPGKGLEWV<u>A</u>**QIRLK
SNNYATHYAESVKGRFTISRDDSKNS<u>V</u>YLQMNSLKTEDTAVYYCTPIDY**WGQGTT
VTVSS (SEQ ID NO: 152)

FIG. 28A

Humanized 12G6 clone light (kappa) chain variable region sequence

12G6-VK1
DIVMTQTPLSLSVTPGQPASISCKSSQSLLYSNGKTYLNWYLQKPGQSPQLLIY
LVSKLDSGVPDRFSGSGSGTDFTLKISRVEAEDVGVYYCVQGSHFHTFGQGTK
LEIK (SEQ ID NO: 153)

12G6-VK10
DIVMTQTPLSLSVTPGQPASISCKSSQSLLYSNGKTYLNWVLQKPGQSPQLLIY
LVSKLDSGVPDRFSGSGSGTDFTLKISRVEAEDVGVYYCVQGSHFHTFGQGTK
LEIK (SEQ ID NO: 154)

12G6-VK11
DIVMTQTPLSLSVTPGQPASISCKSSQSLLYSNGKTYLNWVLQKPGQSPKRLIY
LVSKLDSGVPDRFSGSGSGTDFTLKISRVEAEDVGVYYCVQGSHFHTFGQGTK
LEIK (SEQ ID NO: 155)

12G6-VK12
DIVMTQTPLSLSVTPGQPASISCKSSQSLLYSNGKTYLNWVLQKPGQSPQRLIY
LVSKLDSGVPDRFSGSGSGTDFTLKISRVEAEDVGVYYCVQGSHFHTFGQGTK
LEIK (SEQ ID NO: 156)

12G6-VK13
DIVMTQTPLSLSVTPGQPASISCKSSQSLLYSNGKTYLNWYLQKPGQSPQRLIY
LVSKLDSGVPDRFSGSGSGTDFTLKISRVEAEDVGVYYCVQGSHFHTFGQGTK
LEIK (SEQ ID NO: 157)

FIG. 28B

Humanized 9D9 clone heavy chain variable region sequences

9D9-VH10
EVQLLESGGGLVQPGGSLRLSCAASGFTFSDAWMDWVRQAPGKGLEWVS**EIRNKA
KNHATYYAESVKGRFTISRDNSKNTLYLQMNSLRAEDTAVYYCTTLD**SWGQGTTV
TVSS  (SEQ ID NO: 158)

9D9-VH11
EVQLLESGGGLVQPGGSLRLSCAASGFTFSDAWMDWVRQAPGKGLEL<u>TA</u>**EIRNK
AKNHATYYAESVKGRFTISRDNSK<u>ST</u>VYLQMNSLRAEDTAVYYCTTLD**SWGQGT
TVTVSS  (SEQ ID NO: 159)

9D9-VH15
EVQLLESGGGLVQPGGSLRLSCAASGFTFSDAWMDWVRQAPGKGLEL<u>TA</u>**EIRNK
AKNHATYYAESVKGRFTISRDNSKNTLYLQMNSLRAEDTAVYYCTTLD**SWGQGT
TVTVSS  (SEQ ID NO: 160)

9D9-VH 16
EVQLLESGGGLVQPGGSLRLSCAASGFTFSDAWMDWVRQAPGKGLEL<u>V</u>S**EIRNK
AKNHATYYAESVKGRFTISRDNSKNTLYLQMNSLRAEDTAVYYCTTLD**SWGQGT
TVTVSS  (SEQ ID NO: 161)

9D9-VH 17
EVQLLESGGGLVQPGGSLRLSCAASGFTFSDAWMDWVRQAPGKGLEL<u>T</u>S**EIRNK
AKNHATYYAESVKGRFTISRDNSKNTLYLQMNSLRAEDTAVYYCTTLD**SWGQGT
TVTVSS  (SEQ ID NO: 162)

9D9-VH 18
EVQLLESGGGLVQPGGSLRLSCAASGFTFSDAWMDWVRQAPGKGLEL<u>VA</u>**EIRNK
AKNHATYYAESVKGRFTISRDNSKNTLYLQMNSLRAEDTAVYYCTTLD**SWGQGT
TVTVSS  (SEQ ID NO: 163)

FIG. 30A

Humanized 9D9 clone light (kappa) chain variable region sequences

9D9-VK2
DIVMTQTPLSLSVTPGQPASISCKSSQSLLDSDGKTYLNWYLQKPGQSPQLLIYL
VSALDSGVPDRFSGSGSGTDFTLKISRVEAEDVGVYYCWQGTHFPWTFGQGTK
LEIK  (SEQ ID NO: 164)

9D9-VK12
DIVMTQTPLSLSVTPGQPASISCKSSQSLLDSDGKTYLNWLLQKPGQSPKRLIYL
VSALDSGVPDRFSGSGSGTDFTLKISRVEAEDVGVYYCWQGTHFPWTFGQGTK
LEIK  (SEQ ID NO: 165)

9D9-VK13
DIVMTQTPLSLSVTPGQPASISCKSSQSLLDSDGKTYLNWLLQKPGQSPQRLIYL
VSALDSGVPDRFSGSGSGTDFTLKISRVEAEDVGVYYCWQGTHFPWTFGQGTK
LEIK  (SEQ ID NO: 166)

9D9-VK14
DIVMTQTPLSLSVTPGQPASISCKSSQSLLDSDGKTYLNWYLQKPGQSPQRLIYL
VSALDSGVPDRFSGSGSGTDFTLKISRVEAEDVGVYYCWQGTHFPWTFGQGTK
LEIK  (SEQ ID NO: 167)

9D9-VK15
DIVMTQTPLSLSVTPGQPASISCKSSQSLLDSDGKTYLNWYLQKPGQSPKRLIYL
VSALDSGVPDRFSGSGSGTDFTLKISRVEAEDVGVYYCWQGTHFPWTFGQGTK
LEIK  (SEQ ID NO: 168)

FIG. 30B

| | EC$_{50}$ (nM) | |
|---|---|---|
| | Human CD4+ T cells | huCD52 transgenic mouse CD4+ T cells |
| Campath-1H® | 21.91 | 25.08 |
| 2C3-Chimeric | 25.93 | 30.81 |
| 2C3-SFD1/K12 | 11.00 | 13.61 |
| 12G6-Chimeric | 22.41 | 34.42 |
| 12G6-SFD1/K11 | 7.30 | 13.17 |
| 12G6-SFD1/K12 | 10.58 | |

FIG. 33

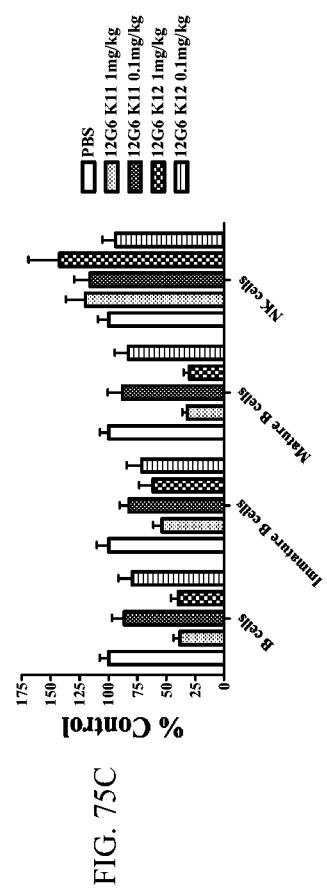
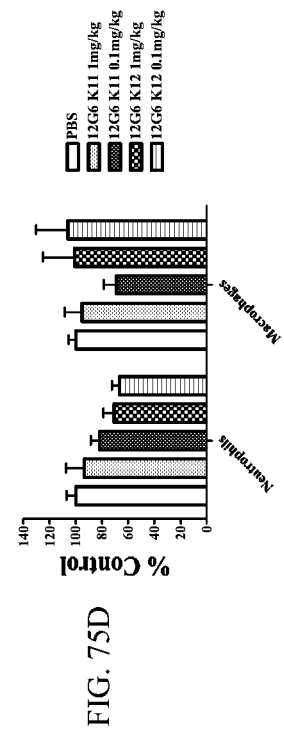
FIG. 75C
FIG. 75D

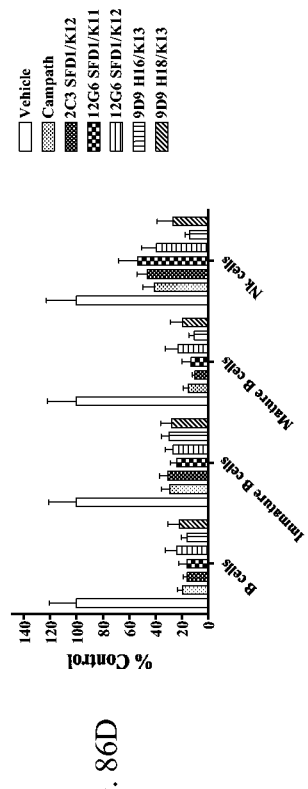
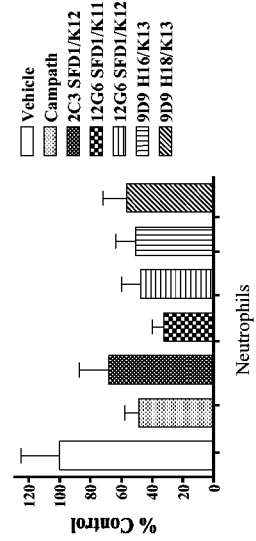
FIG. 86D
FIG. 86E

Humanized 2C3 clone full-length heavy chain sequence

2C3-SFD1
*MEAPAQLLFLLLLWLPDTTG*EVQLVESGGGLVQPGGSLRLSCAAS<u>GFTFNTYWMN</u>WV
RQAPGKGLEWVG<u>QIRLKSNNYATHYAESVKG</u>RFTISRDDSKNSLYLQMNSLKTEDTAV
YYC<u>TPVD</u>FWGQGTTVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
(SEQ ID NO: 272)

Humanized 2C3 clone full-length light chain sequence

2C3-K12
*MEAPAQLLFLLLLWLPDTTG*DIVMTQTPLSLSVTPGQPASISC<u>KSSQSLLYSNGKTYLN</u>W
LLQKPGQSPQRLIY<u>LVSKLDS</u>GVPDRFSGSGSGTDFTLKISRVEAEDVGVYYC<u>VQGTHL</u>
<u>HT</u>FGQGTRLEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C  (SEQ ID NO: 273)

FIG. 106

Humanized 7F11 clone full-length heavy chain sequence

7F11-SFD1
*MEAPAQLLFLLLLWLPDTTG*EVQLVESGGGLVQPGGSLRLSCAAS<u>GFTFTDYYMS</u>WV
RQAPGKGLEWVG<u>FIRNKANGYTTEYNASVKG</u>RFTISRDDSKNSLYLQMNSLKTEDTA
VYYC<u>TRYIFFDY</u>WGQGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSL
SLSPGK   (SEQ ID NO: 274)

Humanized 7F11 clone full-length light chain sequence

7F11-K2
*MEAPAQLLFLLLLWLPDTTG*DIVMTQTPLSLSVTPGQPASISC<u>RSSQSLVHTNGNSYLH</u>
WYLQKPGQSPQLLIY<u>MVSNRFS</u>GVPDRFSGSGSGTDFTLKISRVEAEDVGVYYC<u>SQSTH
VPFT</u>FGQGTKLEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNR
GEC   (SEQ ID NO: 275)

FIG. 107

Humanized 9D9 clone full-length heavy chain sequences

9D9-H16
*MEAPAQLLFLLLLWLPDTTG*EVQLLESGGGLVQPGGSLRLSCAAS<u>GFTFSDAWMD</u>WV
RQAPGKGLELVS<u>EIRNKAKNHATYYAESVKG</u>RFTISRDNSKNTLYLQMNSLRAEDTAV
YYC<u>TTLDS</u>WGQGTTVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
(SEQ ID NO: 276)

9D9-H18
*MEAPAQLLFLLLLWLPDTTG*EVQLLESGGGLVQPGGSLRLSCAAS<u>GFTFSDAWMD</u>WV
RQAPGKGLELVA<u>EIRNKAKNHATYYAESVKG</u>RFTISRDNSKNTLYLQMNSLRAEDTAV
YYC<u>TTLDS</u>WGQGTTVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
(SEQ ID NO: 277)

Humanized 9D9 clone full-length light chain sequence

9D9-K13
*MEAPAQLLFLLLLWLPDTTG*DIVMTQTPLSLSVTPGQPASISC<u>KSSQSLLDSDGKTYLN</u>W
LLQKPGQSPQRLIY<u>LVSALDS</u>GVPDRFSGSGSGTDFTLKISRVEAEDVGVYYC<u>WQGTHF</u>
<u>PWT</u>FGQGTKLEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRG
EC (SEQ ID NO: 278)

FIG. 108

Humanized 12G6 clone full-length heavy chain sequence

12G6-SFD1
*MEAPAQLLFLLLLWLPDTTG*EVQLVESGGGLVQPGGSLRLSCAAS<u>GFPFSNYWMN</u>
WVRQAPGKGLEWVG<u>QIRLKSNNYATHYAESVK</u>GRFTISRDDSKNSLYLQMNSLKTE
DTAVYYC<u>TPIDY</u>WGQGTTVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNT
KVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNH
YTQKSLSLSPGK (SEQ ID NO: 279)

Humanized 12G6 clone full-length light chain sequence

12G6-K12
*MEAPAQLLFLLLLWLPDTTG*DIVMTQTPLSLSVTPGQPASISC<u>KSSQSLLYSNGKTYL
N</u>WVLQKPGQSPQRLIY<u>LVSKLDS</u>GVPDRFSGSGSGTDFTLKISRVEAEDVGVYYC<u>VQ
GSHFH</u>TFGQGTKLEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVT
KSFNRGEC (SEQ ID NO: 280)

FIG. 109

Humanized 4B10 clone full-length heavy chain sequence

4B10-H1
*MEAPAQLLFLLLLWLPDTTG*EVQLVESGGGLVQPGGSLRLSCAAS<u>GFTFSDYYMS</u>W
VRQAPGKGLEWVG<u>FIRNKANGYTTEYSASVK</u>GRFTISRDDSKNSLYLQMNSLKTED
TAVYYC<u>ARYIWFDY</u>WGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEAL
HNHYTQKSLSLSPGK  (SEQ ID NO: 281)

Humanized 4B10 clone full-length light chain sequence

4B10-K1
*MEAPAQLLFLLLLWLPDTTG*DIVMTQTPLSLSVTPGQPASISC<u>RSSQSLVHTNGNTYL
H</u>WYLQKPGQSPQLLIY<u>MVSNRFS</u>GVPDRFSGSGSGTDFTLKISRVEAEDVGVYYC<u>SQ
SAHVPPLT</u>FGQGTRLEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSS
PVTKSFNRGEC  (SEQ ID NO: 282)

FIG. 110

Humanized 2C3 clone full-length heavy chain nucleic acid sequence

2C3-SFD1
ATGGAAGCCCCAGCGCAGCTTCTCTTCCTCCTGCTACTCTGGCTCCCTGATACCACCGGA
GAGGTACAGCTGGTGGAGTCGGGAGGAGGCTTGGTACAGCCTGGGGGTTCTCTGA
GACTCTCCTGTGCAGCTTCTGGATTCACTTTCAATACCTACTGGATGAACTGGGTCC
GCCAGGCTCCAGGGAAGGGACTTGAGTGGGTGGGTCAAATTAGATTGAAATCTAAT
AATTATGCAACACATTATGCGGAGTCTGTGAAAGGGCGGTTCACCATCTCCAGAGA
TGATTCCAAAAACAGCCTCTATCTTCAAATGAATTCCCTGAAAACTGAAGACACTGC
CGTTTATTACTGTACCCCAGTTGACTTTTGGGGCCAAGGCACCACTGTCACAGTCTC
CTCA*GCCTCCACCAAGGGCCCATCGGTCTTCCCCCTGGCACCCTCCTCCAAGAGCACCTCTG*
*GGGGTACAGCGGCCCTGGGCTGCCTGGTCAAGGACTACTTCCCCGAACCGGTGACGGTGTCG*
*TGGAACTCAGGCGCCCTGACCAGCGGCGTGCACACCTTCCCGGCTGTCCTACAGTCCTCAGG*
*ACTCTACTCCCTCAGCAGCGTGGTGACCGTGCCCTCCAGCAGCTTGGGCACCCAGACCTACAT*
*CTGCAACGTGAATCACAAGCCCAGCAACACCAAGGTGGACAAGAAAGTTGAGCCCAAATCTTG*
*TGACAAAACTCACACATGCCCACCGTGCCCAGCACCTGAACTCCTGGGGGGACCGTCAGTCTT*
*CCTCTTCCCCCCAAAACCCAAGGACACCCTCATGATCTCCCGGACCCCTGAGGTCACATGCGT*
*GGTGGTGGACGTGAGCCACGAAGACCCTGAGGTCAAGTTCAACTGGTACGTGGACGGCGTGG*
*AGGTGCATAATGCCAAGACAAAGCCGCGGGAGGAGCAGTACAACAGCACGTACCGTGTGGTC*
*AGCGTCCTCACCGTCCTGCACCAGGACTGGCTGAATGGCAAGGAGTACAAGTGCAAGGTCTCC*
*AACAAAGCCCTCCCAGCCCCCATCGAGAAAACCATCTCCAAAGCCAAAGGGCAGCCCCGAGAA*
*CCACAGGTGTACACCCTGCCCCCATCCCGGGATGAGCTGACCAAGAACCAGGTCAGCCTGAC*
*ATGCCTGGTCAAAGGCTTCTATCCCAGCGACATCGCCGTGGAGTGGGAGAGCAATGGGCAGC*
*CGGAGAACAACTACAAGACCACGCCTCCCGTGCTGGACTCCGACGGCTCCTTCTTCCTCTACA*
*GCAAGCTCACCGTGGACAAGTCCAGGTGGCAGCAGGGGAACGTCTTCTCATGCTCCGTGATG*
*CATGAGGCTCTGCACAACCACTACACGCAGAAGAGCCTCTCCCTGTCTCCGGGTAAA*TGA
(SEQ ID NO: 283)

Humanized 2C3 clone full-length light chain nucleic acid sequence

2C3-K12
ATGGAAGCCCCAGCGCAGCTTCTCTTCCTCCTGCTACTCTGGCTCCCTGATACCACCGGA
GACATTGTGATGACCCAGACTCCACTCAGTTTGTCAGTTACCCCTGGACAACCAGC
CTCAATCTCTTGCAAGTCAAGTCAGAGCCTCTTATATAGTAATGGAAAAACCTATTT
GAACTGGTTATTACAGAAGCCAGGCCAGTCTCCACAGCGCCTAATCTATCTGGTGT
CTAAATTGGACTCTGGAGTCCCTGACAGGTTCAGTGGCAGTGGATCAGGAACAGAT
TTTACACTGAAAATCAGCAGAGTGGAGGCTGAGGATGTGGGAGTTTATTACTGCGT
GCAAGGTACACATCTGCACACGTTCGGTCAAGGGACCAGGCTGGAGATAAAA*CGAA*
*CTGTGGCAGCACCAAGCGTCTTCATCTTCCCGCCATCTGATGAGCAGTTGAAATCTGGAACTGC*
*CTCTGTTGTGTGCCTGCTGAATAACTTCTATCCCAGAGAGGCCAAAGTACAGTGGAAGGTGGAT*
*AACGCCCTCCAATCGGGTAACTCCCAGGAGAGTGTCACAGAGCAGGACAGCAAGGACAGCAC*
*CTACAGCCTCAGCAGCACCCTGACGCTGAGCAAAGCAGACTACGAGAAACACAAAGTCTACGC*
*CTGCGAAGTCACCCATCAGGGCCTGAGCTCGCCCGTCACAAAGAGCTTCAACAGGGGAGAGT*
*GTTAG* (SEQ ID NO: 284)

FIG. 111

Humanized 7F11 clone full-length heavy chain nucleic acid sequence

7F11-SFD1
ATGGAAGCCCCAGCGCAGCTTCTCTTCCTCCTGCTACTCTGGCTCCCTGATACCACCGGA
GAGGTACAGCTGGTGGAGTCGGGAGGAGGCTTGGTACAGCCTGGGGGTTCTCTGA
GACTCTCCTGTGCAGCTTCTGGCTTCACATTCACCGACTATTACATGAGCTGGGTCC
GCCAGGCTCCAGGGAAGGGACTTGAGTGGGTGGGTTTCATAAGGAACAAGGCTAA
CGGTTATACAACCGAGTACAACGCTTCCGTTAAAGGCCGGTTCACCATCTCCAGAG
ATGATTCCAAAAACAGCCTCTATCTTCAAATGAATTCCCTGAAAACTGAAGACACTG
CCGTTTATTACTGTACCAGGTATATCTTTTTCGATTACTGGGGCCAAGGCACCACTG
TCACAGTCTCCTCA*GCCTCCACCAAGGGCCCATCGGTCTTCCCCCTGGCACCCTCCTCCAA*
*GAGCACCTCTGGGGGTACAGCGGCCCTGGGCTGCCTGGTCAAGGACTACTTCCCCGAACGG*
*TGACGGTGTCGTGGAACTCAGGCGCCCTGACCAGCGGCGTGCACACCTTCCCGGCTGTCCTA*
*CAGTCCTCAGGACTCTACTCCCTCAGCAGCGTGGTGACCGTGCCCTCCAGCAGCTTGGGCACC*
*CAGACCTACATCTGCAACGTGAATCACAAGCCCAGCAACACCAAGGTGGACAAGAAAGTTGAG*
*CCCAAATCTTGTGACAAAACTCACACATGCCCACCGTGCCCAGCACCTGAACTCCTGGGGGGA*
*CCGTCAGTCTTCCTCTTCCCCCCAAAACCCAAGGACACCCTCATGATCTCCCGGACCCCTGAG*
*GTCACATGCGTGGTGGTGGACGTGAGCCACGAAGACCCTGAGGTCAAGTTCAACTGGTACGTG*
*GACGGCGTGGAGGTGCATAATGCCAAGACAAAGCCGCGGGAGGAGCAGTACAACAGCACGTA*
*CCGTGTGGTCAGCGTCCTCACCGTCCTGCACCAGGACTGGCTGAATGGCAAGGAGTACAAGT*
*GCAAGGTCTCCAACAAAGCCCTCCCAGCCCCCATCGAGAAAACCATCTCCAAAGCCAAAGGGC*
*AGCCCCGAGAACCACAGGTGTACACCCTGCCCCCATCCCGGGATGAGCTGACCAAGAACCAG*
*GTCAGCCTGACATGCCTGGTCAAAGGCTTCTATCCCAGCGACATCGCCGTGGAGTGGGAGAG*
*CAATGGGCAGCCGGAGAACAACTACAAGACCACGCCTCCCGTGCTGGACTCCGACGGCTCCT*
*TCTTCCTCTACAGCAAGCTCACCGTGGACAAGTCCAGGTGGCAGCAGGGGAACGTCTTCTCAT*
*GCTCCGTGATGCATGAGGCTCTGCACAACCACTACACGCAGAAGAGCCTCTCCCTGTCTCCGG*
*GTAAA*TGA  (SEQ ID NO: 285)

Humanized 7F11 clone full-length light chain nucleic acid sequence

7F11-K2
ATGGAAGCCCCAGCGCAGCTTCTCTTCCTCCTGCTACTCTGGCTCCCTGATACCACCGGA
GATATTGTAATGACCCAAACACCCCTCTCTCTTTCAGTCACACCTGGACAGCCAGCG
TCCATCTCCTGCAGGTCCTCACAGAGTCTCGTGCACACCAATGGCAATTCCTACCTG
CATTGGTACCTGCAGAAGCCCGGGCAGAGCCCCCAGTTGCTGATCTATATGGTGTC
TAATCGGTTCTCCGGAGTCCCCGACAGATTTTCTGGTTCAGGGTCTGGAACTGATTT
TACACTGAAGATTAGTCGGGTCGAGGCCGAGGATGTAGGCGTGTATTACTGCTCAC
AAAGCACACATGTGCCGTTCACTTTCGGCCAAGGAACAAAGCTCGAAATCAAG*CGAA*
*CTGTGGCAGCACCAAGCGTCTTCATCTTCCCGCCATCTGATGAGCAGTTGAAATCTGGAACTGC*
*CTCTGTTGTGTGCCTGCTGAATAACTTCTATCCCAGAGAGGCCAAAGTACAGTGGAAGGTGGAT*
*AACGCCCTCCAATCGGGTAACTCCCAGGAGAGTGTCACAGAGCAGGACAGCAAGGACAGCAC*
*CTACAGCCTCAGCAGCACCCTGACGCTGAGCAAAGCAGACTACGAGAAACACAAAGTCTACGC*
*CTGCGAAGTCACCCATCAGGGCCTGAGCTCGCCCGTCACAAAGAGCTTCAACAGGGGAGAGT*
*GT*TAG  (SEQ ID NO: 286)

FIG. 112

Humanized 9D9 clone full-length heavy chain nucleic acid sequences

9D9-H16
ATGGAAGCCCCAGCGCAGCTTCTCTTCCTCCTGCTACTCTGGCTCCCTGATACCACCGGAGAG
GTACAGCTTCTTGAAAGTGGAGGTGGCCTTGTCCAACCCGGAGGGTCATTGCGGTTGAG
CTGTGCGGCAAGTGGCTTCACCTTCTCTGACGCTTGGATGGACTGGGTGAGACAAGCCC
CCGGTAAGGGACTGGAGTTGGTTTCTGAAATCAGGAACAAGGCCAAGAACCATGCAAC
ATATTATGCCGAAAGTGTGAAGGGAAGGTTCACAATCAGTAGAGATAACAGCAAGAACA
CACTGTACCTCCAGATGAACAGCCTCAGAGCTGAGGACACCGCCGTCTATTATTGTACC
ACTCTCGATTCATGGGGGCAGGGTACCACCGTTACAGTCAGCAGC*GCCTCCACCAAGGGC*
*CCATCGGTCTTCCCCCTGGCACCCTCCTCAAGAGCACCTCTGGGGGTACAGCGGCCCTGGGCTG*
*CCTGGTCAAGGACTACTTCCCCGAACCGGTGACGGTGTCGTGGAACTCAGGCGCCCTGACCAGCG*
*GCGTGCACACCTTCCCGGCTGTCCTACAGTCCTCAGGACTCTACTCCCTCAGCAGCGTGGTGACCG*
*TGCCCTCCAGCAGCTTGGGCACCCAGACCTACATCTGCAACGTGAATCACAAGCCCAGCAACACCA*
*AGGTGGACAAGAAAGTTGAGCCCAAATCTTGTGACAAAACTCACACATGCCCACCGTGCCCAGCAC*
*CTGAACTCCTGGGGGGACCGTCAGTCTTCCTCTTCCCCCCAAAACCCAAGGACACCCTCATGATCT*
*CCCGGACCCCTGAGGTCACATGCGTGGTGGTGGACGTGAGCCACGAAGACCCTGAGGTCAAGTTC*
*AACTGGTACGTGGACGGCGTGGAGGTGCATAATGCCAAGACAAAGCCGCGGGAGGAGCAGTACAA*
*CAGCACGTACCGTGTGGTCAGCGTCCTCACCGTCCTGCACCAGGACTGGCTGAATGGCAAGGAGT*
*ACAAGTGCAAGGTCTCCAACAAAGCCCTCCCAGCCCCATCGAGAAAACCATCTCCAAAGCCAAAG*
*GGCAGCCCCGAGAACCACAGGTGTACACCCTGCCCCCATCCCGGGATGAGCTGACCAAGAACCAG*
*GTCAGCCTGACATGCCTGGTCAAAGGCTTCTATCCCAGCGACATCGCCGTGGAGTGGGAGAGCAAT*
*GGGCAGCCGGAGAACAACTACAAGACCACGCCTCCCGTGCTGGACTCCGACGGCTCCTTCTTCCTC*
*TACAGCAAGCTCACCGTGGACAAGTCCAGGTGGCAGCAGGGGAACGTCTTCTCATGCTCCGTGATG*
*CATGAGGCTCTGCACAACCACTACACGCAGAAGAGCCTCTCCCTGTCTCCGGGTAAA*TGA (SEQ ID NO: 287)

9D9-H18
ATGGAAGCCCCAGCGCAGCTTCTCTTCCTCCTGCTACTCTGGCTCCCTGATACCACCGGAGAG
GTACAGCTTCTTGAAAGTGGAGGTGGCCTTGTCCAACCCGGAGGGTCATTGCGGTTGAG
CTGTGCGGCAAGTGGCTTCACCTTCTCTGACGCTTGGATGGACTGGGTGAGACAAGCCC
CCGGTAAGGGACTGGAGTTGGTTGCTGAAATCAGGAACAAGGCCAAGAACCATGCAAC
ATATTATGCCGAAAGTGTGAAGGGAAGGTTCACAATCAGTAGAGATAACAGCAAGAACA
CACTGTACCTCCAGATGAACAGCCTCAGAGCTGAGGACACCGCCGTCTATTATTGTACC
ACTCTCGATTCATGGGGGCAGGGTACCACCGTTACAGTCAGCAGC*GCCTCCACCAAGGGC*
*CCATCGGTCTTCCCCCTGGCACCCTCCTCAAGAGCACCTCTGGGGGTACAGCGGCCCTGGGCTG*
*CCTGGTCAAGGACTACTTCCCCGAACCGGTGACGGTGTCGTGGAACTCAGGCGCCCTGACCAGCG*
*GCGTGCACACCTTCCCGGCTGTCCTACAGTCCTCAGGACTCTACTCCCTCAGCAGCGTGGTGACCG*
*TGCCCTCCAGCAGCTTGGGCACCCAGACCTACATCTGCAACGTGAATCACAAGCCCAGCAACACCA*
*AGGTGGACAAGAAAGTTGAGCCCAAATCTTGTGACAAAACTCACACATGCCCACCGTGCCCAGCAC*
*CTGAACTCCTGGGGGGACCGTCAGTCTTCCTCTTCCCCCCAAAACCCAAGGACACCCTCATGATCT*
*CCCGGACCCCTGAGGTCACATGCGTGGTGGTGGACGTGAGCCACGAAGACCCTGAGGTCAAGTTC*
*AACTGGTACGTGGACGGCGTGGAGGTGCATAATGCCAAGACAAAGCCGCGGGAGGAGCAGTACAA*
*CAGCACGTACCGTGTGGTCAGCGTCCTCACCGTCCTGCACCAGGACTGGCTGAATGGCAAGGAGT*
*ACAAGTGCAAGGTCTCCAACAAAGCCCTCCCAGCCCCATCGAGAAAACCATCTCCAAAGCCAAAG*
*GGCAGCCCCGAGAACCACAGGTGTACACCCTGCCCCCATCCCGGGATGAGCTGACCAAGAACCAG*
*GTCAGCCTGACATGCCTGGTCAAAGGCTTCTATCCCAGCGACATCGCCGTGGAGTGGGAGAGCAAT*
*GGGCAGCCGGAGAACAACTACAAGACCACGCCTCCCGTGCTGGACTCCGACGGCTCCTTCTTCCTC*
*TACAGCAAGCTCACCGTGGACAAGTCCAGGTGGCAGCAGGGGAACGTCTTCTCATGCTCCGTGATG*
*CATGAGGCTCTGCACAACCACTACACGCAGAAGAGCCTCTCCCTGTCTCCGGGTAAA*TGA (SEQ ID NO: 288)

FIG. 113

Humanized 9D9 clone full-length light chain nucleic acid sequence

9D9-K13
ATGGAAGCCCCAGCGCAGCTTCTCTTCCTCCTGCTACTCTGGCTCCCTGATACCACCGGA
GATATCGTGATGACACAAACTCCCCTGTCTCTGTCTGTAACTCCAGGTCAGCCCGC
GAGTATTTCATGTAAGAGCAGCCAATCCCTGCTGGACAGCGACGGGAAGACCTACC
TGAACTGGTTACTCCAAAAGCCAGGACAAAGTCCCCAACGCCTTATTTACCTGGTGT
CAGCCCTGGACTCTGGCGTGCCCGATCGATTTAGCGGCAGCGGGAGTGGCACAGAT
TTCACCCTGAAAATATCCCGCGTCGAGGCCGAAGATGTGGGCGTGTACTACTGCTG
GCAGGGCACACATTTCCCCTGGACATTTGGTCAGGGGACAAAGCTGGAAATTAAAC
*GAACTGTGGCAGCACCAAGCGTCTTCATCTTCCCGCCATCTGATGAGCAGTTGAAATCTGGAAC*
*TGCCTCTGTTGTGTGCCTGCTGAATAACTTCTATCCCAGAGAGGCCAAAGTACAGTGGAAGGTG*
*GATAACGCCCTCCAATCGGGTAACTCCAGGAGAGTGTCACAGAGCAGGACAGCAAGGACAG*
*CACCTACAGCCTCAGCAGCACCCTGACGCTGAGCAAAGCAGACTACGAGAAACACAAAGTCTA*
*CGCCTGCGAAGTCACCCATCAGGGCCTGAGCTCGCCCGTCACAAAGAGCTTCAACAGGGGAG*
*AGTGT*TAG   (SEQ ID NO: 289)

FIG. 114

Humanized 12G6 clone full-length heavy chain nucleic acid sequence

12G6-SFD1
ATGGAAGCCCCAGCGCAGCTTCTCTTCCTCCTGCTACTCTGGCTCCCTGATACCACCGGA
GAGGTACAGCTGGTGGAGTCGGGAGGAGGCTTGGTACAGCCTGGGGGTTCTCTGA
GACTCTCCTGTGCAGCTTCTGGATTCCCATTCAGTAACTACTGGATGAACTGGGTCC
GCCAGGCTCCAGGGAAGGGACTTGAGTGGGTGGGTCAAATTAGATTGAAATCTAAT
AATTATGCAACACATTATGCGGAGTCTGTGAAAGGGCGGTTCACCATCTCCAGAGA
TGATTCCAAAAACAGCCTCTATCTTCAAATGAATTCCCTGAAAACTGAAGACACTGC
CGTTTATTACTGTACCCCAATTGACTATTGGGGCCAAGGCACCACTGTCACAGTCTC
CTCA*GCCTCCACCAAGGGCCCATCGGTCTTCCCCCTGGCACCCTCCTCCAAGAGCACCTCTG*
*GGGGTACAGCGGCCCTGGGCTGCCTGGTCAAGGACTACTTCCCCGAACCGGTGACGGTGTCG*
*TGGAACTCAGGCGCCCTGACCAGCGGCGTGCACACCTTCCCGGCTGTCCTACAGTCCTCAGG*
*ACTCTACTCCCTCAGCAGCGTGGTGACCGTGCCCTCCAGCAGCTTGGGCACCCAGACCTACAT*
*CTGCAACGTGAATCACAAGCCCAGCAACACCAAGGTGGACAAGAAAGTTGAGCCCAAATCTTG*
*TGACAAAACTCACACATGCCCACCGTGCCCAGCACCTGAACTCCTGGGGGGACCGTCAGTCTT*
*CCTCTTCCCCCCAAAACCCAAGGACACCCTCATGATCTCCCGGACCCCTGAGGTCACATGCGT*
*GGTGGTGGACGTGAGCCACGAAGACCCTGAGGTCAAGTTCAACTGGTACGTGGACGGCGTGG*
*AGGTGCATAATGCCAAGACAAAGCCGCGGGAGGAGCAGTACAACAGCACGTACCGTGTGGTC*
*AGCGTCCTCACCGTCCTGCACCAGGACTGGCTGAATGGCAAGGAGTACAAGTGCAAGGTCTCC*
*AACAAAGCCCTCCCAGCCCCCATCGAGAAAACCATCTCCAAAGCCAAAGGGCAGCCCCGAGAA*
*CCACAGGTGTACACCCTGCCCCCATCCCGGGATGAGCTGACCAAGAACCAGGTCAGCCTGAC*
*ATGCCTGGTCAAAGGCTTCTATCCCAGCGACATCGCCGTGGAGTGGGAGAGCAATGGGCAGC*
*CGGAGAACAACTACAAGACCACGCCTCCCGTGCTGGACTCCGACGGCTCCTTCTTCCTCTACA*
*GCAAGCTCACCGTGGACAAGTCCAGGTGGCAGCAGGGGAACGTCTTCTCATGCTCCGTGATG*
*CATGAGGCTCTGCACAACCACTACACGCAGAAGAGCCTCTCCCTGTCTCCGGGTAAA*TGA
(SEQ ID NO: 290)

Humanized 12G6 clone full-length light chain nucleic acid sequence

12G6-K12
ATGGAAGCCCCAGCGCAGCTTCTCTTCCTCCTGCTACTCTGGCTCCCTGATACCACCGGA
GACATTGTGATGACCCAGACTCCACTCAGTTTGTCAGTTACCCCTGGGCAACCAGC
CTCTATCTCTTGCAAGTCAAGTCAGAGCCTCTTATATAGTAATGGAAAAACCTATTT
GAACTGGGTTTTACAGAAGCCAGGCCAGTCTCCACAGCGCCTAATCTATCTGGTGT
CTAAACTGGACTCTGGAGTCCCTGACAGGTTCTCTGGCAGTGGATCAGGAACAGAT
TTTACACTGAAAATCAGCAGAGTGGAGGCTGAGGATGTGGGAGTTTATTACTGCGT
GCAAGGTTCACATTTTCACACGTTCGGTCAAGGGACCAAGCTGGAGATTAAA*CGAAC*
*TGTGGCAGCACCAAGCGTCTTCATCTTCCCGCCATCTGATGAGCAGTTGAAATCTGGAACTGCC*
*TCTGTTGTGTGCCTGCTGAATAACTTCTATCCCAGAGAGGCCAAAGTACAGTGGAAGGTGGATA*
*ACGCCCTCCAATCGGGTAACTCCCAGGAGAGTGTCACAGAGCAGGACAGCAAGGACAGCACC*
*TACAGCCTCAGCAGCACCCTGACGCTGAGCAAAGCAGACTACGAGAAACACAAAGTCTACGCC*
*TGCGAAGTCACCCATCAGGGCCTGAGCTCGCCCGTCACAAAGAGCTTCAACAGGGGAGAGTG*
*TTAG* (SEQ ID NO: 291)

FIG. 115

Humanized 4B10 clone full-length heavy chain nucleic acid sequence

4B10-H1
ATGGAAGCCCCAGCGCAGCTTCTCTTCCTCCTGCTACTCTGGCTCCCTGATACCACCGGA
GAGGTACAGCTGGTGGAGTCGGGAGGAGGCTTGGTACAGCCTGGGGGTTCTCTGA
GACTCTCCTGTGCAGCTTCTGGATTCACCTTTTCTGATTACTACATGAGCTGGGTCC
GCCAGGCTCCAGGGAAGGGACTTGAGTGGGTGGGTTTTATTAGAAACAAAGCTAAT
GGTTACACAACAGAGTACAGTGCATCTGTGAAGGGTCGGTTCACCATCTCCAGAGA
TGATTCCAAAAACAGCCTCTATCTTCAAATGAATTCCCTGAAAACTGAAGACACTGC
CGTTTATTACTGTGCAAGATATATCTGGTTTGACTACTGGGGCCAAGGCACCACTGT
CACAGTCTCCTCA*GCCTCCACCAAGGGCCCATCGGTCTTCCCCCTGGCACCCTCCTCCAAG*
*AGCACCTCTGGGGGTACAGCGGCCCTGGGCTGCCTGGTCAAGGACTACTTCCCCGAACCGGT*
*GACGGTGTCGTGGAACTCAGGCGCCCTGACCAGCGGCGTGCACACCTTCCCGGCTGTCCTAC*
*AGTCCTCAGGACTCTACTCCCTCAGCAGCGTGGTGACCGTGCCCTCCAGCAGCTTGGGCACCC*
*AGACCTACATCTGCAACGTGAATCACAAGCCCAGCAACACCAAGGTGGACAAGAAAGTTGAGC*
*CCAAATCTTGTGACAAAACTCACACATGCCCACCGTGCCCAGCACCTGAACTCCTGGGGGGAC*
*CGTCAGTCTTCCTCTTCCCCCCAAAACCCAAGGACACCCTCATGATCTCCCGGACCCCTGAGG*
*TCACATGCGTGGTGGTGGACGTGAGCCACGAAGACCCTGAGGTCAAGTTCAACTGGTACGTGG*
*ACGGCGTGGAGGTGCATAATGCCAAGACAAAGCCGCGGGAGGAGCAGTACAACAGCACGTAC*
*CGTGTGGTCAGCGTCCTCACCGTCCTGCACCAGGACTGGCTGAATGGCAAGGAGTACAAGTG*
*CAAGGTCTCCAACAAAGCCCTCCCAGCCCCCATCGAGAAAACCATCTCCAAAGCCAAAGGGCA*
*GCCCCGAGAACCACAGGTGTACACCCTGCCCCCATCCCGGGATGAGCTGACCAAGAACCAGG*
*TCAGCCTGACATGCCTGGTCAAAGGCTTCTATCCCAGCGACATCGCCGTGGAGTGGGAGAGCA*
*ATGGGCAGCCGGAGAACAACTACAAGACCACGCCTCCCGTGCTGGACTCCGACGGCTCCTTCT*
*TCCTCTACAGCAAGCTCACCGTGGACAAGTCCAGGTGGCAGCAGGGGAACGTCTTCTCATGCT*
*CCGTGATGCATGAGGCTCTGCACAACCACTACACGCAGAAGAGCCTCTCCCTGTCTCCGGGTA*
*AA*TGA  (SEQ ID NO: 292)

Humanized 4B10 clone full-length light chain nucleic acid sequence

4B10-K1
ATGGAAGCCCCAGCGCAGCTTCTCTTCCTCCTGCTACTCTGGCTCCCTGATACCACCGGA
GACATTGTGATGACCCAAACTCCACTCTCCCTGTCTGTCACTCCTGGACAACCAGCC
TCCATCTCTTGCAGATCTAGTCAGAGCCTTGTACACACTAATGGAAACACCTATTTA
CATTGGTACCTGCAGAAGCCAGGCCAGTCTCCACAGCTCCTGATTTATATGGTTTCC
AACCGATTTTCTGGGGTCCCAGACAGGTTCAGTGGCAGTGGATCAGGGACAGATTT
CACACTCAAGATCAGCAGAGTGGAGGCTGAGGATGTGGGAGTTTATTACTGCTCTC
AAAGTGCACATGTTCCTCCGCTCACGTTCGGTCAAGGGACCAGGCTGGAGATTAAA
*CGAACTGTGGCAGCACCAAGCGTCTTCATCTTCCCGCCATCTGATGAGCAGTTGAAATCTGGAA*
*CTGCCTCTGTTGTGTGCCTGCTGAATAACTTCTATCCCAGAGAGGCCAAAGTACAGTGGAAGGT*
*GGATAACGCCCTCCAATCGGGTAACTCCCAGGAGAGTGTCACAGAGCAGGACAGCAAGGACA*
*GCACCTACAGCCTCAGCAGCACCCTGACGCTGAGCAAAGCAGACTACGAGAAACACAAAGTCT*
*ACGCCTGCGAAGTCACCCATCAGGGCCTGAGCTCGCCCGTCACAAAGAGCTTCAACAGGGGA*
*GAGTGT*TAG  (SEQ ID NO: 293)

FIG. 116

ANTI-HUMAN CD52 IMMUNOGLOBULINS

This application is a national stage application under 35 U.S.C. §371 of International Application PCT/US2010/034704 (now pending), filed May 13, 2010, which claims priority from U.S. Provisional Application 61/177,837, filed May 13, 2009. The contents of the foregoing priority applications are incorporated by reference herein in their entirety.

A Sequence Listing associated with this application is being submitted electronically via EFS-Web in text format, and is hereby incorporated by reference in its entirety into the specification. The name of the text file containing the Sequence Listing is 001662_0029_301_Sequence_Listing.txt. The text file, created on Nov. 10, 2011, is 182,313 bytes in size.

BACKGROUND OF THE INVENTION

CD52 is a glycosylated, glycosylphosphatidylinositol (GPI)-anchored cell surface protein found in abundance (500,000 molecules/cell) on a variety of normal and malignant lymphoid cells (e.g., T and B cells). See, e.g., Hale et al., *J Biol regul Homeost Agents* 15:386-391 (2001); Huh et al., *Blood* 92: Abstract 4199 (1998); Elsner et al., *Blood* 88:4684-4693 (1996); Gilleece et al., Blood 82:807-812 (1993); Rodig et al., *Clin Cancer Res* 12:7174-7179 (2006); Ginaldi et al., *Leuk Res* 22:185-191 (1998). CD52 is expressed at lower levels on myeloid cells such as monocytes, macrophages, and dendritic cells, with little expression found on mature natural killer (NK) cells, neutrophils, and hematological stem cells. Id. CD52 is also produced by epithelial cells in the epididymis and duct deferens, and is acquired by sperm during passage through the genital tract (Hale et al., 2001, supra; Domagala et al., *Med Sci Monit* 7:325-331 (2001)). The exact biological function of CD52 remains unclear but some evidence suggests that it may be involved in T cell migration and co-stimulation (Rowan et al., *Int Immunol* 7:69-77 (1995); Masuyama et al., *J Exp Med* 189:979-989 (1999); Watanabe et al., *Clin Immunol* 120:247-259 (2006)). Campath-1H® (alemtuzumab, Campath®, MabCampath®) is a humanized anti-human CD52 monoclonal antibody that exhibits potent in vitro cytotoxic effects (antibody-dependent cell mediated cytotoxicity (ADCC) and complement-dependent cytotoxicity (CDC)). Campath® recognizes an epitope which consists of the carboxy terminal four amino acids of the mature CD52 protein and a portion of the negatively charged GPI anchor. Due to its significant cytotoxic effects, Campath® is capable of depleting CD52 positive cells in vivo and it is approved for front line and third line treatment of chronic lymphocytic leukemia (CLL). Campath® has been evaluated for its utility in the treatment of several autoimmune diseases, including rheumatoid arthritis, vasculitis, myositis and Wegener's disease. However, the most advanced studies of Campath® are in treating relapsing remitting multiple sclerosis (MS). These studies showed a significant improvement in time to relapse relative to an active comparator (Rebif® (i.e., interferon beta-1a)).

A need exists for additional therapeutic agents and approaches to target CD52.

SUMMARY OF THE INVENTION

Humanized Immunoglobulins

The invention relates to humanized immunoglobulins that have binding specificity for human CD52 (huCD52). They may comprise the complementarity determining regions (CDRs) of mouse anti-human CD52 antibodies. The humanized immunoglobulins of the invention have amino acid sequences that are different from other humanized immunoglobulins, and in particular from other humanized immunoglobulins that comprise CDRs of murine anti-human CD52 antibodies. The humanized immunoglobulins of the invention are different from the humanized immunoglobulin Campath®. In some embodiments, they provide advantages over humanized antibodies that comprise the CDRs of Campath®.

The humanized immunoglobulins described herein can comprise a humanized heavy chain and a humanized light chain. In one embodiment, the humanized immunoglobulin comprises a light chain comprising one or more CDRs (e.g., all three CDRs) of SEQ ID NO: 3 and a heavy chain comprising one or more CDRs (e.g., all three CDRs) of SEQ ID NO: 16; a light chain comprising one or more CDRs (e.g., all three CDRs) of SEQ ID NO: 4 and a heavy chain comprising one or more CDRs (e.g., all three CDRs) of SEQ ID NO: 17; a light chain comprising one or more CDRs (e.g., all three CDRs) of SEQ ID NO: 5 and a heavy chain comprising one or more CDRs (e.g., all three CDRs) of SEQ ID NO: 18; a light chain comprising one or more CDRs (e.g., all three CDRs) of SEQ ID NO: 6 and a heavy chain comprising one or more CDRs of SEQ ID NO: 19; a light chain comprising one or more CDRs (e.g., all three CDRs) of SEQ ID NO: 7 and a heavy chain comprising one or more CDRs (e.g., all three CDRs) of SEQ ID NO: 20; a light chain comprising one or more CDRs (e.g., all three CDRs) of SEQ ID NO: 8 and a heavy chain comprising one or more CDRs (e.g., all three CDRs) of SEQ ID NO: 21; a light chain comprising one or more CDRs (e.g., all three CDRs) of SEQ ID NO: 9 and a heavy chain comprising one or more CDRs (e.g., all three CDRs) of SEQ ID NO: 22; a light chain comprising one or more CDRs (e.g., all three CDRs) of SEQ ID NO: 10 and a heavy chain comprising one or more CDRs (e.g., all three CDRs) of SEQ ID NO: 23; a light chain comprising one or more CDRs (e.g., all three CDRs) of SEQ ID NO: 11 and a heavy chain comprising one or more CDRs (e.g., all three CDRs) of SEQ ID NO: 24; a light chain comprising one or more CDRs (e.g., all three CDRs) of SEQ ID NO: 12 and a heavy chain comprising one or more CDRs (e.g., all three CDRs) of SEQ ID NO: 25; a light chain comprising one or more CDRs (e.g., all three CDRs) of SEQ ID NO: 12 and a heavy chain comprising one or more CDRs (e.g., all three CDRs) of SEQ ID NO: 137; or a light chain comprising one or more CDRs (e.g., all three CDRs) of SEQ ID NO: 13 and a heavy chain sequence comprising one or more CDRs (e.g., all three CDRs) of SEQ ID NO: 26. The CDRs in the above-mentioned SEQ ID NOs are indicated by FIGS. 2 and 3 and are referred to in Tables 1-6 as provided herein.

In another embodiment, the humanized immunoglobulin that has binding specificity for human CD52 comprises a light chain comprising one or more CDRs (e.g., all three) selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48; a heavy chain comprising one or more CDRs (e.g., all three) selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294; or such a light chain and such a heavy chain; wherein the humanized immunoglobulin is not Campath®.

In another embodiment, the humanized immunoglobulin that has a binding specificity for human CD52 comprises a light chain comprising one or more CDRs (e.g., all three CDRs) of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13; a heavy chain comprising one or more CDRs (e.g., all three CDRs) of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 137; or such a light chain and such a heavy chain; wherein the humanized immunoglobulin is not Campath®.

In some embodiments, the framework region of the humanized immunoglobulin has at least 50% homology to the framework region of the immunoglobulin from which the light chain CDRs and the heavy chain CDRs are obtained. For example, the framework region of the humanized immunoglobulin can be at least 50%, at least 60%, at least 70%, at least 80%, at least 90%, at least 95%, at least 98%, at least 99%, or even 100% identical, to a germline human immunoglobulin sequence. In one embodiment, the framework region of the humanized immunoglobulin can be obtained or derived from an IgG human antibody variable region. In another embodiment the CD52 is wildtype human CD52. In yet another embodiment, the humanized immunoglobulin can compete with alemtuzumab for binding to human CD52, e.g., it can bind to an epitope that is identical to, or which overlaps with, the epitope to which alemtuzumab binds.

The invention also relates to a humanized light chain of a humanized immunoglobulin of the invention. In one embodiment, the humanized light chain comprises one or more CDRs selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48 or a combination thereof, wherein the humanized light chain is not the humanized light chain of Campath®.

In other embodiment, the humanized light chain comprises one or more CDRs (e.g., all three CDRs) of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13, wherein the humanized light chain is not the humanized light chain of Campath®.

The invention also relates to a humanized heavy chain of a humanized immunoglobulin of the invention. In one embodiment, the humanized heavy chain comprises one or more CDRs of an Ig variable domain selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294, or a combination thereof, wherein the humanized heavy chain is not the humanized heavy chain of Campath®.

In other embodiments, the humanized heavy chain comprises one or more CDRs (e.g., all three CDRs) of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 137, wherein the humanized heavy chain is not the humanized heavy chain of Campath®.

Preferably, the humanized immunoglobulins of the present invention comprise both a humanized light chain of the invention and a humanized heavy chain of the invention.

In other embodiments, the invention provides a humanized immunoglobulin which binds to the same epitope on human CD52 as, or competes or cross-competes with, a mouse monoclonal antibody comprising a light chain variable region of SEQ ID NO: 3 and a heavy chain variable region of SEQ ID NO: 16; a light chain variable region of SEQ ID NO: 4 and a heavy chain variable region of SEQ ID NO: 17; a light chain variable region of SEQ ID NO: 5 and a heavy chain variable region of SEQ ID NO: 18; a light chain variable region of SEQ ID NO: 6 and a heavy chain variable region of SEQ ID NO: 19; a light chain variable region of SEQ ID NO: 7 and a heavy chain variable region of SEQ ID NO: 20; a light chain variable region of SEQ ID NO: 8 and a heavy chain variable region of SEQ ID NO: 21; a light chain variable region of SEQ ID NO: 9 and a heavy chain variable region of SEQ ID NO: 22; a light chain variable region of SEQ ID NO: 10 and a heavy chain variable region of SEQ ID NO: 23; a light chain variable region of SEQ ID NO: 11 and a heavy chain variable region of SEQ ID NO: 24; a light chain variable region of SEQ ID NO: 12 and a heavy chain variable region of SEQ ID NO: 25; or a light chain variable region of SEQ ID NO: 13 and a heavy chain variable region of SEQ ID NO: 26. In other embodiments, the humanized immunoglobulin binds to an epitope on human CD52 which overlaps with the epitope to which such a mouse monoclonal antibody binds.

In other embodiments, the invention provides a humanized immunoglobulin which binds to an epitope on human CD52 (e.g., SEQ ID NO: 104) comprising at least residue 1 of the mature human CD52 sequence (where residue 1 is the N-terminus of the mature human CD52 sequence, i.e., the N-terminal glycine [G] residue; see FIG. 4). The humanized immunoglobulin may bind to an epitope comprising at least residues 1, 3, 4 and 5 of the mature human CD52 sequence (these residues being a glycine [G], an asparagine [N], an aspartate [D], and a threonine [T], respectively). The humanized immunoglobulin may bind to an epitope comprising at least residues 1, 2, 3, 4 and 5 of the mature human CD52 sequence (these residues being a glycine [G], a glutamine [Q], an asparagine [N], an aspartate [D], and a threonine [T], respectively). In other embodiments, the invention provides a humanized immunoglobulin which binds to an epitope on human CD52 comprising at least residues 7, 8 and 9 of the mature human CD52 sequence (these residues being a glutamine [Q], a threonine [T], and a serine [S], respectively). In some embodiments, the epitope comprises at least residues 7 (Q), 8 (T) and 11 (P) of the mature human CD52 sequence. In some embodiments, the epitope comprises at least residues 4 (D) and 11 (P) of the mature human CD52 sequence.

In some embodiments, the invention provides a humanized immunoglobulin, which binds to human CD52, and which comprises a light chain comprising one or more CDRs selected from the group consisting of SEQ ID NO: 115, SEQ ID NO: 118, and SEQ ID NO: 121 (e.g., all three of said CDRs), or a heavy chain comprising one or more CDRs selected from the group consisting of SEQ ID NO: 124, SEQ ID NO: 127, and SEQ ID NO: 130 (e.g., all three of said CDRs), or both such light chain and such heavy chain. In other embodiments, the invention provides a humanized immunoglobulin, which binds to human CD52, and which comprises a light chain comprising one or more CDRs selected from the group consisting of SEQ ID NO: 116, SEQ ID NO: 119, and SEQ ID NO: 122 (e.g., all three of said CDRs), or a heavy chain comprising one or more CDRs selected from the group consisting of SEQ ID NO: 125, SEQ ID NO: 128, and SEQ ID NO: 131 (e.g., all three of said CDRs), or both such light chain and heavy chain. In still further embodiments, the invention provides a humanized immunoglobulin, which binds to human CD52, and which comprises a light chain comprising one or more CDRs selected from the group consisting of SEQ ID NO: 117, SEQ ID NO: 120, and SEQ ID NO: 123 (e.g., all three of said CDRs), or a heavy chain comprising one or more CDRs selected from the group consisting of SEQ ID NO: 126, SEQ ID NO: 129, and SEQ ID NO: 132 (e.g., all three of said CDRs), or both such light chain and such heavy chains.

In certain embodiments, the humanized immunoglobulin comprises a light chain comprising the CDRs of SEQ ID NO: 115, SEQ ID NO: 118 and SEQ ID NO: 121 and a heavy chain comprising the CDRs of SEQ ID NO: 124, SEQ ID NO: 127 and SEQ ID NO: 130. In other embodiments, the humanized immunoglobulin comprises a light chain comprising the CDRs of SEQ ID NO: 116, SEQ ID NO: 119 and SEQ ID NO: 122 and a heavy chain comprising the CDRs of SEQ ID NO: 125, SEQ ID NO: 128 and SEQ ID NO: 131. In other embodiments, the humanized immunoglobulin comprises a light chain comprising the CDRs of SEQ ID NO: 117, SEQ ID NO: 120 and SEQ ID NO: 123 and a heavy chain comprising the CDRs of SEQ ID NO: 126, SEQ ID NO: 129 and SEQ ID NO: 132.

The humanized immunoglobulins of the present invention are different from the humanized immunoglobulin Campath®.

The amino acid sequences of the above-mentioned SEQ ID NOs: 115-132 are provided below, and are based on the amino acid sequences that are reported in Tables 1-6 as provided elsewhere herein. In these amino acid sequences, "X" stands for any amino acid, and the symbol "/" indicates that either (or any) of the amino acids depicted adjacent that symbol may be present at the indicated position (e.g., K/R indicates that a lysine or arginine residue is present at the indicated position and F/L/V indicates that a phenylalanine, leucine or valine residue is present at the indicated position).

```
Light Chain CDR-1 Sequences
                            (SEQ ID NO: 115)
K/RSSQSLL/V/IXS/TN/DGXS/TYLX (SEQ ID NO: 116)
K/RSSQSLL/V/IHS/TNGXS/TYLH (SEQ ID NO: 117)
RSSQSLVHTNGNS/TYLH Light Chain CDR-2 Sequences
                            (SEQ ID NO: 118)
XVSXXXS (SEQ ID NO: 119)
XVSXRXS (SEQ ID NO: 120)
MVSXRFS Light Chain CDR-3 Sequences
                            (SEQ ID NO: 121)
XQXXH/R/KF/L/V/IXX (SEQ ID NO: 122)
SQSXH/R/KF/L/V/IPX (SEQ ID NO: 123)
SQSXHVPF/P Heavy Chain CDR-1 Sequences
                            (SEQ ID NO: 124)
GFXFXXYW/YMX (SEQ ID NO: 125)
GFTFXXYW/YMX (SEQ ID NO: 126)
GFTFTDYW/YMS Heavy Chain CDR-2 Sequences
                            (SEQ ID NO: 127)
XIRXKXBXYXTXYXXSVKG (SEQ ID NO: 128)
XIRXKXNXYTTEYXXSVKG (SEQ ID NO: 129)
FIRNKANGYTTEYXXSVKG Heavy Chain CDR-3 Sequences
                            (SEQ ID NO: 130)
TXXXY/F/W (SEQ ID NO: 131)
TRYXY/F/WFDY (SEQ ID NO: 132)
TRYIF/WFDY
```

The invention also relates to a humanized light chain comprising one or more CDRs selected from the group consisting of SEQ ID NO: 115, SEQ ID NO: 118, and SEQ ID NO: 121 (e.g., all three of said CDRs); a humanized light chain comprising one or more CDRs selected from the group consisting of SEQ ID NO: 116, SEQ ID NO: 119, and SEQ ID NO: 122 (e.g., all three of said CDRs); or a humanized light chain comprising one or more CDRs selected from the group consisting of SEQ ID NO: 117, SEQ ID NO: 120, and SEQ ID NO: 123 (e.g., all three of said CDRs).

The invention also relates to a humanized heavy chain comprising one or more CDRs selected from the group consisting of SEQ ID NO: 124, SEQ ID NO: 127, and SEQ ID NO: 130 (e.g., all three of said CDRs); a humanized heavy chain comprising one or more CDRs selected from the group consisting of SEQ ID NO: 125, SEQ ID NO: 128, and SEQ ID NO: 131 (e.g., all three of said CDRs); or a humanized heavy chain comprising one or more CDRs selected from the group consisting of SEQ ID NO: 126, SEQ ID NO: 129, and SEQ ID NO: 132 (e.g., all three of said CDRs).

The humanized light chains and humanized heavy chains of the present invention are different from the humanized light chain and the humanized heavy chains of the humanized immunoglobulin Campath®.

In some embodiments of the present invention, the humanized immunoglobulins of the invention (irrespective of the manner in which they might otherwise be defined, e.g., regardless of whether they might also be defined in terms of the sequence of one or more of their CDRs and/or by their cross-reactivity with a mouse monoclonal antibody or another humanized immunoglobulin): (1) exhibit binding to glycosylated and de-glycosylated CD52 with no apparent preference; (2) exhibit binding specific for glycosylated CD52; (3) exhibit binding specific for de-glycosylated CD52; or (4) exhibit binding preferential for de-glycosylated over glycosylated CD52. In certain embodiments, the humanized immunoglobulins of the invention have a greater binding affinity for glycosylated human CD52 than for non-glycosylated or de-glycosylated human CD52. Indeed, in certain embodiments of the present invention, the humanized immunoglobulins of the present invention exhibit binding that is specific for glycosylated human CD52. Binding affinity for non-glycosylated or de-glycosylated human CD52 may be determined with the use of mature human CD52 that has been de-glycosylated using a glycosidase, e.g., using the endoglycosidase PNGase-F. In certain embodiments of the present invention, the humanized immunoglobulins of the invention bind to an epitope on mature human CD52 which comprises its N-linked carbohydrate moiety. This carbohydrate moiety is a sialylted, polylactosamine-containing core-fucosylated tetraantennary N-linked oligosaccharide (Treumann, A. et al., (1995) *J. Biol. Chem.* 270:6088-6099). This epitope may also comprise at least residue 1 of the mature human CD52 sequence, at least residue 3 of the mature human CD52 sequence, at least residues 1, 3, 4 and 5 of the mature human CD52 sequence, or at least residues 1, 2, 3, 4 and 5 of the mature human CD52 sequence. In some embodiments, the mouse or chimeric antibodies of the present invention may have any of these binding features.

Isolated nucleic acid molecules that encode a humanized immunoglobulin, humanized light chain or humanized heavy chain of the invention, as defined elsewhere herein, are also provided. In some embodiments, the invention is an (one or more) isolated nucleic acid molecule encoding a humanized heavy chain and a humanized light chain which associate together to form a humanized immunoglobulin that has binding specificity for human CD52, wherein the humanized light chain comprises one or more CDRs (e.g., all three CDRs) of SEQ ID NO: 3 and a heavy chain comprising one or more CDRs (e.g., all three CDRs) of SEQ ID NO: 16; a light chain comprising one or more CDRs (e.g., all three CDRs) of SEQ ID NO: 4 and a heavy chain comprising one or more CDRs (e.g., all three CDRs) of SEQ ID NO: 17; a light chain comprising one or more CDRs (e.g., all three CDRs) of SEQ ID NO: 5 and a heavy chain comprising one or more CDRs (e.g., all three CDRs) of SEQ ID NO: 18; a light chain comprising one or more CDRs (e.g., all three CDRs) of SEQ ID NO: 6 and a heavy chain comprising one or more CDRs (e.g., all three CDRs) of SEQ ID NO: 19; a light chain comprising one or more CDRs (e.g., all three CDRs) of SEQ ID NO: 7 and a heavy chain comprising one or more CDRs (e.g., all three CDRs) of SEQ ID NO: 20; a light chain comprising one or more CDRs (e.g., all three CDRs) of SEQ ID NO: 8 and a heavy chain comprising one or more CDRs (e.g., all three CDRs) of SEQ ID NO: 21; a light chain comprising one or more CDRs (e.g., all three CDRs) of SEQ ID NO: 9 and a heavy chain comprising one or more CDRs (e.g., all three CDRs) of SEQ ID NO: 22; a light chain comprising one or more CDRs (e.g., all three CDRs) of SEQ ID NO: 10 and a heavy chain comprising one or more CDRs (e.g., all three CDRs) of SEQ ID NO: 23; a light chain comprising one or more CDRs (e.g., all three CDRs) of SEQ ID NO: 11 and a heavy chain comprising one or more CDRs (e.g., all three CDRs) of SEQ ID NO: 24; a light chain comprising one or more CDRs (e.g., all three CDRs) of SEQ ID NO: 12 and a heavy chain comprising one or more CDRs (e.g., all three CDRs) of SEQ ID NO: 25; a light chain comprising one or more CDRs (e.g., all three CDRs) of SEQ ID NO: 12 and a heavy chain comprising one or more CDRs (e.g., all three CDRs) of SEQ ID NO: 137; or a light chain comprising one or more CDRs (e.g., all three CDRs) of SEQ ID NO: 13 and a heavy chain sequence comprising one or more CDRs (e.g., all three CDRs) of SEQ ID NO: 26.

In some embodiments, the invention is one or more isolated nucleic acid molecules encoding a humanized heavy chain and a humanized light chain which associate together to form a humanized immunoglobulin that has binding specificity for human CD52, wherein the humanized immunoglobulin binds to the same epitope on human CD52 as a mouse monoclonal antibody comprising a light chain variable region of SEQ ID NO: 3 and a heavy chain variable region of SEQ ID NO: 16; a light chain variable region of SEQ ID NO: 4 and a heavy chain variable region of SEQ ID NO: 17; a light chain variable region of SEQ ID NO: 5 and a heavy chain variable region of SEQ ID NO: 18; a light chain variable region of SEQ ID NO: 6 and a heavy chain variable region of SEQ ID NO: 19; a light chain variable region of SEQ ID NO: 7 and a heavy chain variable region of SEQ ID NO: 20; a light chain variable region of SEQ ID NO: 8 and a heavy chain variable region of SEQ ID NO: 21; a light chain variable region of SEQ ID NO: 9 and a heavy chain variable region of SEQ ID NO: 22; a light chain variable region of SEQ ID NO: 10 and a heavy chain variable region of SEQ ID NO: 23; a light chain variable region of SEQ ID NO: 11 and a heavy chain variable region of SEQ ID NO: 24; a light chain variable region of SEQ ID NO: 12 and a heavy chain variable region of SEQ ID NO: 25; or a light chain variable region of SEQ ID NO: 13 and a heavy chain variable region of SEQ ID NO: 26. In other embodiments, the invention is one or more isolated nucleic acid molecules encoding a humanized heavy chain and a humanized light chain which associate together to form a humanized immunoglobulin that has binding specificity for human CD52, wherein the humanized immunoglobulin binds to an epitope on human CD52 which overlaps with the epitope to which such a mouse monoclonal antibody binds.

In other embodiments, the invention is one or more isolated nucleic acid molecules encoding a humanized heavy chain and a humanized light chain which associate together to form a humanized immunoglobulin that has binding specificity for human CD52, wherein the humanized immunoglobulin binds to an epitope comprising at least residue 1 of mature human CD52; the humanized immunoglobulin binds to an epitope comprising at least residues 1, 3, 4 and 5 of mature human CD52; the humanized immunoglobulin binds to an epitope comprising at least residues 1, 2, 3, 4 and 5 of mature human CD52; or the humanized immunoglobulin binds to an epitope comprising at least residues 7, 8 and 9 of mature human CD52. In some embodiments, the epitope comprises at least residues 7, 8 and 11 of the mature human CD52 sequence. In some embodiments, the epitope comprises at least residues 4 and 11 of the mature human CD52 sequence.

In other embodiments, the invention is one or more isolated nucleic acid molecules encoding a humanized heavy chain and a humanized light chain which associate together to form a humanized immunoglobulin that has binding specificity for human CD52, wherein the humanized immunoglobulin comprises a light chain comprising one or more CDRs selected from the group consisting of SEQ ID NO: 115, SEQ ID NO: 118, and SEQ ID NO: 121 (e.g., all three of said CDRs), and/or a heavy chain comprising one or more CDRs selected from the group consisting of SEQ ID NO: 124, SEQ ID NO: 127, and SEQ ID NO: 130 (e.g., all three of said CDRs); a light chain comprising one or more CDRs selected from the group consisting of SEQ ID NO: 116, SEQ ID NO: 119, and SEQ ID NO: 122 (e.g., all three of said CDRs), and/or a heavy chain comprising one or more CDRs selected from the group consisting of SEQ ID NO: 125, SEQ ID NO: 128, and SEQ ID NO: 131 (e.g., all three of said CDRs); or a light chain comprising one or more CDRs selected from the group consisting of SEQ ID NO: 117, SEQ ID NO: 120, and SEQ ID NO: 123

(e.g., all three of said CDRs), and/or a heavy chain comprising one or more CDRs selected from the group consisting of SEQ ID NO: 126, SEQ ID NO: 129, and SEQ ID NO: 132 (e.g., all three of said CDRs).

In certain embodiments, the invention is one or more isolated nucleic acid molecules encoding a humanized heavy chain and a humanized light chain which associate together to form a humanized immunoglobulin that has binding specificity for human CD52, wherein the humanized immunoglobulin comprises a light chain comprising the CDRs of SEQ ID NO: 115, SEQ ID NO: 118 and SEQ ID NO: 121 and a heavy chain comprising the CDRs of SEQ ID NO: 124, SEQ ID NO: 127 and SEQ ID NO: 130; a light chain comprising the CDRs of SEQ ID NO: 116, SEQ ID NO: 119 and SEQ ID NO: 122 and a heavy chain comprising the CDRs of SEQ ID NO: 125, SEQ ID NO: 128 and SEQ ID NO: 131; or a light chain comprising the CDRs of SEQ ID NO: 117, SEQ ID NO: 120 and SEQ ID NO: 123 and a heavy chain comprising the CDRs of SEQ ID NO: 126, SEQ ID NO: 129 and SEQ ID NO: 132.

The one or more nucleic acids of the invention do not encode the humanized immunoglobulin Campath®.

In other embodiments, the invention is one or more isolated nucleic acid molecules encoding a humanized heavy chain and a humanized light chain which associate together to form a humanized immunoglobulin that has binding specificity for human CD52, wherein the humanized immunoglobulin has a greater binding affinity for glycosylated human CD52 than for non-glycosylated or de-glycosylated human CD52, e.g., exhibits binding that is specific for glycosylated human CD52. The humanized immunoglobulin may bind to an epitope on mature human CD52 which comprises its N-linked carbohydrate moiety. This epitope may also comprise at least residue 1 of the mature human CD52 sequence, at least residue 3 of the mature human CD52 sequence, at least residues 1, 3, 4 and 5 of the mature human CD52 sequence, or at least residues 1, 2, 3, 4 and 5 of the mature human CD52 sequence.

In other embodiments, the invention is an isolated nucleic acid molecule encoding a humanized light chain comprising one or more CDRs (e.g., all three CDRs) of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13, wherein the humanized light chain is not the humanized light chain of Campath®.

In other embodiments, the invention is an isolated nucleic acid molecule encoding a humanized heavy chain comprising one or more CDRs (e.g., all three CDRs) of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 137, wherein the humanized heavy chain is not the humanized heavy chain of Campath®.

In other embodiments, the invention is an isolated nucleic acid molecule encoding a humanized light chain comprising one or more CDRs selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, or a combination thereof, wherein the humanized light chain is not the humanized light chain of Campath®.

In other embodiments, the invention is an isolated nucleic acid molecule encoding a humanized heavy chain comprising one or more CDRs selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294, or a combination thereof, wherein the humanized heavy chain is not the humanized heavy chain of Campath®.

In other embodiments, the invention is an isolated nucleic acid molecule encoding a humanized light chain comprising one or more CDRs selected from the group consisting of SEQ ID NO: 115, SEQ ID NO: 118, and SEQ ID NO: 121 (e.g., all three of said CDRs); a humanized light chain comprising one or more CDRs selected from the group consisting of SEQ ID NO: 116, SEQ ID NO: 119, and SEQ ID NO: 122 (e.g., all three of said CDRs); or a humanized light chain comprising one or more CDRs selected from the group consisting of SEQ ID NO: 117, SEQ ID NO: 120, and SEQ ID NO: 123 (e.g., all three of said CDRs).

In other embodiments, the invention is an isolated nucleic acid molecule encoding a humanized heavy chain comprising one or more CDRs selected from the group consisting of SEQ ID NO: 124, SEQ ID NO: 127, and SEQ ID NO: 130 (e.g., all three of said CDRs); a humanized heavy chain comprising one or more CDRs selected from the group consisting of SEQ ID NO: 125, SEQ ID NO: 128 and SEQ ID NO: 131 (e.g., all three of said CDRs); or a humanized heavy chain comprising one or more CDRs selected from the group consisting of SEQ ID NO: 126, SEQ ID NO: 129 and SEQ ID NO: 132 (e.g., all three of said CDRs).

The invention also relates to recombinant vectors (e.g., expression vectors, including mammalian cell expression vectors) that comprise a nucleic acid encoding a humanized immunoglobulin (e.g., a humanized light chain and a humanized heavy chain), a humanized light chain, or a humanized heavy chain of the invention. In some embodiments, the invention is a recombinant vector comprising a nucleic acid encoding a humanized immunoglobulin that comprises a light chain comprising one or more CDRs (e.g., all three CDRs) of SEQ ID NO: 3 and a heavy chain comprising one or more CDRs (e.g., all three CDRs) of SEQ ID NO: 16; a light chain comprising one or more CDRs (e.g., all three CDRs) of SEQ ID NO: 4 and a heavy chain comprising one or more CDRs (e.g., all three CDRs) of SEQ ID NO: 17; a light chain comprising one or more CDRs (e.g., all three CDRs) of SEQ ID NO: 5 and a heavy chain comprising one or more CDRs (e.g., all three CDRs) of SEQ ID NO: 18; a light chain comprising one or more CDRs (e.g., all three CDRs) of SEQ ID NO: 6 and a heavy chain comprising one or more CDRs (e.g., all three CDRs) of SEQ ID NO: 19; a light chain comprising one or more CDRs (e.g., all three CDRs) of SEQ ID NO: 7 and a heavy chain comprising one or more CDRs (e.g., all three CDRs) of SEQ ID NO: 20; a light chain comprising one or more CDRs (e.g., all three CDRs) of SEQ ID NO: 8 and a heavy chain comprising one or more CDRs (e.g., all three CDRs) of SEQ ID NO: 21; a light chain comprising one or more CDRs (e.g., all three CDRs) of SEQ ID NO: 9 and a heavy chain comprising one or more CDRs (e.g., all three CDRs) of SEQ ID NO: 22; a light chain comprising one or more CDRs (e.g., all three CDRs) of SEQ ID NO: 10 and a heavy chain comprising one or more CDRs (e.g., all three CDRs) of SEQ ID NO: 23; a light chain comprising one or more CDRs (e.g., all three CDRs) of SEQ ID NO: 11 and a heavy chain comprising one or more CDRs (e.g., all three CDRs) of SEQ ID NO: 24; a light chain comprising one or more CDRs (e.g., all three CDRs) of SEQ ID NO: 12 and a heavy chain comprising one or more CDRs (e.g., all three CDRs) of SEQ ID NO: 25; a light chain comprising one or more CDRs (e.g., all three CDRs) of SEQ ID NO: 12 and a heavy chain comprising one or more CDRs (e.g., all three CDRs) of SEQ ID NO: 137; or a light chain comprising one or more CDRs (e.g., all three CDRs) of SEQ ID NO: 13 and a heavy chain comprising one or more CDRs (e.g., all three CDRs) of SEQ ID NO: 26.

In other embodiments, the recombinant vector comprises a nucleic acid encoding a humanized light chain, wherein the humanized light chain comprises one or more CDRs selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, or a combination thereof, wherein the humanized light chain is not the humanized light chain of Campath®.

In other embodiments, the recombinant vector comprises a nucleic acid encoding a humanized heavy chain, wherein the humanized heavy chain comprises one or more CDRs selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294, or a combination thereof, wherein the humanized light chain is not the humanized light chain of Campath®.

In some embodiments, the invention provides a recombinant vector comprising a nucleic acid molecule, or a pair of recombinant vectors comprising nucleic acid molecules, encoding a humanized heavy chain and a humanized light chain which associate together to form a humanized immunoglobulin that has binding specificity for human CD52, wherein the humanized immunoglobulin binds to the same epitope on human CD52 as a mouse monoclonal antibody comprising a light chain variable region of SEQ ID NO: 3 and a heavy chain variable region of SEQ ID NO: 16; a light chain variable region of SEQ ID NO: 4 and a heavy chain variable region of SEQ ID NO: 17; a light chain variable region of SEQ ID NO: 5 and a heavy chain variable region of SEQ ID NO: 18; a light chain variable region of SEQ ID NO: 6 and a heavy chain variable region of SEQ ID NO: 19; a light chain variable region of SEQ ID NO: 7 and a heavy chain variable region of SEQ ID NO: 20; a light chain variable region of SEQ ID NO: 8 and a heavy chain variable region of SEQ ID NO: 21; a light chain variable region of SEQ ID NO: 9 and a heavy chain variable region of SEQ ID NO: 22; a light chain variable region of SEQ ID NO: 10 and a heavy chain variable region of SEQ ID NO: 23; a light chain variable region of SEQ ID NO: 11 and a heavy chain variable region of SEQ ID NO: 24; a light chain variable region of SEQ ID NO: 12 and a heavy chain variable region of SEQ ID NO: 25; or a light chain variable region of SEQ ID NO: 13 and a heavy chain variable region of SEQ ID NO: 26. In other embodiments, the invention provides a recombinant vector comprising a nucleic acid molecule, or a pair of recombinant vectors comprising nucleic acid molecules, encoding a humanized heavy chain and a humanized light chain which associate together to form a humanized immunoglobulin that has binding specificity for human CD52, wherein the humanized immunoglobulin binds to an epitope on human CD52 which overlaps with the epitope to which such a mouse monoclonal antibody binds.

In other embodiments, the recombinant vector comprises a nucleic acid molecule, or a pair of recombinant vectors comprise nucleic acid molecules, encoding a humanized heavy chain and a humanized light chain which associate together to form a humanized immunoglobulin that has binding specificity for human CD52, wherein the humanized immunoglobulin binds to an epitope comprising at least residue 1 of mature human CD52; binds to an epitope comprising at least residues 1, 3, 4 and 5 of mature human CD52; binds to an epitope comprising at least residues 1, 2, 3, 4 and 5 of mature human CD52; or binds to an epitope comprising at least residues 7, 8 and 9 of mature human CD52. In some embodiments, the epitope comprises at least residues 7, 8 and 11 of the mature human CD52 sequence. In some embodiments, the epitope comprises at least residues 4 and 11 of the mature human CD52 sequence.

In some embodiments, the recombinant vector comprises a nucleic acid molecule, or a pair of recombinant vectors comprise nucleic acid molecules, encoding a humanized heavy chain and a humanized light chain which associate together to form a humanized immunoglobulin that has binding specificity for human CD52, wherein the humanized immunoglobulin comprises a light chain comprising one or more CDRs selected from the group consisting of SEQ ID NO: 115, SEQ ID NO: 118, and SEQ ID NO: 121 (e.g., all three of said CDRs), and/or a heavy chain comprising one or more CDRs selected from the group consisting of SEQ ID NO: 124, SEQ ID NO: 127, and SEQ ID NO: 130 (e.g., all three of said CDRs); a light chain comprising one or more CDRs selected from the group consisting of SEQ ID NO: 116, SEQ ID NO: 119, and SEQ ID NO: 122 (e.g., all three of said CDRs), and/or a heavy chain comprising one or more CDRs selected from the group consisting of SEQ ID NO: 125, SEQ ID NO: 128, and SEQ ID NO: 131 (e.g., all three of said CDRs); or a light chain comprising one or more CDRs selected from the group consisting of SEQ ID NO: 117, SEQ ID NO: 120, and SEQ ID NO: 123 (e.g., all three of said CDRs), and/or a heavy chain comprising one or more CDRs selected from the group consisting of SEQ ID NO: 126, SEQ ID NO: 129, and SEQ ID NO: 132 (e.g., all three of said CDRs).

In certain embodiments, the recombinant vector comprises a nucleic acid molecule, or a pair of recombinant vectors comprise nucleic acid molecules, encoding a humanized heavy chain and a humanized light chain which associate together to form a humanized immunoglobulin that has binding specificity for human CD52, wherein the humanized immunoglobulin comprises a light chain comprising the CDRs of SEQ ID NO: 115, SEQ ID NO: 118 and SEQ ID NO: 121 and a heavy chain comprising the CDRs of SEQ ID NO: 124, SEQ ID NO: 127 and SEQ ID NO: 130; a light chain comprising the CDRs of SEQ ID NO: 116, SEQ ID NO: 119 and SEQ ID NO: 122 and a heavy chain comprising the CDRs of SEQ ID NO: 125, SEQ ID NO: 128 and SEQ ID NO: 131; or a light chain comprising the CDRs of SEQ ID NO: 117, SEQ ID NO: 120 and SEQ ID NO: 123 and a heavy chain comprising the CDRs of SEQ ID NO: 126, SEQ ID NO: 129 and SEQ ID NO: 132.

The one or more nucleic acids in the recombinant vector or vectors of the present invention do not encode the humanized immunoglobulin Campath®.

In other embodiments, the recombinant vector comprises a nucleic acid molecule, or a pair of recombinant vectors comprise nucleic acid molecules, encoding a humanized heavy chain and a humanized light chain which associate together to form a humanized immunoglobulin that has binding specificity for human CD52, wherein the humanized immunoglobulin has a greater binding affinity for glycosylated human CD52 than for non-glycosylated or de-glycosylated human CD52, e.g., exhibits binding that is specific for glycosylated human CD52. The humanized immunoglobulin may bind to an epitope on mature human CD52 which comprises its N-linked carbohydrate moiety. This epitope may also comprise at least residue 1 of the mature human CD52 sequence, at least residue 3 of the mature human CD52 sequence, at least residues 1, 3, 4 and 5 of the mature human CD52 sequence, or at least residues 1, 2, 3, 4 and 5 of the mature human CD52 sequence.

In other embodiments, the recombinant vector comprises a nucleic acid molecule encoding a humanized light chain comprising one or more CDRs (e.g., all three CDRs) of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13, wherein the humanized light chain is not the humanized light chain of Campath®.

In other embodiments, the recombinant vector comprises a nucleic acid molecule encoding a humanized heavy chain comprising one or more CDRs (e.g., all three CDRs) of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 137, wherein the humanized heavy chain is not the humanized heavy chain of Campath®.

In other embodiments, the recombinant vector comprises a nucleic acid molecule encoding a humanized light chain comprising one or more CDRs selected from the group consisting of SEQ ID NO: 115, SEQ ID NO: 118, and SEQ ID NO: 121 (e.g., all three of said CDRs); a humanized light chain comprising one or more CDRs selected from the group consisting of SEQ ID NO: 116, SEQ ID NO: 119, and SEQ ID NO: 122 (e.g., all three of said CDRs); or a humanized light chain comprising one or more CDRs selected from the group consisting of SEQ ID NO: 117, SEQ ID NO: 120, and SEQ ID NO: 123 (e.g., all three of said CDRs), wherein the humanized light chain is not the humanized light chain of Campath®.

In other embodiments, the recombinant vector comprises a nucleic acid molecule encoding a humanized heavy chain comprising one or more CDRs selected from the group consisting of SEQ ID NO: 124, SEQ ID NO: 127, and SEQ ID NO: 130 (e.g., all three of said CDRs); a humanized heavy chain comprising one or more CDRs selected from the group consisting of SEQ ID NO: 125, SEQ ID NO: 128, and SEQ ID NO: 131 (e.g., all three of said CDRs); or a humanized heavy chain comprising one or more CDRs selected from the group consisting of SEQ ID NO: 126, SEQ ID NO: 129, and SEQ ID NO: 132 (e.g., all three of said CDRs), wherein the humanized heavy chain is not the humanized heavy chain of Campath®.

In particular embodiments, the recombinant vector of the invention is an expression vector, such as a mammalian cell expression vector. In certain embodiments, the vector is a plasmid or a viral vector (e.g., an adenoviral or AAV vector).

The invention also relates to a host cell that comprises a (one or more) nucleic acid (e.g., recombinant) encoding a humanized immunoglobulin (humanized light chain and humanized heavy chain), a humanized light chain or a humanized heavy chain of the invention. In some embodiments, the host cell comprises a recombinant vector (e.g., expression vector, including mammalian cell expression vectors) of the invention.

In a particular embodiment, the host cell comprises a nucleic acid (one or more nucleic acids) encoding a humanized light chain and a humanized heavy chain, wherein the humanized light chain and the humanized heavy chain associate together to form a humanized immunoglobulin that has binding specificity for human CD52 and wherein the humanized immunoglobulin comprises a light chain comprising one or more CDRs (e.g., all three CDRs) of SEQ ID NO: 3 and a heavy chain comprising one or more CDRs (e.g., all three CDRs) of SEQ ID NO: 16; a light chain comprising one or more CDRs (e.g., all three CDRs) of SEQ ID NO: 4 and a heavy chain comprising one or more CDRs (e.g., all three CDRs) of SEQ ID NO: 17; a light chain comprising one or more CDRs (e.g., all three CDRs) of SEQ ID NO: 5 and a heavy chain comprising one or more CDRs (e.g., all three CDRs) of SEQ ID NO: 18; a light chain comprising one or more CDRs (e.g., all three CDRs) of SEQ ID NO: 6 and a heavy chain comprising one or more CDRs (e.g., all three CDRs) of SEQ ID NO: 19; a light chain comprising one or more CDRs (e.g., all three CDRs) of SEQ ID NO: 7 and a heavy chain comprising one or more CDRs (e.g., all three CDRs) of SEQ ID NO: 20; a light chain comprising one or more CDRs (e.g., all three CDRs) of SEQ ID NO: 8 and a heavy chain comprising one or more CDRs (e.g., all three CDRs) of SEQ ID NO: 21; a light chain comprising one or more CDRs (e.g., all three CDRs) of SEQ ID NO: 9 and a heavy chain comprising one or more CDRs (e.g., all three CDRs) of SEQ ID NO: 22; a light chain comprising one or more CDRs (e.g., all three CDRs) of SEQ ID NO: 10 and a heavy chain comprising one or more CDRs (e.g., all three CDRs) of SEQ ID NO: 23; a light chain comprising one or more CDRs (e.g., all three CDRs) of SEQ ID NO: 11 and a heavy chain comprising one or more CDRs (e.g., all three CDRs) of SEQ ID NO: 24; a light chain comprising one or more CDRs (e.g., all three CDRs) of SEQ ID NO: 12 and a heavy chain comprising one or more CDRs (e.g., all three CDRs) of SEQ ID NO: 25; a light chain comprising one or more CDRs (e.g., all three CDRs) of SEQ ID NO: 12 and a heavy chain comprising one or more CDRs (e.g., all three CDRs) of SEQ ID NO: 137; or a light chain comprising one or more CDRs (e.g., all three CDRs) of SEQ ID NO: 13 and a heavy chain sequence comprising one or more CDRs (e.g., all three CDRs) of SEQ ID NO: 26.

In some embodiments, the host cell comprises one or more nucleic acid molecules encoding a humanized heavy chain and a humanized light chain which associate together to form a humanized immunoglobulin that has binding specificity for human CD52, wherein the humanized immunoglobulin binds to the same epitope on human CD52 as a mouse monoclonal antibody comprising a light chain variable region of SEQ ID NO: 3 and a heavy chain variable region of SEQ ID NO: 16; a light chain variable region of SEQ ID NO: 4 and a heavy chain variable region of SEQ ID NO: 17; a light chain variable region of SEQ ID NO: 5 and a heavy chain variable region of SEQ ID NO: 18; a light chain variable region of SEQ ID NO: 6 and a heavy chain variable region of SEQ ID NO: 19; a light chain variable region of SEQ ID NO: 7 and a heavy chain variable region of SEQ ID NO: 20; a light chain variable region of SEQ ID NO: 8 and a heavy chain variable region of SEQ ID NO: 21; a light chain variable region of SEQ ID NO: 9 and a heavy chain variable region of SEQ ID NO: 22; a light chain variable region of SEQ ID NO: 10 and a heavy chain variable region of SEQ ID NO: 23; a light chain variable region of SEQ ID NO: 11 and a heavy chain variable region of SEQ ID NO: 24; a light chain variable region of SEQ ID NO: 12 and a heavy chain variable region of SEQ ID NO: 25; or a light chain variable region of SEQ ID NO: 13 and a heavy chain variable region of SEQ ID NO: 26. In other embodiments, the host cell comprises one or more nucleic acid molecules encoding a humanized heavy chain and a humanized light chain which associate together to form a humanized immunoglobulin that has binding specificity for human CD52, wherein the humanized immunoglobulin binds to an epitope on human CD52 which overlaps with the epitope to which such a mouse monoclonal antibody binds.

In other embodiments, the host cell comprises one or more nucleic acid molecules encoding a humanized heavy chain and a humanized light chain which associate together to form a humanized immunoglobulin that has binding specificity for human CD52, wherein the humanized immunoglobulin binds to an epitope comprising at least residue 1 of mature human CD52; binds to an epitope comprising at least residues 1, 3, 4 and 5 of mature human CD52; binds to an epitope comprising at least residues 1, 2, 3, 4 and 5 of mature human CD52; or binds to an epitope comprising at least residues 7, 8 and 9 of mature human CD52. In some embodiments, the epitope comprises at least residues 7, 8 and 11 of the mature human CD52 sequence. In some embodiments, the epitope comprises at least residues 4 and 11 of the mature human CD52 sequence.

In some embodiments, the host cell comprises one or more nucleic acid molecules encoding a humanized heavy chain and a humanized light chain which associate together to form a humanized immunoglobulin that has binding specificity for human CD52, wherein the humanized immunoglobulin comprises a light chain comprising one or more CDRs selected from the group consisting of SEQ ID NO: 115, SEQ ID NO: 118, and SEQ ID NO: 121 (e.g., all three of said CDRs), and/or a heavy chain comprising one or more CDRs selected from the group consisting of SEQ ID NO: 124, SEQ ID NO: 127, and SEQ ID NO: 130 (e.g., all three of said CDRs); a light chain comprising one or more CDRs selected from the group consisting of SEQ ID NO: 116, SEQ ID NO: 119, and SEQ ID NO: 122 (e.g., all three of said CDRs), and/or a heavy chain comprising one or more CDRs selected from the group consisting of SEQ ID NO: 125, SEQ ID NO: 128, and SEQ ID NO: 131 (e.g., all three of said CDRs); or a light chain comprising one or more CDRs selected from the group consisting of SEQ ID NO: 117, SEQ ID NO: 120, and SEQ ID NO: 123 (e.g., all three of said CDRs), and/or a heavy chain comprising one or more CDRs selected from the group consisting of SEQ ID NO: 126, SEQ ID NO: 129, and SEQ ID NO: 132 (e.g., all three of said CDRs).

In some embodiments, the host cell comprises one or more nucleic acid molecules encoding a humanized heavy chain and a humanized light chain which associate together to form a humanized immunoglobulin that has binding specificity for human CD52, wherein the humanized immunoglobulin comprises a light chain comprising the CDRs of SEQ ID NO: 115, SEQ ID NO: 118 and SEQ ID NO: 121 and a heavy chain comprising the CDRs of SEQ ID NO: 124, SEQ ID NO: 127 and SEQ ID NO: 130; a light chain comprising the CDRs of SEQ ID NO: 116, SEQ ID NO: 119 and SEQ ID NO: 122 and a heavy chain comprising the CDRs of SEQ ID NO: 125, SEQ ID NO: 128 and SEQ ID NO: 131; or a light chain comprising the CDRs of SEQ ID NO: 117, SEQ ID NO: 120 and SEQ ID NO: 123 and a heavy chain comprising the CDRs of SEQ ID NO: 126, SEQ ID NO: 129 and SEQ ID NO: 132.

In other embodiments, the host cell comprises one or more nucleic acid molecules encoding a humanized heavy chain and a humanized light chain which associate together to form a humanized immunoglobulin that has binding specificity for human CD52, wherein the humanized immunoglobulin has a greater binding affinity for glycosylated human CD52 than for non-glycosylated or de-glycosylated human CD52, e.g., exhibits binding that is specific for glycosylated human CD52. The humanized immunoglobulin may bind to an epitope on mature human CD52 which comprises its N-linked carbohydrate moiety. This epitope may also comprise at least residue 1 of the mature human CD52 sequence, at least residue 3 of the mature human CD52 sequence, at least residues 1, 3, 4 and 5 of the mature human CD52 sequence, or at least residues 1, 2, 3, 4 and 5 of the mature human CD52 sequence.

In some embodiments, the host cell comprises a nucleic acid molecule encoding a humanized light chain comprising one or more CDRs (e.g., all three CDRs) of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13. The humanized light chain is not the humanized light chain of Campath®.

In other embodiments, the host cell comprises a nucleic acid molecule encoding a humanized heavy chain comprising one or more CDRs (e.g., all three CDRs) of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 137. The humanized heavy chain is not the humanized heavy chain of Campath®.

In some embodiments, the host cell comprises a nucleic acid encoding a humanized light chain, wherein the humanized light chain comprises one or more CDRs selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48 or a combination thereof, wherein the humanized light chain is not the humanized light chain of Campath®.

In other embodiments, the host cell comprises a nucleic acid encoding a humanized heavy chain, wherein the humanized heavy chain comprises one or more CDRs selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294, or a combination thereof, wherein the humanized heavy chain is not the humanized heavy chain of Campath®.

The invention also relates to a method of preparing a humanized immunoglobulin that has binding specificity for human CD52 comprising maintaining a host cell of the invention (e.g., a host cell that contains one or more recombinant nucleic acids that encode a humanized immunoglobulin of the invention (e.g., a humanized light chain and a humanized heavy chain of the invention)) under conditions appropriate for expression of a humanized immunoglobulin, whereby humanized immunoglobulin chains are expressed and a humanized immunoglobulin is produced. In some embodiments, the method further comprises purifying or isolating the humanized immunoglobulin. In some embodiments, the method further comprises combining the purified or isolated humanized immunoglobulin with a physiologically acceptable vehicle or carrier to produce a pharmaceutical composition.

The invention also relates to a method of preparing a humanized light chain that has binding specificity for human CD52 comprising maintaining a host cell of the invention (e.g., a host cell that contains one or more recombinant nucleic acids that encode a humanized light chain of the invention) under conditions appropriate for expression of a humanized light chain, whereby a humanized light chain is expressed and a humanized light chain is produced. In some embodiments, the method further comprises purifying or isolating the humanized light chain.

The invention also relates to a method of preparing a humanized heavy chain that has binding specificity for human CD52 comprising maintaining a host cell of the invention (e.g., a host cell that contains one or more recombinant nucleic acids that encode a humanized heavy chain of the invention) under conditions appropriate for expression of a humanized heavy chain, whereby a humanized heavy chain is expressed and a humanized heavy chain is produced. In some embodiments, the method further comprises purifying or isolating the humanized heavy chain.

The invention further relates to a pharmaceutical composition comprising a humanized immunoglobulin of the invention (e.g., comprising a humanized light chain of the invention and/or a humanized heavy chain of the invention) and a physiologically acceptable vehicle or carrier. In some embodiments, the pharmaceutical composition comprises a unit dose composition.

The invention also relates to a method of producing a hybridoma that secretes a monoclonal antibody that has binding specificity for human CD52 comprising administering lymphocytes of a mouse transgenic for human CD52 to a non-transgenic mouse of the same, or of a similar, strain (e.g., CD1) as the human CD52 transgenic mouse, thereby producing an immunized, non-transgenic mouse. Splenocytes of the immunized, non-transgenic mouse are fused with immortalized cells, thereby producing a hybridoma. The hybridoma is maintained under conditions in which it will secrete a monoclonal antibody having binding specificity for human CD52. In some embodiments, FACS analysis is used to detect a hybridoma that secretes a monoclonal antibody that has binding specificity for human CD52. In other embodiments, the strain of the transgenic mouse and the strain of the non-transgenic mouse are identical. In certain embodiments, the CD52 is wildtype human CD52. In some embodiments, the CD52 transgenic mouse and the non-transgenic mouse are CD1 mice. In some embodiments, the lymphocytes used for immunization are obtained from the spleen of the human CD52 transgenic mouse. In some embodiments, the immortalized cells are selected from the group consisting of SP2/0 Ag14 cells and NS1 myeloma cells. The invention also relates to a hybridoma produced by the methods of the invention. Optionally, the monoclonal antibody secreted by the hybridoma is collected and can be further purified (e.g., substantially purified, isolated). In other embodiments, the method further comprises determining the nucleotide sequence of the monoclonal antibody secreted by the hybridoma.

The invention also relates to a method for treating an autoimmune disease (e.g., multiple sclerosis (MS), rheumatoid arthritis (RA) (See e.g., Nature Reviews Drug Discovery 6: 75-92 (2007)), vasculitis (See e.g., Rheumatology 39:229-237 (2000)), Behcet's disease (BD) (See e.g., Rheumatology 42:1539-1544 (2003)), lupus and celiac disease (Vivas, S., et al., N Engl. J. Med., 354(23):2514-2515 (2006)), vasculitis, psoriasis, myositis, scleroderma, aplastic anemia, and colitis) in a patient in need thereof, comprising administering to the patient an effective amount of a humanized immunoglobulin of the invention.

In another aspect, an effective amount of a humanized immunoglobulin of the invention can be administered in conjunction with one or more immunosuppressive agents to prepare a patient in need thereof for a solid organ transplant (Agarwal et al., Transplant Immunol., 20:6-11 (2008)) or a CD34+ stem cell transplant (Burt et al., The Lancet, published online Jan. 30, 2009).

The invention also relates to a method for treating cancer in a patient in need thereof, comprising administering to the patient an effective amount of a humanized immunoglobulin of the invention.

The invention also relates to a method for treating multiple sclerosis in a patient in need thereof, comprising administering to the patient an effective amount of a humanized immunoglobulin of the invention.

The invention also relates to a method for treating chronic lymphocytic leukemia in a patient in need thereof, comprising administering to the patient an effective amount of a humanized immunoglobulin of the invention.

The administration of a humanized immunoglobulin of the present invention may comprise the administration of the humanized immunoglobulin per se (e.g., in a pharmaceutical composition), the administration of one or more recombinant vectors encoding the humanized immunoglobulin, or the administration of a host cell which comprises one or more nucleic acids (e.g., one or more recombinant vectors) encoding the humanized immunoglobulins and expresses the humanized immunoglobulin.

The invention also relates to a method of diagnosing a disease selected from the group consisting of autoimmune diseases (e.g., multiple sclerosis, lupus, vasculitis), cancer (e.g., leukemias (e.g., chronic lymphocytic leukemia), and lymphomas (e.g., non-Hodgkin's lymphoma)), transplant (e.g., solid organ transplant (e.g., kidney transplant) and stem cell transplant), 'comprising assaying a patient sample in vitro with a humanized immunoglobulin of the invention.

The invention also relates to a humanized immunoglobulin of the invention (e.g., comprising a humanized light chain of the invention and/or humanized heavy chain of the invention), a recombinant vector of the invention, or a host cell of the invention, for use in medicine, such as for use in therapy and/or diagnosis of a disease such as for use in treating a disease or disorder described herein such as an autoimmune disease (e.g., multiple sclerosis, rheumatoid arthritis, and lupus), cancer, a lymphocyte hyper-proliferative condition (e.g., T or B cell malignancies including leukemia such as B-cell chronic lymphocytic leukemia and lymphomas such as non-Hodgkin's lymphoma). See, e.g., Lundin, J., et al., Blood, 101:4267-4272 (2003); Rodig, S J., et al., Clinical Cancer Research, 12(23):7174-7179 (2006). The invention also relates to the use of a humanized immunoglobulin, humanized light chain or humanized heavy chain of the invention, a recombinant vector of the invention, or a host cell of the invention, for the manufacture of a medicament for treating a disease or disorder described herein (e.g., autoimmune diseases (e.g., multiple sclerosis, lupus, vasculitis), cancer (e.g., leukemias (e.g., chronic lymphocytic leukemia), and lymphomas (e.g., non-Hodgkin's lymphoma)), and transplant (e.g., solid organ transplant (e.g., kidney transplant) and stem cell transplant)').

The invention further provides humanized anti-human CD52 antibodies comprising human light chain framework regions that utilize a human Vk2-A18b gene in which residues 36 (Y) and 46 (L) (Kabat numbering) have been substituted. In some embodiments, residue 36 is V or L and residue 46 is R. The invention also provides humanized anti-human CD52 antibodies comprising human heavy chain framework regions that utilize a human VH 3-23 gene in which residue 47 (W) (Kabat numbering) has been substituted. In some embodiments, residues 47 (W) and 49 (S) (Kabat numbering) both have been substituted. In some embodiments, residue 47 is L and residue 49 is S. In other embodiments, residue 47 is L and residue 49 is A.

In some embodiments, a humanized anti-human CD52 antibody of the invention has an $EC_{50}$ value as determined in a cell-binding assay such as the assay described in Example 29 that is two-fold lower than the $EC_{50}$ value for Campath-1H® antibody. In various embodiments, the humanized anti-human CD52 antibody has an $EC_{50}$ value of 11 nM or less.

In some embodiments, a humanized anti-human CD52 antibody of the invention binds CD52 on cells in the presence of anti-Campath-1H® antibodies from the serum of a human patient who has been treated with Campath-1H®. That is, the binding of a humanized anti-human CD52 antibody of the invention to CD52 on cells is not reduced in the presence of such anti-Campath-1H® antibodies compared to Campath-1H® binding to CD52 or is less reduced in the presence of such anti-Campath-1H® antibodies compared to Campath-1H® binding to CD52.

The invention further provides humanized anti-human CD52 antibodies with a lymphocyte depletion profile in blood and/or spleen of a humanized anti-human CD52 antibody provided herein.

In some embodiments, a humanized anti-human CD52 antibody of the invention increases the circulating level of one or more of TNFalpha, IL-6 and MCP-1 in the serum of a subject.

In some embodiments, a humanized anti-human CD52 antibody of the invention reduces lymphocyte levels in a subject for at least 30 days, at least 50 days, at least 60 days, at least 70 days, at least 80 days or for more than 80 days.

In some embodiments, a humanized anti-human CD52 antibody of the invention delays the onset of disease and/or decreases the severity of disease as measured by clinical score in a mouse EAE model.

In some embodiments, a humanized anti-human CD52 antibody of the invention is less immunogenic than Campath-1H® in an immunogenicity assay such as the assay described in Example 69 or 70.

Mouse Monoclonal Immunoglobulins

The invention also relates to mouse monoclonal antibodies (mouse monoclonal immunoglobulins) that have binding specificity for human CD52. In one embodiment, the invention relates to a mouse monoclonal antibody that has binding specificity for human CD52, comprising a light chain comprising SEQ ID NO: 3 and a heavy chain comprising SEQ ID NO: 16; a light chain comprising SEQ ID NO: 4 and a heavy chain comprising SEQ ID NO: 17; a light chain comprising SEQ ID NO: 5 and a heavy chain comprising SEQ ID NO: 18; a light chain comprising SEQ ID NO: 6 and a heavy chain comprising SEQ ID NO: 19; a light chain comprising SEQ ID NO: 7 and a heavy chain comprising SEQ ID NO: 20; a light chain comprising SEQ ID NO: 8 and a heavy chain comprising SEQ ID NO: 21; a light chain comprising SEQ ID NO: 9 and a heavy chain comprising SEQ ID NO: 22; a light chain comprising SEQ ID NO: 10 and a heavy chain comprising SEQ ID NO: 23; a light chain comprising SEQ ID NO: 11 and a heavy chain comprising SEQ ID NO: 24; a light chain comprising SEQ ID NO: 12 and a heavy chain comprising SEQ ID NO: 25; or a light chain comprising SEQ ID NO: 13 and a heavy chain comprising SEQ ID NO: 26.

In one embodiment, the mouse monoclonal antibody that has binding specificity for human CD52 comprises a light chain variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13, or a heavy chain variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26, or both such light chain variable region and such heavy chain variable region.

The invention also relates to a mouse immunoglobulin light chain comprising the variable region of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13.

The invention also relates to a mouse immunoglobulin heavy chain comprising the variable region of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

Preferably, the mouse monoclonal antibodies of the present invention comprise both a mouse antibody light chain of the invention and a mouse antibody heavy chain of the invention. In some embodiments, the invention provides a mouse monoclonal immunoglobulin which binds to the same epitope on human CD52 as a mouse monoclonal antibody comprising a light chain variable region of SEQ ID NO: 3 and a heavy chain variable region of SEQ ID NO: 16; a light chain variable region of SEQ ID NO: 4 and a heavy chain variable region of SEQ ID NO: 17; a light chain variable region of SEQ ID NO: 5 and a heavy chain variable region of SEQ ID NO: 18; a light chain variable region of SEQ ID NO: 6 and a heavy chain variable region of SEQ ID NO: 19; a light chain variable region of SEQ ID NO: 7 and a heavy chain variable region of SEQ ID NO: 20; a light chain variable region of SEQ ID NO: 8 and a heavy chain variable region of SEQ ID NO: 21; a light chain variable region of SEQ ID NO: 9 and a heavy chain variable region of SEQ ID NO: 22; a light chain variable region of SEQ ID NO: 10 and a heavy chain variable region of SEQ ID NO: 23; a light chain variable region of SEQ ID NO: 11 and a heavy chain variable region of SEQ ID NO: 24; a light chain variable region of SEQ ID NO: 12 and a heavy chain variable region of SEQ ID NO: 25; or a light chain variable region of SEQ ID NO: 13 and a heavy chain variable region of SEQ ID NO: 26. In other embodiments, the invention provides a mouse monoclonal immunoglobulin which binds to an epitope on human CD52 which overlaps with the epitope to which such a mouse monoclonal antibody binds.

In other embodiments, the invention provides a mouse monoclonal immunoglobulin which binds to an epitope on human CD52 comprising at least residue 1 of the mature human CD52 sequence. The mouse monoclonal immunoglobulin may bind to an epitope comprising at least residues 1, 3, 4 and 5 of the mature human CD52 sequence, may bind to an epitope comprising at least residues 1, 2, 3, 4 and 5 of the mature human CD52 sequence, or may bind to an epitope comprising at least residues 7, 8 and 9 of the mature human CD52 sequence. In some embodiments, the epitope comprises at least residues 7, 8 and 11 of the mature human CD52 sequence. In some embodiments, the epitope comprises at least residues 4 and 11 of the mature human CD52 sequence.

The invention also relates to isolated nucleic acid molecules that encode the mouse monoclonal immunoglobulins, mouse immunoglobulin light chains or mouse immunoglobulin heavy chains of the invention. In some embodiments, the invention is an isolated nucleic acid molecule encoding a mouse immunoglobulin heavy chain and a mouse immunoglobulin light chain which associate together to form a mouse monoclonal immunoglobulin that has binding specificity for human CD52, wherein the mouse immunoglobulin light chain comprises a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, or the mouse immunoglobulin heavy chain comprises a variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26, or both such light chain and such heavy chain.

In some embodiments, the isolated nucleic acid encodes a mouse immunoglobulin light chain which comprises a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

In other embodiments, the isolated nucleic acid encodes a mouse immunoglobulin heavy chain which comprises a variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26.

The invention also relates to recombinant vectors (e.g., expression vectors, including mammalian cell expression vectors) that comprise a nucleic acid encoding the mouse monoclonal immunoglobulin (e.g., a mouse immunoglobulin light chain and a mouse immunoglobulin heavy chain), the mouse immunoglobulin light chain, or the mouse immunoglobulin heavy chain of the invention. In some embodiments, the invention is a recombinant vector comprising a nucleic acid, or a pair of recombinant vectors comprising nucleic acids encoding a mouse monoclonal immunoglobulin that comprises a light chain variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, or a heavy chain variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26, or both such light chain variable region and heavy chain variable region.

In other embodiments, the recombinant vector comprises a nucleic acid encoding a mouse immunoglobulin light chain, wherein the mouse immunoglobulin light chain comprises SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13.

In other embodiments, the recombinant vector comprises a nucleic acid encoding a mouse immunoglobulin heavy chain, wherein the mouse immunoglobulin heavy chain comprises SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

In other embodiments, the recombinant vector comprises a nucleic acid encoding a mouse immunoglobulin light chain and a mouse immunoglobulin heavy chain, wherein the mouse immunoglobulin light chain and mouse immunoglobulin heavy chain associate together to form a mouse monoclonal immunoglobulin that has binding specificity for human CD52. In one embodiment, the mouse immunoglobulin light chain comprises a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, and the mouse immunoglobulin heavy chain comprises a variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26.

In particular embodiments, the recombinant vector of the invention is an expression vector, such as a mammalian cell expression vector. In certain embodiments, the vector is a plasmid or a viral vector (e.g., an adenoviral or AAV vector).

The invention also relates to a host cell that comprises one or more nucleic acids encoding the mouse monoclonal immunoglobulin (mouse immunoglobulin light chain and mouse immunoglobulin heavy chain), the mouse immunoglobulin light chain or the mouse immunoglobulin heavy chain of the invention. For example, in some embodiments, the host cell comprises a recombinant vector (e.g., expression vector, mammalian cell expression vector) of the invention.

In some embodiments, the host cell comprises nucleic acid encoding a mouse immunoglobulin light chain and a mouse immunoglobulin heavy chain, wherein the mouse immunoglobulin light chain and the mouse immunoglobulin heavy chain associate together to form a mouse monoclonal immunoglobulin that has binding specificity for human CD52 and wherein the mouse immunoglobulin light chain comprises a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13, and/or the mouse immunoglobulin heavy chain comprises a variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26, or both.

In some embodiments, the host cell comprises nucleic acid encoding a mouse immunoglobulin light chain, wherein the mouse immunoglobulin light chain comprises a light chain variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

In some embodiments, the host cell comprises a nucleic acid encoding a mouse immunoglobulin heavy chain, wherein the mouse immunoglobulin heavy chain comprises a heavy chain variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26.

The invention also relates to a method of preparing a mouse monoclonal immunoglobulin comprising maintaining a host cell of the invention (e.g., a host cell that contains one or more recombinant nucleic acids (e.g., recombinant vectors) that encode a mouse monoclonal immunoglobulin (e.g., a mouse immunoglobulin light chain and a mouse immunoglobulin heavy chain) of the invention) under conditions appropriate for expression of a mouse monoclonal immunoglobulin, whereby mouse monoclonal immunoglobulin chains are expressed and a mouse monoclonal immunoglobulin is produced. In some embodiments, the method further comprises purifying or isolating the mouse monoclonal immunoglobulin.

The invention also relates to a method of preparing a light chain of a mouse monoclonal immunoglobulin, comprising maintaining a host cell of the invention containing a nucleic acid encoding a mouse immunoglobulin light chain of the invention under conditions appropriate for expression of said mouse immunoglobulin light chain, whereby a light chain is expressed. In some embodiments, the method further comprises purifying or isolating the light chain.

The invention also relates to a method of preparing a heavy chain of a mouse monoclonal immunoglobulin, comprising maintaining a host cell of the invention containing a nucleic acid encoding a mouse immunoglobulin heavy chain of the invention under conditions appropriate for expression of said mouse immunoglobulin heavy chain, whereby a mouse immunoglobulin heavy chain is expressed. In some embodiments, the method further comprises purifying or isolating the mouse immunoglobulin heavy chain.

The invention also relates to a method of diagnosing a disease (e.g., autoimmune diseases (e.g., multiple sclerosis, lupus, vasculitis), cancer (e.g., leukemias (e.g., chronic lymphocytic leukemia), and lymphomas (e.g., non-Hodgkin's lymphoma)), and transplant (e.g., solid organ transplant (e.g., kidney transplant) and stem cell transplant)') comprising assaying a patient sample in vitro, with the mouse monoclonal immunoglobulin of the invention (e.g., Lundin, J., et al., *Blood*, 101:4267-4272 (2003); Rodig, S J, et al., *Clin. Cancer res.*, 12(23); 7174-717179 (2006)).

Chimeric Immunoglobulins

The invention also relates to chimeric immunoglobulins that have binding specificity for human CD52. Such chimeric immunoglobulins may include the variable regions of any of the mouse monoclonal immunoglobulin of the present invention. In one embodiment, the chimeric immunoglobulin of the invention comprises the light chain variable region of SEQ ID NO: 3 and the heavy chain variable region of SEQ ID NO: 16; the light chain variable region of SEQ ID NO: 4 and the heavy chain variable region of SEQ ID NO: 17; the light chain variable region of SEQ ID NO: 5 and the heavy chain variable region of SEQ ID NO: 18; the light chain variable region of SEQ ID NO: 6 and the heavy chain variable region of SEQ ID NO: 19; the light chain variable region of SEQ ID NO: 7 and the heavy chain variable region of SEQ ID NO: 20; the light chain variable region of SEQ ID NO: 8 and the heavy chain variable region of SEQ ID NO: 21; the light chain variable region of SEQ ID NO: 9 and the heavy chain variable region of SEQ ID NO: 22; the light chain variable region of SEQ ID NO: 10 and the heavy chain variable region of SEQ ID NO: 23; the light chain variable region of SEQ ID NO: 11 and the heavy chain variable region of SEQ ID NO: 24; the light chain variable region of SEQ ID NO: 12 and the heavy chain variable region of SEQ ID NO: 25; or the light chain variable region of SEQ ID NO: 13 and the heavy chain variable region of SEQ ID NO: 26.

The invention also relates to a chimeric antibody that has binding specificity for human CD52, comprising a light chain variable region sequence selected from the group consisting of the light chain variable region of SEQ ID NO: 3, the light chain variable region of SEQ ID NO: 4, the light chain variable region of SEQ ID NO: 5, the light chain variable region of SEQ ID NO: 6, the light chain variable region of SEQ ID NO: 7, the light chain variable region of SEQ ID NO: 8, the light chain variable region of SEQ ID NO: 9, the light chain variable region of SEQ ID NO: 10, the light chain variable region of SEQ ID NO: 11, the light chain variable region of SEQ ID NO: 12 and the light chain variable region of SEQ ID NO: 13, and/or a heavy chain variable region sequence selected from the group consisting of: the heavy chain variable region of SEQ ID NO: 16, the heavy chain variable region of SEQ ID NO: 17, the heavy chain variable region of SEQ ID NO: 18, the heavy chain variable region of SEQ ID NO: 19, the heavy chain variable region of SEQ ID NO: 20, the heavy chain variable region of SEQ ID NO: 21, the heavy chain variable region of SEQ ID NO: 22, the heavy chain variable region of SEQ ID NO: 23, the heavy chain variable region of SEQ ID NO: 24, the heavy chain variable region of SEQ ID NO: 25 and the heavy chain variable region of SEQ ID NO: 26.

The invention also relates to a chimeric light chain comprising a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

The invention also relates to a chimeric heavy chain comprising a variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26.

Preferably, the chimeric immunoglobulins of the present invention comprise both a chimeric light chain of the invention and a chimeric heavy chain of the invention.

In some embodiments, the invention provides a chimeric immunoglobulin which binds to the same epitope on human CD52 as a mouse monoclonal antibody comprising a light chain variable region of SEQ ID NO: 3 and a heavy chain variable region of SEQ ID NO: 16; a light chain variable region of SEQ ID NO: 4 and a heavy chain variable region of SEQ ID NO: 17; a light chain variable region of SEQ ID NO: 5 and a heavy chain variable region of SEQ ID NO: 18; a light chain variable region of SEQ ID NO: 6 and a heavy chain variable region of SEQ ID NO: 19; a light chain variable region of SEQ ID NO: 7 and a heavy chain variable region of SEQ ID NO: 20; a light chain variable region of SEQ ID NO: 8 and a heavy chain variable region of SEQ ID NO: 21; a light chain variable region of SEQ ID NO: 9 and a heavy chain variable region of SEQ ID NO: 22; a light chain variable region of SEQ ID NO: 10 and a heavy chain variable region of SEQ ID NO: 23; a light chain variable region of SEQ ID NO: 11 and a heavy chain variable region of SEQ ID NO: 24; a light chain variable region of SEQ ID NO: 12 and a heavy chain variable region of SEQ ID NO: 25; or a light chain variable region of SEQ ID NO: 13 and a heavy chain variable region of SEQ ID NO: 26. In other embodiments, the chimeric immunoglobulin binds to an epitope on human CD52 which overlaps with the epitope to which such a mouse monoclonal antibody binds.

In other embodiments, the invention provides a chimeric immunoglobulin which binds to an epitope on human CD52 comprising at least residue 1 of the mature human CD52 sequence. The chimeric immunoglobulin may bind to an epitope comprising at least residues 1, 3, 4 and 5 of the mature human CD52 sequence, may bind to an epitope comprising at least residues 1, 2, 3, 4 and 5 of the mature human CD52 sequence, or may bind to an epitope on human CD52 comprising at least residues 7, 8 and 9 of the mature human CD52 sequence. In some embodiments, the epitope comprises at least residues 7, 8 and 11 of the mature human CD52 sequence. In some embodiments, the epitope comprises at least residues 4 and 11 of the mature human CD52 sequence.

The invention also relates to isolated nucleic acid molecules that encode the chimeric immunoglobulins, chimeric light chains or chimeric heavy chains of the invention. In some embodiments, the invention is an isolated nucleic acid molecule (one or more nucleic acid molecules) encoding a chimeric heavy chain and a chimeric light chain which associate together to form a chimeric immunoglobulin that has binding specificity for human CD52, wherein the chimeric light chain comprises a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13; and/or the chimeric heavy chain comprises a variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26.

In some embodiments, the invention is an isolated nucleic acid molecule encoding a chimeric light chain that comprises the variable region of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13.

In some embodiments, the invention is an isolated nucleic acid molecule encoding a chimeric heavy chain that comprises the variable region of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

The invention also relates to recombinant vectors (e.g., expression vectors, mammalian cell expression vectors) that comprise a nucleic acid encoding the chimeric immunoglobulin (chimeric light chain and chimeric heavy chain), the chimeric light chain, or the chimeric heavy chain of the invention. In some embodiments, the invention is a recombinant vector comprising a nucleic acid (or a pair of recombinant vectors comprising nucleic acids) encoding a chimeric immunoglobulin that comprises a light chain variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13; or a heavy chain variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26; or both such light chain and heavy chain.

In other embodiments, the recombinant vector comprises a nucleic acid encoding a chimeric light chain, wherein the chimeric light chain comprises the variable region of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13.

In other embodiments, the recombinant vector comprises a nucleic acid encoding a chimeric heavy chain, wherein the chimeric heavy chain comprises the variable region of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

In particular embodiments, the recombinant vector of the invention is an expression vector, such as a mammalian cell expression vector. In certain embodiments, the vector is a plasmid or a viral vector (e.g., an adenoviral or AAV vector).

The invention also relates to a host cell that comprises one or more nucleic acids (e.g., one or more recombinant vectors) encoding the chimeric immunoglobulin (chimeric light chain and chimeric heavy chain), the chimeric light chain or the chimeric heavy chain of the invention. For example, in some embodiments, the host cell comprises a recombinant vector (e.g., expression vector, mammalian cell expression vector) of the invention.

In some embodiments, the host cell comprises a recombinant nucleic acid (or a pair of recombinant nucleic acids) encoding a chimeric light chain and a chimeric heavy chain, wherein the chimeric light chain and the chimeric heavy chain associate together to form a chimeric immunoglobulin that has binding specificity for human CD52 and wherein the chimeric light chain comprises a variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13; and/or the chimeric heavy chain comprises a variable region selected from the group consisting of the variable region of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26.

In some embodiments, the host cell comprises a recombinant nucleic acid encoding a chimeric light chain, wherein the chimeric light chain comprises a light chain variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

In some embodiments, the host cell comprises a recombinant nucleic acid encoding a chimeric heavy chain, wherein the chimeric heavy chain comprises a heavy chain variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26.

The invention also relates to a method of preparing a chimeric immunoglobulin comprising maintaining a host cell of the invention (e.g., a host cell that contains one or more isolated nucleic acids that encode a chimeric immunoglobulin (e.g., a chimeric light chain and a chimeric heavy chain) of the invention) under conditions appropriate for expression of a chimeric immunoglobulin, whereby chimeric immunoglobulin chains are expressed and a chimeric immunoglobulin is produced. In some embodiments, the method further comprises purifying or isolating the chimeric immunoglobulin.

The invention also relates to a method of preparing a chimeric light chain comprising maintaining a host cell of the invention (e.g., a host cell that contains a nucleic acid encoding a chimeric light chain of the invention) under conditions appropriate for expression of said chimeric light chain, whereby a chimeric light chain is expressed and a chimeric light chain is produced. In some embodiments, the method further comprises purifying or isolating the chimeric light chain.

The invention also relates to a method of preparing a chimeric heavy chain comprising maintaining a host cell of the invention (e.g., a host cell that contains a nucleic acid encoding a chimeric heavy chain of the invention) under conditions appropriate for expression of said chimeric heavy chain, whereby a chimeric heavy chain is expressed and a chimeric heavy chain is produced. In some embodiments, the method further comprises purifying or isolating the chimeric heavy chain.

The invention also relates to a method of diagnosing a disease selected from the group consisting of autoimmune diseases (e.g., multiple sclerosis, lupus, vasculitis), cancer (e.g., leukemias (e.g., chronic lymphocytic leukemia), and lymphomas (e.g., non-Hodgkin's lymphoma)), and transplant (e.g., solid organ transplant (e.g., kidney transplant) and stem cell transplant', comprising assaying a patient sample in vitro, with the chimeric immunoglobulin of the invention.

Further embodiments of this invention are described as follows. In one aspect, the invention relates to a monoclonal anti-human CD52 antibody or an antigen-binding portion thereof, wherein the light chain and heavy chain of said antibody comprise the three complementarity determining regions (CDRs) found in: SEQ ID NOs: 3 and 16, respectively; SEQ ID NOs: 4 and 17, respectively; SEQ ID NOs: 5 and 18, respectively; SEQ ID NOs: 6 and 19, respectively; SEQ ID NOs: 7 and 20, respectively; SEQ ID NOs: 8 and 21, respectively; SEQ ID NOs: 9 and 22, respectively; SEQ ID NOs: 10 and 23, respectively; SEQ ID NOs: 11 and 24, respectively; SEQ ID NOs: 12 and 25, respectively; SEQ ID NOs: 12 and 137, respectively; or SEQ ID NOs: 13 and 26, respectively. In some embodiments, the invention relates to an antibody that binds to the same epitope on human CD52 as the above monoclonal antibody or antigen-binding portion. In some embodiments, the invention relates to an antibody that competes with the above monoclonal antibody or antigen-binding portion. In some embodiments, the invention relates to an antibody that cross-competes with the above monoclonal antibody or antigen-binding portion.

In some embodiments, any of the above antibodies or antigen-binding portions binds to an amino acid sequence comprising SEQ ID NO: 104. In some related embodiments, the binding of said antibody or portion to SEQ ID NO: 104 may be reduced by an alanine substitution at one or more of residues 4, 7, 8, or 11 of SEQ ID NO: 104.

In some embodiments, the antibody is a humanized antibody, a mouse antibody, or a chimeric antibody. In certain embodiments, the framework regions of the heavy chain of said antibody utilize a VH3-72 or VH3-23 human germline sequence, and the framework regions of the light chain of said antibody utilize a VK2 A18b human germline sequence.

In some embodiments, the invention relates to a monoclonal anti-human CD52 antibody or an antigen-binding portion thereof, wherein said antibody comprises heavy chain (H)-CDR1, H-CDR2, H-CDR3, and light chain (L)-CDR1, L-CDR2, and L-CDR3 whose amino acid sequences are SEQ ID NOs: 51, 59, 69, 29, 36, and 43, respectively; SEQ ID NOs: 50, 60, 69, 29, 37, and 43, respectively; SEQ ID NOs: 50, 61, 68, 29, 38, and 43, respectively; SEQ ID NOs: 50, 61, 69, 29, 36, and 43, respectively; SEQ ID NOs: 50, 62, 69, 29, 39, and 43, respectively; SEQ ID NOs: 52, 61, 70, 30, 40, and 43, respectively; SEQ ID NOs: 53, 63, 71, 31, 36, and 44, respectively; SEQ ID NOs: 54, 64, 71, 31, 36, and 45, respectively; SEQ ID NOs: 55, 63, 72, 31, 36, and 46, respectively; SEQ ID NOs: 56, 65, 73, 32, 41, and 47, respectively; SEQ ID NOs: 56, 65, 294, 32, 41, and 47, respectively; or SEQ ID NOs: 56, 66, 74, 33, 41, and 48, respectively.

In some embodiments, the invention relates to a monoclonal anti-human CD52 antibody or an antigen-binding portion thereof, wherein the light chain and heavy chain of said antibody comprise the amino acid sequences of SEQ ID NOs: 3 and 16, respectively; SEQ ID NOs: 4 and 17, respectively; SEQ ID NOs: 5 and 18, respectively; SEQ ID NOs: 6 and 19, respectively; SEQ ID NOs: 7 and 20, respectively; SEQ ID NOs: 8 and 21, respectively; SEQ ID NOs: 9 and 22, respectively; SEQ ID NOs: 10 and 23, respectively; SEQ ID NOs: 11 and 24, respectively; SEQ ID NOs: 12 and 25, respectively; or SEQ ID NOs: 13 and 26, respectively.

In some embodiments, the invention relates to a monoclonal antibody or antigen-binding portion thereof, wherein the heavy chain and light chain of said antibody comprise the amino acid sequences of SEQ ID NOs: 103 and 102, respectively; SEQ ID NOs: 136 and 138, respectively; SEQ ID NOs: 137 and 138, respectively; SEQ ID NOs: 139 and 147, respectively; SEQ ID NOs: 149 and 155, respectively; SEQ ID NOs: 149 and 156, respectively; SEQ ID NOs: 158 and 165, respectively; SEQ ID NOs: 158 and 166, respectively; SEQ ID NOs: 159 and 165, respectively; SEQ ID NOs: 159 and 166, respectively; SEQ ID NOs: 161 and 166, respectively; or SEQ ID NOs: 163 and 166, respectively. In some embodiments, the invention relates to an antibody that binds to the same epitope on human CD52 as the above monoclonal antibody or antigen-binding portion. In some embodiments, the invention relates to an antibody that competes with the above monoclonal antibody or antigen-binding portion. In some embodiments, the invention relates to an antibody that cross-competes with the above monoclonal antibody or antigen-binding portion.

In certain embodiments, the invention relates to a monoclonal humanized anti-human CD52 antibody or an antigen-binding portion thereof, wherein the heavy chain and the light chain of said antibody comprise the amino acid sequences of SEQ ID NOs: 272 and 273, respectively, without the signal sequences. In certain embodiments, the invention relates to a monoclonal anti-human CD52 antibody or an antigen-binding portion thereof, wherein the heavy chain and the light chain of said antibody comprise the amino acid sequences of SEQ ID NOs: 274 and 275, respectively, without the signal sequences. In certain embodiments, the invention relates to a monoclonal anti-human CD52 antibody or an antigen-binding portion thereof, wherein the heavy chain and the light chain of said antibody comprise the amino acid sequences of SEQ ID NOs: 276 and 278, respectively, without the signal sequences. In certain embodiments, the invention relates to a monoclonal anti-human CD52 antibody or an antigen-binding portion thereof, wherein the heavy chain and the light chain of said antibody comprise the amino acid sequences of SEQ ID NOs: 277 and 278, respectively, without the signal sequences. In certain embodiments, the invention relates to a monoclonal anti-human CD52 antibody or an antigen-binding portion thereof, wherein the heavy chain and the light chain of said antibody comprise the amino acid sequences of SEQ ID NOs: 279 and 280, respectively, without the signal sequences. In certain embodiments, the invention relates to a monoclonal anti-human CD52 antibody or an antigen-binding portion thereof, wherein the heavy chain and the light chain of said antibody comprise the amino acid sequences of SEQ ID NOs: 281 and 282, respectively, without the signal sequences. The invention also provides antibodies that bind to the same epitope on CD52 as one of these humanized antibodies and antibodies that compete or cross-compete with one of these humanized antibodies. In related embodiments, the invention provides compositions comprising one such humanized antibody and a pharmaceutically acceptable carrier.

In some embodiments, the invention relates to a monoclonal anti-human CD52 antibody or an antigen-binding portion thereof, wherein the light chain of said antibody comprises an amino acid sequence selected from the group consisting of SEQ ID NOs: 102, 138, 145-148, 153-157, and 164-168. In certain embodiments, the invention relates to a monoclonal anti-human CD52 antibody or an antigen-binding portion thereof, wherein the light chain of said antibody comprises an amino acid sequence selected from the group consisting of SEQ ID NOs: 273, 275, 278, 280, and 282, without the signal sequences. In certain embodiments, the invention relates to an antibody light chain or a portion thereof, comprising an amino acid sequence selected from the group consisting of SEQ ID NOs: 102, 138, 145-148, 153-157, 164-168, 273, 275, 278, 280, and 282, without the signal sequences if present.

In some embodiments, the invention relates to a monoclonal anti-human CD52 antibody or an antigen-binding portion thereof, wherein the heavy chain of said antibody comprises an amino acid sequence selected from the group consisting of SEQ ID NOs: 103, 136, 137, 139-144, 149-152, and 158-163. In certain embodiments, the invention relates to a monoclonal anti-human CD52 antibody or an antigen-binding portion thereof, wherein the heavy chain of said antibody comprises an amino acid sequence selected from the group consisting of SEQ ID NOs: 272, 274, 276, 277, 279, and 281, without the signal sequences. In certain embodiments, the invention relates to an antibody heavy chain or a portion thereof, comprising an amino acid sequence selected from the group consisting of SEQ ID NOs: 103, 136, 137, 139-144, 149-152, 158-163, 272, 274, 276, 277, 279, and 281, without the signal sequences if present.

In some embodiments, any of the above antibodies may be an IgG, IgM, IgA, IgD or IgE molecule. In certain embodiments, said IgG is IgG1, IgG2, IgG3, or IgG4.

In some embodiments, any of the above antigen-binding portions may be a single chain antibody, Fv, Fab, Fab', F(ab')2, Fd, single chain Fv molecule (scFv), bispecific single chain Fv dimer, diabody, domain-deleted antibody or single domain antibody (dAb).

The invention also relates to any of the above antibodies or antigen-binding portions, wherein said antibody or antigen-binding portion depletes T or B lymphocytes, or both; preferentially depletes T lymphocytes as compared to B lymphocytes; increases circulating serum levels of TNF-alpha, IL-6, or MCP-1 (e.g., by at least 5%, at least 10%, at least 50%, at least 100% or at least 200%); mediates antibody-dependent cell mediated cytotoxicity (ADCC) of CD52-expressing cells; mediates complement-dependent cytotoxicity (CDC) of CD52-expressing cells; binds to human CD52 in spite of the presence of neutralizing antibodies to alemtuzumab in a human patient; and/or promotes intracellular signaling in human T and/or B cells (see, e.g., Hederer et al., *International Immunology* 12:505-616 (2000); Watanabe et al., *Clinical Immunology* 120: 247-259 (2006)).

The invention further relates to an isolated nucleic acid encoding the heavy chain or an antigen-binding portion thereof, or the light chain or an antigen-binding portion thereof, of any of the above antibodies. In some embodiments, said isolated nucleic acid comprises a heavy chain nucleotide sequence selected from the group consisting of SEQ ID NOs: 283, 285, 287, 288, 290, and 292, or said nucleotide sequence without the sequence encoding a signal peptide; a light chain nucleotide sequence selected from the group consisting of SEQ ID NOs: 284, 286, 289, 291, and 293, or said nucleotide sequence without the sequence encoding a signal peptide; or both said heavy chain nucleotide sequence and said light chain nucleotide sequence. In certain embodiments, said isolated nucleic acid comprises a heavy chain nucleotide sequence and a light chain nucleotide sequence selected from the group consisting of SEQ ID NO: 283 and SEQ ID NO: 284, respectively, both without sequences encoding signal peptides; SEQ ID NO: 285 and SEQ ID NO: 286, respectively, both without sequences encoding signal peptides; SEQ ID NO: 287 and SEQ ID NO: 289, respectively, both without sequences encoding signal peptides; SEQ ID NO: 288 and SEQ ID NO: 289, respectively, both without sequences encoding signal peptides; SEQ ID NO: 290 and SEQ ID NO: 291, respectively, both without sequences encoding signal peptides; and SEQ ID NO: 292 and SEQ ID NO: 293, respectively, both without sequences encoding signal peptides.

The invention also relates to the use of an isolated nucleic acid comprising a heavy chain nucleotide sequence and an isolated nucleic acid comprising a light chain nucleotide sequence for the manufacture of a medicament for treating a patient in need thereof, wherein said heavy chain nucleotide sequence and light chain nucleotide sequence are selected from the group consisting of SEQ ID NO: 283 and SEQ ID NO: 284, respectively, both without sequences encoding signal peptides; SEQ ID NO: 285 and SEQ ID NO: 286, respectively, both without sequences encoding signal peptides; SEQ ID NO: 287 and SEQ ID NO: 289, respectively, both without sequences encoding signal peptides; SEQ ID NO: 288 and SEQ ID NO: 289, respectively, both without sequences encoding signal peptides; SEQ ID NO: 290 and SEQ ID NO: 291, both respectively, without sequences encoding signal peptides; and SEQ ID NO: 292 and SEQ ID NO: 293, both respectively, without sequences encoding signal peptides.

The invention also relates to a recombinant vector comprising (1) a nucleic acid sequence encoding the heavy chain or an antigen-binding portion thereof, (2) a nucleic acid sequence encoding the light chain or an antigen-binding portion thereof, or (3) both, of any of the above antibodies. The invention further relates to a host cell comprising a first nucleic acid sequence encoding the heavy chain or an antigen-binding portion thereof of any of the above antibodies, said first nucleic acid sequence operably linked to an expression control element, and a second nucleic acid sequence encoding the light chain or an antigen-binding portion thereof of said antibody, said second nucleic acid sequence operably linked to an expression control element. The invention relates to a method of making an anti-human CD52 antibody or an antigen-binding portion thereof, comprising maintaining said host cell under conditions appropriate for expression of the antibody or portion, and also relates to said method further comprising the step of isolating the antibody or portion.

The invention relates to a composition comprising the monoclonal antibody or antigen-binding portion according to any one of claims 1-24 and a pharmaceutically acceptable vehicle or carrier.

In some embodiments, the invention relates to a method for treating a patient in need thereof, comprising administering to the patient an effective amount of any of the above antibodies or antigen-binding portions, or the above composition. In certain embodiments, said patient is receiving a transplantation.

In some embodiments, the invention relates to a method for treating an autoimmune disease in a patient in need thereof, comprising administering to the patient an effective amount of any of the above antibodies or antigen-binding portions, or the above composition. In certain embodiments, the autoimmune disease is, e.g., multiple sclerosis, rheumatoid arthritis, or systemic lupus erythematosus.

In some embodiments, the invention relates to a method for treating cancer in a patient in need thereof, comprising administering to the patient an effective amount of any of the above antibodies or antigen-binding portions, or the above composition. In certain embodiments, the cancer is, e.g., a lymphoma such as non-Hodgkin's lymphoma; a leukemia such as B-cell chronic lymphocytic leukemia; T cell malignancy, wherein the antibody or portion preferentially depletes T cells as compared to B cells; or a solid tumor.

In some embodiments, any of the above methods of treatment further comprising administering to the patient a neutrophil or NK cell stimulatory agent. In certain embodiments, said agent is G-CSF or GM-CSF. In some embodiments, any of the above methods of treatment further comprises administering to the patient a T regulatory cell stimulatory agent. In certain embodiments, said agent is rapamycin.

In some embodiments, the invention relates to a method for inhibiting angiogenesis in a patient in need thereof, comprising administering an effective amount of any of the above antibodies or antigen-binding portions to the patient. In certain embodiments, the patient has a solid tumor. In certain embodiments, the patient has neovascularization. In certain embodiments, said neovascularization is in the eye.

The invention also relates to the use of any of the above antibodies or antigen-binding portions for the manufacture of a medicament for treating an autoimmune disease in a patient in need thereof. Further, the invention relates to the use of any of the above antibodies or antigen-binding portions for the manufacture of a medicament for treating cancer in a patient in need thereof. The invention relates to the use of any of the above antibodies or antigen-binding portions for the manufacture of a medicament for treating a patient in need of a transplantation. The invention relates to the use of any of the above antibodies or antigen-binding portions for the manufacture of a medicament for treating neovascularization in a patient in need thereof.

The invention also relates to the use of any of the above antibodies or antigen-binding portions as a medicament.

BRIEF DESCRIPTION OF THE DRAWINGS

FIG. 1A-1B is a schematic representation of the development of new anti-CD52 monoclonal antibodies. The general scheme is depicted in FIG. 1A and the names of the mouse anti-human CD52 antibody clones as well as their isotypes in shown in FIG. 1B.

FIG. 2 is an alignment of the amino acid sequences of several mouse anti-human CD52 kappa light chain sequences (SEQ ID NOS:1-13). Campath-1G is the rat monoclonal antibody from which the humanized Campath-1H antibody is derived.

FIG. 3 is an alignment of the amino acid sequences of several mouse anti-human CD52 heavy chain sequences (SEQ ID NOS:14-26).

FIG. 4 is an alignment of wildtype CD52 and 10 mutant CD52 proteins (SEQ ID NOS: 104-114, from top to bottom).

FIG. 8A-8C illustrate the comparative binding of various anti-CD52 antibodies and the Campath-1H® ("C-1H") antibody to defined human lymphocyte populations. These figures show the hierarchy of the binding ability of the chimeric antibodies screened by FACS assay. Curves to the far right demonstrate the highest binding ability, whereas curves to the left bind with lower affinity.

FIG. 16 is an alignment of the mouse anti-human CD52 antibody 4B10 heavy chain variable region (SEQ ID NO: 96) sequence with the closest matched human germline sequence (SEQ ID NO: 97) and the humanized heavy chain variable region sequence (SEQ ID NO: 98). Also shown is an alignment of the mouse anti-human CD52 antibody 4B10 light chain variable region (SEQ ID NO: 99) sequence with the closest matched human germline sequence (SEQ ID NO: 100) and the humanized light chain variable region sequence (SEQ ID NO: 101).

FIG. 17 shows the humanized 4B10 heavy chain (SEQ ID NO: 103) and light chain (SEQ ID NO: 102) variable region sequences.

FIG. 24 shows the humanized 7F11 heavy and light (kappa) chain variable region sequences. Amino acid residues that are back mutated to mouse residues are underlined and the CDRs are shown in boldface.

FIG. 26A shows the humanized 2C3 heavy chain variable region sequences. Amino acid residues that are back mutated to mouse residues are underlined and the CDRs are shown in boldface. FIG. 26B shows the humanized 2C3 light (kappa) chain variable region sequences. Amino acid residues that are back mutated to mouse residues are underlined and the CDRs are shown in boldface.

FIG. 28A shows the humanized 12G6 heavy chain variable region sequences. Amino acid residues that are back mutated to mouse residues are underlined and the CDRs are shown in boldface. FIG. 28B shows the humanized 12G6 light (kappa) chain variable region sequences. Amino acid residues that are back mutated to mouse residues are underlined and the CDRs are shown in boldface.

FIG. 30A shows the humanized 9D9 heavy chain variable region sequences. Amino acid residues that are back mutated to mouse residues are underlined and the CDRs are shown in boldface. FIG. 30B shows the humanized 9D9 light (kappa) chain variable region sequences. Amino acid residues that are back mutated to mouse residues are underlined and the CDRs are shown in boldface.

FIG. 33 is a table showing the relative binding efficiency of Campath-1H®, chimeric 2C3 and 12G6 antibodies, and humanized 2C3 and 12G6 antibodies to huCD52 expressing human and transgenic mouse T cells.

FIGS. 75A-75D show the level of CD4+ T cells, CD8+ T cells, B220+ B cells, NK cells and myeloid cells in the spleen 72 hours after dosing with 12G6-SFD1/K11 ("12G6 K11") and 12G6-SFD1/K12 ("12G6 K12") antibodies.

FIGS. 86A-86E show the level of bulk lymphocyte populations (CD4+ T cells, CD8+ T cells, and B220+ B cells) and CD4+ T cell, CD8+ T cell, B220+ B cell, NK cell, and myeloid cell subtypes in the blood 72 hours after dosing with Campath-1H® ("Campath"), 2C3-SFD1/K12, 12G6-SFD1/K11, 12G6-SFD1/K12, 9D9-H16/K13, and 9D9-H18/K13 antibodies.

FIG. 101A shows no binding between 12G6-SFD1/K12 and the MUT 8 peptide, while FIG. 101B shows binding between 12G6-SFD1/K12 and the MUT 9 peptide.

FIG. 106 shows the full-length humanized heavy chain amino acid sequence of 2C3-SFD1 (SEQ ID NO: 272) and the full-length humanized light chain amino acid sequence of 2C3-K12 (SEQ ID NO: 273). The signal sequences are boldfaced and italicized and the CDRs are underlined.

FIG. 107 shows the full-length humanized heavy chain amino acid sequence of 7F11-SFD1 (SEQ ID NO: 274) and the full-length humanized light chain amino acid sequence of 7F11-K2 (SEQ ID NO: 275). The signal sequences are boldfaced and italicized and the CDRs are underlined.

FIG. 108 shows the full-length humanized heavy chain amino acid sequences of 9D9-H16 (SEQ ID NO: 276) and 9D9-H18 (SEQ ID NO: 277), and the full-length humanized light chain amino acid sequence of 9D9-K13 (SEQ ID NO: 278). The signal sequences are boldfaced and italicized and the CDRs are underlined.

FIG. 109 shows the full-length humanized heavy chain amino acid sequence of 12G6-SFD1 (SEQ ID NO: 279) and the full-length humanized light chain amino acid sequence of 12G6-K12 (SEQ ID NO: 280). The signal sequences are boldfaced and italicized and the CDRs are underlined.

FIG. 110 shows the full-length humanized heavy chain amino acid sequence of 4B10-H1 (SEQ ID NO: 281) and the full-length humanized light chain amino acid sequence of 4B10-K1 (SEQ ID NO: 282). The signal sequences are boldfaced and italicized and the CDRs are underlined.

FIG. 111 shows the full-length humanized heavy chain nucleic acid sequence of 2C3-SFD1 (SEQ ID NO: 283) and the full-length humanized light chain nucleic acid sequence of 2C3-K12 (SEQ ID NO: 284). The signal sequences are underlined, the variable domains are in boldface, and the constant regions are italicized.

FIG. 112 shows the full-length humanized heavy chain nucleic acid sequence of 7F11-SFD1 (SEQ ID NO: 285) and the full-length humanized light chain nucleic acid sequence of 7F11-K2 (SEQ ID NO: 286). The signal sequences are underlined, the variable domains are in boldface, and the constant regions are italicized.

FIG. 113 shows the full-length humanized heavy chain nucleic acid sequences of 9D9-H16 (SEQ ID NO: 287) and 9D9-H18 (SEQ ID NO: 288). The signal sequences are underlined, the variable domains are in boldface, and the constant regions are italicized.

FIG. 114 shows the full-length humanized light chain nucleic acid sequence of 9D9-K13 (SEQ ID NO: 289). The signal sequence is underlined, the variable domain is in boldface, and the constant region is italicized.

FIG. 115 shows the full-length humanized heavy chain nucleic acid sequence of 12G6-SFD1 (SEQ ID NO: 290) and the full-length humanized light chain nucleic acid sequence of 12G6-K12 (SEQ ID NO: 291). The signal sequences are underlined, the variable domains are in boldface, and the constant regions are italicized.

FIG. 116 shows the full-length humanized heavy chain nucleic acid sequence of 4B10-H1 (SEQ ID NO: 292) and the full-length humanized light chain nucleic acid sequence of 4B10-K1 (SEQ ID NO: 293). The signal sequences are underlined, the variable domains are in boldface, and the constant regions are italicized.

DETAILED DESCRIPTION OF THE INVENTION

Figure 5A:
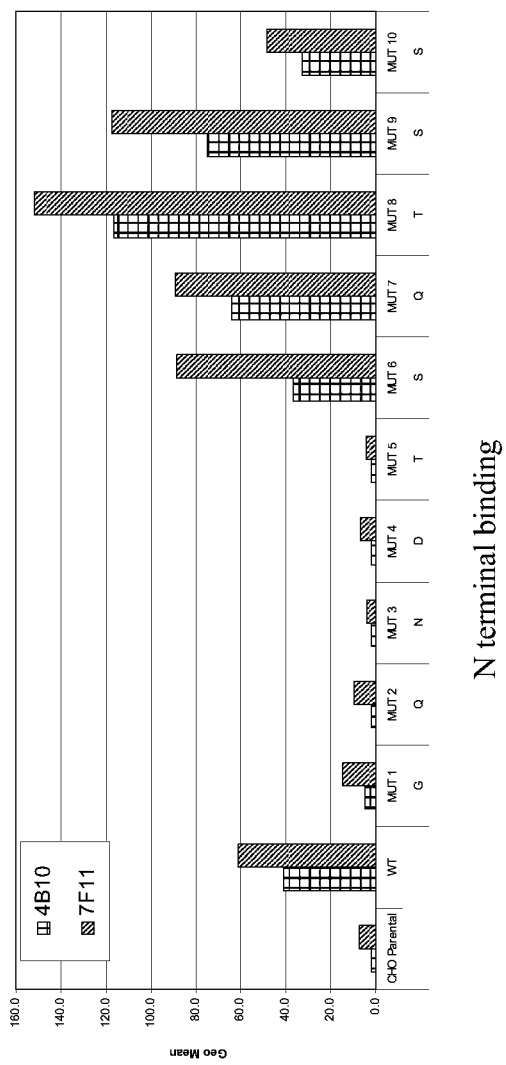
FIG. 5A illustrates the FACS-based N-terminal binding profile of antibodies 4B10 and 7F11 on cells expressing CD52 alanine scanning mutants.

CD52 is a glycosylated, GPI anchored cell surface abundant protein (approximately $5 \times 10^5$ antibody binding sites per cell) present on at least 95% of all human peripheral blood lymphocytes and monocytes/macrophages (Hale G, et al., "The CAMPATH-1 antigen (CD52)," *Tissue Antigens*, 35:178-327 (1990)), but is absent from hematopoietic stem cells. This invention is directed to immunoglobulins (anti-CD52) which have binding specificity (e.g., epitopic specificity) for, or are selective for binding to, human CD52 or a portion thereof. These immunoglobulins bind specifically to a CD52, and do not bind specifically to non-CD52 molecules. Specific binding between an anti-CD52 immunoglobulin and CD52 can be determined, for example, by measuring $EC_{50}$ of the immunoglobulin's binding to CD52+ cells by flow cytometry. Specific binding can be indicated by an $EC_{50}$ range of, e.g., 0.5-10 µg/ml. The immunoglobulins described herein can have binding specificity for all or a portion of a human CD52 wherein the human CD52 is an isolated and/or recombinant human CD52, or on the surface of a cell which expresses human CD52. In addition, the immunoglobulins can have binding specificity for one or more forms of human CD52 (e.g., glycosylated human CD52; de-glycosylated human CD52; non-glycosylated human CD52; and allelic variants). In one embodiment, the immunoglobulins have binding specificity for a naturally occurring, endogenous or wildtype human CD52. The amino acid sequence of a wildtype human CD52 is set out in FIG. 4 (SEQ ID NO: 104).

The immunoglobulins described herein can be purified or isolated using known techniques. Immunoglobulins that are "purified" or "isolated" have been separated away from molecules (e.g., peptides) of their source of origin (e.g., the supernatant of cells; in a mixture such as in a mixture of immunoglobulins in a library), and include immunoglobulins obtained by methods described herein or other suitable methods. Isolated immunoglobulins include substantially pure (essentially pure) immunoglobulins, and immunoglobulins produced by chemical synthesis, recombinant techniques and a combination thereof.

More specifically, the invention relates to anti-human CD52 immunoglobulins, antigen-binding fragments (i.e., portions) of the immunoglobulins, the light chains of the immunoglobulins, the heavy chains of the immunoglobulins, and fragments of these light chains or heavy chains. The invention also relates to mature immunoglobulins or chains thereof, such as glycosylated immunoglobulins. The invention also relates to immature or precursor immunoglobulin (protein). The invention also relates to nucleic acid molecules (e.g., vectors) that encode both these immature or mature proteins, to vectors and host cells that comprise such nucleic acid, to methods of producing immature and mature proteins and to methods of using the immunoglobulins.

The immunoglobulins of this invention can be used to treat a subject in need thereof (e.g., a human patient) to deplete the subject's lymphocytes and other CD52+ cells (e.g., CD52+ cancerous cells) as needed. As used herein, "lymphocyte depletion" is a type of immunosuppression by reducing the population of circulating lymphocytes, e.g., T cells and/or B cells, resulting in lymphopenia. The immunoglobulins of this invention can also be used to inhibit angiogenesis as further described below. The immunoglobulins of this invention also can be used to enrich hematopoietic stem cells, for example, in ex vivo applications (see, e.g., Lim et al., *J. Hematology & Oncology* 1:19 (2008)).

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain (also called the $V_L$ domain) is a C-terminal portion known as the J region. Within the variable region of the heavy chain (also called the $V_H$ domain), there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. The locations of CDR and FR regions and a numbering system have been defined by Kabat et al. (Kabat, E. A., et al., *Sequences of Proteins of Immunological Interest*, Fifth Edition, U.S. Department of Health and Human Services, U.S. Government Printing Office (1991), Chothia & Lesk, *Canonical Structures for the Hypervariable Regions of Immunoglobulins*, J. Mol. Biol., 196, 901-917 (1987), and the IMGT® numbering system (The International ImMunoGeneTics Iinformation System®, Lefranc, M.-P., *The Immunologist* 7, 132-136 (1999). Visual inspection and sequence analysis can be carried out to identify the CDR boundaries. For this invention, the CDR sequences are defined by using both the Kabat system and the IMGT system; that is, when the CDRs defined by the two systems do not entirely overlap, we include all the residues from the sequences defined by both systems.

Human immunoglobulins can be divided into classes and subclasses, depending on the isotype of the heavy chain. The classes include IgG, IgM, IgA, IgD and IgE, in which the heavy chains are of the gamma (γ), mu (μ), alpha (α), delta (δ) or epsilon (ε) type, respectively. Subclasses include IgG1, IgG2, IgG3, IgG4, IgA1 and IgA2, in which the heavy chains are of the γ1, γ2, γ3, γ4, α1 and α2 type, respectively. Human immunoglobulin molecules of a selected class or subclass may contain either a kappa (κ) or lambda (λ) light chain. See e.g., *Cellular and Molecular Immunology, Wonsiewicz, M. J., Ed., Chapter* 45, pp. 41-50, W. B. Saunders Co., Philadelphia, Pa. 91991); Nisonoff, A., *Introduction to Molecular Immunology*, 2$^{nd}$ Ed., Chapter 4, pp. 45-65, Sinauer Associates, Inc., Sunderland, Mass. (1984).

As used herein, the terms "immunoglobulin" and "antibody," which are used interchangeably, refer to whole antibodies and antigen-binding fragments (i.e., "antigen-binding portions"—the two terms are used interchangeably herein unless otherwise indicated). Antigen-binding fragments of antibodies can be in the format of, for example, single chain antibodies, Fv fragments, Fab fragments, Fab' fragments, F(ab')$_2$ fragments, Fd fragments, single chain Fv molecules (scFv), bispecific single chain Fv dimers (PCT/US92/09665), diabodies, domain-deleted antibodies and single domain antibodies (dAbs). See e.g., *Nature Biotechnology* 22(9):1161-1165 (2004)). Also within the invention are antigen-binding molecules comprising a VH and/or a VL. In the case of a VH, the molecule may also comprise one or more of a CH1, hinge, CH2 and CH3 region. Such single chain antibodies are also intended to be encompassed within the term "antigen-binding portion" of an antibody.

Antibody portion or fragments can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CH$_1$ domain and hinge region of the heavy chain. Preferred antigen-binding fragments have binding specificity for a wild-type human CD52.

In another aspect, the invention provides a variant of an antibody or portion thereof as described herein, wherein said variant binds to human CD52 specifically but differs from the reference antibody or portion thereof by 1, 2, 3, 4, 5, 6, 7, 8, 9 or 10 amino acid substitutions (for example, in a CDR region, a FR region, or a constain domain). For example, the variant antibody is at least 90%, at least 91%, at least 93%, at least 95%, at least 97% or at least 99% identical to the reference antibody in the heavy chain, the heavy chain variable domain, the light chain, or the light chain variable domain.

Sequence similarity or identity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997); herein incorporated by reference.

According to the invention, one type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical. Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another aspect of the invention, the antibody may be deimmunized to reduce its immunogenicity using the techniques described in, e.g., PCT Publication WO98/52976 and WO00/34317.

Another type of amino acid substitution that may be made in one of the variants according to the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g., Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., Science 256:1443-45 (1992). A "moderately conservative" replacement is any change having a nonnegative value in the PAM250 log-likelihood matrix.

In certain embodiments, amino acid substitutions to an antibody or antigen-binding portion of the invention are those which: (1) reduce susceptibility to proteolysis, (2) reduce susceptibility to oxidation, (3) alter binding affinity for forming protein complexes, for example, to enhance ADCC and CDC activity of the antibody, (4) confer or modify other physicochemical or functional properties of such analogs, but still retain specific binding to human CD52, (5) remove C-terminal lysine, and (6) add or remove glycosylation sites.

In an aspect, the invention provides a new and novel polypeptide that is the heavy or light chain of an antibody of this invention, or that is a variable domain-containing portion of the heavy or light chain. Such a polypeptide is useful because it can partner with an opposite (light or heavy) antibody chain to form a CD52-binding molecule.

Humanized Immunoglobulins

Described herein are humanized immunoglobulins comprising the CDRs of novel mouse anti-human CD52 antibodies. In one embodiment, the humanized immunoglobulin comprises a humanized light chain and a humanized heavy chain that have CDR amino acid sequences which differ from the amino acid sequence of other humanized versions of anti-CD52 antibodies (e.g., Campath®).

The term "humanized immunoglobulin" as used herein refers to an immunoglobulin comprising chains that comprise one or more light chain CDRs (CDR1, CDR2 and CDR3) and one or more heavy chain CDRs (CDR1, CDR2 and CDR3) of an anti-CD52 antibody of non-human origin, also referred to herein as the donor antibody (e.g., a murine anti-CD52 antibody), and at least a portion of an immunoglobulin of human origin (e.g., framework regions, or framework and constant regions, derived from a light and/or heavy chain of human origin, such as CDR-grafted antibodies with or without framework changes). The humanized immunoglobulin of the invention comprises at least one CDR that differs from at least one CDR (e.g., from the corresponding CDR) present in Campath®. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., *Science,* 242: 423-426 (1988)), regarding single chain antibodies. In some embodiments, humanized immunoglobulins are de-immunized antibodies. See, e.g., Carr et al., U.S. Pat. No. 7,264,806, regarding de-immunized immunoglobulins that have been modified to reduce the number of potential T-cell epitopes, thereby reducing the propensity for the immunoglobulin to elicit an immune response upon administration to a human.

In particular embodiments, the humanized immunoglobulin comprises one or more light chain CDRs and one or more heavy chain CDRs of one or more of the following murine monoclonal antibodies: mouse 8G3.25.3.5, mouse 4G7.F3, mouse 9D9.A2, mouse 11C11.C5, mouse 3G7.E9, mouse 5F7.1.1.4, mouse 12G6.15.1.2, mouse 23E6.2.2.1, mouse 2C3.3.8.1, mouse 7F11.1.9.7, and mouse 4B10.1.2.4.

In another embodiment, the humanized immunoglobulins bind human CD52 with an affinity similar to or better than that of Campath®. In a particular embodiment, the humanized immunoglobulin of the present invention has the binding specificity of a murine anti-human CD52 antibody of the invention (e.g., having specificity for human CD52, having the same or similar epitopic specificity) and/or it has the same inhibitory function. The humanized immunoglobulin can have the binding specificity and/or inhibitory activity of a murine anti-human CD52 antibody or humanized anti-human CD52 antibody described herein, and/or the epitopic specificity of a murine anti-human CD52 antibody or humanized anti-human CD52 antibody described herein (e.g., it can compete with the murine anti-human CD52 antibody, or another humanized anti-CD52 antibody (e.g., Campath®) for binding to CD52, and/or it can have the inhibitory function of the murine or humanized anti-human CD52 antibody). In a particular embodiment, the humanized immunoglobulin has the binding specificity, epitopic specificity and/or inhibitory activity of any one of mouse antibodies 8G3, 4G7, 9D9, 11C11, 3G7, 5F7, 12G6, 23E6, 2C3, 7F11, andr 4B10.

The portion of the humanized immunoglobulin or immunoglobulin chain which is of human origin (e.g., framework region; constant region) can be derived from any suitable human immunoglobulin or immunoglobulin chain. For example, a human constant region or portion thereof in a humanized or chimeric antibody can be derived from a human κ or λ light chain gene, and/or from a human γ (e.g., γ1, γ2, γ3, γ4), μ, α (e.g., α1, α2), δ or ε heavy chain gene, including allelic variants. A particular constant region (e.g., IgG1), variant or portion thereof can be selected in order to tailor effector function. For example, a mutated constant region (variant) can be incorporated into the immunoglobulin or immunoglobulin chain so as to minimize binding to Fc receptors and/or ability to fix complement. (See e.g., Winter et al., GB 2,209,757 B; Morrison et al., WO 89/07142; Morgan et al., WO 94/29351, Dec. 22, 1994). In one embodiment, the human framework has no variation or mutation in its structure or sequence. In a particular embodiment, the framework is a germline framework sequence that has no mutations or variations in its sequence.

As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence.

In other embodiments, the human framework has minimal variation or mutation from germline sequence in its structure or sequence (e.g., less than 3, 4, 5, 6, 7, 8, 9, or 10 acceptor framework residues have been replaced with donor framework residues to improve binding affinity, see Queen et al., U.S. Pat. No. 5,530,101). In a particular embodiment, a limited number of amino acids in the framework of a humanized immunoglobulin chain (e.g., 1, 2, 3, 4, 5, 6, 7, 8, 9, or 10 amino acids) are chosen to be the same as the amino acids at those positions in the donor sequence (i.e., "back-mutated"), rather than in the acceptor sequence, to increase the affinity of an antibody comprising the humanized immunoglobulin chain for human CD52.

Human framework regions (e.g., of the heavy and/or light chain variable regions) are preferably obtained or derived from a human antibody variable region having sequence similarity to the analogous or equivalent region (e.g., heavy or light chain variable regions) of the antigen-binding region of the donor immunoglobulin (murine anti-CD52 antibody). Other sources of framework regions for portions of human origin of a humanized immunoglobulin include human variable region consensus sequences (See e.g., Kettleborough, C. A. et al., *Protein Engineering* 4:773-783 (1991); Carter et al., WO 94/04679; Carter U.S. Pat. No. 6,407,213)). For example, the region of the donor sequence of the antibody (e.g., the sequence of the variable region) used to obtain the nonhuman portion can be compared to human sequences as described in Kabat, E. A. et al. *Sequences of Proteins of Immunological Interest*, Fifth Edition, U.S. Department of Health and Human Services, U.S. Government Printing Office (1991) to select a particular source of the human portions of the humanized immunoglobulin, e.g., a source of the framework regions.

In one embodiment, the framework regions of the humanized immunoglobulin chains are obtained, or derived, from a human Ig variable region having at least about 50%, at least about 55%, at least about 60%, at least about 65%, at least about 70%, at least about 75%, at least about 80%, at least about 85%, at least about 90% or at least about 95% overall sequence identity, with the variable region of the nonhuman donor. In a particular embodiment, the framework regions of the humanized immunoglobulin chains are obtained or derived from human variable region framework regions having at least about 50%, at least about 55%, at least about 60%, at least about 65%, at least about 70%, at least about 75%, at least about 80%, at least about 85%, at least about 90%, or at least about 95% overall sequence identity, with the framework regions of the variable region of the nonhuman donor immunoglobulin.

In one embodiment, at least one of the framework regions (FR) of the humanized immunoglobulin is obtained or derived from one or more chains of an antibody of human origin. Thus, the FR can include a FR1 and/or FR2 and/or FR3 and/or FR4 obtained or derived from one or more antibodies of human origin (e.g., from a human immunoglobulin chain, from a human consensus sequence).

The immunoglobulin portions for use in the present invention have sequences identical, or similar, to immunoglobulins from which they are derived or to variants thereof. Such variants include mutants differing by the addition, deletion or substitution (e.g., conservative substitution) of one or more residues, e.g., differing by up to 3, 4, 5, 6, 7, 8, 9, or 10 residues from the parental sequence by one or more additions, deletions or substitutions. As indicated above, the humanized immunoglobulin of the invention comprises one or more CDRs from one or more of the murine anti-CD52 antibodies (donor antibodies) described herein. Changes in the framework region, such as those which substitute a residue of the framework region of human origin with a residue from the corresponding position of the donor antibody, can be made. One or more mutations, including deletions, insertions and substitutions of one or more amino acids in the framework region, can be made. If desired, framework mutations can be included in a humanized antibody or chain, and sites for mutation can be selected using any suitable method, for example as described in WO 98/06248, the entire teachings of which are incorporated by reference.

It will be appreciated by one of skill in the art that in some cases residues flanking the one or more CDRs of the murine anti-CD52 antibody(ies) may contribute, and in some cases, may be essential, either directly or indirectly, to function (e.g., binding). Thus, in some embodiments, one or more amino acids flanking one or more CDRs (e.g., 1, 2, 3, 4, 5, 6, 7, 8, 9, 10 flanking amino acids) of the murine framework are also included in the humanized immunoglobulin.

In some embodiments, the human heavy chain framework regions of the humanized antibodies of this invention utilize the human VH3-72 or VH3-23 germline sequence. In some embodiments, the human light chain framework regions of the humanized antibodies of this invention utilize the human Vk2-A18b germline sequence. Back mutations may optionally be made in these FR regions at one or more of the residues as described in the Working Examples below to improve CD52-binding affinity of the humanized antibody.

"Affinity" is a term of art that describes the strength of a binding interaction and typically refers to the overall strength of binding of the immunoglobulin to human CD52.

In a particular embodiment, the immunoglobulin has a binding activity measured as an $EC_{50}$ value of less than 10 μg/ml (e.g., as determined by flow cytometry). In another embodiment, the immunoglobulin has a binding activity measured as an $EC_{50}$ value of less than 5.0 μg/ml, or less than 1.0 μg/ml (e.g., as determined by flow cytometry).

In some embodiments, the immunoglobulin binds to human CD52 with an affinity ($K_D$; $K_D=K_{off}(kd)/Kon(ka)$) of 300 nM to 1 pM (i.e., $3\times10^{-7}$ to $1\times10^{-12}$M), preferably 50 nM to 1 pM, more preferably 5 nM to 1 pM and most preferably 1 nM to 1 pM, for example, a $K_D$ of $1\times10^{-7}$ M or less, preferably $1\times10^{-8}$ M or less, more preferably $1\times10^{-9}$ M or less, advantageously $1\times10^{-10}$ M or less and most preferably $1\times10^{-11}$ M or $1\times\times10^{-12}$ or less; and/or a $K_{off}$ rate constant of $5\times10^{-1}$ s−1 to $1\times10^{-7}$ s−1, preferably $1\times10^{-2}$ s−1 to $1\times10^{-6}$ s−1, more preferably $5\times10^{-3}$ s−1 to $1\times10^{-5}$ s−1, for example $5\times10^{-1}$ s−1 or less, preferably $1\times10^{-2}$ s−1 or less, advantageously $1\times10^{-3}$ s−1 or less, more preferably $1\times10^{4}$ s−1 or less, still more preferably $1\times10^{-5}$ s−1 or less, and most preferably $1\times10^{-6}$ s−1 or less as determined by surface plasmon resonance.

As is apparent to one of skill in the art, a variety of methods can be used to confirm that immunoglobulins produced according to methods provided herein and known in the art have the requisite specificity (e.g., binding specificity, epitopic specificity). For example, the binding function of a humanized anti-CD52 immunoglobulin of the invention having binding specificity for human CD52 can be detected using any suitable method, e.g., assays which monitor formation of a complex between humanized immunoglobulin and human CD52 (e.g., a membrane fraction comprising human CD52; a cell bearing human CD52, such as a human T cell, a human B cell; a CHO cell or a recombinant host cell comprising and expressing a nucleic acid encoding human CD52; a peptide (e.g., a synthetic peptide) having an amino acid sequence of CD52; a solid support comprising human CD52).

The ability of an immunoglobulin of the invention (e.g., a humanized immunoglobulin of the invention) to bind to the same epitope on human CD52 as a particular murine, chimeric, or humanized monoclonal antibody, or to bind to an epitope on human CD52 which overlaps with the epitope on human CD52 to which a particular murine, chimeric, or humanized monoclonal antibody binds, can be readily determined using a variety of techniques known to those of skill in the art, including e.g., competitive binding assays. These may involve the use of a labeled form of said particular antibody, and a measurement of the binding of that labeled antibody to human CD52 in the presence and in the absence of an immunoglobulin of the invention.

An "epitope" as used herein includes any protein determinant capable of specific binding to an immunoglobulin. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e., the antibodies compete for binding to the antigen.

In one embodiment, to determine if a test antibody binds to the same or overlapping epitope of a humanized antibody of this invention, one allows the anti-CD52 antibody of the invention to bind to CD52 under saturating conditions and then measures the ability of the test antibody to bind to CD52. If the test antibody is able to bind to CD52 at the same time as the reference anti-CD52 antibody, then the test antibody binds to a different epitope than the reference anti-CD52 antibody. However, if the test antibody is not able to bind to CD52 at the same time, then the test antibody binds to the same epitope, an overlapping epitope, or an epitope that is in close proximity to the epitope bound by the anti-CD52 antibody of the invention. This experiment can be performed using ELISA, RIA, BIACORE™, or flow cytometry. To test whether an anti-CD52 antibody cross-competes with another anti-CD52 antibody, one may use the competition method described above in two directions, i.e., determining if the reference antibody blocks the test antibody and vice versa. In a some embodiment, the experiment is performed using BIACORE™.

Epitope binning can also be useful to characterize the antibodies of this invention. The term "binning" refers to a method to group antibodies based on their antigen binding characteristics. A high throughput process for "binning" antibodies based upon their cross-competition is described in International Patent Application No. WO 03/48731. The "epitope binning" can be investigated by allowing an unlabeled form of an anti-CD52 antibody "A" to bind to a synthetic peptide corresponding to the sequence of CD52 or to CD52 positive cells. Subsequently a labeled second anti-CD52 antibody "B" is added and one can assess the amount of labeled antibody that can bind relative to a control sample where the cells or synthetic peptide have not been exposed previously to anti-CD52 antibody "A." Alternatively, anti-CD52 antibodies "A" and "B" can both be labeled with different fluorochromes or chemicals enabling detection, and one can measure the quantities of both labeled antibodies that can engage the CD52 peptide at the same time using a device capable of detecting the label or measure the amounts of both antibodies that simultaneously engage CD52 positive cells by flow cytometry. Biacore and Octet technologies enable one to investigate the competitive binding of unlabelled forms of antibodies. This use of unlabelled forms of antibodies is desired as the chemical modification of some antibodies can compromise the binding activity. See also the technology described in See also Jia et al., *J. Immunol. Methods* 288:91-98 (2004), which is useful in performing epitope binning as well.

Also provided herein are portions of the humanized immunoglobulins such as light chains, heavy chains and portions of light and heavy chains. These immunoglobulin portions can be obtained or derived from immunoglobulins (e.g., by reduction and/or cleavage), or produced or expressed by nucleic acids encoding a portion of an immunoglobulin or chain thereof having the desired property (e.g., binds human CD52, sequence similarity). They can be prepared by e.g., de novo synthesis of the relevant portion. Humanized immunoglobulins comprising the desired portions (e.g., antigen-binding region, CDR, FR, C region) of human and nonhuman origin can be produced using synthetic and/or recombinant nucleic acids to prepare constructs (e.g., cDNA) encoding the desired humanized chain. For example, to prepare a portion of an immunoglobulin (e.g., a portion of a chain), one or more stop codons can be introduced at the desired position. Nucleic acid (e.g., DNA) sequences coding for humanized variable regions can be constructed using PCR mutagenesis methods to alter existing DNA sequences (see e.g., Kamman, M., et al., *Nucl. Acids Res.* 17:5404 (1989)). PCR primers coding for the new CDRs can be hybridized to a DNA template of a previously humanized variable region which is based on the same, or a very similar, human variable region (Sato, K., et al., *Cancer Research* 53:851-856 (1993)). If a similar DNA sequence is not available for use as a template, a nucleic acid comprising a sequence encoding a variable region sequence can be constructed from synthetic oligonucleotides (see e.g., Kolbinger, F., *Protein Engineering* 8:971-980 (1993)). A sequence encoding a signal peptide can also be incorporated into the nucleic acid (e.g., on synthesis, upon insertion into a vector). If a signal peptide sequence is unavailable (e.g., not typically present), a signal peptide sequence from another antibody can be used (see, e.g., Kettleborough, C. A., *Protein Engineering* 4:773-783 (1991)). Using these methods, methods described herein or other suitable methods, variants can readily be produced.

The invention relates to a humanized immunoglobulin that has binding specificity for human CD52 and comprises a humanized light chain and a humanized heavy chain and/or portions thereof. In one embodiment, the humanized immunoglobulin comprises a light chain comprising one or more CDRs (e.g., all three CDRs) of SEQ ID NO: 3 and a heavy chain comprising one or more CDRs (e.g., all three CDRs) of SEQ ID NO: 16; a light chain comprising one or more CDRs (e.g., all three CDRs) of SEQ ID NO: 4 and a heavy chain comprising one or more CDRs (e.g., all three CDRs) of SEQ ID NO: 17; a light chain comprising one or more CDRs (e.g., all three CDRs) of SEQ ID NO: 5 and a heavy chain comprising one or more CDRs (e.g., all three CDRs) of SEQ ID NO: 18; a light chain comprising one or more CDRs (e.g., all three CDRs) of SEQ ID NO: 6 and a heavy chain comprising one or more CDRs (e.g., all three CDRs) of SEQ ID NO: 19; a light chain comprising one or more CDRs (e.g., all three CDRs) of SEQ ID NO: 7 and a heavy chain comprising one or more CDRs (e.g., all three CDRs) of SEQ ID NO: 20; a light chain comprising one or more CDRs (e.g., all three CDRs) of SEQ ID NO: 8 and a heavy chain comprising one or more CDRs (e.g., all three CDRs) of SEQ ID NO: 21; a light chain comprising one or more CDRs (e.g., all three CDRs) of SEQ ID NO: 9 and a heavy chain comprising one or more CDRs (e.g., all three CDRs) of SEQ ID NO: 22; a light chain comprising one or more CDRs (e.g., all three CDRs) of SEQ ID NO: 10 and a heavy chain comprising one or more CDRs (e.g., all three CDRs) of SEQ ID NO: 23; a light chain comprising one or more CDRs (e.g., all three CDRs) of SEQ ID NO: 11 and a heavy chain comprising one or more CDRs (e.g., all three CDRs) of SEQ ID NO: 24; a light chain comprising one or more CDRs (e.g., all three CDRs) of SEQ ID NO: 12 and a heavy chain comprising one or more CDRs (e.g., all three CDRs) of SEQ ID NO: 25; or a light chain comprising one or more CDRs (e.g., all three CDRs) of SEQ ID NO: 13 and a heavy chain sequence comprising one or more CDRs (e.g., all three CDRs) of SEQ ID NO: 26.

In one embodiment, a humanized immunoglobulin of the invention comprises heavy chain (H)-CDR1, H-CDR2, H-CDR3, light chain (L)-CDR1, L-CDR2, and L-CDR3 whose amino acid sequences are: a) SEQ ID NOs: 51, 59, 69, 29, 36, and 43, respectively; b) SEQ ID NOs: 50, 60, 69, 29, 37, and 43, respectively; c) SEQ ID NOs: 50, 61, 68, 29, 38, and 43, respectively; d) SEQ ID NOs: 50, 61, 69, 29, 36, and 43, respectively; e) SEQ ID NOs: 50, 62, 69, 29, 39, and 43, respectively; f) SEQ ID NOs: 52, 61, 70, 30, 40, and 43, respectively; g) SEQ ID NOs: 53, 63, 71, 31, 36, and 44, respectively; h) SEQ ID NOs: 54, 64, 71, 31, 36, and 45, respectively; i) SEQ ID NOs: 55, 63, 72, 31, 36, and 46, respectively; j) SEQ ID NOs: 56, 65, 73, 32, 41, and 47, respectively; k) SEQ ID NOs: 56, 65, 294, 32, 41, and 47; or l) SEQ ID NOs: 56, 66, 74, 33, 41, and 48, respectively.

In another embodiment, a humanized immunoglobulin of this invention comprises H-CDR3 and L-CDR3 whose sequences are a) SEQ ID NOs: 69 and 43, respectively; b) SEQ ID NOs: 68 and 43, respectively; c) SEQ ID NOs: 70 and 43, respectively; d) SEQ ID NOs: 71 and 44, respectively; e) SEQ ID NOs: 71 and 45, respectively; f) SEQ ID NOs: 72 and 46, respectively; g) SEQ ID NOs: 73 and 47, respectively; h) SEQ ID NOs: 294 and 47, respectively; or i) SEQ ID NOs: 74 and 48, respectively.

In another embodiment, the humanized immunoglobulin has binding specificity for human CD52 and comprises a light chain comprising one or more CDRs selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, or a combination thereof; and a heavy chain comprising one or more CDRs selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294, or a combination thereof, wherein the humanized immunoglobulin is not Campath®.

In another embodiment, the humanized immunoglobulin that has a binding specificity for human CD52 comprises a light chain comprising one or more CDRs (e.g., all three CDRs) of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13, and a heavy chain comprising one or more CDRs (e.g., all three CDRs) of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 137, wherein the humanized immunoglobulin is not Campath®.

The invention also relates to a humanized immunoglobulin light chain of the humanized immunoglobulin described herein. In one embodiment, the humanized immunoglobulin light chain comprises one or more CDRs selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, and a combination thereof, wherein the humanized immunoglobulin light chain is not the light chain of Campath®. For example, the humanized antibody has L-CDR1, L-CDR2, and L-CDR3 whose amino acid sequences are: a) SEQ ID NOs: 29, 36, and 43, respectively; b) SEQ ID NOs: 29, 37, and 43, respectively; c) SEQ ID NOs: 29, 38, and 43, respectively; d) SEQ ID NOs: 29, 36, and 43, respectively; e) SEQ ID NOs: 29, 39, and 43, respectively; f) SEQ ID NOs: 30, 40, and 43, respectively; g) SEQ ID NOs: 31, 36, and 44, respectively; h) SEQ ID NOs: 31, 36, and 45, respectively; i) SEQ ID NOs: 31, 36, and 46, respectively; j) SEQ ID NOs: 32, 41, and 47, respectively; or k) SEQ ID NOs: 33, 41, and 48, respectively.

The invention also relates to humanized heavy chain comprising one or more CDRs selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, and SEQ ID NO: 294, or a combination thereof, wherein the humanized immunoglobulin heavy chain is not the heavy chain of Campath®. For example, the humanized antibody has H-CDR1, H-CDR2, and H-CDR3 whose amino acid sequences are: a) SEQ ID NOs: 51, 59, and 69, respectively; b) SEQ ID NOs: 50, 60, and 69, respectively; c) SEQ ID NOs: 50, 61, and 68, respectively; d) SEQ ID NOs: 50, 61, and 69, respectively; e) SEQ ID NOs: 50, 62, and 69, respectively; f) SEQ ID NOs: 52, 61, and 70, respectively; g) SEQ ID NOs: 53, 63, and 71, respectively; h) SEQ ID NOs: 54, 64, and 71, respectively; i) SEQ ID NOs: 55, 63, and 72, respectively; j) SEQ ID NOs: 56, 65, and 73, respectively; k) SEQ ID NOs: 56, 65, and 294; or l) SEQ ID NOs: 56, 66, and 74, respectively.

In one embodiment, a humanized antibody of this invention comprises a light chain comprising a variable domain ($V_L$) sequence of one of SEQ ID NOs: 102, 138, 145-148, 153-157, and 164-168. In a related embodiment, the humanized antibody comprises a light chain whose amino acid sequence comprises or consists of one of SEQ ID NOs: 273, 275, 278, 280, and 282.

In one embodiment, a humanized antibody of this invention comprises a heavy chain comprising a variable domain ($V_H$) sequence of one of SEQ ID NOs: 103, 136, 137, 139-144, 149-152, and 158-163. In a related embodiment, the humanized antibody comprises a heavy chain whose amino acid sequence comprises or consists of one of SEQ ID NOs: 272, 274, 276, 277, 279, and 281.

In some embodiments, a humanized antibody of this invention comprises a $V_H$ and a $V_L$ whose amino acid sequences comprise or consist of a) SEQ ID NOs: 103 and 102, respectively (4B10-H1/K1);

b) SEQ ID NOs: 136 and 138, respectively (7F11-SFD1/K2);

c) SEQ ID NOs: 137 and 138, respectively (7F11-SFD2/K2)

d) SEQ ID NO: 139 and one of SEQ ID NOs: 145-148, respectively (e.g., SEQ ID NOs: 139 and 146, respectively (2C3-SFD1/K11); and SEQ ID NOs: 139 and 147, respectively (2C3-SFD1/K12));

e) SEQ ID NO: 140 and one of SEQ ID NOs: 145-148, respectively;

f) SEQ ID NO: 141 and one of SEQ ID NOs: 145-148, respectively;

g) SEQ ID NO: 142 and one of SEQ ID NOs: 145-148, respectively;

h) SEQ ID NO: 143 and one of SEQ ID NOs: 145-148, respectively;

i) SEQ ID NO: 144 and one of SEQ ID NOs: 145-148, respectively;

j) SEQ ID NO: 149 and one of SEQ ID NOs: 153-157, respectively (e.g., SEQ ID NOs: 149 and 155, respectively (12G6-SFD1/K11); SEQ ID NOs: 149 and 156, respectively (12G6-SFD1/K12); and SEQ ID NOs: 149 and 157, respectively (12G6-SFD1/K13));

k) SEQ ID NO: 150 and one of SEQ ID NOs: 153-157, respectively;

l) SEQ ID NO: 151 and one of SEQ ID NOs: 153-157, respectively;

m) SEQ ID NO: 152 and one of SEQ ID NOs: 153-157, respectively;

n) SEQ ID NO: 158 and one of SEQ ID NOs: 164-168, respectively (e.g., SEQ ID NOs: 158 and 165, respectively (9D9-H10/K12); and SEQ ID NOs: 158 and 166, respectively (9D9-H10/K13));

o) SEQ ID NO: 159 and one of SEQ ID NOs: 164-168, respectively (e.g., SEQ ID NOs: 159 and 165, respectively (9D9-H11/K12); and SEQ ID NOs: 159 and 166, respectively (9D9-H11/K13));

p) SEQ ID NO: 160 and one of SEQ ID NOs: 164-168, respectively;

q) SEQ ID NO: 161 and one of SEQ ID NOs: 164-168, respectively (e.g., SEQ ID NOs: 161 and 166, respectively (9D9-H16/K13));

r) SEQ ID NO: 162 and one of SEQ ID NOs: 164-168, respectively; or s) SEQ ID NO: 163 and one of SEQ ID NOs: 164-168, respectively (e.g., SEQ ID NOs: 163 and 166, respectively (9D9-H18/K13)).

The antibodies included in the parentheses are further described below in the working examples.

In one embodiment, a humanized antibody of this invention comprises a light chain (LC) and a heavy chain (HC) whose amino acid sequences comprise or consist of a) SEQ ID NOs: 273 and 272, respectively; b) SEQ ID NOs: 275 and 274, respectively; c) SEQ ID NOs: 278 and 276, respectively; d) SEQ ID NOs: 278 and 277, respectively; e) SEQ ID NOs: 280 and 279, respectively; or f) SEQ ID NOs: 282 and 281, respectively.

This invention also provides anti-human CD52 antibodies (except those, in any, known in the prior art) that binds to the same epitope as, or competes or cross-competes with, an antibody exemplified herein. These antibodies can be, for example, humanized, chimeric, or mouse antibodies. For example, the invention provides anti-human CD52 antibodies that bind to the same epitope as, or competes or cross-competes with, one of mouse antibodies 8G3, 4F7, 9D9, 11C11, 3G7, 5F7, 12G6, 23E6, 2C3, 7F11, and 4B10, and humanized and chimeric versions of these mouse antibodies. The ability of an antibody to bind to the same epitope as, or competes or cross-competes with a reference antibody can be determined as described above. For example, we have found that the CD52 epitope bound by the humanized antibodies 2C3-SFD1/K12 and 12G6-SFD1/K12 includes residues 7, 8, and 11 in SEQ ID NO: 104, and that the epitope bound by the humanized antibody 9D9-H16/K13 includes residues 4 and 11 in SEQ ID NO: 104. Thus, in some embodiments, this invention provides anti-CD52 antibodies that bind to the same epitope as, or competes or cross-competes with, those humanized antibodies.

If desired, for example, for diagnostic or assay purposes (e.g., imaging to allow, for example, monitoring of therapies), the humanized immunoglobulin (e.g., antigen-binding fragment thereof) can comprise a detectable label. Suitable detectable labels and methods for labeling a humanized immunoglobulin or antigen-binding fragment thereof are well known in the art. Suitable detectable labels include, for example, a radioisotope (e.g., as Indium-111, Technetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group or a chemiluminescent group. When labels are not employed, complex formation (e.g., between humanized immunoglobulin and human CD52) can be determined by surface plasmon resonance, ELISA, FACS, or other suitable methods.

Anti-CD52 antibodies used in the invention also may be conjugated, via, for example, chemical reactions or genetic modifications, to other moieties (e.g., pegylation moieties) that improve the antibodies' pharmacokinetics such as half-life. In some embodiments, the anti-CD52 antibodies used in this invention can be linked to a suitable cytokine via, e.g., chemical conjugation or genetic modifications (e.g., appending the coding sequence of the cytokine in frame to an antibody coding sequence, thereby creating an antibody:cytokine fusion protein).

The invention also relates to immunoconjugates in which the humanized immunoglobulin (e.g., antigen-binding fragment thereof) of the invention is coupled to another therapeutic agent, such as a bioactive compound (e.g., cytokines, superantigens, cytotoxic agents and toxins). For example, the humanized immunoglobulin that has binding specificity for human CD52 (e.g., antigen binding fragment thereof) can be coupled to a biological protein, a molecule of plant or bacterial origin (or derivative thereof), an interleukin-2 antibody or diptheria toxin antibodies.

Mouse Monoclonal Immunoglobulins

As described herein, mouse monoclonal immunoglobulins having binding specificity for human CD52 have been produced Humanized and chimeric antibodies of this invention can be derived from the mouse monoclonal antibodies of this invention. That is, in some embodiments, humanized and chimeric anti-CD52 antibodies of the invention comprise sequences taken from a mouse monoclonal antibody of the invention, such as one or more CDR sequences. A mouse monoclonal immunoglobulin of this invention comprises a light chain and a heavy chain that have CDR amino acid sequences which differ from the CDR amino acid sequences of known mouse anti-CD52 monoclonal antibodies (e.g., from CF1D12).

As used herein, the term "mouse monoclonal immunoglobulin" refers to an immunoglobulin containing light chain CDRs (L-CDR1, L-CDR2 and L-CDR3) and heavy chain CDRs (H-CDR1, H-CDR2 and H-CDR3) of a murine anti-human CD52 antibody, and framework and constant regions of murine origin. Mouse monoclonal immunoglobulins are homogeneous antibodies of a single specificity prepared, for example, by the use of hybridoma technology or recombinant methods.

The invention relates to the mouse monoclonal immunoglobulins described herein, including antigen-binding fragments (i.e., portions) of the mouse monoclonal immunoglobulins, the light chains of the mouse monoclonal immunoglobulins, the heavy chains of the mouse monoclonal immunoglobulins, and fragments of these heavy and light chains. In a particular embodiment, the mouse monoclonal antibody is the mouse 8G3.25.3.5 (also called GENZ 8G3.25.3.5 or 8G3), mouse GMA 4G7.F3 (also called 4G7.F3 or 4G7), mouse GMA 9D9.A2 (also called 9D9.A2 or 9D9), mouse GMA 11C11.C5 (also called 11C11.C5 or 11C11), mouse GMA 3G7.E9 (also called 3G7.E9 or 3G7), mouse 5F7.1.1.4 (also called GENZ 5F7.1.1.4 or 5F7), mouse 12G6.15.1.2 (also called GENZ 12G6.15.1.2 or 2G6), mouse 23E6.2.2.1 (also called GENZ 23E6.2.2.1 or 23E6), mouse 2C3.3.8.1 (also called GENZ 2C3.3.8.1 or 2C3), mouse 7F11.1.9.7 (also called GENZ 7F11.1.9.7 or 7F11), or mouse 4B10.1.2.4 (also called GENZ 4B10.1.2.4 or 4B10). The invention relates to mature mouse monoclonal immunoglobulin, such as the mouse monoclonal immunoglobulin following processing to remove the heavy and light chain signal peptides and/or to the glycosylated immunoglobulin. The invention also relates to immature or precursor protein, such as a mouse immunoglobulin light chain or a mouse immunoglobulin heavy chain comprising a signal peptide. The invention also relates to nucleic acid molecules (e.g., vectors) that encode these immature or mature proteins, to host cells that comprise such nucleic acids and to methods of producing these immature and mature proteins.

The binding function of a mouse monoclonal immunoglobulin having binding specificity for human CD52 can be detected using any suitable method, for example using assays which monitor formation of a complex between mouse monoclonal immunoglobulin and human CD52 (e.g., a membrane fraction comprising human CD52, or a cell bearing human CD52, such as a human T cell, a human B cell, CHO cell or a recombinant host cell comprising a nucleic acid encoding human CD52; a peptide (e.g., a synthetic peptide) having an amino acid sequence of CD52).

Also provided herein are portions of the murine immunoglobulins which include light chains, heavy chains and portions of light and heavy chains. These immunoglobulin portions can be obtained or derived from immunoglobulins (e.g., by reduction and/or cleavage), or nucleic acids encoding a portion of an immunoglobulin or chain thereof having the desired property (e.g., binds human CD52, sequence similarity) can be produced and expressed. They can be prepared by e.g., de novo synthesis of a portion of mouse monoclonal immunoglobulins comprising the desired portions (e.g., antigen-binding region, CDR, FR, and/or C region) of murine origin can be produced using synthetic and/or recombinant nucleic acids to prepare constructs (e.g., cDNA) encoding the desired monoclonal immunoglobulin chain. To prepare a portion of a chain, one or more stop codons can be introduced at the desired position. A sequence encoding a signal peptide can also be incorporated into the nucleic acid (e.g., on synthesis, upon insertion into a vector). If the natural signal peptide sequence is unavailable, a signal peptide sequence from another antibody can be used (see, e.g., Kettleborough, C. A., *Protein Engineering* 4:773-783 (1991)). Using these methods, methods described herein or other suitable methods, variants can be readily produced.

In one embodiment, a mouse monoclonal immunoglobulin of this invention comprises a light chain comprising SEQ ID NO: 3 and a heavy chain comprising SEQ ID NO: 16; a light chain comprising SEQ ID NO: 4 and a heavy chain comprising SEQ ID NO: 17; a light chain comprising SEQ ID NO: 5 and a heavy chain comprising SEQ ID NO: 18; a light chain comprising SEQ ID NO: 6 and a heavy chain comprising SEQ ID NO: 19; a light chain comprising SEQ ID NO: 7 and a heavy chain comprising SEQ ID NO: 20; a light chain comprising SEQ ID NO: 8 and a heavy chain comprising SEQ ID NO: 21; a light chain comprising SEQ ID NO: 9 and a heavy chain comprising SEQ ID NO: 22; a light chain comprising SEQ ID NO: 10 and a heavy chain comprising SEQ ID NO: 23; a light chain comprising SEQ ID NO: 11 and a heavy chain comprising SEQ ID NO: 24; a light chain comprising SEQ ID NO: 12 and a heavy chain comprising SEQ ID NO: 25; or a light chain comprising SEQ ID NO: 13 and a heavy chain comprising SEQ ID NO: 26.

In another embodiment, the invention also relates to a mouse monoclonal antibody that has binding specificity for human CD52, comprising a light chain variable region selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9; SEQ ID NO: 10; SEQ ID NO: 11, SEQ ID NO: 12, and SEQ ID NO: 13; and a heavy chain variable region selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23; SEQ ID NO: 24, SEQ ID NO: 25 and SEQ ID NO: 26.

If desired, for example, for diagnostic or assay purposes (e.g., imaging), the mouse monoclonal immunoglobulin (e.g., antigen binding fragment thereof) can comprise a detectable label. Suitable detectable labels and methods for labeling a mouse monoclonal immunoglobulin are well known in the art. Suitable detectable labels include, for example, a radioisotope (e.g., as Indium-111, Technnetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group or a chemiluminescent group. When labels are not employed, complex formation (e.g., between mouse monoclonal immunoglobulin and CD52) can be determined by surface plasmon resonance or other suitable methods. All suitable methods and techniques described above for humanized antibodies of this invention can also be used herein.

Chimeric Immunoglobulins

As described herein, chimeric immunoglobulins having binding specificity for human CD52 have been produced. The chimeric immunoglobulin comprises a chimeric light chain and/or a chimeric heavy chain that have amino acid sequences which differ from the amino acid sequence of known chimeric antibodies having binding specificity for human CD52.

As used herein, the term "chimeric immunoglobulin" refers to a recombinant protein that contains the variable domains including the complementarity determining regions (CDRs) of an antibody derived from one species, preferably a murine anti-human CD52 monoclonal antibody, while the constant domains of the antibody molecule are derived from those of a different species, e.g., from a human antibody.

The invention relates to the chimeric immunoglobulins described herein, including antigen-binding fragments (i.e., portions) of the chimeric immunoglobulins, the chimeric light chains and chimeric heavy chains of the chimeric immunoglobulins and fragments of these chimeric light and heavy chains. The invention relates to mature chimeric immunoglobulin, such as the chimeric immunoglobulin following processing to remove the heavy and light signal peptides and/or to the glycosylated immunoglobulin. The invention also relates to immature or precursor protein, such as a chimeric heavy chain comprising a signal peptide. The invention also relates to nucleic acid molecules (e.g., vectors) that encode these immature or mature proteins, to host cells that comprise such nucleic acids and to methods of producing these immature and mature proteins.

The binding function of a chimeric immunoglobulin having binding specificity for human CD52 can be detected using any suitable method, for example using assays which monitor formation of a complex between chimeric immunoglobulin and human CD52 (e.g., a membrane fraction comprising human CD52, on a cell bearing human CD52, such as a human T cell, a human B cell, CHO cell or a recombinant host cell comprising a nucleic acid encoding human CD52, a peptide (e.g., synthetic peptide) having an amino acid sequence of CD52).

Also provided herein are portions of the chimeric immunoglobulins which include light chains, heavy chains and portions of light and heavy chains. These immunoglobulin portions can be obtained or derived from immunoglobulins (e.g., by reduction and/or cleavage), or nucleic acids encoding a portion of an immunoglobulin or chain thereof having the desired property (e.g., binds human CD52, sequence similarity) can be produced and expressed. They may be prepared by e.g., de novo synthesis of a portion. Chimeric immunoglobulins comprising the desired portions (e.g., antigen-binding region, CDR, FR, and/or C region) of human and non-human origin can be produced using synthetic and/or recombinant nucleic acids to prepare constructs (e.g., cDNA) encoding the desired chimeric chain. To prepare a portion of a chain, one or more stop codons can be introduced at the desired position. A sequence encoding a signal peptide can also be incorporated into the nucleic acid (e.g., on synthesis, upon insertion into a vector). If the natural signal peptide sequence is unavailable (e.g., typically not present), a signal peptide sequence from another antibody can be used (see, e.g., Kettleborough, C. A., *Protein Engineering* 4:773-783 (1991)). Using these methods, methods described herein or other suitable methods, variants can be readily produced.

In one embodiment, a chimeric immunoglobulin of this invention comprises the light chain variable region of SEQ ID NO: 3 and the heavy chain variable region of SEQ ID NO: 16; the light chain variable region of SEQ ID NO: 4 and the heavy chain variable region of SEQ ID NO: 17; the light chain variable region of SEQ ID NO: 5 and the heavy chain variable region of SEQ ID NO: 18; the light chain variable region of SEQ ID NO: 6 and the heavy chain variable region of SEQ ID NO: 19; the light chain variable region of SEQ ID NO: 7 and the heavy chain variable region of SEQ ID NO: 20; the light chain variable region of SEQ ID NO: 8 and the heavy chain variable region of SEQ ID NO: 21; the light chain variable region of SEQ ID NO: 9 and the heavy chain variable region of SEQ ID NO: 22; the light chain variable region of SEQ ID NO: 10 and the heavy chain variable region of SEQ ID NO: 23; the light chain variable region of SEQ ID NO: 11 and the heavy chain variable region of SEQ ID NO: 24; the light chain variable region of SEQ ID NO: 12 and the heavy chain variable region of SEQ ID NO: 25; or the light chain variable region of SEQ ID NO: 13 and the heavy chain variable region of SEQ ID NO: 26.

The invention also relates to a chimeric antibody that has binding specificity for human CD52, comprising a light chain variable region sequence selected from the group consisting of the light chain variable region of SEQ ID NO: 3, the light chain variable region of SEQ ID NO: 4, the light chain variable region of SEQ ID NO: 5, the light chain variable region of SEQ ID NO: 6, the light chain variable region of SEQ ID NO: 7, the light chain variable region of SEQ ID NO: 8, the light chain variable region of SEQ ID NO: 9, the light chain variable region of SEQ ID NO: 10, the light chain variable region of SEQ ID NO: 11, the light chain variable region of SEQ ID NO: 12 and the light chain variable region of SEQ ID NO: 13, and a heavy chain variable region sequence selected from the group consisting of: the heavy chain variable region of SEQ ID NO: 16, the heavy chain variable region of SEQ ID NO: 17, the heavy chain variable region of SEQ ID NO: 18, the heavy chain variable region of SEQ ID NO: 19, the heavy chain variable region of SEQ ID NO: 20, the heavy chain variable region of SEQ ID NO: 21, the heavy chain variable region of SEQ ID NO: 22, the heavy chain variable region of SEQ ID NO: 23, the heavy chain variable region of SEQ ID NO: 24, the heavy chain variable region of SEQ ID NO: 25 and the heavy chain variable region of SEQ ID NO: 26.

The invention also relates to a chimeric light chain comprising the variable region of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

The invention also relates to a chimeric heavy chain comprising the variable region of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23; SEQ ID NO: 24, SEQ ID NO: 25 or SEQ ID NO: 26

If desired, for example, for diagnostic or assay purposes (e.g., imaging), the chimeric immunoglobulin (e.g., antigen-binding fragment thereof) can comprise a detectable label. Suitable detectable labels and methods for labeling a chimeric immunoglobulin are well known in the art. Suitable detectable labels include, for example, a radioisotope (e.g., as Indium-111, Technnetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group or a chemiluminescent group. When labels are not employed, complex formation (e.g., between chimeric immunoglobulin and human CD52) can be determined by surface plasmon resonance or other suitable methods. All suitable methods and techniques described above for humanized antibodies of this invention can also be used herein.

Nucleic Acids and Recombinant Vectors

The present invention also relates to isolated and/or recombinant (including, e.g., essentially pure) nucleic acids comprising sequences which encode a humanized immunoglobulin, humanized light chain, humanized heavy chain, mouse monoclonal immunoglobulin, mouse immunoglobulin light chain, mouse immunoglobulin heavy chain, chimeric immunoglobulin, chimeric light chain or chimeric heavy chain of the present invention.

Nucleic acids referred to herein as "isolated" or "purified" are nucleic acids which have been separated away from the nucleic acids of the genomic DNA or cellular RNA of their source of origin (e.g., as they exist in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.,* 19(9): 2471-2476 (1991); Lewis, A. P. and J. S. Crowe, *Gene,* 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

The present invention also relates more specifically to isolated and/or recombinant nucleic acids comprising a nucleotide sequence which encodes a humanized immunoglobulin, mouse immunoglobulin or chimeric immunoglobulin that has binding specificity for human CD52 (e.g., a humanized immunoglobulin of the present invention in which the nonhuman portion (e.g., the CDRs) is derived from a murine anti-CD52 monoclonal antibody; a mouse immunoglobulin of the present invention; or a chimeric immunoglobulin of the present invention in which the nonhuman portion (e.g., the $V_H$ and $V_L$) is derived from a murine anti-CD52 monoclonal antibody) or portion (e.g., antigen-binding portion) thereof (e.g., heavy or light chain thereof).

Nucleic acids of the present invention can be used to produce humanized immunoglobulins having binding specificity for human CD52, mouse immunoglobulins having binding specificity for human CD52 and chimeric immunoglobulins having binding specificity for human CD52. For example, a nucleic acid (e.g., DNA (such as cDNA), or RNA) or one or more nucleic acids encoding a humanized immunoglobulin, mouse immunoglobulin or chimeric immunoglobulin of the present invention can be incorporated into a suitable construct (e.g., a recombinant vector) for further manipulation of sequences or for production of the encoded immunoglobulins in suitable host cells.

Constructs or vectors (e.g., expression vectors) suitable for the expression of a humanized immunoglobulin having binding specificity for human CD52, mouse immunoglobulin having binding specificity for human CD52 or chimeric immunoglobulin having binding specificity for human CD52 are also provided. A variety of vectors are available, including vectors which are maintained in single copy or multiple copies in a host cell, or which become integrated into the host cell's chromosome(s). The constructs or vectors can be introduced into a suitable host cell, and cells which express a humanized immunoglobulin, mouse immunoglobulin or chimeric immunoglobulin of the present invention, can be produced and maintained in culture. A single vector or multiple vectors can be used for the expression of a humanized immunoglobulin, mouse immunoglobulin or chimeric immunoglobulin having binding specificity for human CD52.

Suitable expression vectors, for example mammalian cell expression vectors, can also contain a number of components, including, but not limited to one or more of the following: an origin of replication; a selectable marker gene; one or more expression control elements, such as a transcriptional control element (e.g., a promoter, an enhancer, a terminator), and/or one or more translation signals; a signal sequence or leader sequence for membrane targeting or secretion. In a construct or vector, a signal peptide sequence can be provided by the construct or vector or other source. For example, the transcriptional and/or translational signals of an immunoglobulin can be used to direct expression.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic (e.g., lac, tac, T3, T7 promoters for *E. coli*) and eukaryotic (e.g., yeast alcohol dehydrogenase (ADH1), SV40, CMV) hosts are available. Those of skill in the art will be able to select the appropriate promoter for expressing an anti-CD52 antibody or portion thereof of the invention.

In addition, the vectors (e.g., expression vectors) typically comprise a selectable marker for selection of host cells carrying the vector, and, in the case of a replicable vector, an origin of replication. Genes encoding products which confer antibiotic or drug resistance are common selectable markers and may be used in prokaryotic (e.g., β-lactamase gene (ampicillin resistance), Tet gene (tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

The invention thus relates to isolated nucleic acid molecules that encode the humanized immunoglobulin, humanized light chain, humanized heavy chain, mouse immunoglobulin, mouse immunoglobuin light chain, mouse immunoglobuin heavy chain, chimeric immunoglobulin, chimeric light chain, or chimeric heavy chain of this invention. The invention also relates to isolated nucleic acid molecules that encode an antigen-binding portion of the immunoglobulins and their chains. Polypeptide sequences encoded by the nucleic acids of this invention are described above and in the following Examples.

In some embodiments, a nucleic acid and vector of this invention encodes a heavy chain (or an antigen-binding portion thereof) or a light chain (or an antigen-binding portion thereof) of this invention. A host cell containing both the heavy chain-encoding nucleic acid and the light chain-encoding nucleic acid can be used to make an antibody comprising the heavy and light chain (or an antigen-binding portion of the antibody). The heavy chain-encoding nucleic acid and the light chain-encoding nucleic acid can be placed on separate expression vectors. They can also be placed on a single expression vector under the same or different expression control. See, e.g., Cabilly U.S. Pat. No. 6,331,415; Fang U.S. Pat. No. 7,662,623.

Method of Producing Immunoglobulins Having Specificity for Human CD52

Another aspect of the invention relates to a method of making an anti-human CD52 antibody of this invention. The antibody of this invention can be produced, for example, by the expression of one or more recombinant nucleic acids encoding the antibody in a suitable host cell. The host cell can be produced using any suitable method. For example, the expression constructs (e.g., the one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Suitable host cells can be prokaryotic, including bacterial cells such as *E. coli* (e.g., strain DH5α™ (Invitrogen, Carlsbad, Calif.)), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/26087 (O'Connor), TN5B1-4 (HIGH 5) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L A., *Proc. Natl. Acac. Sci. USA,* 77(7):4216-4220 (1980)), 293 (ATCC Accession No. CRL-1573), HeLa (ATCC Accession No. CCL-2), CV1 (ATCC Accession No. CCL-70), WOP (Dailey, L., et al., *J. Virol.,* 54:739-749 (1985)), 3T3, 293T (Pear, W. S., et al., *Proc. Natl. Acad. Sci. U.S.A.,* 90:8392-8396 (1993)), NS0 cells, SP2/0 cells, HuT 78 cells and the like)), or plants (e.g., tobacco, lemna (duckweed), and algae). (See, for example, Ausubel, F. M. et al., eds. *Current Protocols in Molecular Biology,* Greene Publishing Associates and John Wiley & Sons Inc. (1993)). In some embodiments, the host cell is not part of a multicellular organism (e.g., plant or animal), e.g., it is an isolated host cell or is part of a cell culture.

The present invention also relates to cells comprising a nucleic acid, e.g., a vector, of the invention (e.g., an expression vector). For example, a nucleic acid (i.e., one or more nucleic acids) encoding the heavy and light chains of a humanized immunoglobulin, the heavy and light chains of mouse immunoglobulin, or the heavy and light chains of a chimeric immunoglobulin, said immunoglobulin having binding specificity for human CD52, or a construct (i.e., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded protein (e.g., humanized immunoglobulin, mouse immunoglobulin, chimeric immunoglobulin) can be isolated, for example, from the host cells, culture medium, or milk. This process encompasses expression in a host cell (e.g., a mammary gland cell) of a transgenic animal or plant (e.g., tobacco) (see e.g., WO 92/03918).

Fusion proteins can be produced in which an immunoglobulin portion (e.g., a humanized immunoglobulin; immunoglobulin chain) is linked to a non-immunoglobulin moiety (i.e., a moiety which does not occur in immunoglobulins as found in nature) in an N-terminal location, C-terminal location or internal to the fusion protein. For example, some embodiments can be produced by the insertion of a nucleic acid encoding an immunoglobulin sequence(s) into a suitable expression vector, such as a pET vector (e.g., pET-15b, Novagen), a phage vector (e.g., pCANTAB 5 E, Pharmacia), or other vector (e.g., pRIT2T Protein A fusion vector, Pharmacia). The resulting construct can be introduced into a suitable host cell for expression. Upon expression, some fusion proteins can be isolated or purified from a cell lysate by means of a suitable affinity matrix (see, e.g., *Current Protocols in Molecular Biology* (Ausubel, F. M. et al., Eds., Vol. 2, Suppl. 26, pp. 16.4.1-16.7.8 (1991)).

The invention relates to a host cell that comprises recombinant nucleic acid(s) encoding an immunoglobulin provided herein (e.g., a humanized immunoglobulin, a humanized light chain or a humanized heavy chain, a mouse immunoglobulin, a mouse light chain or a mouse heavy chain, a chimeric immunoglobulin, a chimeric heavy chain, or a chimeric light chain of the invention). The invention also relates to a host cell that comprises recombinant nucleic acid(s) encoding an antigen-binding portion of the immunoglobulin or their chains. In some embodiments, the host cell comprises a recombinant vector (e.g., expression vector, mammalian cell expression vector) of the invention as referred to herein.

The invention also relates to a method of preparing an immunoglobulin or an immunoglobulin polypeptide chain of this invention. In one embodiment, the method comprises maintaining a host cell of the invention as described herein (e.g., a host cell that contains one or more isolated nucleic acids that encode the immunoglobulin or polypeptide chain (e.g., a light chain and a heavy chain, a light chain only, or a heavy chain only, of the invention) under conditions appropriate for expression of the immunoglobulin or polypeptide chain. For example a host cell can be cultured on a substrate or in suspension. In some embodiments, the method further comprises the step of purifying or isolating the immunoglobulin or polypeptide chain.

The invention further relates to a method of preparing immunoglobulins through phage display. For example, a naïve antibody phage display library on CD52 antigen can be panned. Alternatively, a method of preparing immunoglobulins through guided selection can be used (U.S. Patent Application Publication US 2006-0251658 A1.) A custom library built around, for example, a fixed heavy chain (and/or light chain) CDR3 region of a known anti-CD52 antibody can be created. The CDR1 and CDR2 regions of the heavy and light chains can be derived from a naïve repertiore (Osburn et al., *Methods*, 36:61-68 (2005)). In one embodiment, anti-CD52 ScFvs can be generated from ScFv naïve antibody libraries which are used to obtain mouse-human chimeric antibodies with the desired binding properties. These libraries may be screened for antibodies with the desired binding properties. ScFv phage libraries may be used. For example, ScFvs which recognize human CD52 can be isolated from scFv guided selection libraries following a series of repeated selection cycles on recombinant human CD52 essentially as described in Vaughan et al. (1996). In brief, following incubation with the library, the immobilized antigen, which is pre-coupled to paramagnetic beads, and bound phage can be recovered by magnetic separation while unbound phage is washed away. Bound phage can then be rescued as described by Vaughan et al. (1996) and the selection process repeated.

In a particular embodiment, a library is constructed consisting of the entire variable domain of the heavy chain of a mouse anti-CD52 antibody fused in a single chain format to a repertoire of naive human light chain variable regions. After selection the pool of human light chain variable regions that complement the mouse heavy chain variable region are identified. A library is then constructed consisting of the repertoire of human light chain variable regions selected above fused in a single chain format to a chimeric heavy chain variable region consisting of naive human CDR1 and CDR2 regions and a fixed CDR3 region from the mouse anti-CD52 antibody heavy chain variable domain. After selection for CD52 binders, the best binding clones are selected. Five of the 6 CDR regions can be human in origin while the CDR-3 of the heavy chain variable region can be identical to the original CDR3 of the mouse heavy chain variable domain.

Selections can be performed using CD52 coupled to DYNABEADS M-270 amine (Dynal) according to the manufacturer's recommendations. Alternatively, selections using biotinylated CD52 can be prepared using the primary amine specific reagent succinimidyl-6-(biotinamido)hexanoate following the manufacturer's instructions (EZ link NHS LC Biotin, Pierce).

Outputs from selections can be tested as periplasmic preparations in high throughput screens based on competition assays which measure the ability of the scFvs present in the periplasmic preparation to compete for binding to CD52.

Samples that are able to compete in the high throughput screens may be subjected to DNA sequencing as described in Vaughan et al. (1996) and Osburn et al. (1996). Clones would then be expressed and purified as scFvs or IgGs and assessed for their ability to bind CD52, neutralize CD52 or a combination thereof, e.g., using assays such as antibody-dependent cell mediated cytotoxicity (ADCC) assay and complement dependent cytotoxicity (CDC) assay. Purified scFv preparations can then be prepared as described in Example 3 of WO 01/66754. Protein concentrations of purified scFv preparations were determined using the BCA method (Pierce). Similar approaches can be used to screen for an optimal partner (the opposite chain) of a fixed immunoglobulin heavy or light chain (or $V_H$ or $V_L$).

In a particular embodiment, the invention is directed to a method of producing a hybridoma that secretes a monoclonal antibody that has binding specificity for human CD52 comprising administering lymphocytes of a CD52 transgenic mouse to a non-transgenic mouse having the same strain (e.g., CD1) as the human CD52 transgenic mouse, thereby producing an immunized, non-transgenic mouse. Splenocytes of the immunized, non-transgenic mouse are contacted with immortalized cells, thereby producing fused cells, and the fused cells are maintained under conditions in which hybridomas that secrete a monoclonal antibody having binding specificity for human CD52 are produced, thereby producing a hybridoma that secretes a monoclonal antibody that has binding specificity for human CD52.

Immunoglobulins Containing a Toxin Moiety or Toxin

The invention also relates to immunoglobulins that comprise a toxin moiety or toxin. Suitable toxin moieties comprise a toxin (e.g., surface active toxin, cytotoxin). The toxin moiety or toxin can be linked or conjugated to the immunoglobulin using any suitable method. For example, the toxin moiety or toxin can be covalently bonded to the immunoglobulin directly or through a suitable linker. Suitable linkers can include noncleavable or cleavable linkers, for example, pH cleavable linkers or linkers that comprise a cleavage site for a cellular enzyme (e.g., cellular esterases, cellular proteases such as cathepsin B). Such cleavable linkers can be used to prepare an immunoglobulin that can release a toxin moiety or toxin after the immunoglobulin is internalized.

A variety of methods for linking or conjugating a toxin moiety or toxin to an immunoglobulin can be used. The particular method selected will depend on the toxin moiety or toxin and immunoglobulin to be linked or conjugated. If desired, linkers that contain terminal functional groups can be used to link the immunoglobulin and toxin moiety or toxin. Generally, conjugation is accomplished by reacting toxin moiety or toxin that contains a reactive functional group (or is modified to contain a reactive functional group) with a linker or directly with an immunoglobulin. Covalent bonds are formed by reacting a toxin moiety or toxin that contains (or is modified to contain) a chemical moiety or functional group that can, under appropriate conditions, react with a second chemical group thereby forming a covalent bond. If desired, a suitable reactive chemical group can be added to an immunoglobulin or to a linker using any suitable method. (See, e.g., Hermanson, G. T., *Bioconjugate Techniques*, Academic Press: San Diego, Calif. (1996).) Many suitable reactive chemical group combinations are known in the art, for example an amine group can react with an electrophilic group such as tosylate, mesylate, halo (chloro, bromo, fluoro, iodo), N-hydroxysuccinimidyl ester (NHS), and the like. Thiols can react with maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)).

Suitable toxin moieties and toxins include, for example, a maytansinoid (e.g., maytansinol, e.g., DM1, DM4), a taxane, a calicheamicin, a duocarmycin, or derivatives thereof. The maytansinoid can be, for example, maytansinol or a maytansinol analogue. Examples of maytansinol analogs include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl, 4,5-deoxy). Maytansinol and maytansinol analogs are described, for example, in U.S. Pat. Nos. 5,208,020 and 6,333,410, the contents of which are incorporated herein by reference. Maytansinol can be coupled to antibodies and antibody fragments using, e.g., an N-succinimidyl 3-(2-pyridyldithio)proprionate (also known as N-succinimidyl 4-(2-pyridyldithio)pentanoate (or SPP)), 4-succinimidyl-oxycarbonyl-a-(2-pyridyldithio)-toluene (SMPT), N-succinimidyl-3-(2-pyridyldithio)butyrate (SDPB), 2 iminothiolane, or S-acetylsuccinic anhydride. The taxane can be, for example, a taxol, taxotere, or novel taxane (see, e.g., WO 01/38318). The calicheamicin can be, for example, a bromo-complex calicheamicin (e.g., an alpha, beta or gamma bromo-complex), an iodo-complex calicheamicin (e.g., an alpha, beta or gamma iodo-complex), or analogs and mimics thereof. Bromo-complex calicheamicins include I1-BR, I2-BR, I3-BR, I4-BR, J1-BR, J2-BR and K1-BR. Iodo-complex calicheamicins include I1-I, I2-I, I3-I, J1-I, J2-I, L1-I and K1-BR. Calicheamicin and mutants, analogs and mimics thereof are described, for example, in U.S. Pat. Nos. 4,970,198; 5,264,586; 5,550,246; 5,712,374, and 5,714,586, the contents of each of which are incorporated herein by reference. Duocarmycin analogs (e.g., KW-2189, DC88, DC89 CBI-TMI, and derivatives thereof) are described, for example, in U.S. Pat. No. 5,070,092, U.S. Pat. No. 5,187,186, U.S. Pat. No. 5,641,780, U.S. Pat. No. 5,641,780, U.S. Pat. No. 4,923,990, and U.S. Pat. No. 5,101,038, the contents of each of which are incorporated herein by reference.

Examples of other toxins include, but are not limited to antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065 (see U.S. Pat. Nos. 5,475,092, 5,585,499, 5,846,545), melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, mitomycin, puromycin anthramycin (AMC)), duocarmycin and analogs or derivatives thereof, and anti-mitotic agents (e.g., vincristine, vinblastine, taxol, auristatins (e.g., auristatin E) and maytansinoids, and analogs or homologs thereof).

The toxin can also be a surface active toxin, such as a toxin that is a free radical generator (e.g., selenium containing toxin moieties), or radionuclide containing moiety. Suitable radionuclide containing moieties, include for example, moieties that contain radioactive iodine (131I or 125I), yttrium (90Y), lutetium (177Lu), actinium (225Ac), praseodymium, astatine (211At), rhenium (186Re), bismuth (212Bi or 213Bi), indium (111In), technetium (99mTc), phosphorus (32P), rhodium (188Rh), sulfur (35S), carbon (14C), tritium (3H), chromium (51Cr), chlorine (36Cl), cobalt (57Co or 58Co), iron (59Fe), selenium (75Se), or gallium (67Ga).

The toxin can be a protein, polypeptide or peptide, from bacterial sources, e.g., diphtheria toxin, pseudomonas exotoxin (PE) and plant proteins, e.g., the A chain of ricin (RTA), the ribosome inactivating proteins (RIPs) gelonin, pokeweed antiviral protein, saporin, and dodecandron are contemplated for use as toxins.

Antisense compounds of nucleic acids designed to bind, disable, promote degradation or prevent the production of the mRNA responsible for generating a particular target protein can also be used as a toxin. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching, et al., *Proc. Natl. Acad. Sci. U.S.A.* 86: 10006-10010 (1989); Broder, et al., *Ann. Int. Med.* 113: 604-618 (1990); Loreau, et al., *FEBS Letters* 274: 53-56 (1990). Useful antisense therapeutics include for example: Veglin™ (VasGene) and OGX-011 (Oncogenix).

Toxins can also be photoactive agents. Suitable photoactive agents include porphyrin-based materials such as porfimer sodium, the green porphyrins, chlorin E6, hematoporphyrin derivative itself, phthalocyanines, etiopurpurins, texaphrin, and the like.

The toxin can be an antibody or antibody fragment that binds an intracellular target. Such antibodies or antibody fragments can be directed to defined subcellular compartments or targets. For example, the antibodies or antibody fragments can bind an intracellular target selected from erbB2, EGFR, BCR-ABL, p21Ras, Caspase3, Caspase7, Bcl-2, p53, Cyclin E, ATF-1/CREB, HPV16 E7, HP1, Type IV collagenases, cathepsin L as well as others described in Kontermann, R. E., *Methods,* 34:163-170 (2004), incorporated herein by reference in its entirety.

Therapeutic Methods and Compositions

The antibodies of this invention are useful in immuno-suppression and immuno-ablation. The antibodies target CD52-expressing cells (e.g., T and B cells) and reduce (or "deplete" as used herein) their population in a subject in need thereof. Lymphocyte depletion may be useful in treating a variety of diseases and conditions such as inflammation, autoimmune diseases and cancer (e.g., lymphocyte (either B or T cell) malignancy) See, e.g., Reiff, A., *Hematology,* 10(2): 79-93 (2005). Examples of diseases and conditions that can be treated with the antibodies or antigen-binding portions of this invention include, without limitation, multiple sclerosis, lupus, rheumatoid arthritis, graft versus host disease (GVHD), inflammatory bowel disease, vasculitis, Behcet's disease, Wegener's granulomatosis, Sjogren's syndrome, uveitis, psoriasis, scleroderma, polymyositis, type I (autoimmune-based) diabetes, autoimmune cytopenias (e.g., autoimmune neutropenia, transfusion-dependent refractory PRCA, leukemia and lymphoma such as non-Hodgkin's lymphoma with bulky disease and B-cell chronic lymphocytic leukemia.

Accordingly, aspects of this invention are methods for lymphocyte depletion, and for treating inflammation, an autoimmune disease or cancer by administering an effective amount of an antibody of the invention to a subject in need thereof (e.g., a human patient having an autoimmune disease, a blood cancer, or a patient who is to receive a transplantation). The antibody also can be administered prophylactically to prevent onset of inflammation or relapse of an autoimmune disease or cancer. For example, the antibody of this invention can be administered as part of a conditioning regimen to prepare a patient for a transplantation (e.g., a stem cell transplant, an infusion of autologous of allogeneic T cells, or a solid organ transplant).

Some anti-CD52 antibodies of this invention preferentially target certain populations of CD52+ cells. One possible explanation is that epitopes to which these antibodies bind include one or more carbohydrate groups on the CD52 protein, and such carbohydrate groups may be more prevalent on CD52 expressed on one cell type versus another. For example, we have found that antibody 7F11, 5F7, 3G7, and 11C11 deplete T cells to a greater extent than B cells. Thus, the humanized and chimeric versions of these antibodies may be used to treat T cell malignancy with milder immunosuppressing side effects.

Because antibodies of this invention target CD52-expressing cells, the antibodies also can be used to deplete CD52+ cell types other than T cells and B cells. For example, studies have shown that vascular leukocytes (VLC) and Tie2+ monocytes—myeloid cells expressing high levels of CD52—promote tumor angiogenesis and contribute to tumor resistance to anti-VEGF therapy. Pulaski et al., *J. Translational Med.* 7:49 (2009). Anti-CD52 antibodies of this invention thus can be used to inhibit tumor angiogenesis by targeting VLC and Tie2+ monocytes. For this purpose, the anti-CD52 antibodies can be administered systemically, or locally at a site of neovascularization, such as a tumor site. Anti-CD52 antibody therapy can be used in conjunction with standard-of-care cancer treatment such as chemotherapy, surgery, or radiation, or with another targeted therapy such as anti-VEGF antibody therapy. Anti-CD52 antibody therapy can be used to treat, for example, breast cancer, lung cancer, glioma, colorectal cancer, and any other indications of anti-VEGF antibodies. Anti-CD52 antibody therapy also can be used in other neovascularization conditions including non-oncological neovascular conditions.

Antibodies of this invention can be administered to an individual (e.g., a human) alone or in conjunction with another agent (e.g., an immunosuppressant) in a combination therapy. The antibody can be administered before, along with or subsequent to administration of the additional agent. In some embodiments, the additional agent is, for example, an anti-inflammatory compound such as sulfasalazine, another non-steroidal anti-inflammatory compound, or a steroidal anti-inflammatory compound. In some embodiments, the additional agent is another lympho-depleting antibody such as another anti-CD52 antibody, an anti-CD20 antibody, an anti-BAFF antibody, an anti-BAFF-R antibody, and the like. In some embodiments, the additional agent is, e.g., a cytokine (e.g., IL-7), anti-cytokine receptor antibody, or a soluble receptor, that skews, manipulates, and/or augments the reconstitution process that occurs following lymphodepletion mediated by an anti-CD52 antibody (see, e.g., Sportes et al., "*Cytokine Therapies: Ann. N.Y. Acad. Sci.* 1182:28-38 (2009)). In another embodiment, a synthetic peptide mimetic can be administered in conjunction with an immunoglobulin of the present invention.

Studies have shown that lymphocyte depletion by alemtuzumab is mediated by neutrophils and NK cells (Hu et al., *Immunology* 128:260-270 (2009). Thus, in an embodiment of combination therapy, an agent that stimulates neutrophils and NK cells can be administered to a patient, before, during or after anti-CD52 antibody therapy, to augment the antibody therapy. Stimulating neutrophils and/or NK cells include, without limitation, (1) increasing their rates of division, (2) increasing their cell surface expression of the Fc receptors corresponding to the isotype of the anti-CD52 antibody (e.g., FcγRIIIa and FcγRIIIb, FcγRII, FcγRI, and FcαRI), (3) mobilizing and increasing the number of circulating cells, (4) recruiting the cells to target sites (e.g., sites of tumors, inflammation, or tissue damage), (5) and increasing their cytotoxic activity. Examples of agents that stimulate neutrophils and/or NK cells include, for example, granulocyte monocyte colony stimulating factor (GM-CSF) (e.g., LEUKINE® or sargramostim and molgramostim); granulocyte colony stimulating factor (G-CSF) (e.g., NEUPOGEN® or filgrastim, pegylated filgrastim, and lenograstim); interferon gamma (e.g., ACTIMMUNE®); CXC chemokine receptor 4 (CXCR4) antagonists (e.g., MOZOBIL™ or plerixafor); and CXC chemokine receptor 2 (CXCR2) agonists. The neutrophil count of the patient may be monitored periodically to ensure optimal treatment efficacy. The neutrophil count of the patient also can be measured prior to the start of the anti-CD52 antibody treatment. The stimulator's amount can be adjusted based on the patient's neutrophil count. A higher dose of the stimulator may be used if the patient has a lower than normal neutrophil count. During periods of neutropenia, which may be caused by treatment with the anti-CD52 antibody, a higher dose of the neutrophil stimulator may also be administered to maximize the effect of the anti-CD52 antibody.

Because neutrophil and/or NK stimulation improves the efficacy of anti-CD52 antibody therapy, this embodiment of combination therapy allows one to use less antibody in a patient while maintaining similar treatment efficacy. Using less anti-CD52 antibody while maintaining treatment efficacy may help reduce side effects of the anti-CD52 antibody, which include immune response in the patient against the administered antibody as well as development of secondary autoimmunity (autoimmunity that arises during or after anti-CD52 antibody treatment). This embodiment of combination of therapy is also useful in an oncology setting, e.g., when the patient has neutropenia.

In another embodiment of combination therapy, one can use a stimulator of regulatory T cells to augment anti-CD52 antibody therapy. Our data show that anti-CD52 antibodies deplete CD4$^+$CD25$^+$FoxP3$^+$ regulatory T cells to a much lesser extent as compared to other CD4$^+$ T cells. Regulatory T cells (also known as "Treg" or suppressor T cells) are cells that are capable of inhibiting the proliferation and/or function of other lymphoid cells via contact-dependent or contact-independent (e.g., cytokine production) mechanisms. Several types of regulatory T cells have been described, including γδ T cells, natural killer T (NKT) cells, CD8$^+$T cells, CD4$^+$T cells, and double negative CD4$^-$CD8$^-$T cells. See, e.g., Bach et al., *Immunol.* 3:189-98 (2003). CD4$^+$CD25$^+$FoxP3$^+$ regulatory T cells have been referred as "naturally occurring" regulatory T cells; they express CD4, CD25 and forkhead family transcription factor FoxP3 (forkhead box p3). Thus, in this embodiment of combination therapy, one can administer an agent that stimulates CD4$^+$CD25$^+$FoxP3$^+$ regulatory T cells before, during or after the anti-CD52 antibody therapy, to skew the composition of the immune system following lympho-depletion. The agent may, for example, activate those T cells, stabilize and/or expand the population of the cells, mobilize and increase circulation of the cells, and/or recruit the cells to target sites. Examples of such agents are rapamycin, active or latent TGF-β (e.g., TGF-β1, TGF-β2, TGF-β3, TGF-β4, and TGF-β5), IL-10, IL-4, IFN-α, vitamin D3, dexamethasone, and mycophenolate mofetil (see, e.g., Barrat et al., *J. Exp. Med.* 195:603-616 (2002); Gregori et al., *J Immunol.* 167: 1945-1953 (2001); Battaglia et al., *Blood* 105: 4743-4748 (2005); Battaglia et al., *J. Immunol.* 177:8338-8347 (2006)).

In this invention, an effective amount of anti-CD52 antibody for treating a disease is an amount that helps the treated subject to reach one or more desired clinical end points. For example, for lupus (whose manifestations include systemic lupus erythematosus, lupus nephritis, cutaneous lupus erythematosus, CNS lupus, cardiovascular manifestations, pulmonary manifestations, hepatic manifestations, haematological manifestations, gastrointestinal manifestations, musculoskeletal manifestations, neonatal lupus erythematosus, childhood systemic lupus erythematosus, drug-induced lupus erythematosus, anti-phospholipid syndrome, and complement deficiency syndromes resulting in lupus manifestations; see, e.g., Robert G. Lahita, Editor, *Systemic Lupus Erythematosus,* 4th Ed., Elsevier Academic Press, 2004), clinical endpoints can be measured by monitoring of an affected organ system (e.g., hematuria and/or proteinuria for lupus nephritis) and/or using a disease activity index that provides a composite score of disease severity across several organ systems (e.g., BILAG, SLAM, SLEDAI, ECLAM). See, e.g., Mandl et al., "Monitoring patients with systemic lupus erythematosus" in *Systemic Lupus Erythematosus,* 4$^{th}$ edition, pp. 619-631, R. G. Lahita, Editor, Elsevier Academic Press, (2004).

In another example of autoimmune disease, multiple sclerosis (including relapsing-remitting, secondary progressive, primary progressive, and progressive relapsing multiple sclerosis ((Lublin et al., *Neurology* 46 (4), 907-11 (1996)), diagnosed is made by, for example, the history of symptoms and neurological examination with the help of tests such as magnetic resonance imaging (MRI), spinal taps, evoked potential tests, and laboratory analysis of blood samples. In MS, the goal of treatment is to reduce the frequency and severity of relapses, prevent disability arising from disease progression, and promote tissue repair (Compston and Coles, 2008). Thus, an amount of anti-CD52 antibody that helps achieve a clinical endpoint consistent with that goal is an effective amount of antibody for the treatment.

To minimize immunogenicity, it is preferred that a humanized antibody be used to treat a human patient in therapeutic methods and compositions of this invention. In cases where repeated administration is not necessary, it may also be appropriate to administer a mouse:human chimeric antibody of this invention to a human patient.

The antibodies of the invention can be used to treat an individual who has previously been treated with Campath-1H® who has developed neutralizing antibodies to Campath-1H® (e.g., a Campath-1H®-refractory individual). For example, one could treat an individual having an autoimmune disease (e.g., multiple sclerosis, lupus, vasculitis) and/or a cancer (e.g., a leukemia (e.g., chronic lymphocytic leukemia), a lymphoma (e.g., non-Hodgkin's lymphoma)) who has previously been treated with Campath-1H® (e.g., with one or more courses of Campath-1H® treatment) and who has developed neutralizing antibodies to Campath-1H® that reduce the efficacy of further Campath-1H® treatment. We have shown that the humanized antibodies of this invention (e.g., humanized 2C3, 12G6, and 9D9) can bind to human CD52 despite the presence of neutralizing antibodies to alemtuzumab. In another embodiment, one could treat an individual who had become refractory to treatment with a particular humanized antibody described herein with one of the other humanized antibodies described herein.

The antibody of this invention can be administered in a single unit dose or multiple doses at any time point deemed appropriate by a health care provider. The dosage can be determined by methods known in the art and can be dependent, for example, upon the individual's age, sensitivity, tolerance and overall well-being. A variety of routes of administration can be used, including, but not necessarily limited to, parenteral (e.g., intravenous, intraarterial, intramuscular, intrathecal, intraperitoneal, subcutaneous injection), oral (e.g., dietary), locally, topical, inhalation (e.g., intrabronchial, intranasal or oral inhalation, intranasal drops), or rectal, depending on the disease or condition to be treated. Parenteral administration may be one preferred mode of administration.

In one embodiment, the antibodies of the invention are administered to a patient using the same dosing regimen as Campath-1H® (e.g., the dosing regimen of Campath-1H® for chronic lymphocytic leukemia). In another embodiment, an antibody of the invention is administered to a patient having an autoimmune disease (e.g., multiple sclerosis (MS)) in a regimen comprising administration of a first cycle of the antibody followed by at least one further cycle of the antibody, in which each treatment cycle comprises 1-5 doses that are applied on consecutive days, and wherein each treatment cycle is separated from the next cycle by at least 1-24 months (e.g., 12 months). For example, in one embodiment, a patient having multiple sclerosis is treated with a first cycle of the antibody comprising 5 daily doses of the antibody followed by at least one further cycle of antibody treatment, in which the treatment occurs 12 months after the first cycle and comprises 3 doses of the antibody applied on consecutive days. In another embodiment, a patients having MS is only re-treated once evidence of renewed MS activity has been observed (see, e.g., WO 2008/031626; the teachings of which are incorporated herein by reference in their entirety). In some embodiments, it may be necessary to administer more frequent courses of treatment (e.g., every four months, every six months) if patients with more advanced forms of MS or more progressive forms of other autoimmune diseases (such as vasculitis; see, e.g., Walsh et al., *Ann Rheum Dis* 67:1322-1327 (2008)) experience a relapse early on after their last course of treatment. Evidence of renewed MS activity may be determined based on the professional judgment of the treating clinician, using any means that may be available to such clinician. A variety of techniques are currently available to clinicians to diagnose renewed MS activity including, without limitation, by clinical means (relapse or progression of neurological disability) or by magnetic resonance imaging (MRI) of the brain or spinal cord. As is well understood by medical practitioners, disease activity detected via MRI may be indicated by the occurrence of new cerebral or spinal lesions on T1 (enhanced or non-enhanced)- or T2-weighted images or by the increase of the volume of such lesions. As diagnostic methods for MS are continually evolving, it is anticipated there may be additional methods in the future that will detect renewed MS activity (e.g., magnetization transfer ratio or MR-spectroscopy). The particular diagnostic method used to detect renewed MS activity is not a limitation of the claimed invention. In certain embodiments, repeated MRIs are performed in fixed intervals after a treatment cycle in order to determine whether re-treatment of any given patient is necessary and the optimal time point for re-treatment of such patient. In general, it is desirable for re-treatment to occur before the disease re-manifests clinically.

Formulation will vary according to the route of administration selected (e.g., solution, emulsion). An appropriate composition comprising the antibody to be administered can be prepared in a physiologically acceptable vehicle or carrier. The composition can comprise multiple doses or be a single unit dose composition. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Sciences*, 17th Edition, Mack Publishing Co., PA, 1985). For inhalation, the compound can be solubilized and loaded into a suitable dispenser for administration (e.g., an atomizer, nebulizer or pressurized aerosol dispenser).

Diagnostic Methods and Compositions

The immunoglobulins of the present invention also are useful in a variety of processes with applications in research and diagnosis. For instance, they can be used to detect, isolate, and/or purify human CD52 or variants thereof (e.g., by affinity purification or other suitable methods such as flow cytometry, e.g., for cells, such as lymphocytes, in suspension), and to study human CD52 structure (e.g., conformation) and function. For in vitro applications, wherein immunogenicity of the antibody is not a concern, the mouse and chimeric antibodies of this invention will be useful in addition to humanized antibodies.

The immunoglobulins of the present invention can be used in diagnostic applications (e.g., in vitro, ex vivo). For example, the humanized immunoglobulins of the present invention can be used to detect and/or measure the level of human CD52 in a sample (e.g., on cells expressing human CD52 in tissues or body fluids, such as an inflammatory exudate, blood, serum, bowel fluid, tissues bearing human CD52). A sample (e.g., tissue and/or body fluid) can be obtained from an individual and an immunoglobulin described herein can be used in a suitable immunological method to detect and/or measure human CD52 expression, including methods such as flow cytometry (e.g., for cells in suspension such as lymphocytes), enzyme-linked immunosorbent assays (ELISA), including chemiluminescence assays, radioimmunoassay, and immunohistology.

In one embodiment, a method of detecting human CD52 in a sample is provided, comprising contacting a sample with an immunoglobulin of the present invention under conditions suitable for specific binding of the immunoglobulin to human CD52 and detecting antibody-CD52 complexes which are formed. In an application of the method, the immunoglobulins described herein can be used to analyze normal versus inflamed tissues (e.g., from a human) for human CD52 reactivity and/or expression (e.g., immunohistologically) to detect associations between e.g., inflammatory bowel disease (IBD), autoimmune diseases (such as multiple sclerosis and lupus), cancer (such as non-Hodgkin's lymphoma and chronic lymphocytic leukemia), or other conditions and increased expression of human CD52 (e.g., in affected tissues). Thus, the immunoglobulins of the present invention permit immunological methods of assessment of the presence of human CD52 in normal and inflamed tissues, through which the presence of disease, disease progress and/or the efficacy of anti-human CD52 therapy in the treatment of disease, e.g., inflammatory disease can be assessed.

In addition, the immunoglobulins can be used to examine tissues after treatment with a depleting anti-CD52 therapeutic antibody to gauge how effective the depletion has been as well as to determine whether there has been any downregulation in the expression of CD52 (Rawstrom et al., *Br. J. Heam.*, 107:148-153 (1999)).

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

EXEMPLIFICATION

Example 1

Generation of Mouse Anti-Human CD52 Antibodies

The mouse anti-human CD52 antibodies in the following working examples were generated by immunizing CD1 strain mice with splenocytes from human CD52 transgenic mice with a CD1 background (FIG. 1A), where display of human CD52 on the surface of mouse B and T cells of the transgenic mice was verified by flow cytometry. Because the transgenic mice had the same background (CD1) as the immunized mice, splenocytes from the transgenic mice presented human CD52 at the cell surface as a unique, non-self antigen in a native format, and the immunized nontransgenic mice mounted an antibody response primarily towards the human CD52.

To collect splenocytes from the human CD52 transgenic mice, the mice were euthanized, spleens were harvested and single cell suspensions were prepared by passing through a syringe. CD1 mice were then immunized with the collected human CD52 positive spleen cells at $5 \times 10^6$ in 100 µl per mouse with or without Freund's Complete Adjuvant by intraperitoneal (i.p.) injection. Mice were given two booster doses every two weeks after first immunization with transgenic mouse human CD52 positive spleen cells at $5 \times 10^6$ in 100 µl per mouse with Freund's Incomplete Adjuvant, ip.

Eye bleeds were collected 100-200 µl per mouse in yellow-capped serum separator tubes from all mice before immunization to determine base level reactivity, and a week after every round of immunization to determine base level reactivity, and a week after every round of immunization to determine anti-human CD52 specific immune response. Mice that mounted high levels of anti-human CD52 reactivity as measured by FACS on CHO K1 cells engineered to express human CD52 protein, but not on parental CHO K1 cells were sacrificed, blood was harvested and spleens were collected under sterile conditions to generate hybridomas. Hybridomas were generated by using a non-secreting mouse myeloma cell-line SP2/0 Ag14 or NS1 myeloma cells as fusion partners 3-4 days post immunization. Fused cells were placed in complete growth medium containing hypoxanthine, aminopterin and thymidine to generate hybridomas. After screening many hybridoma supernatants, several clones were selected that produced specific anti-human CD52 antibodies and were further subcloned to derive a clonal population. Hybridoma clones that produced anti-human CD52 antibodies were scaled up for further development.

Example 2

PCR Analysis of Heavy and Light Chains of Mouse Anti-Human CD52 Antibodies

A number of mouse anti-human CD52 monoclonal antibodies (FIG. 1B) were identified by testing hybridoma supernatants for the presence of anti-human CD52 reactivity. Individual clones were selected and the mouse heavy and light chain variable sequences were identified by PCR cloning and sequencing. The sequences of the light chains are shown in FIG. 2 as compared to YTH 34.5 HL (i.e., Campath IG Kappa (rat) and a reagent antibody CF1D12 (CF1D12 Kappa) (Invitrogen Life Science Technologies). Similarly, the sequences of the heavy chains are shown in FIG. 3 as compared to YTH 34.5 HL and a reagent antibody CF1D12.

A total of 10 Zunique light chain variable sequences and 11 unique heavy chain variable sequences were identified. If one includes Campath® and CF1D12, 7 unique CDR-1 regions (Table 1), 8 unique CDR-2 regions (Table 2) and 7 unique CDR-3 regions (Table 3) were identified within the light chains of anti-human CD52 antibodies.

TABLE 1

Light Chain CDR-1 Sequences

| Light Chain CDR-1 | Sequence |
| --- | --- |
| A | KASQNIDKYLN (SEQ ID NO: 27) |
| B | KSSQSLLESDGRTYLN (SEQ ID NO: 28) |
| C | KSSQSLLDSDGKTYLN (SEQ ID NO: 29) |
| D | KSSQSLLDSDGRTYLN (SEQ ID NO: 30) |
| E | KSSQSLLYSNGKTYLN (SEQ ID NO: 31) |
| F | RSSQSLVHTNGNSYLH (SEQ ID NO: 32) |
| G | RSSQSLVHTNGNTYLH (SEQ ID NO: 33) |

TABLE 2

Light Chain CDR-2 Sequences

| Light Chain CDR-2 | Sequence |
| --- | --- |
| A | NTNNLQT (SEQ ID NO: 34) |
| B | LVSNLDS (SEQ ID NO: 35) |
| C | LVSKLDS (SEQ ID NO: 36) |
| D | LVSNLGS (SEQ ID NO: 37) |
| E | LVSALDS (SEQ ID NO: 38) |
| F | LVSNLNS (SEQ ID NO: 39) |
| G | LVSHLDS (SEQ ID NO: 40) |
| H | MVSNRFS (SEQ ID NO: 41) |

TABLE 3

Light Chain CDR-3 Sequences

| Light Chain CDR-3 | Sequence |
|---|---|
| A | LQHISRPRT (SEQ ID NO: 42) |
| B | WQGTHFPWT (SEQ ID NO: 43) |
| C | VQGSHFHT (SEQ ID NO: 44) |
| D | VQGTRFHT (SEQ ID NO: 45) |
| E | VQGTHLHT (SEQ ID NO: 46) |
| F | SQSTHVPFT (SEQ ID NO: 47) |
| G | SQSAHVPPLT (SEQ ID NO: 48) |

If one includes Campath® and CF1D12, a total of 8 unique CDR-1 regions (Table 4), 10 unique CDR-2 regions (Table 5) and 8 unique CDR-3 regions (Table 6) have been identified within the heavy chains of anti-human CD52 antibodies.

TABLE 4

Heavy Chain CDR-1 Sequences

| Heavy Chain CDR-1 | Sequence |
|---|---|
| A | GFTFTDFYMN (SEQ ID NO: 49) |
| B | GFTFSDAWMD (SEQ ID NO: 50) |
| C | RFTFSDAWMD (SEQ ID NO: 51) |
| D | GLTFSDAWMD (SEQ ID NO: 52) |
| E | GFPFSNYWMN (SEQ ID NO: 53) |
| F | GFTFNKYWMN (SEQ ID NO: 54) |
| G | GFTFNTYWMN (SEQ ID NO: 55) |
| H | GFTFTDYYMS (SEQ ID NO: 56) |

TABLE 5

Heavy Chain CDR-2 Sequences

| Heavy Chain CDR-2 | Sequence |
|---|---|
| A | FIRDKAKGYTTEYNPSVKG (SEQ ID NO: 57) |
| B | EIRNKAKNHVAYYAESVKG (SEQ ID NO: 58) |
| C | EIRNKANNHATYYAESVKG (SEQ ID NO: 59) |
| D | EIRNKAKNHVKYYAESVKG (SEQ ID NO: 60) |
| E | EIRNKAKNHATYYAESVKG (SEQ ID NO: 61) |
| F | EIRKKVNNHATYYAESVKG (SEQ ID NO: 62) |
| G | QIRLKSNNYATHYAESVKG (SEQ ID NO: 63) |
| H | QIRLKSDNYATHYAESVKG (SEQ ID NO: 64) |
| I | FIRNKANGYTTEYNASVKG (SEQ ID NO: 65) |
| J | FIRNKANGYTTEYSASVKG (SEQ ID NO: 66) |

TABLE 6

Heavy Chain CDR-3 Sequences

| Heavy Chain CDR-3 | Sequence |
|---|---|
| A | AREGHTAAPFDY (SEQ ID NO: 67) |
| B | TTLDS (SEQ ID NO: 68) |
| C | TSLDY (SEQ ID NO: 69) |
| D | TGLDY (SEQ ID NO; 70) |
| E | TPIDY (SEQ ID NO: 71) |
| F | TPVDF (SEQ ID NO: 72) |
| G | TRYIFFDY (SEQ ID NO: 73) |
| H | TRYIWFDY (SEQ ID NO: 74) |

The association of specific light and heavy chain CDR regions within 13 different anti-human CD52 antibodies is depicted in Table 7.

TABLE 7

Classification of Anti-Human CD52 Antibodies on the Basis of CDR Composition

| Clone Name | Heavy Chain CDR-1 | | | Light Chain | | |
|---|---|---|---|---|---|---|
| | CDR-1 | CDR-2 | CDR-3 | CDR-1 | CDR-2 | CDR-3 |
| Campath | A | A | A | A | A | A |
| CF1D12 | B | B | B | B | B | B |
| 8G3.25.3.5 | C | C | C | C | C | B |
| GMA 4G7.F3 | B | D | C | C | D | B |
| GMA 9D9.A2 | B | E | B | C | E | B |
| GMA 11C11.C5 | B | E | C | C | C | B |

TABLE 7-continued

Classification of Anti-Human CD52 Antibodies on the Basis of CDR Composition

| Clone | Heavy Chain CDR-1 | | | Light Chain | | |
|---|---|---|---|---|---|---|
| Name | CDR-1 | CDR-2 | CDR-3 | CDR-1 | CDR-2 | CDR-3 |
| GMA 3G7.E9 | B | F | C | C | F | B |
| 5F7.1.1.4 | D | E | D | D | G | B |
| 12G6.15.1.2 | E | G | E | E | C | C |
| 23E6.2.2.1 | F | H | E | E | C | D |
| 2C3.3.8.1 | G | G | F | E | C | E |
| 7F11.1.9.7 | H | I | G | F | H | F |
| 4B10.1.2.4 | H | J | H | G | H | G |

Clones 8G3.25.3.5, 4G7.F3, 9D9.A2, 11C11.C5, 3G7.E9, 5F7.1.1.4, 12G6.15.1.2, 23E6.2.2.1, 2C3.3.8.1, 7F11.1.9.7 and 4B10.1.2.4 are hereafter referred to as 8G3, 4G7, 9D9, 11C11, 3G7, 5F7, 12G6, 23E6, 2C3, 7F11 and 4B10, respectively.

TABLE 7.1

SEQ ID NOs of the CDRs of the Anti-Human CD52 Antibodies

| Clone | Heavy Chain | | | Light Chain | | |
|---|---|---|---|---|---|---|
| Name | CDR-1 | CDR-2 | CDR-3 | CDR-1 | CDR-2 | CDR-3 |
| Campath | 49 | 57 | 67 | 27 | 34 | 42 |
| CF1D12 | 50 | 58 | 68 | 28 | 35 | 43 |
| 8G3 | 51 | 59 | 69 | 29 | 36 | 43 |
| 4G7 | 50 | 60 | 69 | 29 | 37 | 43 |
| 9D9 | 50 | 61 | 68 | 29 | 38 | 43 |
| 11C11 | 50 | 61 | 69 | 29 | 36 | 43 |
| 3G7 | 50 | 62 | 69 | 29 | 39 | 43 |
| 5F7 | 52 | 61 | 70 | 30 | 40 | 43 |
| 12G6 | 53 | 63 | 71 | 31 | 36 | 44 |
| 23E6 | 54 | 64 | 71 | 31 | 36 | 45 |
| 2C3 | 55 | 63 | 72 | 31 | 36 | 46 |
| 7F11 | 56 | 65 | 73 | 32 | 41 | 47 |
| 4B10 | 56 | 66 | 74 | 33 | 41 | 48 |

Example 3

Cloning of Mouse IgG Variable Region Genes from Mouse Hybridoma Cells to Generate a Mouse/Human Chimeric IgG1 Antibody Actively proliferating and antibody secreting hybridoma cells were used to isolate RNA using Trizol reagent (Gibco/BRL) following the manufacturer's suggested protocol. RNA was quantified by measuring OD using Nanodrop, and the integrity of the RNA was determined by running it on a gel or by using a bioanalyzer. Total RNA was reverse transcribed to cDNA and the variable regions for the heavy and light chains were amplified by polymerase chain reaction (PCR). The cDNA was generated using BD Sprint PowerScript Reverse Transcriptase (Clontech) and Oligo(dT) primer at 0.5 µg/µl (Invitrogen Cat#Y01212) and reverse primers (located in the constant region of the heavy and light chains) listed numerically below at 10 µM following the manufacturer's protocol. Specifically, primers numbered 3 (SEQ ID NO: 77), 11 (SEQ ID NO: 85), 19 (SEQ ID NO: 93), 20 (SEQ ID NO: 94) and 21 (SEQ ID NO: 95) were employed. PCR amplification of the heavy and light chain variable regions was carried out using cDNA generated as described above. 1 µl of cDNA was mixed with forward primer and reverse primers at 10 µM each for both heavy and light chains and mixed with PCR super mix (Invitrogen) in the presence of 2 µl of MgCl$_2$ at 25 mM. The PCR program was run in the following steps: 1) 95° C. for 2 minutes; 2) 95° C. for 30 seconds; 3) 56° C. for 30 seconds; 4) 68° C. for 45 seconds; 5) Repeat steps 2 to 4 25 times; 6) 68° C. for 10 minutes and hold at 16° C. The PCR product was analyzed on a 2% gel for the presence of variable region sequence product of about 300-400 bp in size and the appropriate bands were cloned into pCR2.1-TOPO TA cloning Kit (Invitrogen) following the manufacturer's instructions and the cloned and sequence confirmed using M13 primers. Primers used for reverse transcribing and for PCR amplification of light chain and heavy chain sequences are provided:

Light chain primers (SEQ ID NO: 75)
1) Lead-ML kappa = 5' ATGGGCWTCAARATGRARWCWCAT 3'
(Forward primer in leader sequence)

(SEQ ID NO: 76)
2) FR1-ML kappa = 5' GAYATTGTGMTRACMCARKMTCAA 3'
(Forward primer in the frame work 1)

(SEQ ID NO: 77)
3) ML kappa const = 5' ACTGGATGGTGGGAAGATGGA 3'
(Reverse primer in constant region)

(SEQ ID NO: 78)
4) VK-MK = 5' GAYATTGTGMTSACMCARWCTMCA 3'
(Forward primer in the frame work 1)

(SEQ ID NO: 79)
5) MKC-Const = 5' GGATACAGTTGGTGCAGCATC 3'
(Reverse primer in constant region)

Heavy chain primers (SEQ ID NO: 80)
6) MH-SP-ALT1 = 5' ATGRASTTSKGGYTMARCTKGRTT 3'
(Forward primer in leader sequence)

(SEQ ID NO: 81)
7) MH-SP-ALT2 = 5' ATGRAATGSASCTGGGTYWTYCTCT 3'
(Forward primer in leader sequence)

(SEQ ID NO: 82)
8) MH-FR1 = 5' SAGGTSMARCTGCAGSAGTCT 3'
(Forward primer in the frame work 1)

(SEQ ID NO: 83)
9) MH-FR1-1 = 5' SAGGTGMAGCTCSWRSARYCSGGG 3'
(Forward primer in the frame work 1)

(SEQ ID NO: 84)
10) MH-J2 = 5' TGAGGAGACTGTGAGAGTGGTGCC 3'
(Reverse primer in J region)

(SEQ ID NO: 85)
11) MH-gamma-const = 5' AYCTCCACACACAGGRRC CAGTGGATAGAC 3'
(Reverse primer in constant region)

(SEQ ID NO: 86)
12) VH MH1 = 5' SARGTNMAGCTGSAGSAGTC 3'
(Forward primer in the frame work 1)

(SEQ ID NO: 87)
13) VH MH2 = 5' SARGTNMAGCTGSAGSAGTCWGG 3'
(Forward primer in the frame work 1)

(SEQ ID NO: 88)
14) VH MH3 = 5' CAGGTTACTCTGAAAGWGTSTG 3'
(Forward primer in the frame work 1)

(SEQ ID NO: 89)
15) VH MH4 = 5' GAGGTCCARCTGCAACARTC 3'
(Forward primer in the frame work 1)

(SEQ ID NO: 90)
16) VH MH5 = 5' CAGGTCCAACTVCAGCARCC 3'
(Forward primer in the frame work 1)

-continued

```
                                           (SEQ ID NO: 91)
17) VH MH6 = 5' GAGGTGAASSTGGTGGAATC 3'
(Forward primer in the frame work 1)

(SEQ ID NO: 92)
18) VH MH7 = 5' GATGTGAACTTGGAAGTGTC 3'
(Forward primer in the frame work 1)

(SEQ ID NO: 93)
19) IgG1 = 5' ATAGACAGATGGGGGTGTCGTTTTGGC 3'
(Reverse primer in mouse IgG1 CH1 constant
region)

(SEQ ID NO: 94)
20) IgG2A = 5' CTTGACCAGGCATCCTAGAGTCA 3'
(Reverse primer in mouse IgG2A CH1 constant
region)

(SEQ ID NO: 95)
21) IgG2B = 5' AGGGGCCAGTGGATAGAGTGATGG 3'
(Reverse primer in mouse IgG2B CH1 constant
region)
```

Degenerate primers led to some degeneracy in the 5' end of the frame work 1 region of both heavy and light chains. The consensus DNA sequence from several independent heavy chain variable region clones and from light chain variable region clones was used to derive the amino acid sequence.

Functional chimeric anti-CD52 antibodies were produced by joining the heavy chain and light chain variable regions to the DNA encoding human IgG1 heavy chain (identical sequence to that found in Campath-1H®) and human kappa light chain constant region (identical sequence to that found in Campath-1H®), respectively. To generate pCEP4 (Invitrogen) light chain vector encoding CD52 antibody light chain, the light chain variable sequence was PCR amplified and engineered by ligase independent cloning into the pCEP4 LIC light chain vector to have the human kappa signal sequence in the 5' end and the light chain constant region in the 3' end. Similarly, to generate pCEP4 heavy chain vector, the variable region of the heavy chain sequence was engineered by ligase independent cloning into the pCEP4 LIC heavy chain vector to have the human kappa chain signal sequence in the 5' end and the heavy chain constant region encompassing CH1, hinge, CH2 and CH3 regions in the 3' end. The constant region amino acid sequences for both heavy and light chains are identical to that of the constant regions present in Campath1H antibody.

Briefly, pCEP4 LIC vector was digested with BfuA1 (New England Biolabs-NEB) in appropriate buffer following the manufacturer's recommendations and after complete digestion, the vector was purified using PureLink PCR Purification Kit (Invitrogen). The linearized plasmid was then treated with T4 DNA polymerase (New England Biolabs) to generate single-stranded ends and was used to clone the variable region fragment. Heavy chain specific pCEP4 LIC vector was used for cloning heavy chain variable region and light chain specific pCEP4 LIC vector was used for cloning light chain variable region. Variable region insert was generated by PCR using pCR2.1-TOPO heavy chain variable region containing plasmid or pCR2.1-TOPO light chain variable region containing plasmid as template and primers that contain variable chain specific sequence and vector overhangs. VENT DNA polymerase (New England Biolabs) was used for PCR amplification of the insert. PCR-amplified insert was gel purified and treated with T4 DNA polymerase to generate single-stranded ends. Prepared vectors for heavy chain and light chain and respective variable region insert fragments were combined and incubated at room temperature for 10 minutes and used to transform TOPO10 cells (Invitrogen), ampicillin resistant colonies were picked and sequence verified. pCEP4 heavy chain and pCEP4 light chain clones that had the correct heavy chain and light chain sequences inserted in-frame were amplified and used for protein production. The heavy chain construct was co-transfected with the corresponding light chain construct in a 1:1 ratio into HEK293 cells (Invitrogen) using the cationic lipid Lipofectamine™ 2000 (Invitrogen). The conditioned medium was harvested three days after the transfection and the chimeric antibody was purified using protein A chromatography. For this chromatography method, the medium was added to protein A and washed with 50 column volumes of PBS. The chimeric antibody was eluted with 5 column volumes of 12.5 mM citric acid, pH 3.0. The pH of the eluted antibody was neutralized by addition of 0.5 M HEPES. The buffer was exchanged into PBS by using a PD-10 gel filtration column.

Example 4

Figure 5B:
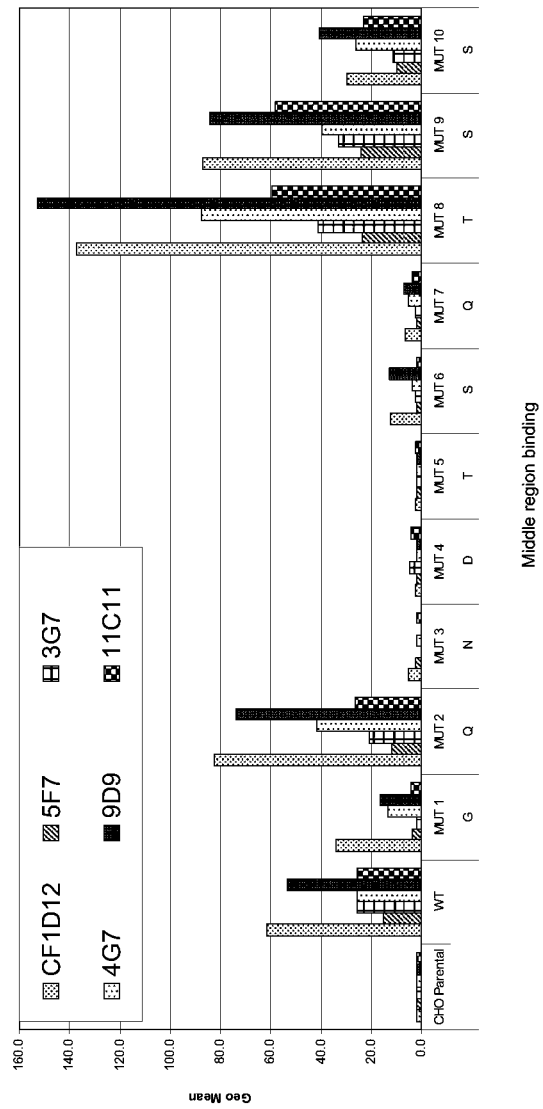
FIG. 5B illustrates the FACS-based middle region binding profile of antibodies CF1D12, 3G7, 9D9, 5F7, 4G7, and 11C11 on cells expressing CD52 alanine scanning mutants.
Figure 5C:
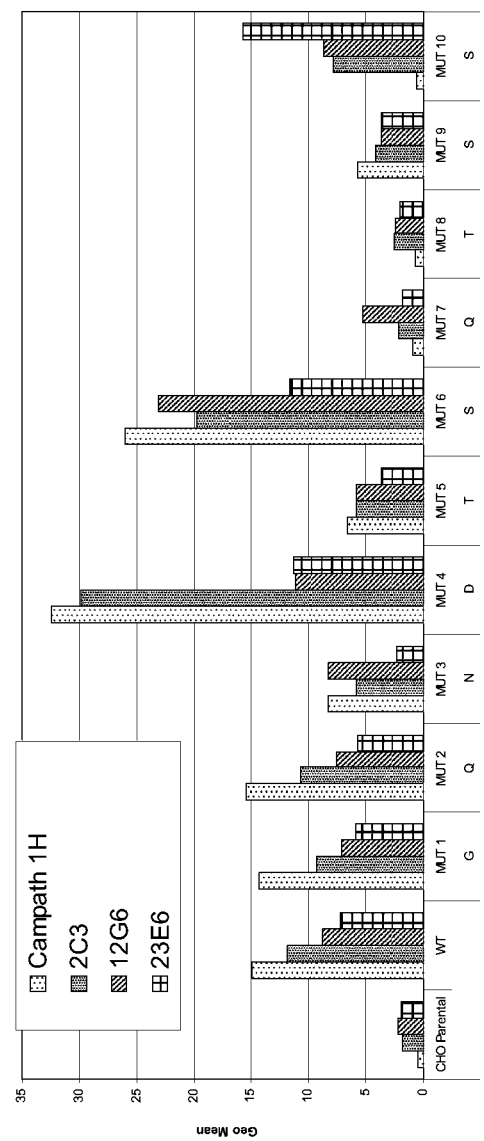
FIG. 5C illustrates the FACS-based binding profile of antibodies Campath-1H® ("Campath 1H"), 2C3, 12G6, and 23E6 on cells expressing CD52 alanine scanning mutants.

Analysis of the Epitope Specificities of Chimeric Anti-Human CD52 Monoclonal Antibodies The epitope specificities of the clones were determined by assessing the ability of the chimeric antibodies to bind to a panel of cell lines engineered to express mutants of human CD52 (FIG. 4) generated by alanine scanning mutagenesis. Antibody substitution of the first 10 amino acids of the 12 amino acid extracellular region of CD52 was conducted on human CD52 cDNA in pcDNA3.1 expression vector (Invitrogen) using the STRATAGENE QUIKCHANGE II XL site-directed mutagenesis kit. pcDNA3.1 vector encoding wild type or mutant CD52 sequence was sequence-verified and transfected into CHO cells using Lipofectamine™ and by selecting in media containing G418 to generate CHO cell lines that expressed wild type or alanine mutant CD52. Epitope specific binding of anti-human CD52 chimeric antibodies was determined by measuring the binding of the antibodies against the wild type and mutant CD52 expressing cells by FACS. FACS analysis was carried out by detecting the binding of chimeric anti-CD52 antibodies using PE-conjugated goat anti-human secondary antibody (Jackson ImmunoResearch Labs). FIGS. 5A-5C show the Mean Fluorescence Intensity (MFI) of anti-CD52 monoclonal antibodies to wild type and mutant CD52 expressing cell lines. Even though CD52 is a very short, 12 amino acid, GPI anchored protein, the FACS results clearly define that there are three sets of antibodies: (1) N-terminal binding group (such as 4B10); (2) middle binding group (such as 4G7, 9D9 and 11C1) and (3) C-terminal binding group (such as 23E6, 12G6, and 2C3). The epitope specificities of the anti-human CD52 monoclonal antibodies (identified by the abbreviated names described at the end of Example 2) are summarized in Table 8.

TABLE 8

Characteristics of 11 Mouse Anti-Human CD52 Monoclonal Antibodies

| Clone | Isotype | Epitope Specificity |
|---|---|---|
| Rat YTH34.5HL | IgG2a | 9-10-11-12 |
| Mouse CF1D12 | IgG3 | 3-4-5-6-7 |
| 8G3.25.3.5 | IgG3 | Not confirmed |
| 4G7.F3 | IgG3 | 3-4-5-6-7 |
| 9D9.A2 | IgG3 | 3-4-5-6-7 |

TABLE 8-continued

Characteristics of 11 Mouse Anti-
Human CD52 Monoclonal Antibodies

| Clone | Isotype | Epitope Specificity |
|---|---|---|
| 11C11.C5 | IgG3 | 1-3-4-5-6-7 |
| 3G7.E9 | IgG2b | 1-3-4-5-6-7 |
| 5F7.1.1.4 | IgG3 | 1-3-4-5-6-7-10 |
| 12G6.15.1.2 | IgG3 | 7-8-9 |
| 23E6.2.2.1 | IgG3 | 7-8-9 |
| 2C3.3.8.1 | IgG3 | 7-8-9-10 |
| 7F11.1.9.7 | IgG1 | 1-2-3-4-5 |
| 4B10.1.2.4 | IgG2a | 1-2-3-4-5 |

Figure 5D:
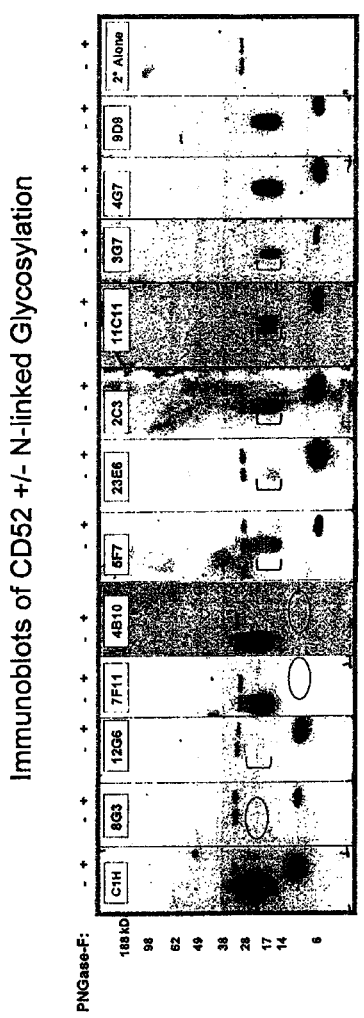
FIG. 5D depicts immunoblots of CD52+/– N-linked glycosylation probed with the panel of chimeric monoclonal antibodies. "C1H" stands for Campath-1H®.

CD52 is an extremely small antigen but possesses a relatively large, hydrophilic N-linked glycan moiety as well as a hydrophobic GPI-anchor. To explore the possibility that the sugars might constitute all or part of an epitope recognized by the anti-CD52 antibodies, samples of affinity purified CD52 from CHO-CD52 cells were treated with the endoglycosidase, PNGase-F, to completely remove N-linked sugars from the antigen. Treated and mock-treated control samples were then resolved by SDS-PAGE, blotted to polyvinylidene fluoride (PVDF) membrane (Invitrogen), probed with 3 μg/ml final of each of the anti-CD52 chimeric monoclonal antibodies indicated, and subsequently developed according to standard western blotting procedures using enhanced chemiluminescent detection. Blots with Campath-1H® (C1H) and with secondary antibody alone (2° Alone) were run as positive and negative controls, respectively, and probed with each of the monoclonal antibodies (FIG. 5D). The results revealed different binding preferences amongst the antibodies for glycosylated versus de-glycosylated CD52. This characterization allowed for the categorization of the eleven antibodies into four types of binding groups:
1. Antibodies exhibiting binding with no apparent preference for glycosylated versus de-glycosylated CD52 (4G7, 9D9)
2. Antibodies exhibiting binding specific for glycosylated CD52 (7F11, 4B10)
3. Antibodies exhibiting binding specific for de-glycosylated CD52 (8G3)
4. Antibodies exhibiting binding preferential for de-glycosylated over glycosylated CD52 (12G6, 5F7, 23E6, 2C3, 11C11, 3G7)

Example 5

CDC Activity of Chimeric Anti-CD52 Antibodies

A complement-dependent cytotoxicity (CDC) assay was performed as described below. Briefly, CHO K1 cells engineered to express CD52 protein (CHO-CD52) were used as target cells and labeled with $Na_2^{51}CrO_4$ (New England Nuclear, Boston, Mass.) at 37° C. for 1-2 hrs. The cells were washed, resuspended with X-Vivo media, and mixed with anti-human CD52 antibodies to final concentration of 2.2 μg/ml. Human complement (Sigma) was added to the experimental wells to a final concentration of 10%. After a 1-5-hour incubation, 25 μl of cell-free supernatant was collected from each well and counted in a MICROBETA TRILUX Scintillation Counter (Wallac, Gaithersburg, Md.). The amount of $^{51}Cr$ spontaneously released was obtained by incubating target cells in medium alone. Spontaneous release from target cells was typically less than 20%. The total amount of $^{51}Cr$ incorporated was determined by adding 1% Triton X-100 in distilled water, and the percentage lysis was calculated as follows: [(sample counts per minute (c.p.m.)−spontaneous c.p.m.)/(total c.p.m.−spontaneous c.p.m.)]×100.

Figure 6:
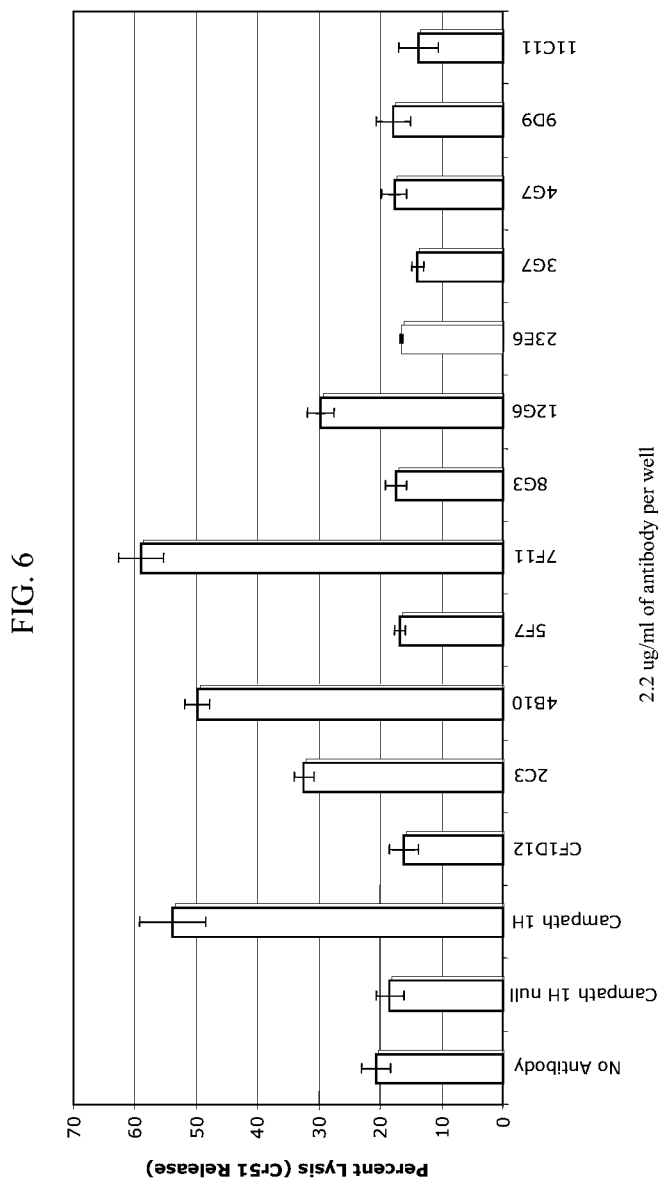
FIG. 6 is a graph showing the results of a 1.5 hour CDC assay on various chimeric anti-CD52 antibodies screened on CHO-K1 CD52 #67 cells. The results show that chimeric antibodies 4B10 and 7F11 are comparable to or better than Campath-1H® ("Campath 1H").

Twelve different chimeric anti-CD52 antibodies (mouse variable region and human IgG1 constant region) were tested in CDC assay with human complement on CHO-CD52 cells. Campath-1H® humanized antibody was used as a positive control. A negative control was Campath-1H® null (a non-cell-binding minimal mutant of Campath-1H®—two point mutations in H2 loop-heavy chain CDR2 region (K52bD and K53D; Gilliland L K et al., *Journal of Immunology*, 162: 3663-3671 (1999)). The results indicate that the chimeric antibodies are capable of mediating CDC killing on CD52-expressing cells. Some of the chimeric antibodies mediated robust killing equivalent or better than Campath® (FIG. 6).

Example 6

ADCC Activity of Chimeric Anti-CD52 Antibodies

An antibody-dependent cytotoxicity (ADCC) assay was performed as described below. Briefly, CHO K1 cells engineered to express CD52 protein (CHO-CD52) were used as target cells and labeled with $Na_2^{51}CrO_4$ (New England Nuclear, Boston, Mass.) at 37° C. for 1-2 hrs. The cells were washed, resuspended with X-Vivo media, and mixed with anti-human CD52 antibodies to final concentration of 1.1 μg/ml. Human PBMC were used as effectors cells and were added at a 1:100 target-to-effector cell ratio. After a 6 hr-overnight incubation, 25 μl of cell-free supernatant was collected from each well and counted in a MICROBETA TRILUX Scintillation Counter (Wallac, Gaithersburg, Md.). The amount of $^{51}Cr$ spontaneously released was obtained by incubating target cells in medium alone. Spontaneous release from target cells was typically less than 20%. The total amount of $^{51}Cr$ incorporated was determined by adding 1% Triton X-100 in distilled water, and the percentage lysis was calculated as follows: [(sample c.p.m.−spontaneous c.p.m.)/(total c.p.m.−spontaneous c.p.m.)]×100.

Figure 7:
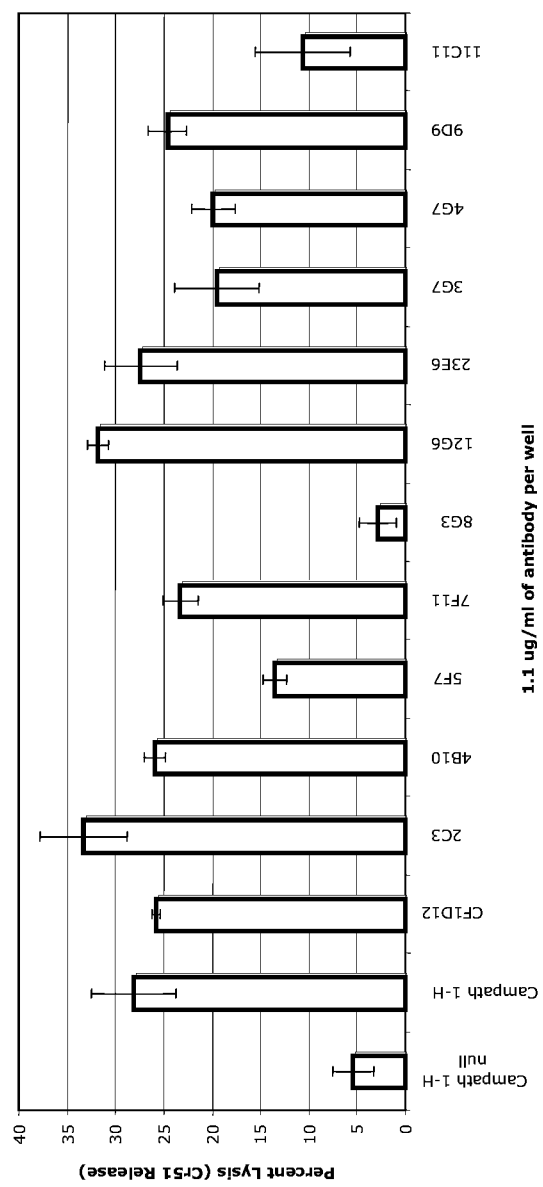
FIG. 7 is a graph showing the results of a 14 hour ADCC assay on various chimeric IgG1 antibodies to CD52 screened on CHO-K1 CD52 #67 cells. The results show that chimeric antibodies 2C3 and 12G6 are comparable to or better than Campath-1H® ("Campath 1-H").

Twelve different chimeric anti-CD52 antibodies (mouse variable region and human IgG1 constant region) were tested in ADCC assay using human PBMC as effector cells. Campath-1H® humanized antibody was used as a positive control. Used as a negative control was Campath-1H® null (a non-cell-binding minimal mutant of Campath-1H®—two point mutations in H2 loop-heavy chain CDR2 region (K52bD and K53D; Gilliland, 1999, supra). The results indicate that the chimeric antibodies are capable of mediating ADCC killing on CD52-expressing cells. Some of the chimeric antibodies mediated robust killing equivalent or better than Campath-1H® (FIG. 7).

Example 7

Evaluation of the Binding of Chimeric Anti-CD52 Antibodies to Defined Lymphocyte Population The following fluorochrome conjugated antibodies were used for flow cytometric analysis: anti-CD3-FITC, anti-CD27-PE, anti-CD62L-PE Cy5, anti-CD56-PE Cy7, anti-CD16-APC Cy7 (BD Biosciences, San Diego, Calif.), anti-CD45RA-ECD (Beckman Coulter), anti-CD19-Pacific Blue, anti-CD4-APC Cy5.5 and anti-CD8 pacific orange (Invitrogen, CA). All the mouse chimeric anti-human CD52 antibodies as well as the humanized Campath-1H® were conjugated to Alexa fluor 647 (BD Pharmingen). Healthy human peripheral blood mononuclear cells were obtained either from cryopreserved buffy coats or from mononuclear cells separated from blood of normal donors obtained from commercial vendors (Bioreclamation, NY, USA). For enrichment of mononuclear cells, human peripheral blood was diluted 1:1 with sterile phosphate buffered saline (PBS) and carefully layered over Ficoll-hypaque (GE Healthcare Bio-Sciences, Uppsala, Sweden) and centrifuged for 30 min at room temperature. The interphase layer of mononuclear cells was drawn out and washed in PBS containing 5% fetal bovine serum (FACS buffer). Contaminating red blood cells (RBCs) were lysed with RBC lysing solution (Sigma, St. Louis, Mo., USA). Cells were resuspended in cold FACS buffer and the debris was removed using a 40 micron filter. Ten color flow cytometry was performed to evaluate the binding ability of 9 chimeric anti-human CD52 antibodies (4B10, 7F11, 9D9, 5F7, 2C3, 4G7, 23E6, 8G3, 3G7) as compared to Campath-1H®.

Figure 8A:
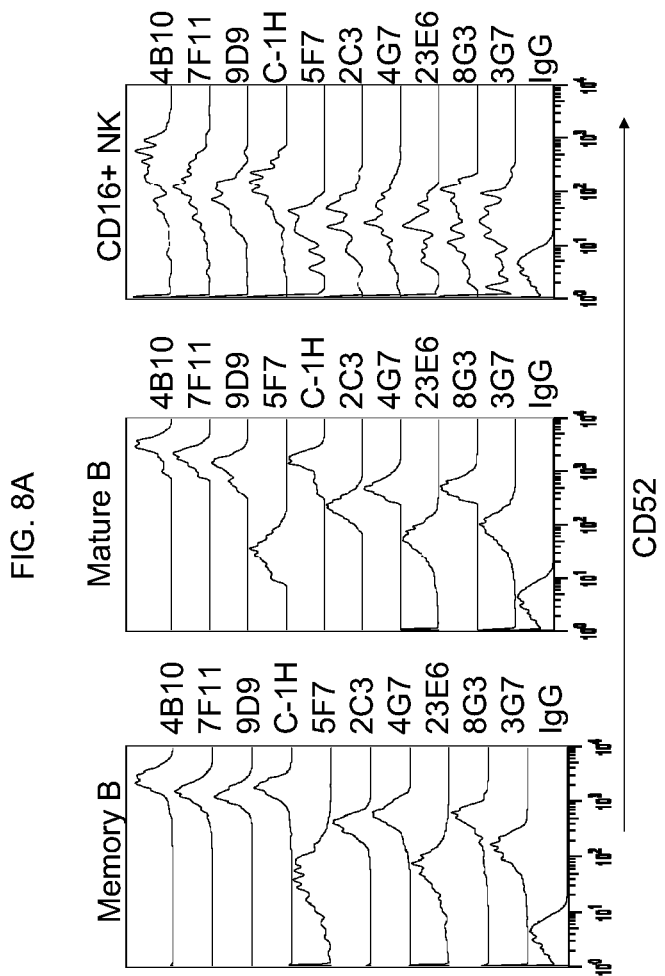
Figure 8C:
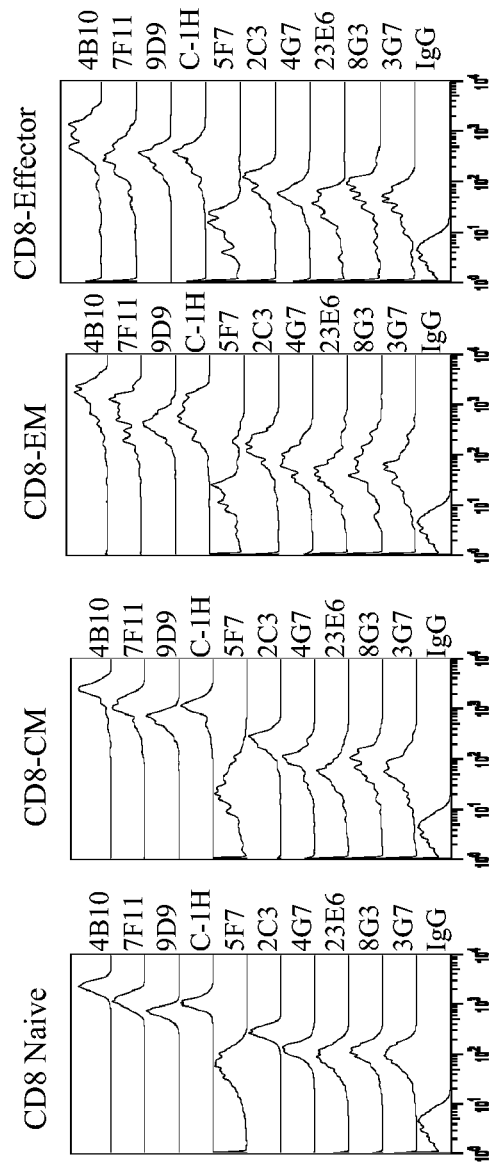

Briefly, replicates of $1 \times 10^6$ PBMC's in FACS buffer were incubated with a cocktail of pre-titrated dilutions of antibodies against CD3, CD27, CD45RA, CD62L, CD56, CD19, CD8, CD4, CD16 along with one of 9 chimeric anti-human CD52 antibodies (4B10, 7F11, 9D9, 5F7, 2C3, 4G7, 23E6, 8G3, 3G7) for 30 min at 4° C. Cells were washed and fixed in PBS containing 1% paraformaldehyde. 100,000 events of the stained cells were acquired on BD LSR-II (BD Biosciences, San Jose, Calif.) and the data was analyzed using FlowJo 7.2 version Software (Tree Star, Inc, Oregon, USA). Multiple subsets with distinct phenotypic characteristics have been defined among B and T lymphocytes and CD52 has been shown to be expressed on all human lymphocytes. Ten color flow cytometry analysis was performed to identify the lymphocyte subsets, and to assess similarities and the differences in the binding characteristics of anti-CD52 antibodies to cell surface CD52 on defined subsets. Using a combination of markers, 11 phenotypically distinct cell populations corresponding to B, T and NK cell lineages were first defined from the lymphocyte gate. The intensity of staining which corresponds to the ability of anti-CD52 antibodies to detect CD52 expression was then assessed. The histograms (FIGS. 8A-8C) show a comparison of the level of detection of CD52 with each antibody on individual lymphocyte populations. The data shows that the antibodies exhibit significant differences in binding to CD52. The level of detection with 4B10, 9D9, 7F11 and Campath-1H® are comparable, although 4B10 consistently shows the highest level of detection than other antibodies including Campath-1H®, on almost all the cell subsets examined. On the other hand, the detection level of CD52 with 3G7, 4G7, 8G3 and 23E6 antibodies is significantly lower. The results indicate a hierarchy within the antibodies with respect to their ability to recognize CD52 on different cell populations with 4B10 being highest and 3G7 being the lowest. Interestingly, these differences are less obvious on CD4 effector and more so on NK cell subsets on which CD52 appears to be expressed at relatively lower levels. The variations in the binding characteristics indicate that the properties of the chimeric antibodies not only differ significantly from Campath-1H® but also reflect differences in properties among the antibodies.

Example 8

Analysis of Chimeric Anti-CD52 Antibodies in Human CD52 Transgenic Mice (7F11, 8G3, 23E6, 12G6, 4B10 and 5F7)

Human CD52 transgenic mice were administered either Campath® or chimeric anti-CD52 antibodies (7F11, 8G3, 23E6, 12G6, 4B10 and 5F7) to examine the level of lymphocyte depletion. Mice were injected intra-peritoneally with either Campath® or the chimeric anti-CD52 antibodies in a 100 µl volume at a dose of 1 mg/kg. Three days later mice were sacrificed and blood and spleens were collected to determine the level of B and T-cell depletion. Flow cytometry was utilized to evaluate the absolute numbers of total T helper cells, cytotoxic T cells, and B cells present in the circulating peripheral blood or spleens of huCD52 transgenic mice. These lymphocyte populations were defined by their surface expression of the following protein antigens: CD4 expression identifies the T helper cell population, CD8 expression identifies the cytotoxic T cell population and CD19 expression identifies all mature B cell populations. A significant level of T and B-cell depletion was observed for both the 12G6 and 4B10 antibodies, which was comparable to the depletion observed with Campath®. Treatment with either Campath®, the chimeric 12G6 or the chimeric 4B10 antibody significantly reduced T and B cells in both the blood and spleens of treated mice at this dose level. The 7F11 and 5F7 chimeric antibodies resulted in significant levels of T cell depletion level in the blood and spleen but were less effective at depleting B cells in both compartments. Treatment with the 23E6 antibody resulted in a moderate level of depletion at this dose while little to no depletion was observed with the lower affinity 8G3 antibody.

Figure 9A:
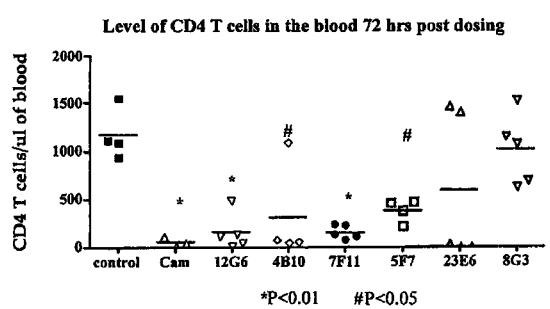
FIGS. 9A-9C are graphs illustrating the level of CD4 T cells (FIG. 9A), CD8 T cells (FIG. 9B) and CD19 B cells (FIG. 9C) in the blood 72 hours after dosing with chimeric antibodies 7F11, 8G3, 23E6, 12G6, 4B10, or 5F7, or Campath-1H® ("Cam").
Figure 9B:
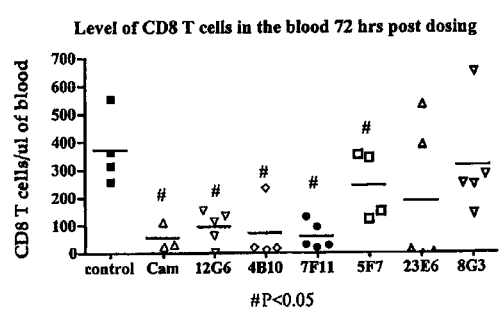
Figure 9C:
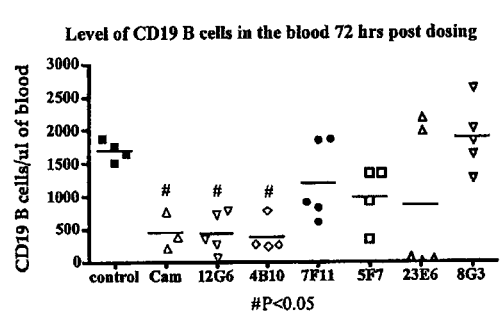
Figure 10:
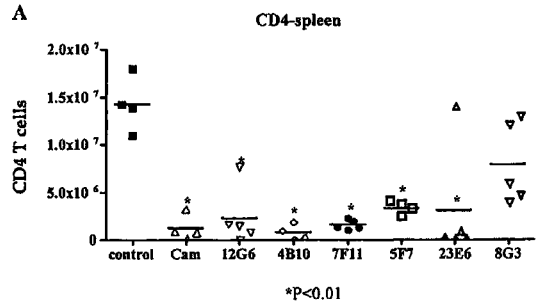
FIGS. 10A-10C are graphs illustrating the level of CD4 T cells (FIG. 10A), CD8 T cells (FIG. 10B) and CD19 B cells (FIG. 10C) in the spleen 72 hours after dosing with chimeric antibodies 7F11, 8G3, 23E6, 12G6, 4B10, or 5F7, or Campath-1H® ("Cam").
Figure 10:
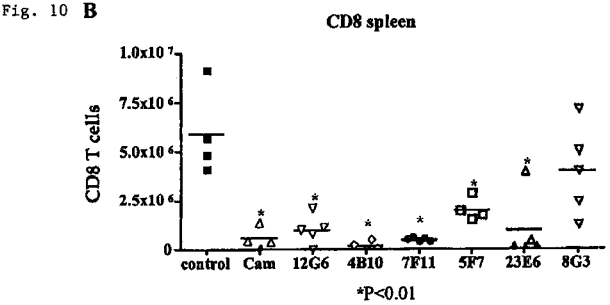
Figure 10:
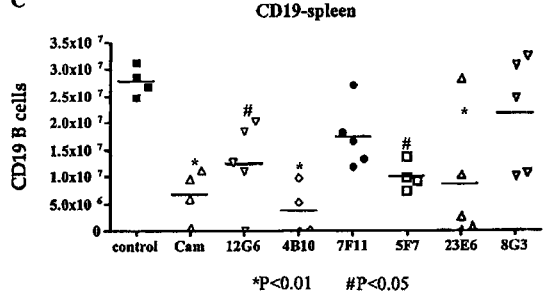

FIGS. 9A-9C show the level of CD4 T cells, CD8 T cells and CD19 B cells in the blood 72 hours after dosing with the chimeric antibodies. FIGS. 10A-10C show the level of CD4 T cells, CD8 T cells and CD19 B cells in the spleen 72 hours after dosing.

Example 9

Analysis of Chimeric Anti-CD52 Antibodies in Human CD52 Transgenic Mice (2C3, 3G7, 4B10, 9D9, and 11C11)

Human CD52 transgenic mice were administered either Campath® or chimeric anti-CD52 antibodies (2C3, 3G7, 4B10, 9D9 and 11C11) to examine the level of lymphocyte depletion. Mice were injected intravenously with either Campath® or the chimeric anti-CD52 antibodies in a 100 µl volume at a dose of 1 mg/kg. Three days later mice were sacrificed and blood and spleens were collected to determine the level of B and T-cell depletion. Flow cytometry was utilized to evaluate the absolute numbers of total T helper cells, cytotoxic T cells, and B cells present in the circulating peripheral blood of huCD52 transgenic mice. These lymphocyte populations were defined by their surface expression of the following protein antigens: CD4 expression identifies the T helper cell population, CD8 expression identifies the cytotoxic T cell population and CD19 expression identifies all mature B cell populations. A significant level of T and B cell depletion was observed for several antibodies in both the blood and spleen. The depleting activity for 2C3 and 9D9 was comparable to that observed with Campath® with significant levels of CD4 and CD8 T cells and CD19 B cells being depleted. Treatment with chimeric 4B10 also resulted in a significant decrease in the numbers of lymphocytes in the blood of transgenic mice. While treatment with either the chimeric antibody 3G7 or 11C11 antibody significantly depleted T cells in the blood, the level of B cells present were not significantly affected at this dose.

Figure 11:
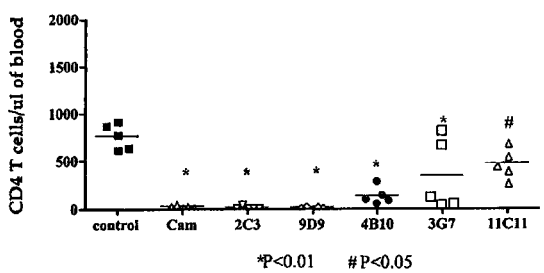
FIGS. 11A-11C are graphs showing the level of CD4 T cells (FIG. 11A), CD8 T cells (FIG. 11B) and CD19 B cells (FIG. 11C) in the blood 72 hours after dosing with chimeric antibodies 2C3, 9D9, 4B10, 3G7, or 11C11, or Campath-1H® ("Cam").
Figure 11:
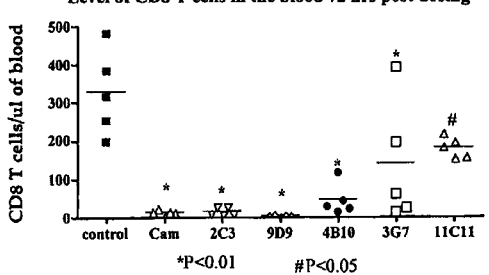
Figure 11:
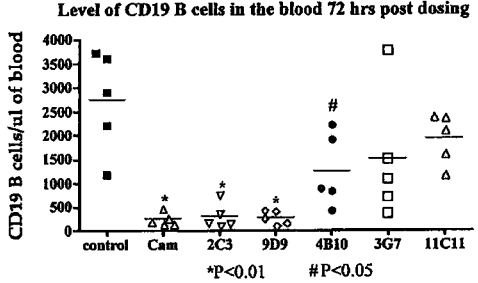

FIGS. 11A-11C show the level of CD4 T cells, CD8 T cells and CD19 B cells in the blood 72 hours after dosing with the chimeric antibodies.

Example 10

Analysis of the Efficacy of Anti-CD52 Antibodies (7F11, 4B10 and 12G6)

Figure 12:
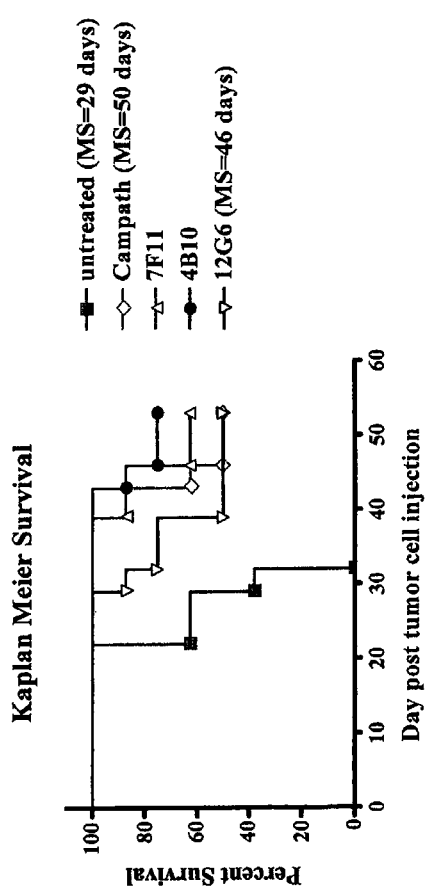
FIG. 12 is a Kaplan Meier Survival graph illustrating the percent of surviving mice after treatment with 7F11, 4B10, or 12G6 chimeric monoclonal antibodies, or Campath-1H® ("Campath").

Forty SCID mice (n=8 per group) were injected with $1 \times 10^6$ B104 tumor cells in 100 µl volume on the right flank. On day 11 post tumor cell injection, treatment began with Campath®, 7F11, 4B10 or 12G6 chimeric antibodies. Antibodies were administered once weekly at 10 mg/kg by intraperitoneal injection throughout the remainder of the experiment. All mice in the untreated group developed progressively growing tumors requiring sacrifice with a median survival of 29 days. Treatment with Campath® resulted in a statistically significant increase in survival compared to the untreated group (median survival (MS) of 50 days and p<0.0001). Treatment with the chimeric anti-CD52 antibodies also resulted in a statistically significant increase in survival compared to untreated mice (p<0.0001 for 7F11 and 4B10 and p=0.0020 for 12G6). Based on survival rates, the activity of both 7F11 and 4B10 antibodies appears to be greater than Campath® (63% survival for 7F11 and 75% survival for 4B10 compared to 50% survival for Campath®). FIG. 12 shows the percent survival of the mice after treatment.

Example 11

Analysis of the Efficacy of Anti-CD52 Antibodies (2C3, 8G3 and 23E6)

Forty SCID mice (n=8 per group) were injected with $1 \times 10^6$ B104 tumor cells in a 100 µl volume on the right flank. On day 11 post tumor cell injection, treatment began with either Campath®, 2C3, 8G3 or 23E6 chimeric antibodies. Antibodies were administered once weekly at 10 mg/kg by intraperitoneal injection throughout the remainder of the experiment. All mice in the untreated group developed progressively growing tumors requiring sacrifice with a median survival of 26 days. Treatment with Campath®, 23E6, and the 2C3 antibody resulted in statistically significant increases in survival (p=0.0025, p=0.0007, and p=0.0002 respectively).

Figure 13:
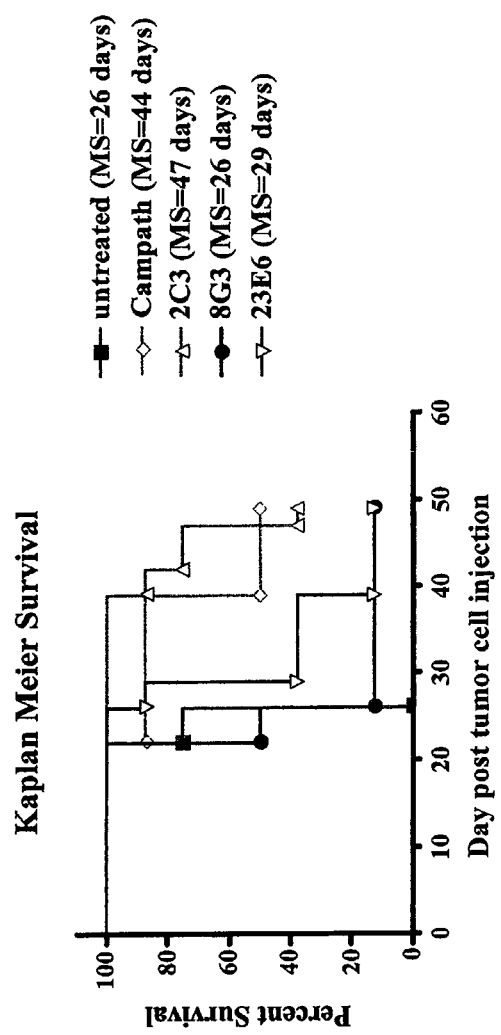
FIG. 13 is a Kaplan Meier Survival graph illustrating the percent of surviving mice after treatment with 2C3, 8G3, or 23E6 chimeric monoclonal antibodies, or Campath-1H® ("Campath").

FIG. 13 shows the percent survival of the mice after treatment.

Example 12

Analysis of the Efficacy of Chimeric Anti-CD52 Antibodies in a Xenograft Tumor Model (9D9 and 4B10)

Figure 14:
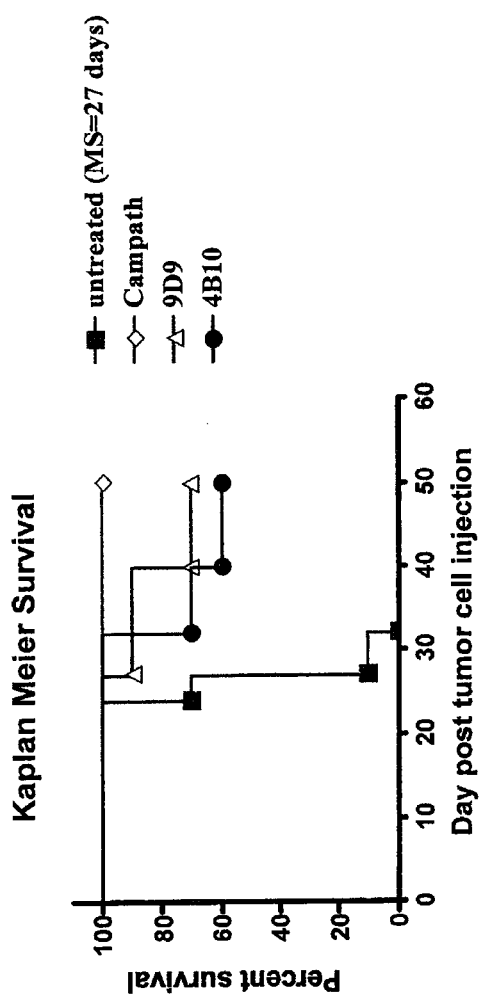
FIG. 14 is a Kaplan Meier Survival graph illustrating the percent of surviving mice after treatment with 9D9 or 4B10 chimeric monoclonal antibodies, or Campath-1H® ("Campath").

Forty SCID mice (n=8 per group) were injected with $1 \times 10^6$ B104 tumor cells in a 100 µl volume on the right flank. On day 11 post tumor cell injection, treatment began with either Campath®, 9D9 or 4B10 chimeric antibody. Antibodies were administered once weekly at 10 mg/kg by intraperitoneal injection throughout the remainder of the experiment. All mice in the untreated group developed progressively growing tumors requiring sacrifice with a median survival of 27 days. Treatment with Campath® resulted in a statistically significant increase in survival compared to the untreated group (median survival not achieved and p<0.0001). Treatment with the chimeric anti-CD52 antibodies also resulted in a statistically significant increase in survival compared to untreated mice (p<0.0001 for 9D9 and 4B10). Statistical analysis of the survival curves reveals that the 9D9 chimeric antibody displayed activity comparable to Campath® (p=0.0675) in this experiment. FIG. 14 shows the percent survival of the mice after treatment.

Example 13

Analysis of the Efficacy of Chimeric Anti-CD52 Antibodies in a Xenograft Tumor Model (2C3 and 11C11)

Figure 15:
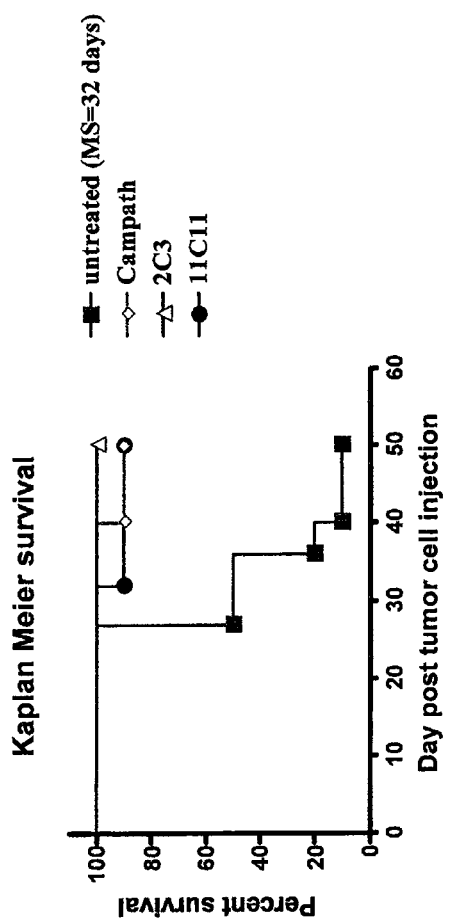
FIG. 15 is a Kaplan Meier Survival graph illustrating the percent of surviving mice after treatment with 2C3 or 11C11 chimeric monoclonal antibodies, or Campath-1H® ("Campath").

Forty SCID mice (n=8 per group) were injected with $1 \times 10^6$ B104 tumor cells in a 100 µl volume on the right flank. On day 11 post tumor cell injection, treatment began with either Campath®, 2C3 or 11C11 chimeric antibody. Antibodies were administered once weekly at 10 mg/kg by intraperitoneal injection throughout the remainder of the experiment. All mice in the untreated group developed progressively growing tumors requiring sacrifice with a median survival of 32 days. Treatment with Campath® resulted in a statistically significant increase in survival compared to the untreated group (median survival not achieved and p<0.0001). Treatment with the chimeric anti-CD52 antibodies also resulted in a statistically significant increase in survival compared to untreated mice (p<0.0001 for 2C3 and p=0.0004 for 11C11). Statistical analysis of the survival curves reveals that both the 2C3 and 11C11 chimeric antibodies displayed activity comparable to Campath® (p=0.3173 for 2C3 and p=0.9703 for 11C11). FIG. 15 shows the percent survival of the mice after treatment with Campath®, 2C3 chimeric antibody or 11C11 chimeric antibody.

Example 14

Generation and Analysis of Humanized Anti-CD52 Antibody 4B10

Humanized anti-human CD52 antibody 4B10 was generated by grafting the CDR regions from the mouse 4B10 antibody into a human antibody variable region framework. Mouse 4B10 heavy chain and light chain sequences were evaluated by a web-based sequence alignment in order to identify a human germline heavy chain and light chain framework sequence that would serve as a suitable acceptor for the CDR graft (FIG. 16). The residues defining the CDR regions by Kabat and IMGT® were superimposed into human framework regions that have high sequence identity to generate humanized heavy chain and light chain sequences. Visual inspection and sequence analysis of the superimposed 4B10 heavy and light chain sequences was carried out to identify the most suitable acceptor sequence. Of all the germline sequences that have high similarity, the VH3-72 germline sequence for heavy chain and the VK2-A18b for light chain (human germ line sequences can be found at the website described in the publication by Tomlinson, I M, et al., *EMBO J.*, 14(18):4628-4638 (1995); Cook, G P., et al., *Nature Genetics*, 7:162-168 (1994)) were selected from their high degree of homology, sequence similarity to mouse framework regions and for minimal disruption of CDR loop structure as CDR acceptor sequence. CDR1, 2, and 3 sequences of heavy chain and light chain for 4B10 were grafted into VH3-72 and VK2-A18b human framework regions respectively to generate humanized heavy chain and light chain sequences for 4B10 (illustrated in FIG. 17; FIG. 110).

Example 15

Figure 18:
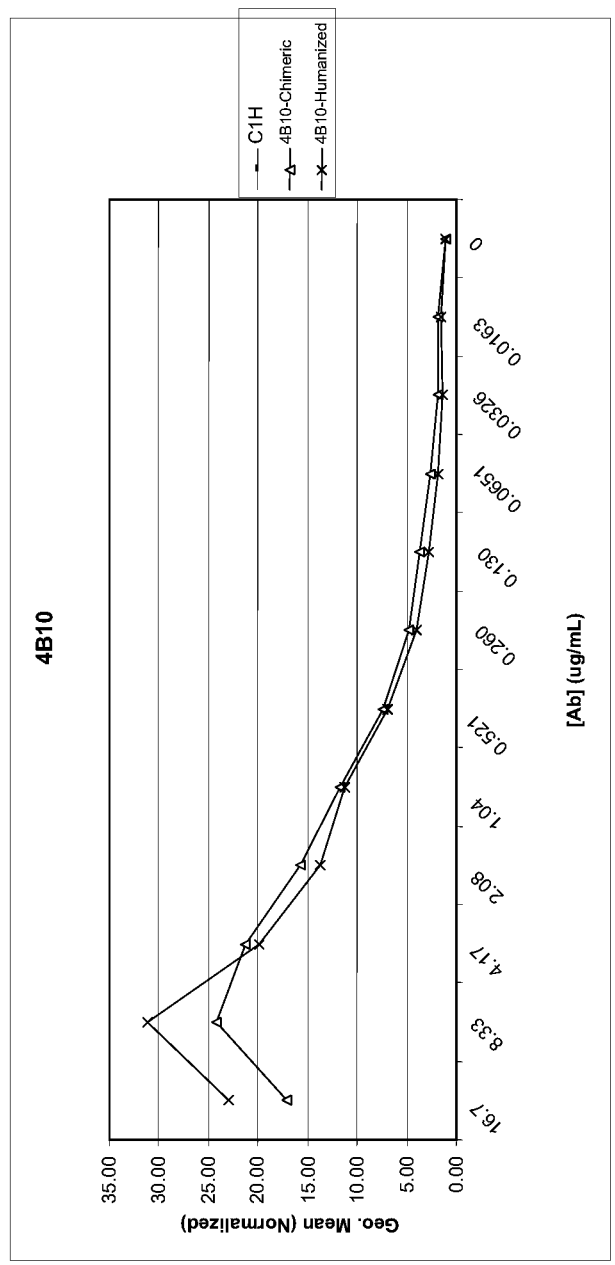
FIG. 18 is a graph showing that humanized antibody 4B10-H1/K1 ("4B10-Humanized") and chimeric antibody 4B10 bind equivalently to cells expressing CD52.

Assessment of the Binding Activities of Chimeric and Humanized 4B10 Monoclonal Antibodies Chimeric and humanized 4B10 antibodies were produced and purified as described in Example 3 and analyzed for their ability to bind to the B cell line B104, which endogenously expresses CD52, by FACS. Briefly, 2×10$^5$ B104 cells were incubated with antibody (0.02 µg/ml to 16.7 µg/ml) in PBS containing 5% fetal bovine serum and 5% goat serum. The bound antibody was detected with FITC labeled goat anti-human secondary antibody which detected chimeric or humanized anti-CD52 antibodies. Labeled cells were analyzed using a FACSCalibur system (Becton Dickinson). FIG. 18 shows the fold increase in Geometric mean fluorescence intensity of each sample normalized (divided) to that of 2°-only sample. The 11 different concentrations (12$^{th}$ point on X axis is secondary alone) of the humanized and chimeric antibody used in the assay is shown on the X axis and the Geo Mean fold increase in the mean fluorescence is on the Y axis. The results indicate that the humanized 4B10 antibody bound as well or slightly better than chimeric 4B10 antibody to CD52 expressing cells.

Example 16

Assessment of the ADCC Activities of Chimeric and Humanized 4B10 Monoclonal Antibodies Humanized and chimeric 4B10 antibodies were evaluated for their ability to mediate ADCC killing of CD52-expressing cells. An ADCC assay was carried out as described above in Example 6. Briefly, CHO K1 cells engineered to express CD52 protein (CHO-CD52) were used as target cells and labeled with Na$_2^{51}$CrO$_4$ (New England Nuclear, Boston, Mass.) at 37° C. for 1-2 hrs. The cells were washed, resuspended in RPMI 1640 media with 10% FCS, and mixed with chimeric or humanized 4B10 antibodies at various concentrations ranging from 10 µg/ml to 0.01 µg/ml. Human PBMC were used as effectors cells and were added at 1:50 target-to-effector cell ratio. After a 6 hr-overnight incubation, 25 µl of cell-free supernatant was collected from each well and counted in a MICROBETA TRILUX Scintillation Counter (Wallac, Gaithersburg, Md.). The amount of $^{51}$Cr spontaneously released was obtained by incubating target cells in medium alone. Spontaneous release from target cells was typically less than 20%. The total amount of $^{51}$Cr incorporated was determined by adding 1% Triton X-100 in distilled water, and the percentage lysis was calculated as follows: [(sample c.p.m.−spontaneous c.p.m.)/(total c.p.m.−spontaneous c.p.m.)]×100.

Figure 19:
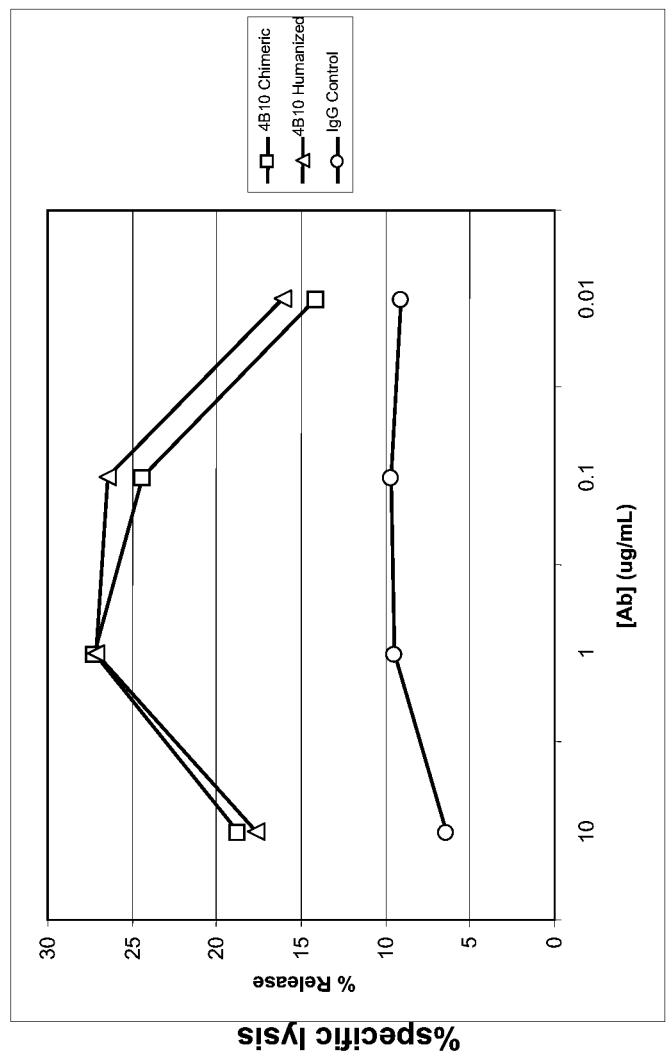
FIG. 19 is a graph showing that humanized antibody 4B10-H1/K1 ("4B10 Humanized") and chimeric antibody 4B10 mediate equivalent ADCC activity on cells expressing CD52.

FIG. 19 illustrates the concentrations of control, chimeric and humanized 4B10 antibodies used in the assay (X axis) and the Y axis shows % specific killing. The results indicate that humanized 4B10 antibody mediated equivalent or slightly better ADCC killing than chimeric 4B10 antibody. The control IgG1 isotype control showed only low levels of background killing at the concentrations tested.

Example 17

Figure 20:
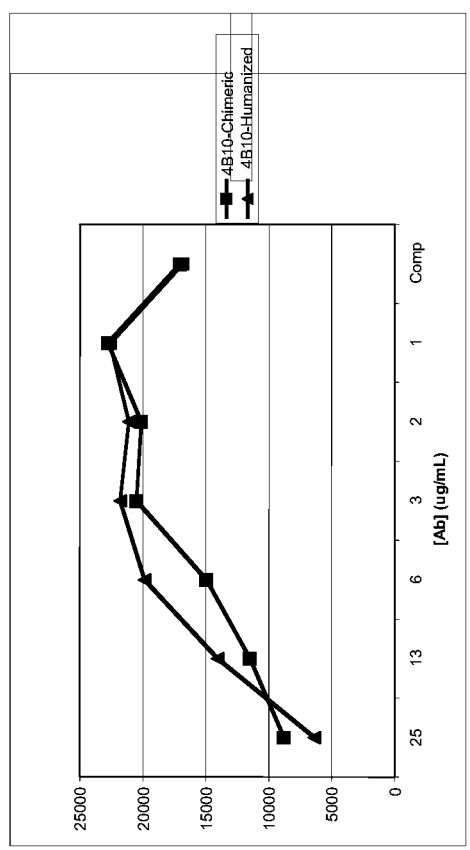
FIG. 20 is a graph showing that humanized antibody 4B10-H1/K1 ("4B10-Humanized") and chimeric antibody 4B10 mediate equivalent CDC activity on cells expressing CD52.

Assessment of the CDC Activities of Chimeric and Humanized 4B10 Monoclonal Antibodies Humanized and chimeric 4B10 antibodies were evaluated for their ability to mediate cytotoxic effect on B104 cells that endogenously express CD52 in the presence of human complement. CellTiter Glo kit (Promega) was used to determine the live cells remaining in the assay. Briefly, B104 cells (target cells) were plated at 2.5×10$^4$ cells/well in a 96 well plate and were mixed with chimeric or humanized 4B10 antibody at various concentrations ranging from 1 µg/ml to 25 µg/ml and human complement to a final concentration of 10%. Complement alone without the antibody and antibody alone without complement were used as controls to determine the background. After three hours of incubation at 37° C., plates were centrifuged for 3 min at 1500 rpm and the live cells present in the pellet were determined using CellTiter Glo assay. Plates were read on Envision machine. FIG. 20 shows the live cells present in the assay as measured using CellTiter Glo assay. Again, with the increasing concentrations of the humanized and chimeric 4B10 antibody there is a decrease in the number of live cells. These results suggest that the humanized antibody performed as well as or slightly better than chimeric 4B10 antibody in CDC mediated killing of B104 cells.

Example 18

Analysis of Pharmacokinetic Profile of Chimeric And Humanized Anti-CD52 Antibodies in CD52 Transgenic Mice (12G6, 7F11, Chimeric and Humanized 4B10)

Figure 21:
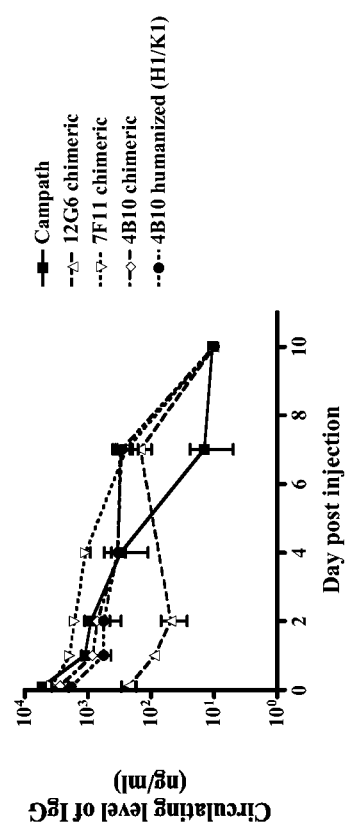
FIG. 21 is a graph illustrating the pharmacokinetic profile of chimeric anti-CD52 antibodies (12G6, 7F11 and 4B10), Campath-1H® ("Campath"), and humanized anti-CD52 antibody 4B10-H1/K1 ("4B10 humanized (H1/K1)") in heterozygous huCD52 transgenic mice.

Human CD52 transgenic mice were administered one of Campath®, 12G6, 7F11, and chimeric and humanized 4B10 anti-CD52 antibodies to examine the level of lymphocyte depletion. Mice were injected intravenously with one of those antibodies in a 100 µl volume at a dose of 1 mg/kg. For analysis of anti-antibody responses, 100 µl of blood was collected into serum separator tubes via puncture of the retro-orbital plexus at 2 hours, 1, 2, 4, 7, and 10 days post antibody injection. ELISA analysis was used to determine the level of circulating human IgG1 in each serum sample. Based on circulating levels of antibody, there appears to be little to no difference between Campath®, 7F11, and the chimeric and humanized forms of 4B10. The 12G6 antibody displayed lower cmax values following injection, suggesting that this antibody may be degraded more quickly. FIG. 21 shows the pharmacokinetic profile of Campath®, 12G6 (chimeric), 7F11 (chimeric), 4B10 (chimeric) and 4B10 (humanized) antibodies.

Example 19

Analysis of the Depleting Activity of Chimeric and Humanized Anti-CD52 Antibodies in CD52 Transgenic Mice (Chimeric and Humanized 4B10)

Figure 22:
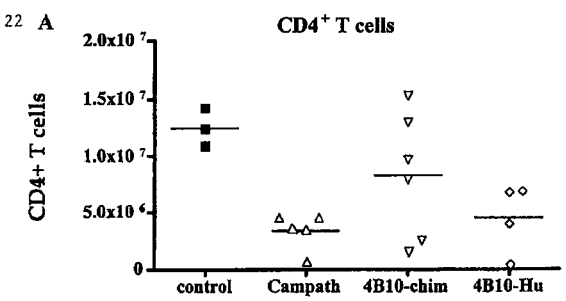
FIGS. 22A-22C are graphs showing the level of CD4 T cells (FIG. 22A), CD8 T cells (FIG. 22B) and CD19 B cells (FIG. 22C) in the blood 72 hours after dosing with chimeric antibody 4B10 or humanized antibody 4B10-H1/K1 ("4B10-Hu") or Campath-1H® ("Campath").
Figure 22:
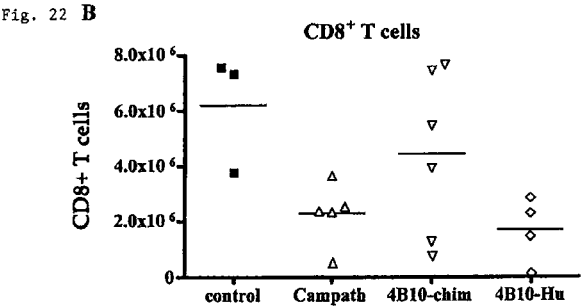
Figure 22:
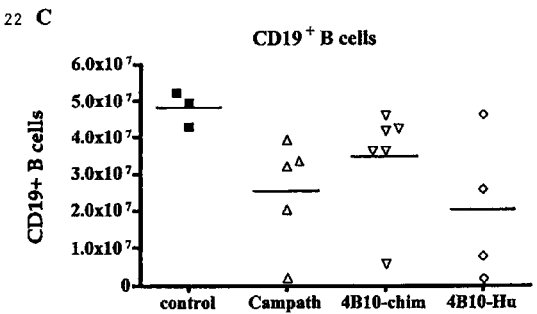

Human CD52 transgenic mice were administered either Campath® or chimeric or humanized 4B10 anti-human CD52 antibody to examine the level of lymphocyte depletion. Mice were injected intravenously with either Campath® or the chimeric or humanized 4B10 anti-human CD52 antibody in a 100 µl volume at a dose of 0.1 mg/kg. Three days later mice were sacrificed and blood and spleens were collected to determine the level of B and T-cell depletion. Flow cytometry was utilized to evaluate the absolute numbers of total T helper cells, cytotoxic T cells, and B cells present in the circulating peripheral blood of the huCD52 transgenic mice. These lymphocyte populations were defined by their surface expression of the following protein antigens: CD4 expression identifies the T helper cell population, CD8 expression identifies the cytotoxic T cell population and CD19 expression identifies all mature B cell populations. Comparison of the depleting activity in the spleen revealed that there was no difference in the level of T cells depleted following administration of either Campath® or the chimeric or humanized forms of 4B10. Due to the low dose used, only a modest level of depletion of B cells was observed in the spleen. On a per animal basis it appears that the humanized 4B10 antibody is as good or slightly better than Campath® at mediating lymphocyte depletion. FIGS. 22A-22C show the level of CD4 T cells, CD8 T cells and CD19 B cells in the blood 72 hours after dosing with the chimeric and humanized antibodies.

Example 20

Relative Binding Efficiency of Anti-Human CD52 Antibodies

The EC50 values of selected anti-CD52 antibodies were estimated using CHO cells engineered to express CD52. CHO-CD52 cells were trypsinized in 0.25% trypsin, collected, and rinsed with PBS/5% FBS. Cells were then deposited into round-bottom 96 well plates at 1E5 cells per well. Primary antibody staining was done with a 12 point serial dilution (1:2) of each anti-CD52 chimeric antibody starting at 50 µg/mL. FITC-conjugated goat FAB2 fragment of anti-human Fc gamma at 10 µg/mL (Jackson 109-096-098) secondary was used. Cells were washed 3 times in ice-cold PBS/5% FBS before and after each incubation. Cells were fixed with PBS containing 2% methanol-free paraformaldehyde and evaluated by flow cytometry. The flow cytometry data was analyzed using Graph pad Prizm software to determine EC50 value with 95% confidence interval.

Figure 23:
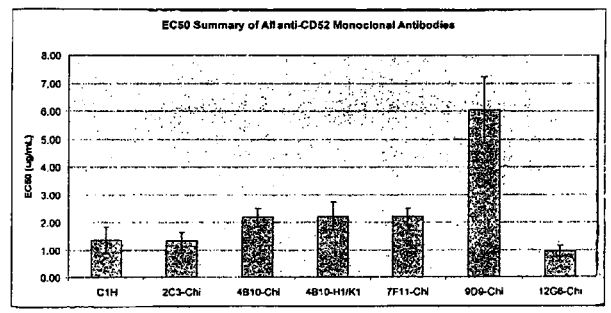
FIG. 23 is a graph showing the summary of the relative binding affinities of the anti-CD52 monoclonal antibodies.

Binding data (FIG. 23) indicates that the new CD52 antibodies not only have different epitope specificities as mentioned earlier, but also have different binding characteristics as shown in the table given below. Campath-1H®, 7F11, 4B10, 2C3 and 12G6 chimeric antibodies showed relatively similar EC 50 values between 0.5 to 2.5 µg/ml/. 9D9 chimeric antibody showed slightly different binding characteristics with EC50 value around 5 to 7 µg/ml. 4B10 humanized antibody showed similar binding characteristics as that of chimeric 4B10 antibody, indicating that the humanized antibody retained the binding characteristics as that of chimeric 4B10 antibody.

TABLE 9

| Clone ID | EC50 (µg/mL) | |
|---|---|---|
| | Mean | STDEV |
| C1H* | 1.36 | 0.46 |
| 2C3-Chi | 1.32 | 0.33 |
| 4B10-Chi | 2.18 | 0.33 |
| 4B10-H1/K1 | 2.23 | 0.50 |
| 7F11-Chi | 2.22 | 0.29 |
| 9D9-Chi | 6.05 | 1.18 |
| 12G6-Chi | 0.95 | 0.21 |

*C1H refers to Campath-1H ®.

Example 21

Humanization of Anti-CD52 Antibody Clone 7F11

Humanization of anti-human CD52 antibody clone 7F11 was performed by grafting the CDR regions from the mouse 7F11 antibody into a human antibody variable region framework as described in Example 14 for 4B10 antibody humanization. CDR-1, CDR-2, and CDR-3 sequences of the heavy chain and light chain of 7F11 were grafted into VH3-72 and VK2 A18b human framework regions, respectively. The human JH6 (WGQGTTVTVSS: SEQ ID NO: 133) and JK2 (FGQGTKLEIK: SEQ ID NO: 134) sequences were selected as the C-terminal peptides for the humanized heavy and light chains, respectively, to generate humanized heavy chain (7F11-SFD1 and 7F11-SFD2) and humanized light chain (7F11-VK2) variable region sequences for 7F11 (FIG. 24). The two humanized heavy chain variable region sequences (7F11-SFD1 and 7F11-SFD2) differ by one amino acid residue in the CDR-3 region. The 7F11-SFD1 version has a threonine at position 93 (denoted by the Kabat numbering system), while the 7F11-SFD2 version has an alanine at this position. Position 93 is underlined for both 7F11-SFD1 and 7F11-SFD2 in FIG. 24.

The full-length heavy chain amino acid sequence of 7F11-SFD1 (SEQ ID NO: 274) and the full-length light chain amino acid sequence of 7F11-K2 (SEQ ID NO: 275) are shown in FIG. 107.

Example 22

Figure 25:
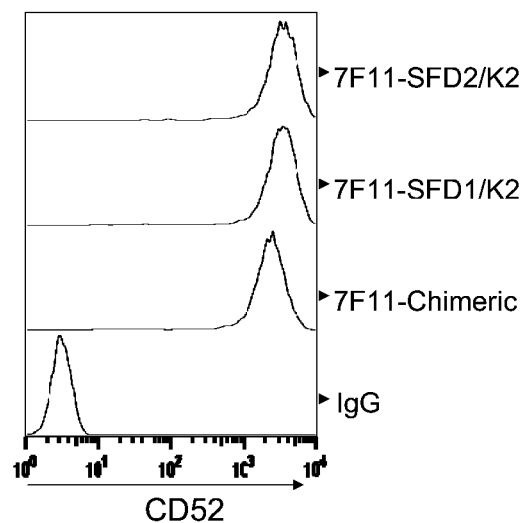
FIG. 25 is a histogram showing that chimeric and humanized 7F11 antibodies bind equivalently to cells expressing CD52. The X axis represents the fluorescence emitted by the bound anti-CD52 antibody, while the area of each peak represents the total cell population.

Assessment of the Binding Activities of Chimeric and Humanized 7F11 Monoclonal Antibodies Chimeric and humanized 7F11 antibodies (7F11-SFD1/K2 and 7F11-SFD2/K2) were produced and purified using the methods described in Example 3, and analyzed for their ability to bind to CD52 expressed on the surface of CHO-CD52 cells (CHO cells engineered to express human CD52) by flow cytometry. Briefly, $2 \times 10^5$ CHO-CD52 cells were incubated with an antibody at 10 µg/ml in PBS containing 5% fetal bovine serum and 5% goat serum. Bound antibody was detected with a FITC-labeled goat anti-human secondary antibody which detected chimeric or humanized anti-CD52 antibodies. Labeled cells were analyzed using a FACSCalibur system (Becton Dickinson) and the data was analyzed using FlowJo version 7.2 software (Tree Star, Inc, Oregon, USA). The histogram in FIG. 25 compares the levels of CD52 detected with chimeric and humanized 7F11 antibodies. The results indicate that the humanized 7F11 antibodies bound as well or slightly better than the chimeric 7F11 antibody to CD52 expressing cells.

Example 23

Humanization of Anti-CD52 Antibody Clone 2C3

Humanization of anti-human CD52 antibody clone 2C3 was performed by grafting the CDR regions from the mouse 2C3 antibody into a human antibody variable region framework as described in Example 14 for clone 4B10 antibody humanization. CDR-1, CDR-2, and CDR-3 sequences of the heavy chain and light chain of 2C3 were grafted into VH3-72 and VK2 A18b human framework regions, respectively. The human JH6 (WGQGTTVTVSS: SEQ ID NO: 133) and JK5 (FGQGTRLEIK: SEQ ID NO: 135) sequences were selected as the C-terminal peptides for the humanized heavy and light chains, respectively, to generate humanized heavy chain (2C3-SFD1) and light chain (2C3-VK1) variable region sequences for 2C3 (FIGS. 26A and B). Unlike humanized clones 4B10 and 7F11, the binding affinity for the CDR-grafted humanized 2C3 antibody was greatly reduced. Binding affinity was restored by introducing back mutations to the CDR-grafted structure, with the aim of limiting the number of back mutations to a minimum to keep the reshaped antibody as "human" as possible, thus reducing the possibility of immunogenicity. Single or multiple back mutations were incorporated into both the humanized heavy and light variable region sequences. The positions of the back mutations (as denoted by the Kabat numbering system) are depicted in Table 10 and Table 11 below. Antibodies generated with these back mutations were evaluated for restored binding affinity. Three light chain variants (2C3-VK1(L46R), also referred to as 2C3-VK11; 2C3-VK1(Y36L-L46R), also referred to as 2C3-VK12; and 2C3-VK1(M4I-A19V-Y36L-Q45K-L46R), also referred to as 2C3-VK13) and 5 heavy chain variants (2C3-SFD1(L78V), also referred to as 2C3-VH12; 2C3-SFD1(G49A), also referred to as 2C3-VH15; 2C3-SFD1(G49A-L78V), also referred to as 2C3-VH16; 2C3-SFD1(L18M-G49A-L78V), also referred to as 2C3-VH17; and 2C3-SFD1(L18M-G42E-G49A-L78V), also referred to as 2C3-VH19) were generated using standard molecular biology techniques. The amino acid sequences for CDR-grafted heavy chain variable region sequence 2C3-SFD1 and back mutants 2C3-VH12, 2C3-VH15, 2C3-VH16, 2C3-VH17, and 2C3-VH19 are shown in FIG. 26A with the back mutated amino acids underlined and the CDRs boldfaced. Similarly, for the light chain sequences, CDR-grafted variable region sequence 2C3-VK1 and back mutants 2C3-VK11, 2C3-VK12, and 2C3-VK13 are shown in FIG. 26B with the back mutated amino acids underlined and the CDRs boldfaced.

The full-length heavy chain amino acid sequence of 2C3-SFD1 (SEQ ID NO: 272) and the full-length light chain amino acid sequence of 2C3-K12 (SEQ ID NO: 273) are shown in FIG. 106.

TABLE 10

2C3 clone heavy chain back mutants

| Clone ID | Mutation (Kabat numbering position) |
| --- | --- |
| 2C3-VH12 | L to V (78) |
| 2C3-VH15 | G to A (49) |
| 2C3-VH16 | G to A (49), L to V (78) |
| 2C3-VH17 | L to M (18), G to A (49), L to V (78) |
| 2C3-VH19 | L to M (18), G to E (42), G to A (49), L to V (78) |

TABLE 11

2C3 clone light (kappa) chain back mutants

| Clone ID | Mutation (Kabat numbering position) |
| --- | --- |
| 2C3-VK11 | L to R (46) |
| 2C3-VK12 | Y to L (36) and L to R (46) |
| 2C3-VK13 | M to I (4), A to V (19), Y to L (36), QL to KR (45, 46) |

Example 24

Figures 27A, 27B:
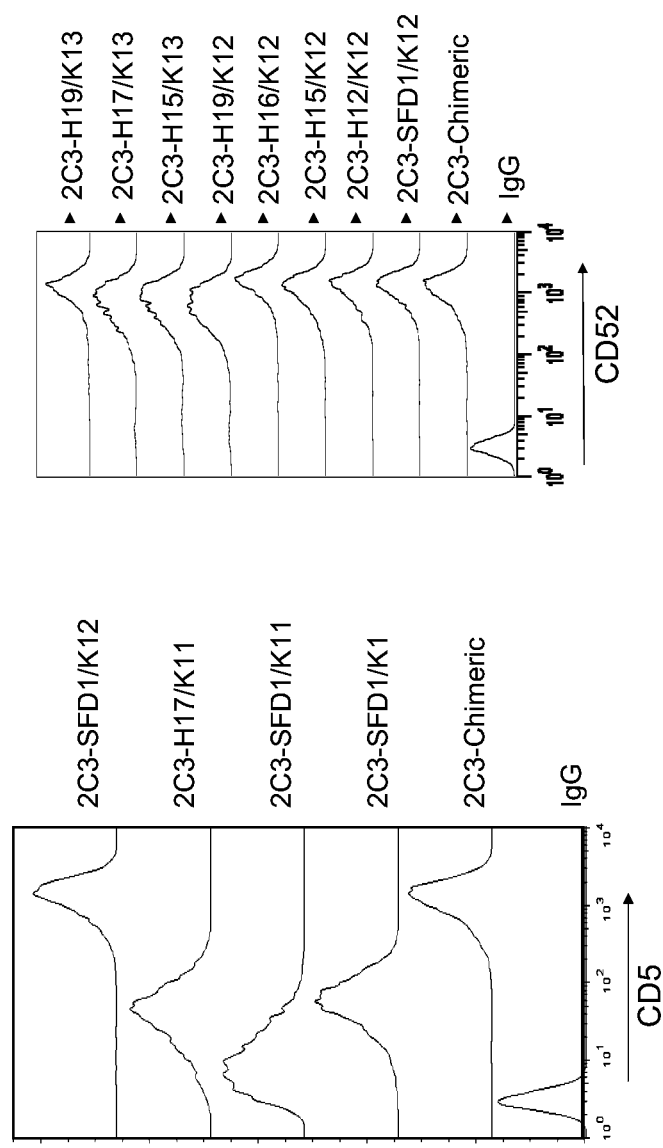
FIG. 27A is a histogram showing binding of humanized and chimeric 2C3 antibodies to cells expressing CD52. The X axis represents the fluorescence emitted by the bound anti-CD52 antibody, while the area of each peak represents the total cell population.
FIG. 27B is a histogram showing that chimeric and a subset of the humanized 2C3 antibodies bind equivalently to cells expressing CD52. The X axis represents the fluorescence emitted by the bound anti-CD52 antibody, while the area of each peak represents the total cell population.

Assessment of the Binding Activities of Chimeric and Humanized 2C3 Monoclonal Antibodies Chimeric and humanized 2C3 antibodies were produced and purified using the methods described in Example 3. A number of the humanized antibodies produced by pairing heavy chain variants with light chain variants, and a corresponding chimeric antibody, were analyzed by flow cytometry for their ability to bind to CD52 expressed on the surface of CHO-CD52 cells, using the methods described in Example 22. The binding data suggest that clones generated by pairing heavy chain variants with light chain variants 2C3-VK1 or 2C3-VK11 had reduced binding ability, while clones generated by pairing heavy chain variants with 2C3-VK12 or 2C3-VK13 showed binding equivalent to or better than that of a chimeric 2C3 antibody. A representative histogram of selected clones (FIG. 27A) compares the level of CD52 detected by chimeric and humanized 2C3 antibodies. Binding of 2C3-SFD1/K1 is reduced significantly compared to that of the corresponding chimeric antibody. Incorporating a single mouse residue at position 46 (leucine to arginine) in the light chain (resulting in 2C3-VK11) did not restore the binding when paired with heavy chain 2C3-SFD1 to make antibody 2C3-SFD1/K11. Further, binding was not restored by incorporating three back mutations in the heavy chain (resulting in 2C3-VH17) to make antibody 2C3-H17/K11. However, binding was completely restored when the 2C3-SFD1 heavy chain was paired with 2C3-VK12, which has two back mutations, to make antibody 2C3-SFD1/K12, suggesting that specific back mutations need to be incorporated to restore binding avidity. FIG. 27B shows a histogram of selected humanized clones that demonstrate binding equivalent to that of a chimeric 2C3 antibody. These results indicate that the back mutation of two amino acid residues in the 2C3-VK12 light chain was sufficient to completely restore antibody avidity. The changes at residues 36 (Y to L) and 46 (L to R) were able to restore binding when paired with almost any heavy chain variant. As such, the humanized 2C3 clone showing restored binding with minimal framework residues derived from the original mouse antibody is 2C3-SFD1/K12.

Example 25

Humanization of Anti-CD52 Antibody Clone 12G6

Humanization of anti-human CD52 antibody clone 12G6 was performed by grafting the CDR regions from the mouse 12G6 antibody into a human antibody variable region framework as described in Example 14 for clone 4B10 antibody humanization. CDR-1, CDR-2, and CDR-3 sequences of the heavy chain and light chain of 12G6 were grafted into VH3-72 and VK2 A18b human framework regions, respectively. The human JH6 (WGQGTTVTVSS: SEQ ID NO: 133) and JK2 (FGQGTKLEIK: SEQ ID NO: 134) sequences were selected as the C-terminal peptides for the humanized heavy and light chains, respectively, to generate humanized heavy chain (12G6-SFD1) and light chain (12G6-VK1) variable region sequences for 12G6 (FIGS. 28A and 28B). When the 12G6-SFD1 heavy chain variable region and 12G6-VK1 light chain variable region were combined in the humanized 12G6-SFD1/K1 antibody, the binding affinity for CD52 was greatly reduced. Binding affinity was restored by introducing back mutations to the CDR grafted structure. Single or multiple back mutations were incorporated into both the humanized heavy and light chain variable region sequences. The positions of these back mutations (as denoted by the Kabat numbering system) are depicted in Table 12 and Table 13 below. Antibodies generated with these back mutations were evaluated for restored binding affinity. Four light chain variants (12G6-VK1(Y36V), also referred to as 12G6-VK10; 12G6-VK1(Y36V-Q45K-L46R), also referred to as 12G6-VK11; 12G6-VK1(Y36V-L46R), also referred to as 12G6-VK12; and 12G6-VK1(L46R), also referred to as 12G6-VK13) and three heavy chain variants (12G6-SFD1(L78V), also referred to as 12G6-VH10; 12G6-SFD1(G49A), also referred to as 12G6-VH11; and 12G6-SFD1(G49A-L78V), also referred to as 12G6-VH12) were generated using standard molecular biology techniques. The amino acid sequences for the CDR grafted heavy chain variable region sequence 12G6-SFD1 and back mutants 12G6-VH10, 12G6-VH11, and 12G6-VH12 are shown in FIG. 28A with the back mutated amino acids underlined and the CDRs boldfaced. Similarly, for the light chain sequences, CDR grafted variable region sequence 12G6-VK1 and back mutants 12G6-VK10, 12G6-VK11, 12G6-VK12, and 12G6-VK13 are shown in FIG. 28B with the back mutated amino acids underlined and the CDRs boldfaced.

The full-length heavy chain amino acid sequence of 12G6-SFD1 (SEQ ID NO: 279) and the full-length light chain amino acid sequence of 12G6-K12 (SEQ ID NO: 280) are shown in FIG. 109.

TABLE 12

12G6 clone heavy chain back mutants

| Clone ID | Mutation (Kabat numbering position) |
| --- | --- |
| 12G6-VH10 | L to V (78) |
| 12G6-VH11 | G to A (49) |
| 12G6-VH12 | G to A (49) and L to V (78) |

TABLE 13

12G6 clone light (kappa) chain back mutants

| Clone ID | Mutation (Kabat numbering position) |
| --- | --- |
| 12G6-VK10 | Y to V (36) |
| 12G6-VK11 | Y to V (36), QL to KR (45, 46) |
| 12G6-VK12 | Y to V (36), L to R (46) |
| 12G6-VK13 | L to R (46) |

Example 26

Figure 29:
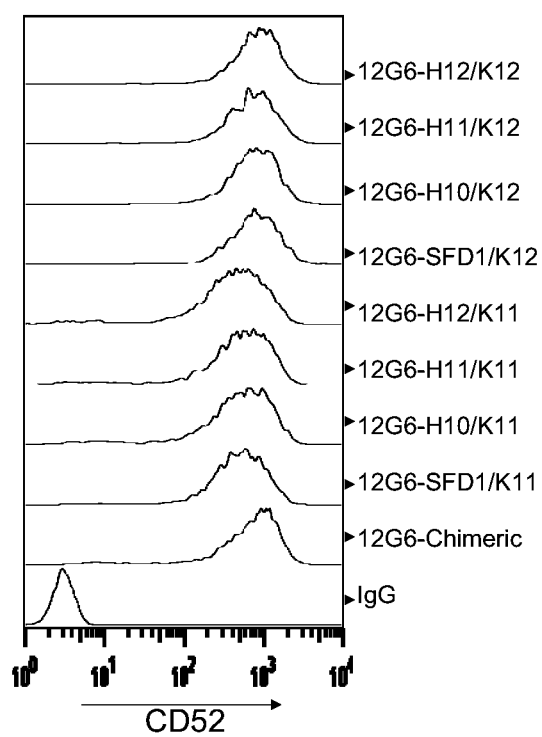
FIG. 29 is a histogram showing that chimeric and a subset of the humanized 12G6 antibodies bind equivalently to cells expressing CD52. The X axis represents the fluorescence emitted by the bound anti-CD52 antibody, while the area of each peak represents the total cell population.

Assessment of the Binding Activities of Chimeric and Humanized 12G6 Monoclonal Antibodies Chimeric and humanized 12G6 antibodies were produced and purified using the methods described in Example 3. A number of the humanized antibodies produced by pairing heavy chain variants with light chain variants, and a corresponding chimeric antibody, were analyzed by flow cytometry for their ability to bind to CD52 expressed on the surface of CHO-CD52 cells, using the methods described in Example 22. The binding data suggest that clones generated by pairing heavy chain variants with light chain variants 12G6-VK1, 12G6-VK10, or 12G6-VK13 had reduced binding ability, while clones generated by pairing heavy chain variants with 12G6-VK11 or 12G6-VK12 showed binding equivalent to or better than that of the corresponding chimeric 12G6 antibody. A representative histogram of selected clones (FIG. 29) compares the level of CD52 detected by chimeric and humanized 12G6 antibodies. These results indicate that the back mutation of two amino acid residues in the 12G6 light chain variable region (clone 12G6-VK12) was sufficient to completely restore antibody specificity. The changes at Kabat numbering residues 36 (Y to V) and 46 (L to R) were able to restore binding when paired with almost any heavy chain variant. As such, the humanized 12G6 clone showing restored binding with minimal framework residues derived from the original mouse antibody is 12G6-SFD1/K12.

Example 27

Humanization of Anti-CD52 Antibody Clone 9D9

Humanization of anti-human CD52 antibody clone 9D9 was performed by grafting the CDR regions from the mouse 9D9 antibody into a human antibody variable region framework as described in Example 14 for clone 4B10 antibody humanization. CDR-1, CDR-2, and CDR-3 sequences of the heavy chain and light chain of 9D9 were grafted into VH3-23 and VK2 A18b human framework regions, respectively. The human JH6 (WGQGTTVTVSS: SEQ ID NO: 133) and JK2 (FGQGTKLEIK: SEQ ID NO: 134) sequences were selected as the C-terminal peptides for the humanized heavy and light chains, respectively, to generate humanized heavy chain (9D9-VH10) and light chain (9D9-VK2) variable region sequences (FIGS. 30A and 30B). When the 9D9-VH10 heavy chain and 9D9-VK2 light chain were combined in the humanized 9D9-H10/K2 antibody, the binding affinity for CD52 was greatly reduced. Binding affinity was restored by introducing back mutations to the CDR grafted structure. Single or multiple back mutations were incorporated into both the humanized heavy and light chain variable region sequences. The positions of the back mutations (as denoted by the Kabat numbering system) are depicted in Table 14 and Table 15 below. Antibodies generated with these back mutations were evaluated for restored binding affinity. Four light chain variants (9D9-VK2(Y36L-Q45K-L46R), also referred to as 9D9-VK12; 9D9-VK2(Y36L-L46R), also referred to as 9D9-VK13; 9D9-VK2(L46R), also referred to as 9D9-VK14; and 9D9-VK2(Q45K-L46R), also referred to as 9D9-VK15) and five heavy chain variants (9D9-VH10(W47L-V48T-549A-N765-L78V), also referred to as 9D9-VH11; 9D9-VH10 (W47L-V48T-S49A), also referred to as 9D9-VH15; 9D9-VH10(W47L), also referred to as 9D9-VH16; 9D9-VH10 (W47L-V48T), also referred to as 9D9-VH17; and 9D9-VH10(W47L-S49A), also referred to as 9D9-VH18) were generated using standard molecular biology techniques. The amino acid sequences for CDR-grafted heavy chain variable region sequence 9D9-VH10 and back mutants 9D9-VH11, 9D9-VH15, 9D9-VH16, 9D9-VH17, and 9D9-VH18 are shown in FIG. 30A with the back mutated amino acids underlined and the CDRs boldfaced. Similarly, for the light chain sequences, CDR-grafted variable region sequence 9D9-VK2 and back mutants 9D9-VK12, 9D9-VK13, 9D9-VK14, and 9D9-VK15 are shown in FIG. 30B with the back mutated amino acids underlined and the CDRs boldfaced.

The full-length heavy chain amino acid sequences of 9D9-H16 (SEQ ID NO: 276) and 9D9-H18 (SEQ ID NO: 277), and the full-length light chain amino acid sequence of 9D9-K13 (SEQ ID NO: 278) are shown in FIG. 108.

TABLE 14

9D9 heavy chain back mutants

| Clone ID | Mutation (Kabat numbering position) |
| --- | --- |
| 9D9-VH11 | WVS to LTA (47-49), N to S (76), L to V (78) |
| 9D9-VH15 | WVS to LTA (47-49) |
| 9D9-VH16 | W to L (47) |
| 9D9-VH17 | WV to LT (47, 48) |
| 9D9-VH18 | W to L (47) and S to A (49) |

TABLE 15

9D9 light (kappa) chain back mutants

| Clone ID | Mutation (Kabat numbering position) |
| --- | --- |
| 9D9-VK12 | Y to L (36) and QL to KR (45, 46) |
| 9D9-VK13 | Y to L (36) and L to R (46) |
| 9D9-VK14 | L to R (46) |
| 9D9-VK15 | QL to KR (45, 46) |

Example 28

Figure 31:
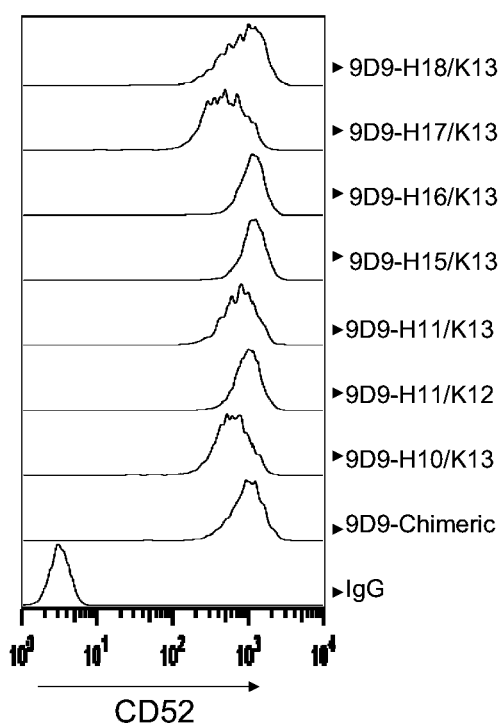
FIG. 31 is a histogram showing that chimeric and a subset of the humanized 9D9 antibodies bind equivalently to cells expressing CD52. The X axis represents the fluorescence emitted by the bound anti-CD52 antibody, while the area of each peak represents the total cell population.

Assessment of the Binding Activities of Chimeric and Humanized 9D9 Monoclonal Antibodies Chimeric and humanized 9D9 antibodies were produced and purified using the methods described in Example 3. A number of the humanized antibodies produced by pairing heavy chain variants with light chain variants, and a corresponding chimeric antibody, were analyzed by flow cytometry for their ability to bind to CD52 expressed on the surface of CHO-CD52 cells (CHO cells engineered to express human CD52), using the methods described in Example 22. The binding data suggest that clones generated by pairing heavy chain variants with light chain variants 9D9-VK2, 9D9-VK14, or 9D9-VK15 had reduced binding ability, while clones generated by pairing 9D9-VK12 or 9D9-VK13 light chain variants with back mutated heavy chain variants 9D9-VH11, 9D9-VH15, 9D9-VH16, and 9D9-VH18 showed binding equivalent to or better than that of the corresponding chimeric 9D9 antibody. When light chain variants 9D9-VK12 and 9D9-VK13 were paired with the parental CDR grafted heavy chain 9D9-VH10 or the back mutated 9D9-VH17 sequence, binding was significantly reduced, suggesting that for humanized 9D9 clones, both heavy chain and light chain sequences have to be engineered with back mutations to restore binding ability. A representative histogram of selected clones (FIG. 31) compares the level of CD52 detected by chimeric and humanized 9D9 antibodies. These results indicate that the back mutation of two amino acid residues (e.g., Y to L at position 36, and L to R at position 46) in the 9D9 light chain variable region (clone 9D9-VK13) was necessary to restore antibody specificity when paired with heavy chains that were mutated at one position (e.g., W to L, at position 47) or at two positions (e.g., W to L at position 47 and S to A at position 49). As such, the humanized 9D9 clones showing restored binding with minimal framework residues derived from the original mouse antibody are 9D9-H16/K13 and 9D9-H18/K13.

Example 29

Figure 32A:
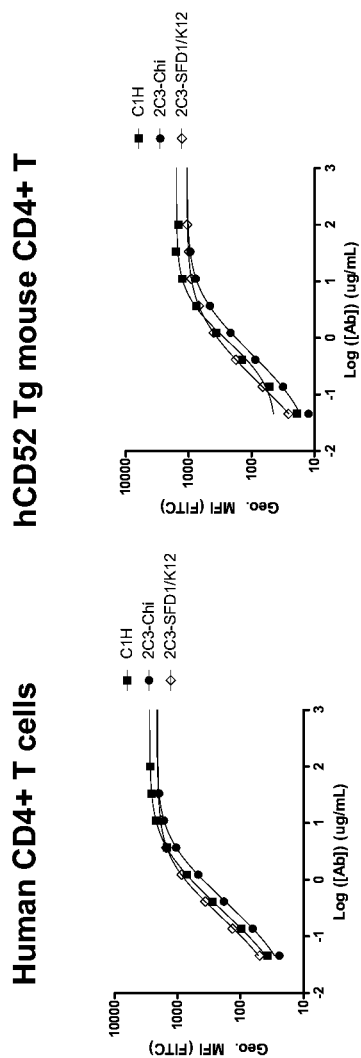
FIG. 32A shows the binding curves of Campath-1H® ("C1H"), a chimeric 2C3 antibody, and a humanized 2C3-SFD1/K12 antibody to primary human T cells and huCD52 transgenic mouse T cells.
Figure 32B:
FIG. 32B shows the binding curves of Campath-1H® ("C1H"), a chimeric 9D9 antibody, and humanized 9D9 antibodies to primary human T cells and huCD52 transgenic mouse T cells.
Figure 32C:
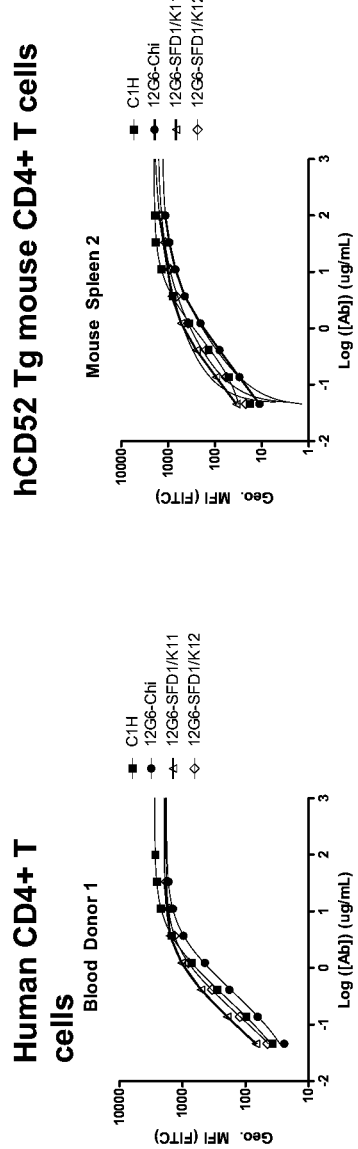
FIG. 32C shows the binding curves of Campath-1H® ("C1H"), a chimeric 12G6 antibody, and humanized 12G6 antibodies to primary human T cells and huCD52 transgenic mouse T cells.

Determination of Relative Binding Efficiency of Humanized Anti-Human CD52 Antibodies The $EC_{50}$ values of chimeric and humanized anti-CD52 antibodies were estimated using CD4+ T cells isolated from healthy donor PBMCs obtained from commercial sources (Bioreclamation, NY, USA). CD4+ T cells were isolated by negative selection using an EasySep kit (Stem Cell Technologies). CD4+ T cells isolated from huCD52 transgenic CD1 mouse spleen tissue were also used (Stem Cell Technologies) according to the methods described above in Example 20 for CHO-CD52 cells. Briefly, human CD4+ T cells were isolated from 50 ml of peripheral blood from healthy volunteers (Bioreclamation), and huCD52 transgenic mouse CD4+ T cells were isolated from spleen tissue. Cells were rinsed with PBS/5% FBS and deposited into round-bottom 96 well plates at $1 \times 10^5$ cells per well. Primary antibody staining was done with an 8 point serial dilution (1:3) of each anti-CD52 chimeric and humanized antibody starting at 100 µg/mL. A FITC-conjugated goat $F(ab)_2$ fragment of anti-human Fc gamma at 10 µg/mL (Jackson 109-096-098) secondary antibody was used. Cells were washed 3 times in ice-cold PBS/ 5% FBS before and after each incubation. Cells were fixed with PBS containing 2% methanol-free paraformaldehyde and evaluated by flow cytometry. The flow cytometry data was analyzed using GraphPad Prism software to determine an $EC_{50}$ value with 95% confidence interval. Based on the binding of anti-CD52 antibodies to CD4+ T cells isolated from human PBMCs and to CD4+ T cells isolated from spleen tissue of human CD52 transgenic mice, binding curves (FIGS. 32A, 32B, 32C) were generated and $EC_{50}$ values estimated and shown in FIG. 33. All of the antibodies showed similar binding characteristics to both human CD4+ T cells and to CD4+ T cells isolated from human CD52 transgenic mice. Binding data indicate that the humanized antibodies have equivalent or better binding affinities compared to their parental chimeric antibodies, suggesting that binding affinity is retained or improved upon humanization. Humanized 2C3 and 12G6 antibodies have at least two fold lower $EC_{50}$ values than a Campath-1H® antibody as determined by this cell binding assay.

Example 30

Evaluation of the Binding of Humanized Anti-CD52 Antibodies to a Defined Lymphocyte Population Campath-1H® (C1H) and humanized 2C3 (2C3-SFD1/K12), 9D9 (9D9-H16/K13 and 9D9-H18/K13), and 12G6 (12G6-SFD1/K11, 12G6-SFD1/K12) antibodies were evaluated for their binding to various PBMC subsets in normal donor PBMCs using the methods described above in Example 7 for chimeric anti-CD52 antibodies. A number of fluorochrome conjugated antibodies were used for flow cytometric analysis. Anti-CD27-PE, anti-CD19 and anti-CD11c-PE Cy5, anti-CD56 and anti-CD123-PE Cy7, anti-CD16-APC Cy7, and CD4-APC were obtained from BD Biosciences (San Diego, Calif.), while anti-CD54RA-ECD and anti-HLA-DR-ECD were obtained from Beckman Coulter. Anti-CD3-Pacific Blue, anti-CD8 and anti-CD14-Pacific Orange, and anti-CD4-APC cy5.5 were obtained from Invitrogen (CA). All of the humanized anti-human CD52 antibodies (9D9-H18/K13, 9D9-H16/K13, 12G6-SFD1/K11, 12G6-SFD1/K12, and 2C3-SFD1/K12) as well as the Campath-1H® were conjugated to FITC. Healthy human peripheral blood mononuclear cells were obtained either from cryopreserved buffy coats or from mononuclear cells separated from the blood of normal donors obtained from commercial vendors (Bioreclamation, NY, USA) as described above in Example 7. For enrichment of mononuclear cells, human peripheral blood was diluted 1:1 with sterile phosphate buffered saline (PBS) and carefully layered over Ficoll-Hypaque (GE Healthcare Bio-Sciences, Uppsala, Sweden) and centrifuged for 30 min at room temperature. The interphase layer of mononuclear cells was drawn out and washed in PBS containing 5% fetal bovine serum (FACS buffer). Contaminating red blood cells (RBCs) were lysed with RBC lysing solution (Sigma, St. Louis, Mo., USA). Cells were resuspended in cold FACS buffer and the debris was removed using a 40 µm filter. Multi color flow cytometry was performed to evaluate the binding ability of humanized anti-human CD52 antibodies 2C3 (2C3-SFD1/K12), 9D9 (9D9-H16/K13 and 9D9-H18/K13) and 12G6 (12G6-SFD1/K11 and 12G6-SFD1/K12) as compared to Campath-1H®.

Figure 34:
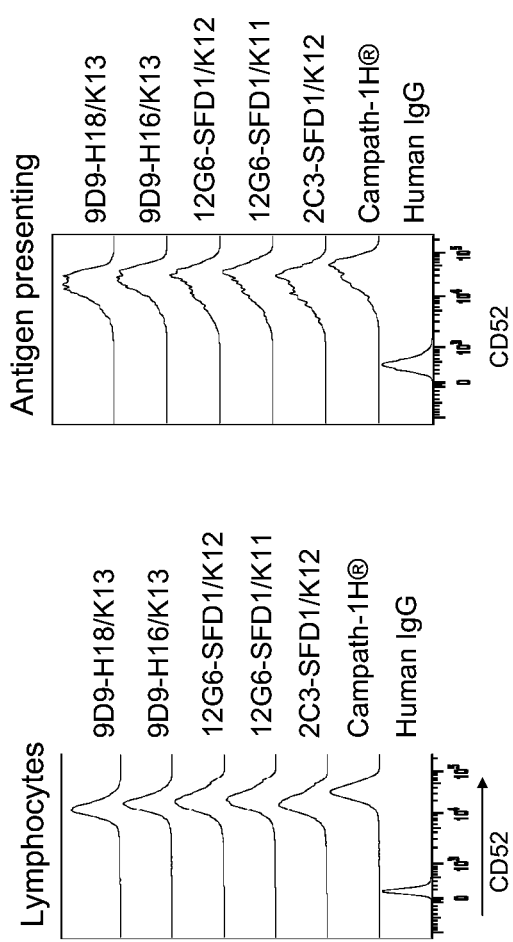
FIG. 34 illustrates the comparative binding patterns of humanized anti-CD52 Campath-1H®, 2C3, 12G6, and 9D9 antibodies to defined subsets of human peripheral blood mononuclear cell populations by flow cytometry. These histograms show that the humanized anti-CD52 antibody binding is equivalent to that of Campath-1H® for various CD52 expressing human PBMC subsets. The X axis represents the fluorescence emitted by the bound anti-CD52 antibody, while the area of each peak represents the total cell population.

Briefly, replicates of $1 \times 10^6$ PBMCs in FACS buffer were incubated with cocktails of pre-titrated dilutions of antibodies to examine either lymphocyte or myeloid derived cells. The lymphocyte cocktail comprised antibodies against CD3, CD27, CD45RA, CD56, CD19, CD8, CD4, and CD16. The antibody cocktail to define myeloid populations included antibodies against HLA-DR, CD11c, CD123, CD4, and CD14. In each of the cocktails, one of the anti-CD52 antibodies was included at 10 μg/ml concentration. The cells were stained for 30 min at 4° C. and were washed and fixed in PBS containing 1% paraformaldehyde. 100,000 events of the stained cells were acquired on a BD LSR II flow cytometer (BD Biosciences, San Jose, Calif.), and the data was analyzed using FlowJo version 7.2 software (Tree Star, Inc, Oregon, USA). Multiple subsets with distinct phenotypic characteristics have been defined among B and T lymphocytes, and CD52 has been shown to be expressed on all human lymphocytes. Multi color flow cytometry analysis was performed to identify the lymphocyte subsets, and to assess similarities and differences in the binding characteristics of the humanized anti-CD52 antibodies to cell surface CD52 on defined subsets. Using a combination of markers, phenotypically distinct cell populations corresponding to B, T, NK and antigen presenting cell lineages were first defined. The intensity of staining, which corresponds to the ability of humanized anti-CD52 antibodies to detect CD52 expression on each of the defined cell populations, was assessed and compared to that of Campath-1H®. The histograms (FIG. 34) compare the level of CD52 detected by each antibody on individual populations. The results indicate that all of the humanized anti-CD52 antibodies bind to cell surface CD52 to a similar extent. Further, no differences were observed between Campath-1H® and humanized anti-CD52 antibodies with respect to the level of detection of cell surface CD52. Analysis was performed on six different donors. Representative data generated using cells derived from one donor is shown in FIG. 34. A similar binding pattern was observed with cells from other donors.

Example 31

Figure 35:
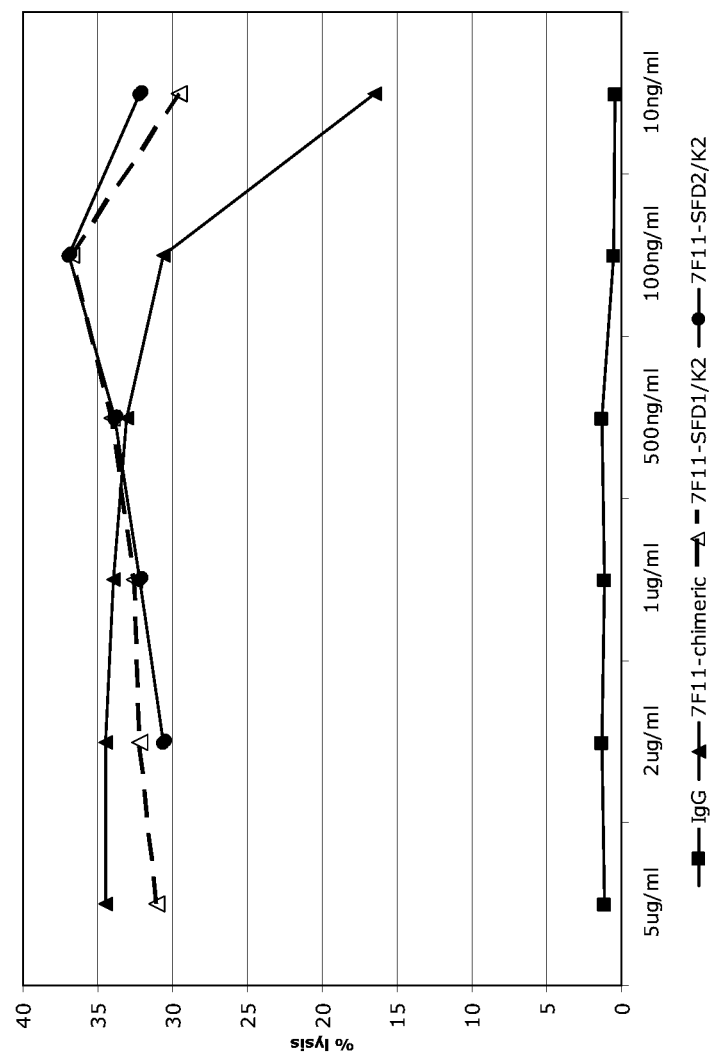
FIG. 35 is a graph showing that chimeric and humanized 7F11 antibodies mediate equivalent ADCC activity on cells expressing CD52.

Assessment of the ADCC Activities of Chimeric and Humanized 7F11 Monoclonal Antibodies Humanized and chimeric 7F11 antibodies were evaluated for their ability to mediate ADCC killing of CD52 expressing cells. An ADCC assay was carried out using the methods described above in Example 6. Briefly, CHO K1 cells engineered to express CD52 protein (CHO-CD52) were used as target cells. The target cells were labeled with $Na_2{}^{51}CrO_4$ (New England Nuclear, Boston, Mass.) at 37° C. for 2-3 hrs. The cells were washed, re-suspended in RPMI 1640 media with 10% FCS, and mixed with an IgG control antibody, a chimeric 7F11 antibody, or a humanized 7F11 antibody (7F11-SFD1/K2 or 7F11-SFD2/K2) at various concentrations ranging from 5 μg/ml to 0.01 μg/ml. Human NK cells isolated from PBMCs using an NK cell isolation kit (Stem Cell Technologies) were used as effector cells and were added at a 1:5 target to effector cell ratio. After 2-6 hrs incubation, 25 μl of cell-free supernatant were collected from each well and counted in a MicroBeta Trilux Scintillation Counter (Wallac, Gaithersburg, Md.). The amount of $^{51}Cr$ spontaneously released was obtained by incubating target cells in medium alone. Spontaneous release from target cells was typically less than 20%. The total amount of $^{51}Cr$ incorporated was determined by adding 1% Triton X-100 in distilled water, and the percentage lysis was calculated as follows: [(sample c.p.m.−spontaneous c.p.m.)/(total c.p.m.−spontaneous c.p.m.)]×100. FIG. 35 illustrates the concentrations of control IgG, chimeric 7F11 antibody, and humanized 7F11 antibodies used in the assay (X axis) vs. % specific lysis (Y axis). The results indicate that humanized 7F11 antibodies (7F11-SFD1/K2 and 7F11-SFD2/K2) mediated equivalent or slightly better ADCC killing as compared to a chimeric 7F11 antibody. The control IgG1 isotype showed only low levels of background killing at the concentrations tested.

Example 32

Figure 36:
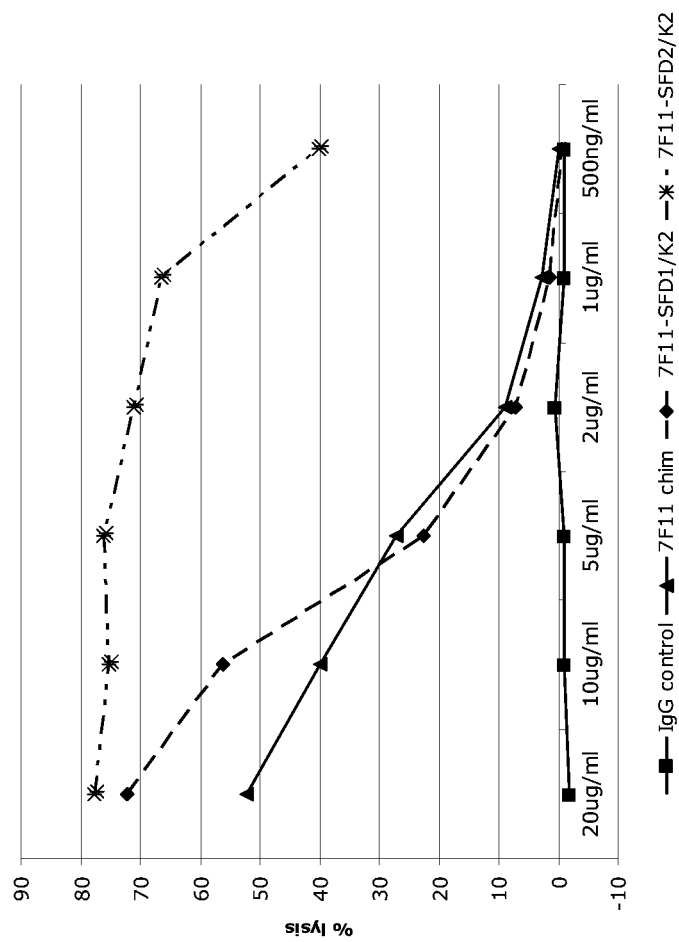
FIG. 36 is a graph showing that chimeric and humanized 7F11 antibodies mediate CDC activity on cells expressing CD52.

Assessment of the CDC Activities of Chimeric and Humanized 7F11 Monoclonal Antibodies Humanized and chimeric 7F11 antibodies were evaluated for their ability to mediate complement dependent cytotoxicity (CDC) of CD52 expressing cells. A CDC assay was carried out using the methods described above in Example 5 for chimeric anti-CD52 antibodies. Briefly, CHO K1 cells engineered to express CD52 protein (CHO-CD52) were used as target cells and labeled with $Na_2{}^{51}CrO_4$ (New England Nuclear, Boston, Mass.) at 37° C. for 2-3 hrs. The cells were washed, resuspended in RPMI 1640 media, and mixed with an IgG control antibody, a chimeric 7F11 antibody, or a humanized 7F11 antibody (7F11-SFD1/K2 or 7F11-SFD2/K2) at various concentrations ranging from 20 μg/ml to 500 ng/ml. Human complement (Sigma) was added to the experimental wells to a final concentration of 10%. After a 1-5-hour incubation, 25 μl of cell-free supernatant were collected from each well and counted in a MicroBeta Trilux Scintillation Counter (Wallac, Gaithersburg, Md.). The amount of $^{51}Cr$ spontaneously released was obtained by incubating target cells in medium alone. Spontaneous release from target cells was typically less than 20%. The total amount of $^{51}Cr$ incorporated was determined by adding 1% Triton X-100 in distilled water, and the percentage lysis was calculated as follows: [(sample counts per minute (c.p.m.)−spontaneous c.p.m.)/(total c.p.m.−spontaneous c.p.m.)]×100. FIG. 36 illustrates the concentrations of control IgG, chimeric 7F11 antibody, and humanized 7F11 antibodies (7F11-SFD1/K2 and 7F11-SFD2/K2) used in the assay (X axis) vs. % specific lysis (Y axis). The results indicate that the chimeric 7F11 antibody and humanized antibody 7F11-SFD1/K2 mediated equivalent killing, while humanized antibody 7F11-SFD2/K2 mediated significantly better CDC killing than the chimeric 7F11 antibody. The control IgG1 isotype antibody showed only low levels of background killing at the concentrations tested.

Example 33

Figure 37:
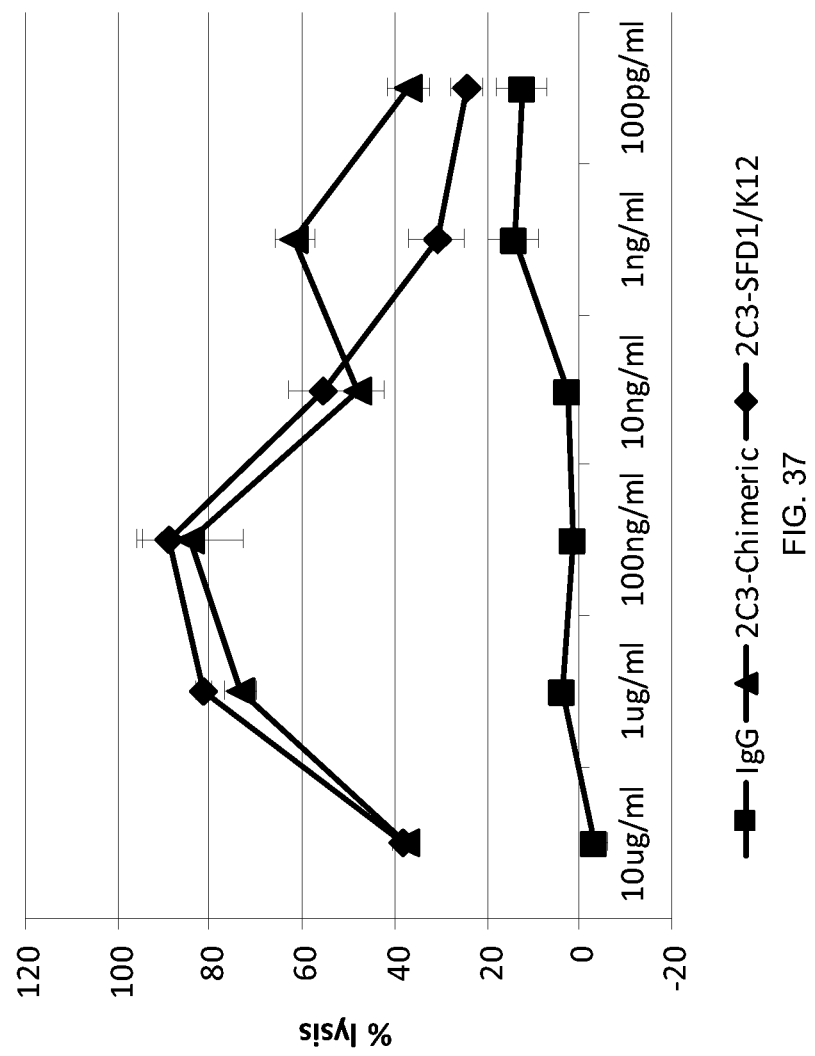
FIG. 37 is a graph showing that chimeric and humanized 2C3 antibodies mediate ADCC activity on cells expressing CD52.

Assessment of the ADCC Activities of Chimeric and Humanized 2C3 Monoclonal Antibodies Humanized and chimeric 2C3 antibodies were evaluated for their ability to mediate ADCC killing of CD52 expressing cells. An ADCC assay was carried out using the methods described above in Example 6, with slight modifications. Briefly, T cells isolated from healthy donor PBMCs using a CD4+ T cell isolation kit (Stem Cell Technologies) were used as target cells. The target cells were labeled overnight with $Na_2{}^{51}CrO_4$ (New England Nuclear, Boston, Mass.) at 37° C. The cells were washed, re-suspended in RPMI 1640 media with 10% FCS, and mixed with an IgG control antibody, a chimeric 2C3 antibody, or a humanized 2C3 antibody (2C3-SFD1/K12) at various concentrations ranging from 10 μg/ml to 100 pg/ml. Human NK cells isolated from PBMCs (using an NK cell isolation kit from Stem Cell Technologies) were used as effector cells and were added at a 1:5 target to effector cell ratio. After 2-6 hrs of incubation, 25 μl of cell-free supernatant were collected from each well and counted in a MicroBeta Trilux Scintillation Counter (Wallac, Gaithersburg, Md.). The amount of $^{51}Cr$ spontaneously released was obtained by incubating target cells in medium alone. Spontaneous release from target cells was typically less than 20%. The total amount of $^{51}$Cr incorporated was determined by adding 1% Triton X-100 in distilled water, and the percentage lysis was calculated as follows: [(sample c.p.m.–spontaneous c.p.m.)/(total c.p.m.–spontaneous c.p.m.)]×100. FIG. 37 illustrates the concentrations of control IgG, chimeric 2C3 antibody, and humanized 2C3 antibody (2C3-SFD1/K12) used in the assay (X axis) vs. % specific lysis (Y axis). The results indicate that the humanized 2C3 antibody 2C3-SFD1/K12 mediated ADCC killing equivalent to that of the 2C3 chimeric antibody. The IgG1 isotype control showed only low levels of background killing at the concentrations tested.

Example 34

Figure 38:
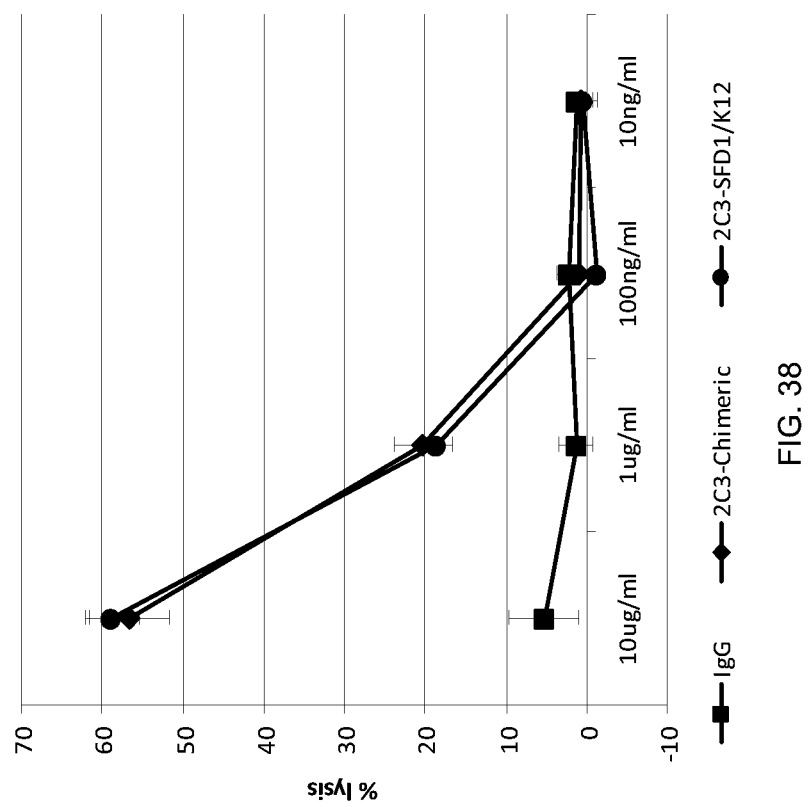
FIG. 38 is a graph showing that chimeric and humanized 2C3 antibodies mediate CDC activity on cells expressing CD52.

Assessment of the CDC Activities of Chimeric and Humanized 2C3 Monoclonal Antibodies Humanized and chimeric 2C3 antibodies were evaluated for their ability to mediate complement dependent cytotoxicity (CDC) of CD52 expressing cells. A CDC assay was carried out using the methods described above in Example 5, with slight modifications. Briefly, T cells isolated from healthy donor PBMCs were used as target cells and labeled overnight with Na$_2$$^{51}$CrO$_4$ (New England Nuclear, Boston, Mass.) at 37° C. After overnight labeling, the cells were washed, re-suspended in RPMI 1640 media with 10% FCS, and mixed with an IgG control antibody, a chimeric 2C3 antibody, or a humanized 2C3 antibody (2C3-SFD1/K12) at various concentrations ranging from 10 µg/ml to 10 ng/ml. Human complement (Sigma) was added to the experimental wells to a final concentration of 10%. After a 1-5 hour incubation, 25 µl of cell-free supernatant were collected from each well and counted in a MicroBeta Trilux Scintillation Counter (Wallac, Gaithersburg, Md.). The amount of $^{51}$Cr spontaneously released was obtained by incubating target cells in medium alone. Spontaneous release from target cells was typically less than 20%. The total amount of $^{51}$Cr incorporated was determined by adding 1% Triton X-100 in distilled water, and the percentage lysis was calculated as follows: [(sample counts per minute (c.p.m.)–spontaneous c.p.m.)/(total c.p.m.–spontaneous c.p.m.)]×100. FIG. 38 illustrates the concentrations of control IgG, chimeric 2C3 antibody, and humanized 2C3 antibody (2C3-SFD1/K12) used in the assay (X axis) vs. % specific lysis (Y axis). The results indicate that the chimeric 2C3 antibody and the humanized 2C3 antibody (2C3-SFD1/K12) mediated equivalent lysis. The control IgG1 isotype antibody showed only low levels of background killing at the concentrations tested.

Example 35

Figure 39:
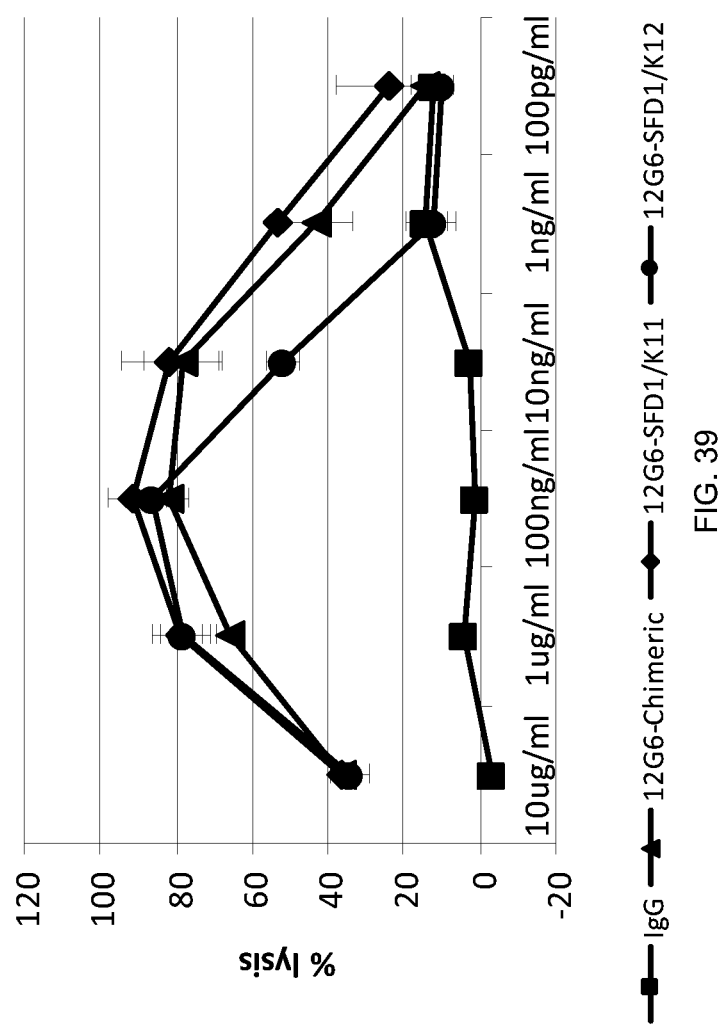
FIG. 39 is a graph showing that chimeric and humanized 12G6 antibodies mediate ADCC activity on cells expressing CD52.

Assessment of the ADCC Activities of Chimeric and Humanized 12G6 Monoclonal Antibodies Humanized and chimeric 12G6 antibodies were evaluated for their ability to mediate ADCC killing of CD52 expressing cells. An ADCC assay was carried out by chromium release assays using T cells isolated from healthy donor PBMCs as target cells, as described above in Example 31. FIG. 39 illustrates the concentrations of control IgG, chimeric 12G6 antibody, and humanized 12G6 antibodies (12G6-SFD1/K11 or 12G6-SFD1/K12) used in the assay (X axis) vs. % specific lysis (Y axis). The results indicate that humanized 12G6 antibodies 12G6-SFD1/K11 and 12G6-SFD1/K12 mediated equivalent ADCC killing as compared to the 12G6 chimeric antibody. The IgG1 isotype control showed only low levels of background killing at the concentrations tested.

Example 36

Figure 40:
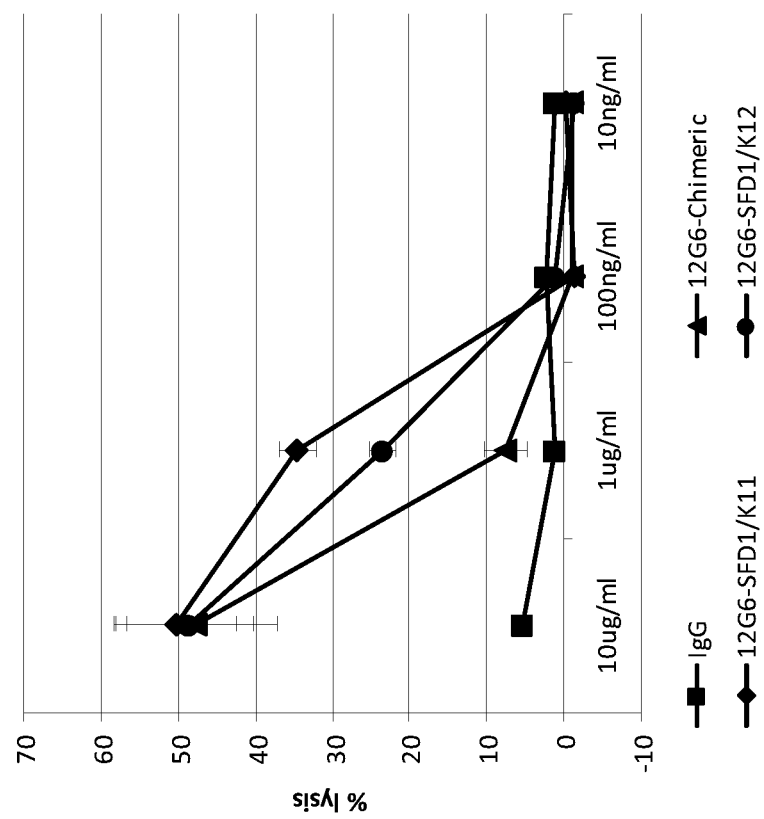
FIG. 40 is a graph showing that chimeric and humanized 12G6 antibodies mediate CDC activity on cells expressing CD52.

Assessment of the CDC Activities of Chimeric and Humanized 12G6 Monoclonal Antibodies Humanized and chimeric 12G6 antibodies were evaluated for their ability to mediate complement dependent cytotoxicity (CDC) of CD52 expressing cells. A CDC assay was carried out by chromium release assays using T cells isolated from healthy donor PBMCs as target cells, as described above in Example 32. FIG. 40 illustrates the concentrations of control IgG, chimeric 12G6 antibody, and humanized 12G6 antibodies (12G6-SFD1/K11 and 12G6-SFD1/K12) used in the assay (X axis) vs. % specific lysis (Y axis). The results indicate that the chimeric 12G6 antibody mediated equivalent lysis as compared to humanized 12G6 antibodies (12G6-SFD1/K11 and 12G6-SFD1/K12). The control IgG1 isotype antibody showed only low levels of background killing at the concentrations tested.

Example 37

Figure 41:
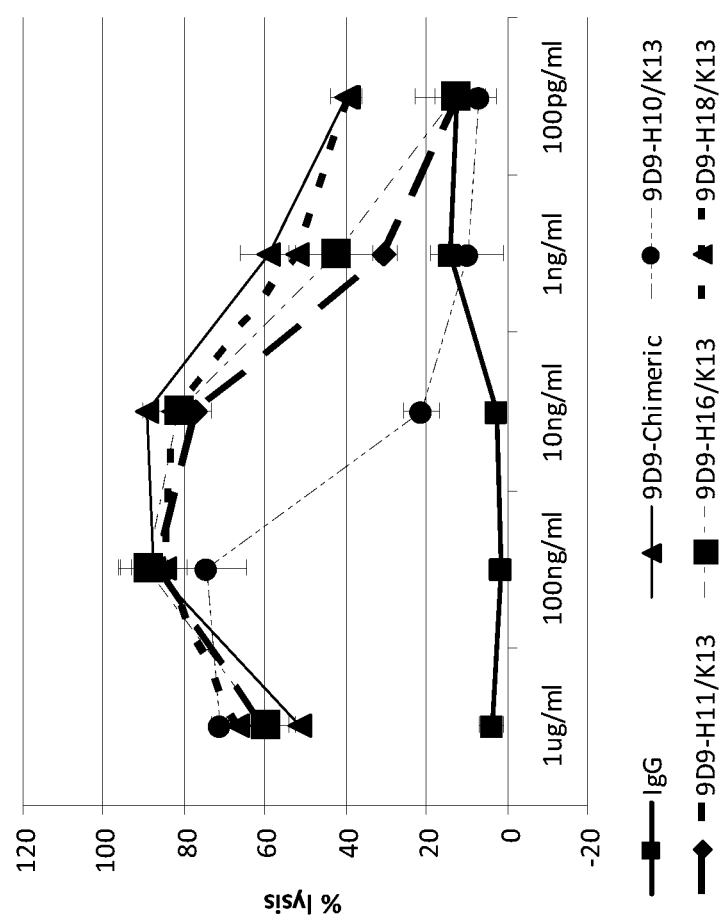
FIG. 41 is a graph showing that chimeric and humanized 9D9 antibodies mediate ADCC activity on cells expressing CD52.

Assessment of the ADCC Activities of Chimeric and Humanized 9D9 Monoclonal Antibodies Humanized and chimeric 9D9 antibodies were evaluated for their ability to mediate ADCC killing of CD52 expressing cells. An ADCC assay was carried out by chromium release assays using T cells isolated from healthy donor PBMCs as target cells, as described above in Example 31. FIG. 41 illustrates the concentrations of control IgG, chimeric 9D9 antibody, and humanized 9D9 antibodies (9D9-H10/K13, 9D9-H11/K13, 9D9-H16/K13, and 9D9-H18/K13) used in the assay (X axis) vs. % specific lysis (Y axis). The results indicate that the chimeric and humanized 9D9 antibodies (with the exception of 9D9-H10/K13) mediated equivalent ADCC killing. The IgG1 isotype control showed only low levels of background killing at the concentrations tested.

Example 38

Figure 42:
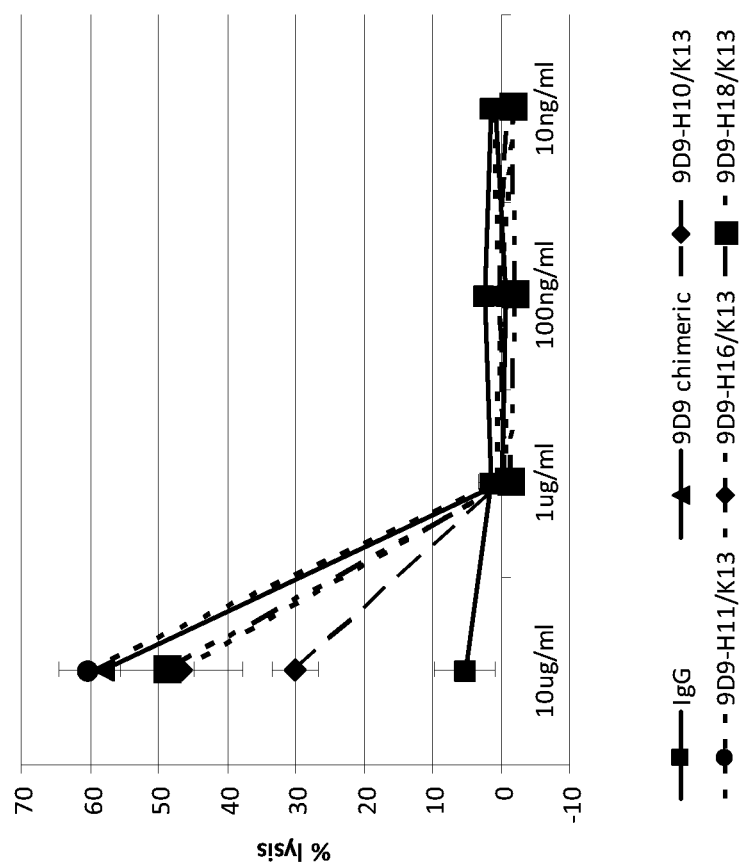
FIG. 42 is a graph showing that chimeric and humanized 9D9 antibodies mediate CDC activity on cells expressing CD52.

Assessment of the CDC Activities of Chimeric and Humanized 9D9 Monoclonal Antibodies Humanized and chimeric 9D9 antibodies were evaluated for their ability to mediate complement dependent cytotoxicity (CDC) of CD52 expressing cells. A CDC assay was carried out by chromium release assays using T cells isolated from healthy donor PBMCs as target cells, as described above in Example 32. FIG. 42 illustrates the concentrations of control IgG, chimeric 9D9 antibody, and humanized 9D9 antibodies (9D9-H10/K13, 9D9-H11/K13, 9D9-H16/K13, and 9D9-H18/K13) used in the assay (X axis) vs. % specific lysis (Y axis). The results indicate that a chimeric 9D9 antibody mediated equivalent lysis as compared to humanized 9D9 antibodies (with the exception of 9D9-H10/K13). The control IgG1 isotype antibody showed only low levels of background killing at the concentrations tested.

Example 39

Figure 43:
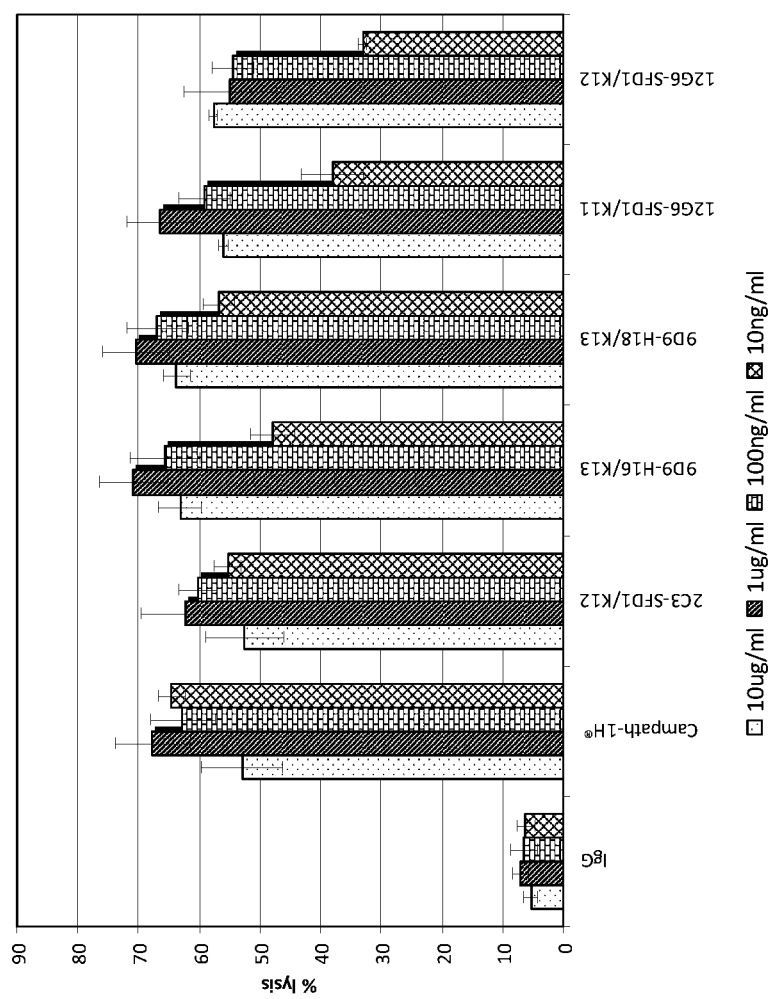
FIG. 43 is a graph showing the ADCC activity of humanized anti-CD52 antibodies on primary T cells.

Assessment of the ADCC Activities of Campath-1H® and Humanized Anti-CD52 Antibodies on Primary T Cells Campath-1H® and humanized anti-CD52 antibodies were evaluated for their ability to mediate ADCC killing of CD52 expressing cells. An ADCC assay was carried out by chromium release assays using T cells isolated from healthy donor PBMCs as target cells, as described above in Example 31. FIG. 43 illustrates the concentrations of control IgG, Campath-1H®, and humanized 2C3-SFD1/K12, 9D9-H16/K13, 9D9-H18/K13, 12G6-SFD1/K11, and 12G6-SFD1/K12 antibodies used in the assay (X axis) vs. % specific lysis (Y axis). The results indicate that the above humanized 2C3, 9D9, and 12G6 antibodies mediated ADCC killing equivalent to that of Campath-1H® at concentrations in excess of 10 ng/ml. The IgG1 isotype control showed only low levels of background killing at the concentrations tested.

Example 40

Figure 44:
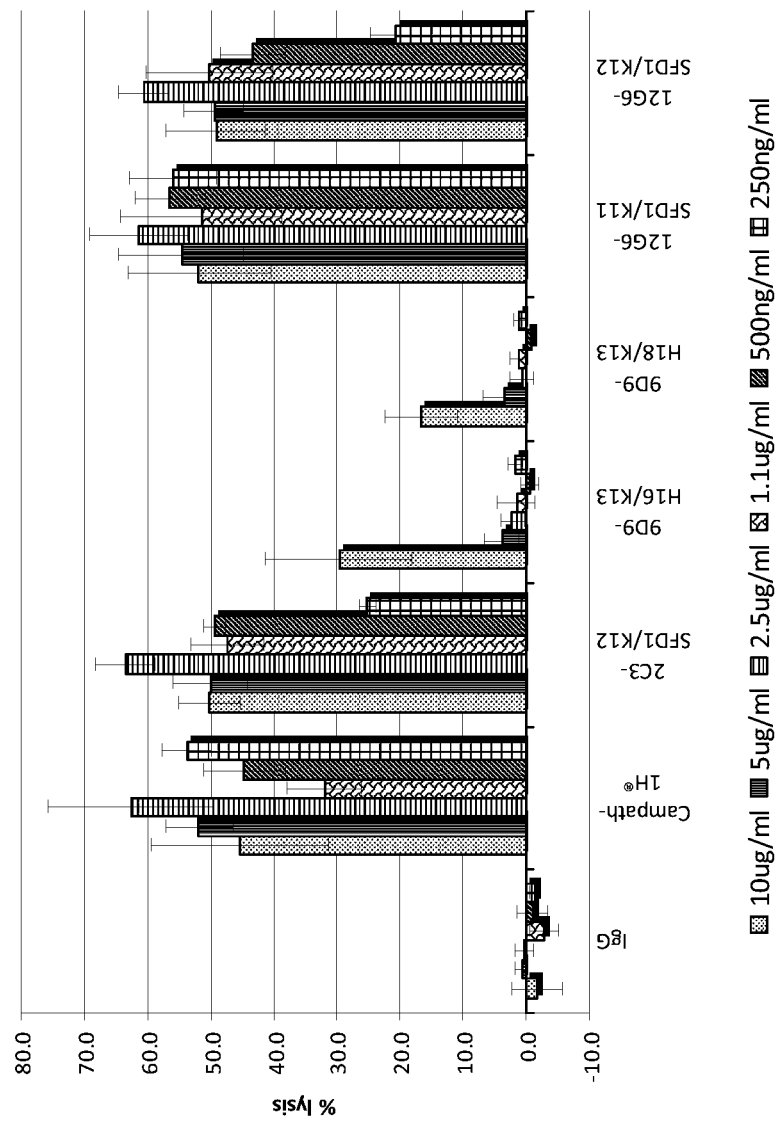
FIG. 44 is a graph showing the CDC activity of humanized anti-CD52 antibodies on primary T cells.

Assessment of the CDC Activities of Campath-1H® and Humanized Anti-CD52 Antibodies on Primary T Cells Campath-1H® and humanized anti-CD52 antibodies were evaluated for their ability to mediate complement dependent cytotoxicity (CDC) of CD52 expressing cells. A CDC assay was carried out by chromium release assays using T cells isolated from healthy donor PBMCs as target cells, as described above in Example 32. FIG. 44 illustrates the concentrations of control IgG, Campath-1H®, and humanized 2C3-SFD1/K12, 9D9-H16/K13, 9D9-H18/K13, 12G6-SFD1/K11, and 12G6-SFD1/K12 antibodies used in the assay (X axis) vs. % specific lysis (Y axis). The results indicate that humanized 2C3 and 12G6 antibodies mediated CDC killing equivalent to Campath-1H®, while humanized 9D9 antibodies demonstrated significantly reduced CDC activity, similar to their corresponding chimeric antibody. The IgG1 isotype control showed only low levels of background killing at the concentrations tested.

Example 41

Figure 45:
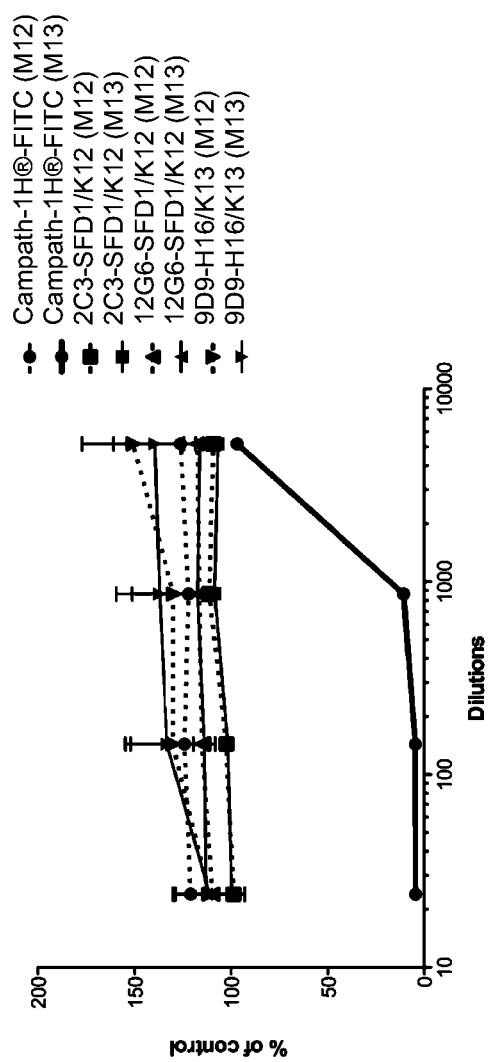
FIG. 45 is a graph showing neutralization of Campath-1H but not other anti-CD52 antibodies with CAMMS223 study human serum samples that contain anti-Campath-1H® neutralizing antibodies. Serum samples were taken from a representative patient (MS-1) at month 12 (M12) and month 13 (M13).
Figure 46A:
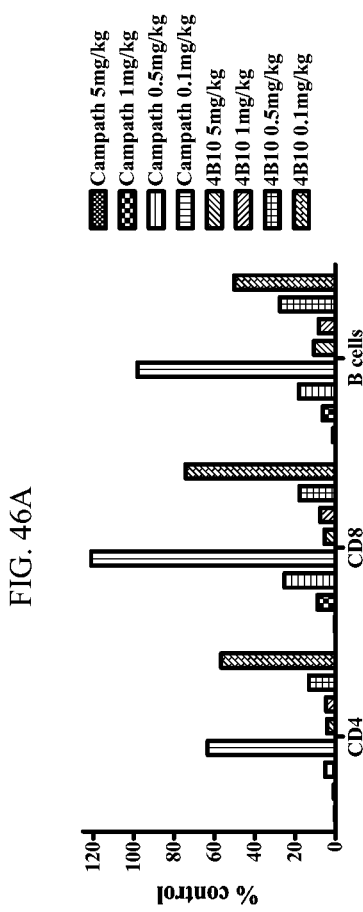
FIGS. 46A-46E show the level of CD4+ T cells, CD8+ T cells, B220+ B cells, NK cells, myeloid cells, and neutrophils in the blood 72 hours after dosing with Campath-1H® ("Campath") and humanized 4B10-H1/K1 ("4B10") antibodies.
Figure 46B:
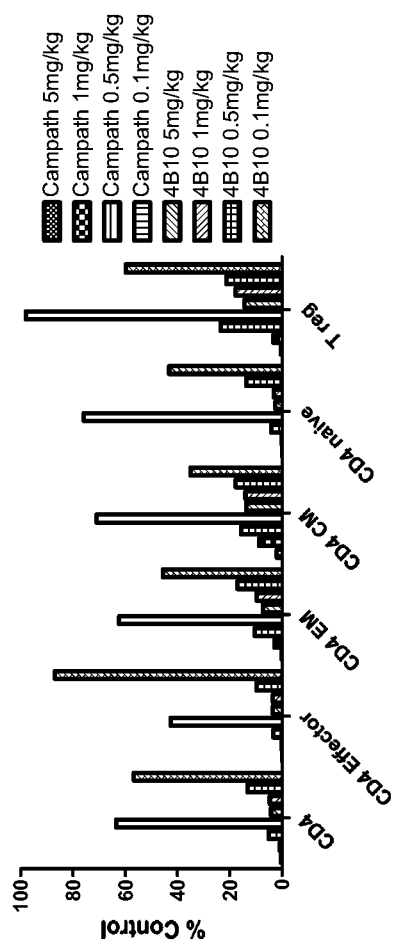
Figure 46C:
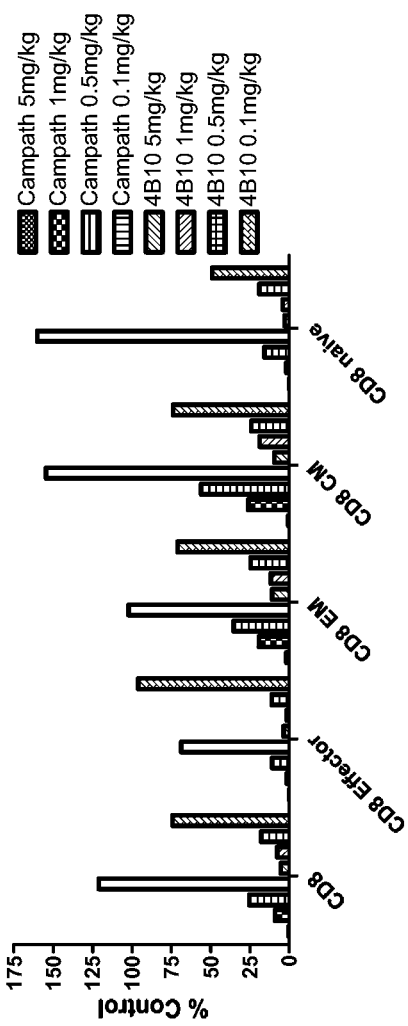
Figures 46D, 46E:
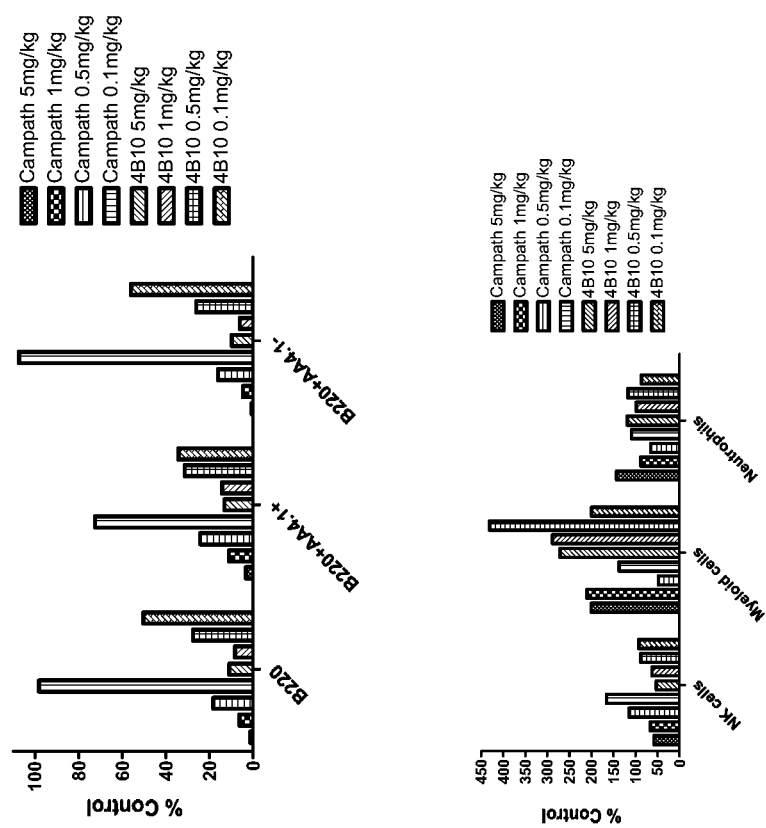
Figure 47A:
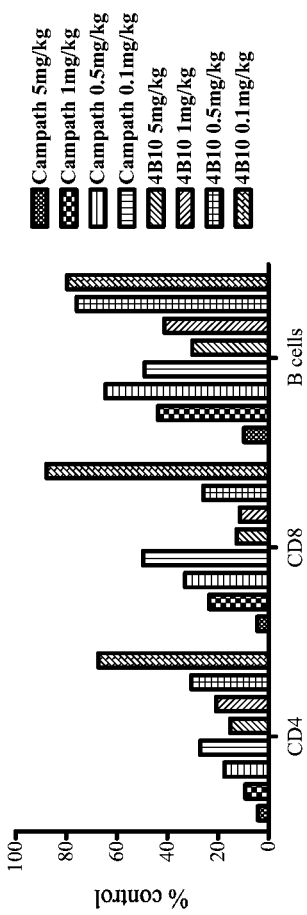
FIGS. 47A-47E show the level of CD4+ T cells, CD8+ T cells, B220+ B cells, NK cells, myeloid cells, neutrophils, and macrophages in the spleen 72 hours after dosing with Campath-1H® ("Campath") and humanized 4B10-H1/K1 ("4B10") antibodies.
Figure 47B:
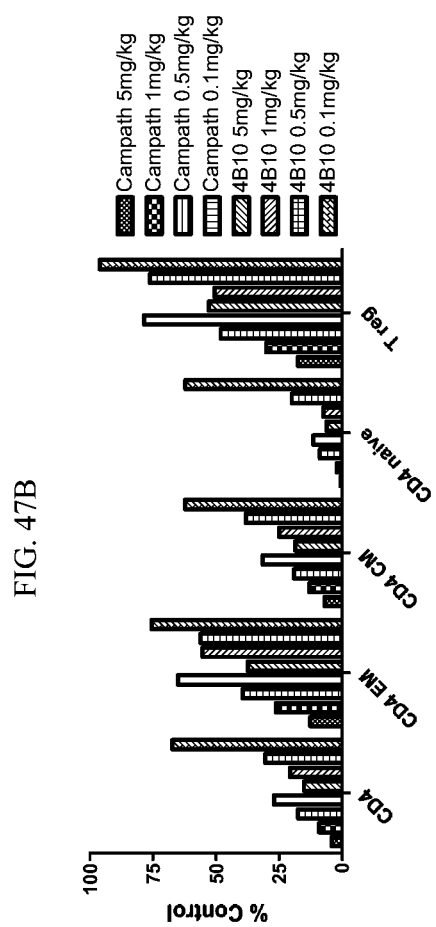
Figure 47C:
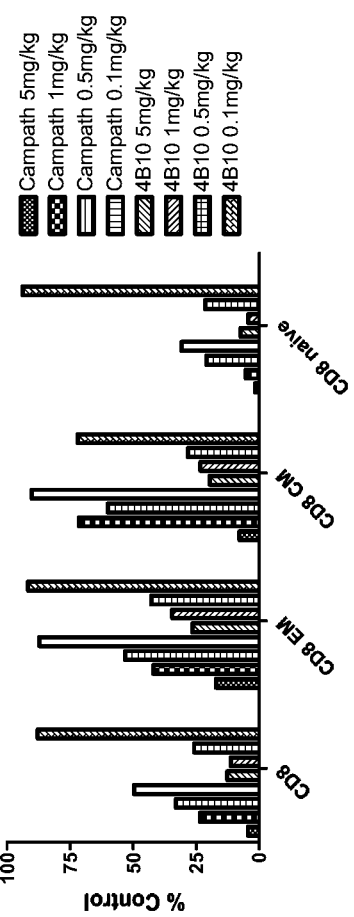
Figure 47D:
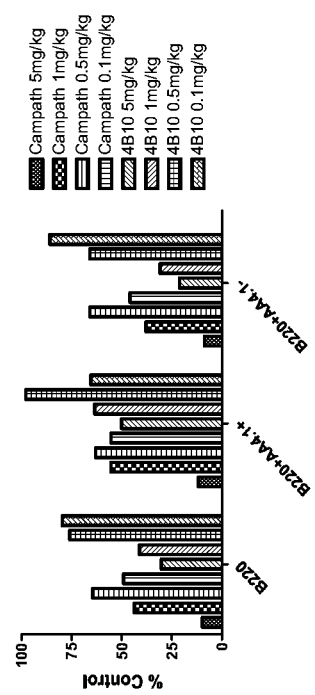
Figure 47E:
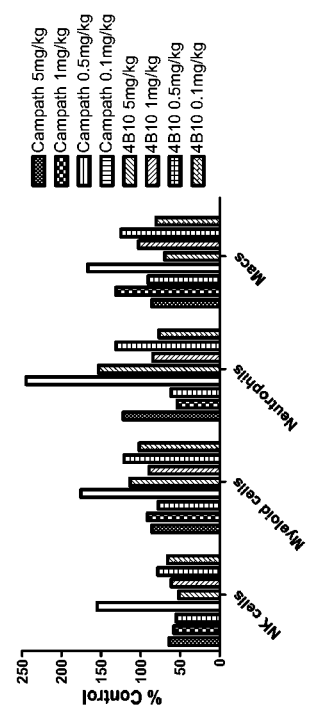
Figure 48:
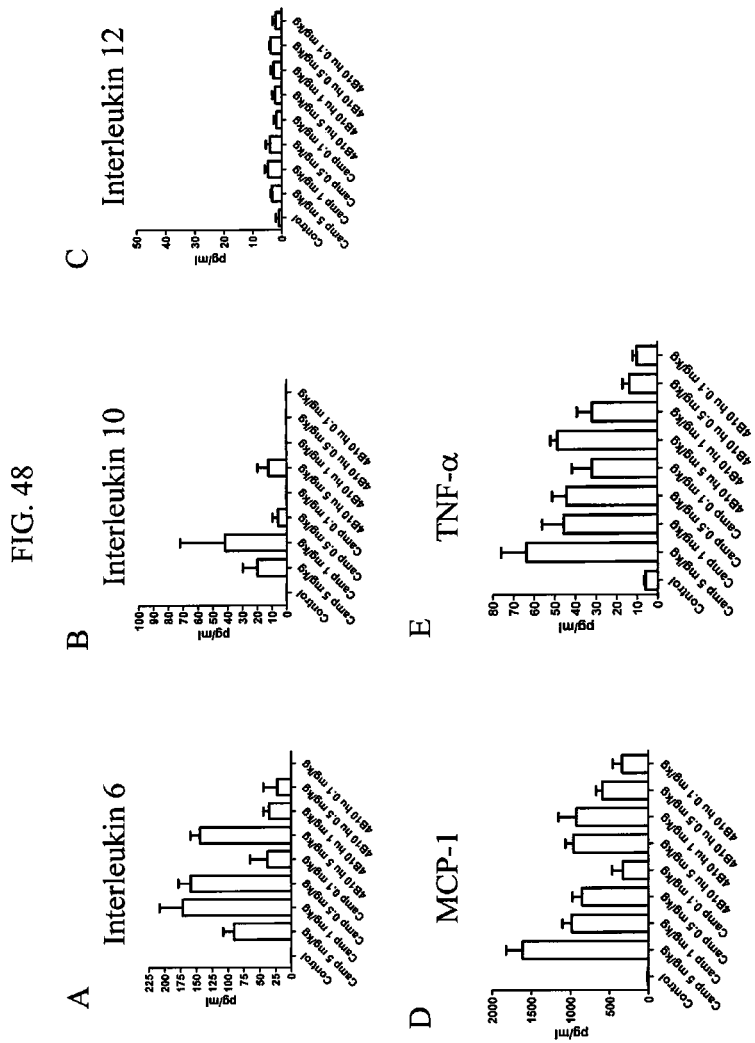
FIGS. 48A-48E show the levels of circulating cytokines 2 hours after dosing with Campath-1H® ("Campath") and humanized 4B10-H1/K1 ("4B10") antibodies.

Assessment of Neutralizing Ability of Serum Samples Containing Anti-Campath-1H® Neutralizing Antibodies to Block Humanized 2C3, 12G6, and 9D9 Anti-CD52 Antibody Activity To assess the ability of humanized antibodies to bind to CD52 expressing cells in the presence of neutralizing antibodies against Campath-1H®, anti-CD52 antibodies (Campath-1H®, 2C3-SFD1/K12, 9D9-H16/K13 and 12G6-SFD1/K12) were reacted with human serum containing anti-Campath-1H® antibody reactivity and evaluated for binding to CD52 expressing Raji cells. Serum samples obtained from relapsing remitting multiple sclerosis patients who were enrolled in the CAMMS223 study (The CAMMS223 Trial Investigators, "Alemtuzumab vs. interferon Beta-1a in early multiple sclerosis," *N Engl J Med* 359:1786-1801 (2008)) were used in the assay. Repeated administration of the Campath-1H® antibody resulted in generation of anti-Campath-1H® antibody responses in most patients. The anti-Campath-1H antibody titer is very low at month 12 in most patients, and increased significantly upon administration of a second cycle of Campath-1H® resulting in a high titer anti-Campath-1H® response in the sera at month 13. Anti-CD52 antibody neutralization assays were carried out using month 12 and month 13 serum samples obtained from five different MS patients (MS-1 to MS-5) who had been treated with Campath-1H® under the CAMMS223 protocol. FITC-conjugated anti-CD52 antibodies Campath-1H®, 2C3-SFD1/K12, 12G6-SFD1/K12, and 9D9-H16/K13 (used in Example 30 and shown to bind to CD52 expressing cells) were used to stain Raji cells that express human CD52 in the absence or presence of a range of dilutions of serum obtained from patients who have been treated with Campath-1H. Briefly, MS patient serum samples (month 12 and month 13) were made into 6 fold serial dilutions and incubated with 10 µg/ml of FITC-conjugated anti-CD52 antibodies (Campath-1H®, 2C3-SFD1/K12, 12G6-SFD1/K12, and 9D9-H16/K13) for 1 hr at 37° C. Raji cells were rinsed with a staining buffer containing HBSS, 5% FBS, and 0.1% azide, and then deposited into round-bottom 96 well plates at $1 \times 10^5$ cells per well. Cells were blocked with 10 µg/ml of human IgG Fc fragment for 30 min on ice in staining buffer. The cells were then washed with staining buffer and re-suspended in 100 µl of the antibody-serum mix as described above. After 30 minutes on ice, cells were washed and fixed with BD Cytofix and the FITC-labeled antibody coated cells were analyzed using a FACSCalibur system (Becton Dickinson), after which the data was analyzed using FlowJo version 7.2 software (Tree Star, Inc, Oregon, USA). Binding of FITC-conjugated anti-CD52 antibodies in the presence of anti-Campath-1H® neutralizing antibodies in the serum was assessed by flow cytometry and % binding relative to control, as a measure of inhibition was calculated as (MFI with serum/MFI control (no serum))×100. Representative data from one of the donors (MS-1) is shown in FIG. 45. The X axis denotes the serum dilution factor and the Y axis denotes the % control binding as a measure of antibody neutralizing activity. The data clearly demonstrate that month 12 serum samples have no inhibitory effect on Campath-1H® or other anti-CD52 antibodies, suggesting that there are low or no anti-Campath-1H® blocking antibodies in the serum. Month 13 serum samples mediated complete inhibition of Campath-1H® binding even at a 1:1000 dilution of serum, but did not mediate inhibition of 2C3, 12G6, and 9D9 humanized anti-CD52 antibodies even at the highest concentration (1:24 dilution) tested. Two of the five patients developed anti-Campath-1H® neutralizing antibody titers of >1:1000, whereas three other patients had about 1:100 Campath-1H® neutralizing antibody titers. Even though two of the patients' month 13 sera had relatively high neutralizing antibody titers of >1:1000 against Campath-1H®, these sera did not inhibit binding of humanized 2C3-SFD1/K12, 12G6-SFD1/K12, and 9D9-H16/K13 antibodies, suggesting that the anti-Campath-1H® antibody reactivity in patients treated with Campath-1H® did not block binding of these humanized antibodies to CD52 as presented on cells.

Example 42

Analysis of Depletion and Repopulation of Anti-CD52 Antibodies in huCD52 Transgenic Mice (4B10-H1/K1)

The depleting activities of Campath-1H® and the humanized anti-CD52 antibody (4B10-H1/K1) at different dose levels were examined in the huCD52 transgenic mouse. Mice were injected intravenously with 0.1, 0.5, 1.0 or 5.0 mg/kg of each antibody. Two hours post dosing, serum was collected to examine the level of circulating cytokines. Three days post dosing, mice were sacrificed, and blood and spleens were collected from each mouse (N=5) to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. A subset of mice (N=5) were kept alive to monitor the repopulation kinetics. Depletion was greatest in the T cell compartment with CD4+ T cells being depleted most followed by CD8+ T cells, B cells, NK cells, and other myeloid cells. Within the CD4+ T cell compartment, naïve CD4+ T cells were depleted the most followed by CD4+ central memory (CM), CD4+ effector memory (EM), and CD4+ regulatory T cells (Treg). A similar pattern was observed for CD8+ T cells (Naïve>CM>EM). Conversely, mature B cells were depleted to a greater extent than immature B cells. Comparison of Campath-1H® treated mice to 4B10-H1/K1 treated mice demonstrated similar patterns of cells in both the blood and spleen at each of the doses examined.

Serum cytokine analysis demonstrated dose dependent increases for TNFα, IL-6 and MCP-1. The circulating level of these cytokines remained elevated compared to untreated mice at the 0.5 and 0.1 mg/kg doses as well. Slight increases were also observed for IL-10 in the Campath-1H® treated group at the three highest doses but only for the highest dose of the humanized 4B10-H1/K1 treated group. No significant increases in the level of circulating IL-12 or IFNg (not shown) were noted.

By 50-60 days post dosing, with the exception of the 1.0 mg/kg group, lymphocyte levels in all of the Campath-1H® dosed groups had rebounded to the levels of untreated mice. In the 1.0 mg/kg group, lymphocytes had returned to normal levels by 80 days post dosing. Similar repopulation kinetics were also observed for the humanized 4B10-H1/K1 antibody treated mice. Lymphocytes had rebounded to control levels by 50 days post dosing in all 4B10-H1/K1 treated groups with the exception of the 0.5 mg/kg level. Levels of circulating lymphocytes in the 0.5 mg/kg group remained decreased throughout the course of the monitoring period. Total lymphocytes were monitored for repopulation in the blood.

Figure 49:
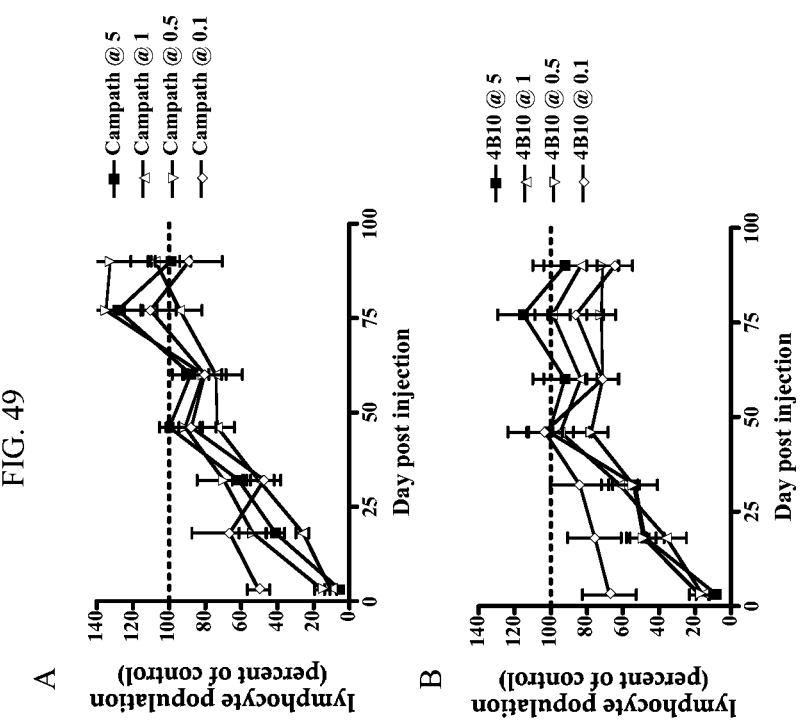
FIGS. 49A and 49B show the repopulation of circulating lymphocytes over a time course after dosing with Campath-1H® ("Campath") and humanized 4B10-H1/K1 ("4B10") antibodies, (mg/kg).
Figure 50A:
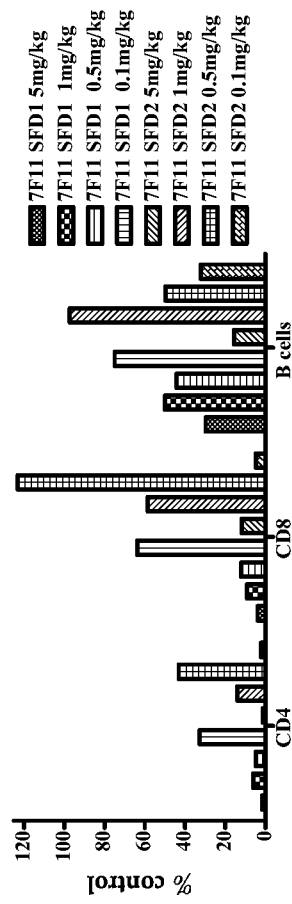
FIGS. 50A-50E show the level of CD4+ T cells, CD8+ T cells, B220+ B cells, NK cells, myeloid cells, and neutrophils in the blood 72 hours after dosing with the humanized 7F11-SFD1/K2 ("7F11 SFD1") and 7F11-SFD2/K2 ("7F11 SFD2") antibodies.
Figure 50B:
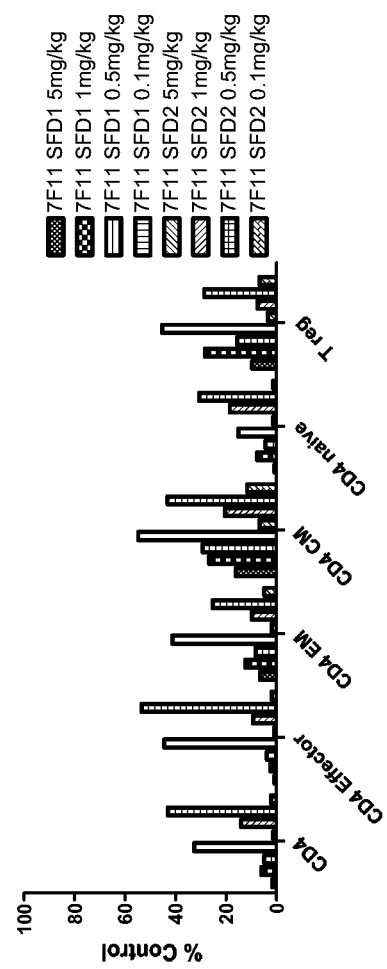
Figure 50C:
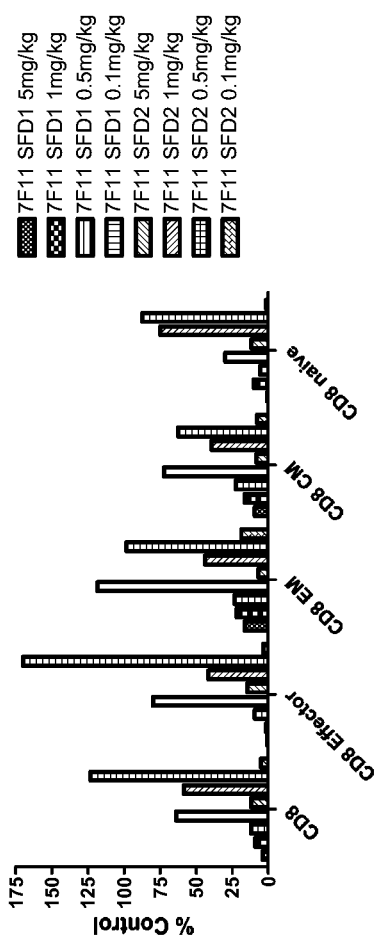
Figure 50D:
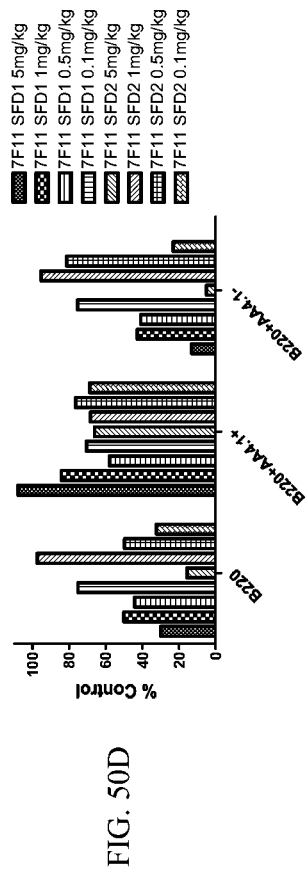
Figure 50E:
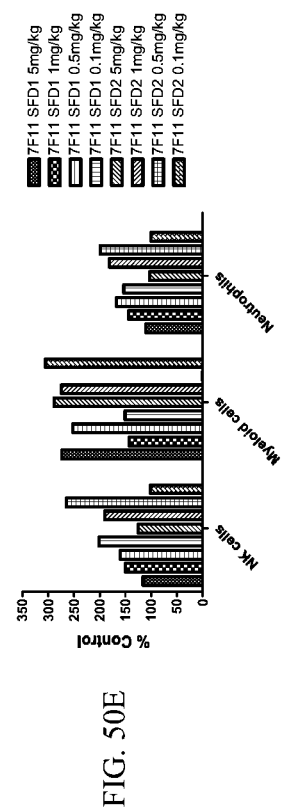
Figure 51A:
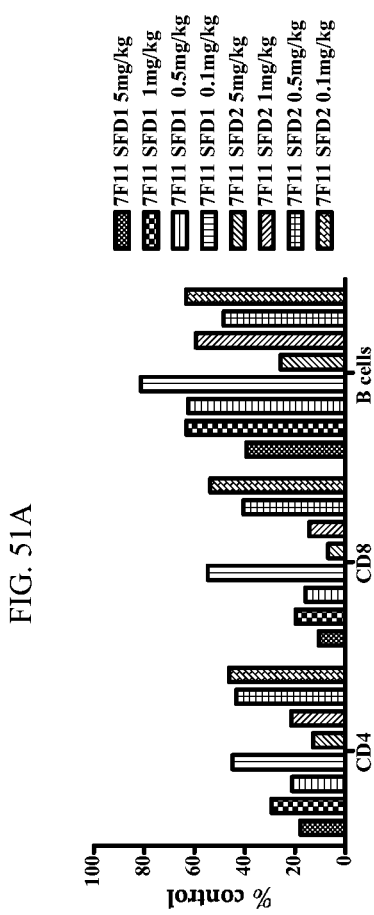
FIGS. 51A-51E show the level of CD4+ T cells, CD8+ T cells, B220+ B cells, NK cells, myeloid cells, and neutrophils in the spleen 72 hours after dosing with the humanized 7F11-SFD1/K2 ("7F11 SFD1") and 7F11-SFD2/K2 ("7F11 SFD2") antibodies.
Figure 51B:
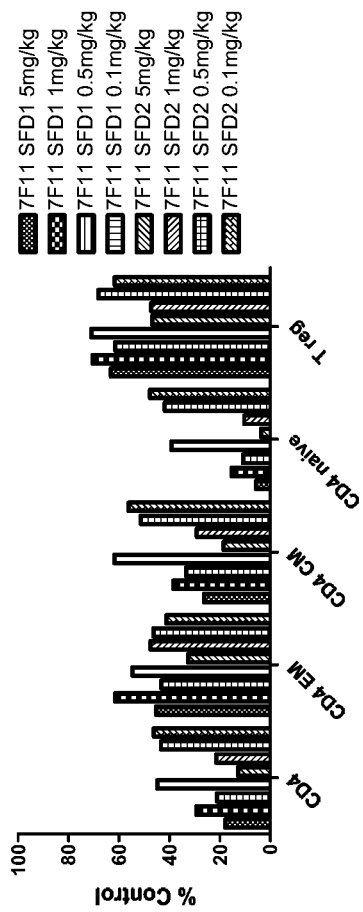
Figure 51C:
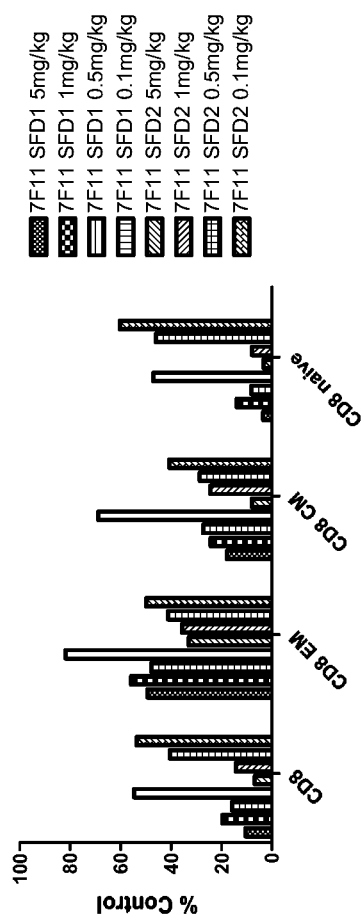
Figure 51D:
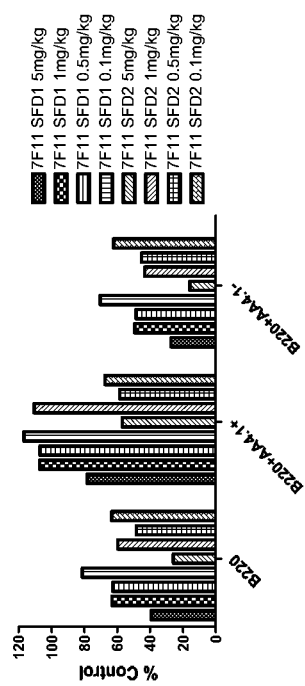
Figure 51E:
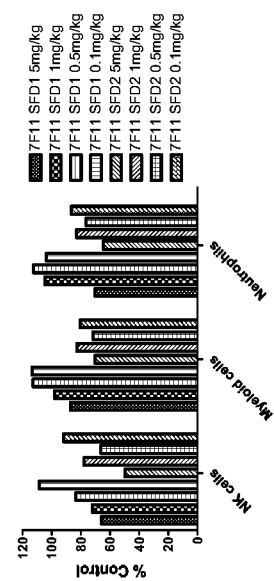
Figure 52:
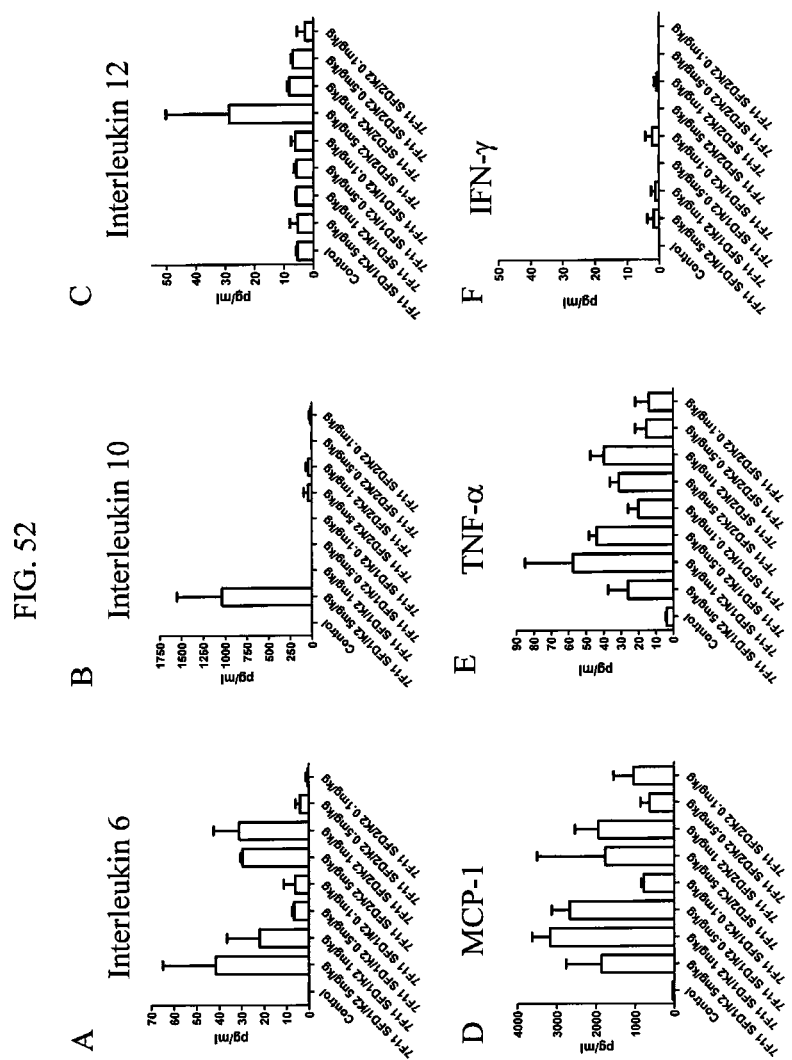
FIGS. 52A-52F show the levels of circulating cytokines 2 hours after dosing with the humanized 7F11-SFD1/K2 ("7F11 SFD1") and 7F11-SFD2/K2 ("7F11 SFD2") antibodies.

FIGS. 46A-46E show the level of CD4+ T cells, CD8+ T cells and B220+ B cells in the blood 72 hours after dosing with Campath-1H® ("Campath") and humanized 4B10-H1/K1 ("4B10") antibodies. FIGS. 47A-47E show the level of CD4+ T cells, CD8+ T cells and B220+ B cells in the spleen 72 hours after dosing with Campath-1H® ("Campath") and humanized 4B10-H1/K1 ("4B10") antibodies. FIGS. 48A-48E show the levels of circulating cytokines 2 hours after dosing with Campath-1H® ("Campath") and humanized 4B10-H1/K1 ("4B10") antibodies. FIGS. 49A-49B show the repopulation of circulating lymphocytes over a timecourse after dosing with Campath-1H® ("Campath") and humanized 4B10-H1/K1 ("4B10") antibodies.

Example 43

Analysis of Depletion and Repopulation of Anti-CD52 Antibodies in huCD52 Transgenic Mice (7F11-SFD1/K2 and 7F11-SFD2/K2)

The depleting activity of humanized antibodies (7F11-SFD1/K2 and 7F11-SFD2/K2) at different dose levels was examined in huCD52 transgenic mice. Mice were injected intravenously with 0.1, 0.5, 1.0 or 5.0 mg/kg of each antibody. Two hours post dosing, serum was collected to examine the level of circulating cytokines. Three days post dosing, mice were sacrificed, and blood and spleens were collected from each mouse (N=5) to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice In addition, T and B cell subset analysis was performed to determine the overall depleting effect. A subset of mice (N=5) were kept alive to monitor the repopulation kinetics. Administration of each humanized 7F11 antibody (7F11-SFD1/K2 and 7F11-SFD2/K2) at all doses resulted in depletion of a significant number of both T cells and B cells in the blood. These data also demonstrated that various T and B cell subsets are depleted to differing degrees depending on the dose of antibody used. Naïve T cells (both CD4 and CD8) demonstrated the most depletion with other cell populations (including memory and T reg cells) being depleted to a lesser degree. In the B cell compartment, mature B cells were depleted more readily than immature B cells. In the spleen, dose dependent depletion was observed with significant depletion of lymphocytes being observed at the 5 and 1 mg/kg dose levels. Similar to the case with blood, naïve T cells were more readily depleted than memory cells. B cells were depleted to a lesser extent than T cells with each of the humanized 7F11 clones (7F11-SFD1/K2 and 7F11-SFD2/K2). Depletion was not observed for NK cells or neutrophils in the blood or the spleen at any of the doses injected. Serum cytokine analysis demonstrated dose dependent increases for both TNFα and IL-6. Levels of these cytokines remained elevated compared to untreated mice at the 0.5 and 0.1 mg/kg doses as well. Dose dependent increases in the level of circulating MCP-1 were also noted.

By 30 days post dosing, lymphocyte levels in the 0.5 and 0.1 mg/kg dosed groups had rebounded to the levels of untreated mice. In the 1.0 and 5.0 mg/kg groups, lymphocytes had returned to normal levels by 50 and 80 days, respectively, for clone 7F11-SFD1/K2 and by 80 days post dosing for both the 1.0 and 5.0 mg/kg groups of clone 7F11-SFD2/K2. Total lymphocytes were monitored for repopulation in the blood.

Figure 53:
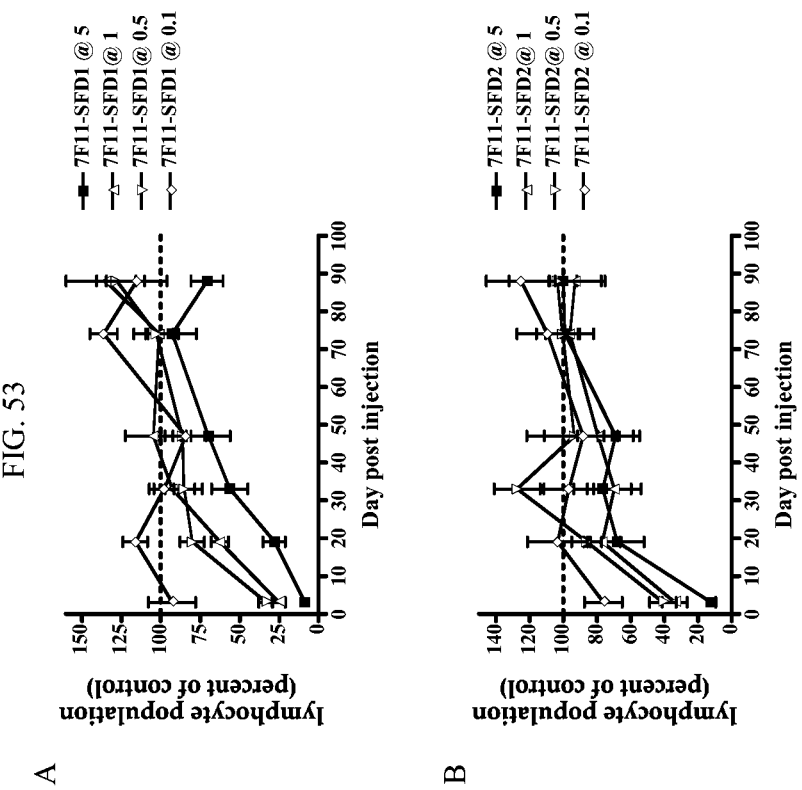
FIGS. 53A and 53B show the repopulation of circulating lymphocytes over a timecourse after dosing with the humanized 7F11-SFD1/K2 ("7F11 SFD1") and 7F11-SFD2/K2 ("7F11 SFD2") antibodies, (mg/kg).

FIGS. 50A-50E show the level of CD4+ T cells, CD8+ T cells and B220+ B cells in the blood 72 hours after dosing with the humanized 7F11-SFD1/K2 ("7F11 SFD1") and 7F11-SFD2/K2 ("7F11 SFD2") antibodies. FIGS. 51A-51E show the level of CD4+ T cells, CD8+ T cells and B220+ B cells in the spleen 72 hours after dosing with the humanized 7F11-SFD1/K2 ("7F11 SFD1") and 7F11-SFD2/K2 ("7F11 SFD2") antibodies. FIGS. 52A-52F show the levels of circulating cytokines 2 hours after dosing with the humanized 7F11-SFD1/K2 ("7F11 SFD1") and 7F11-SFD2/K2 ("7F11 SFD2") antibodies. FIGS. 53A-53B show the repopulation of circulating lymphocytes over a timecourse after dosing with the humanized 7F11-SFD1/K2 ("7F11 SFD1") and 7F11-SFD2/K2 ("7F11 SFD2") antibodies.

Example 44

Analysis of 7F11 Humanized Anti-CD52 Antibodies in CD52 Transgenic Mice (7F11-SFD1/K2 and 7F11-SFD2/K2)

The depleting activity of the chimeric 7F11 antibodies and humanized 7F11-SFD1/K2 and 7F11-SFD2/K2 antibodies in comparison to Campath-1H® was examined in the huCD52 transgenic mouse. Mice were injected intravenously with 1.0 mg/kg of each antibody. Three days post dosing, mice were sacrificed, and blood and spleens were collected from each mouse (N=5) to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice Administration of Campath-1H® resulted in depletion of a significant number of both T cells and B cells in the blood and spleen. Although a comparable level of T cell depletion was observed in the blood for both the chimeric and humanized 7F11 antibodies (7F11-SFD1/K2 and 7F11-SFD2/K2), B cells were depleted to a lesser extent. This observation was also apparent in the spleen, where significant T cell depletion was noted, but only a modest level of B cell depletion was achieved with the 7F11 antibodies (7F11-SFD1/K2 and 7F11-SFD2/K2).

Figure 54:
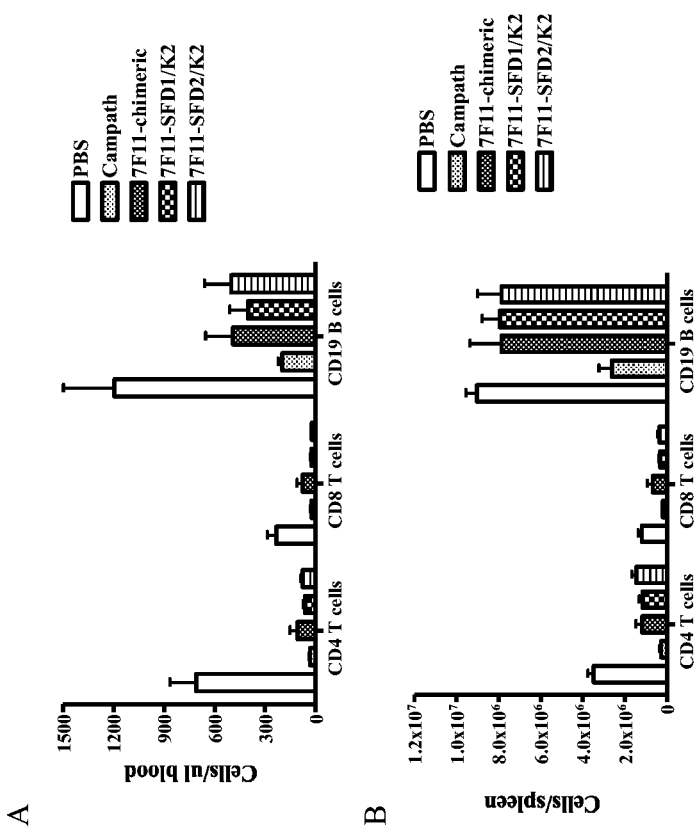
FIGS. 54A and 54B show the level of CD4+ T cells, CD8+ T cells and B220+ B cells in the blood 72 hours after dosing with Campath-1H® ("Campath"), 7F11-chimeric antibodies, and humanized 7F11-SFD1/K2 and 7F11-SFD2/K2 antibodies.

FIGS. 54A-54B show the level of CD4+ T cells, CD8+ T cells and B220+ B cells in the blood 72 hours after dosing with Campath-1H® ("Campath"), 7F11-chimeric antibodies, and humanized 7F11-SFD1/K2 and 7F11-SFD2/K2 antibodies.

Example 45

Analysis of PK Profiles of Anti-CD52 Antibodies in CD52 Transgenic Mice (7F11-SFD1/K2 and 7F11-SFD2/K2)

To ensure that the humanization process did not alter the clearance rate of the antibody, the pharmacokinetic profile of the chimeric 7F11 anti-CD52 antibody and humanized 7F11-SFD1/K2 and 7F11-SFD2/K2 anti-CD52 antibodies was determined in huCD52 transgenic mice. Mice were injected intravenously with antibodies at 5 mg/kg and blood was collected at various timepoints beginning two hours post dosing. The circulating levels of each antibody were evaluated using an anti-human IgG ELISA. For each of the humanized clones, there was a slight difference in the Cmax noted at 2 hours post dosing. Clearance rates for the chimeric 7F11 antibody and humanized 7F11-SFD1/K2 and 7F11-SFD2/K2 antibodies were similar to each other as well as to Campath-1H® over the course of the experiment, indicating that the humanization process did not significantly alter the pharmacokinetic profile of the antibodies.

Figure 55:
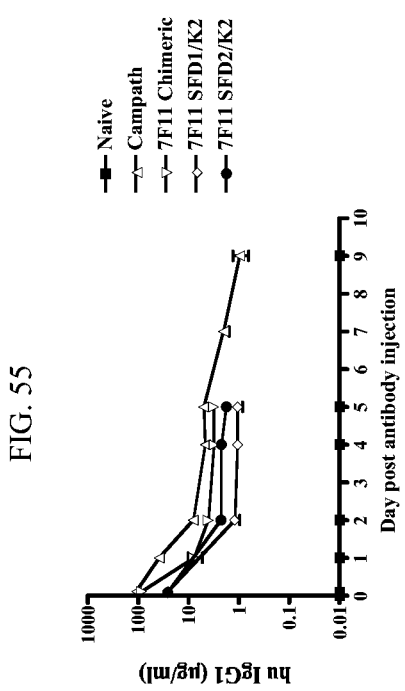
FIG. 55 shows the level of Campath-1H® ("Campath"), 7F11-chimeric antibody and humanized 7F11-SFD1/K2 and 7F11-SFD2/K2 antibodies in the blood over a timecourse after dosing.
Figure 56A:
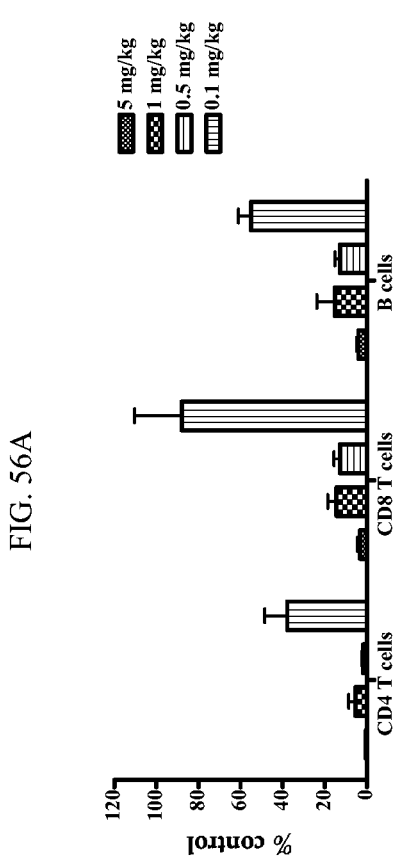
FIGS. 56A-56E show the level of CD4+ T cells, CD8+ T cells, B220+ B cells, NK cells, and neutrophils in the blood 72 hours after dosing with 2C3-SFD1/K12 antibodies.
Figure 56B:
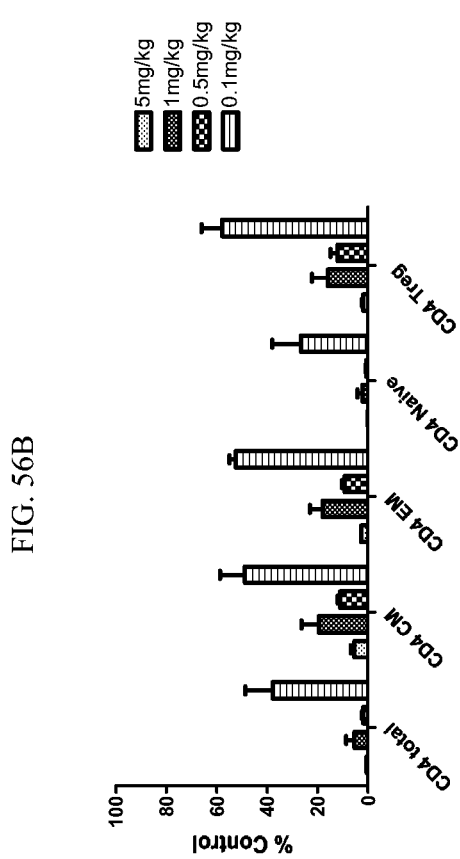
Figure 56C:
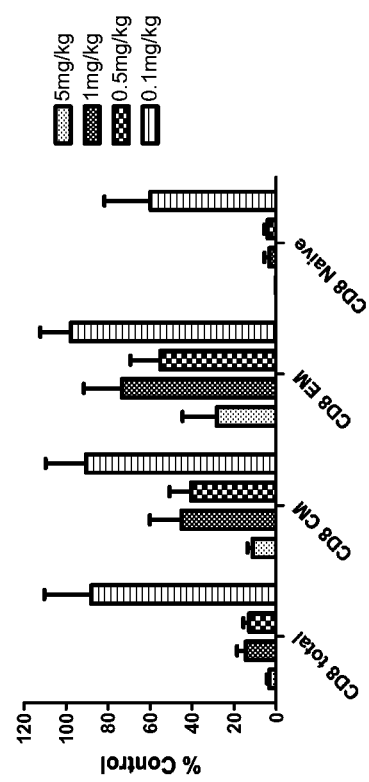
Figures 56D, 56E:
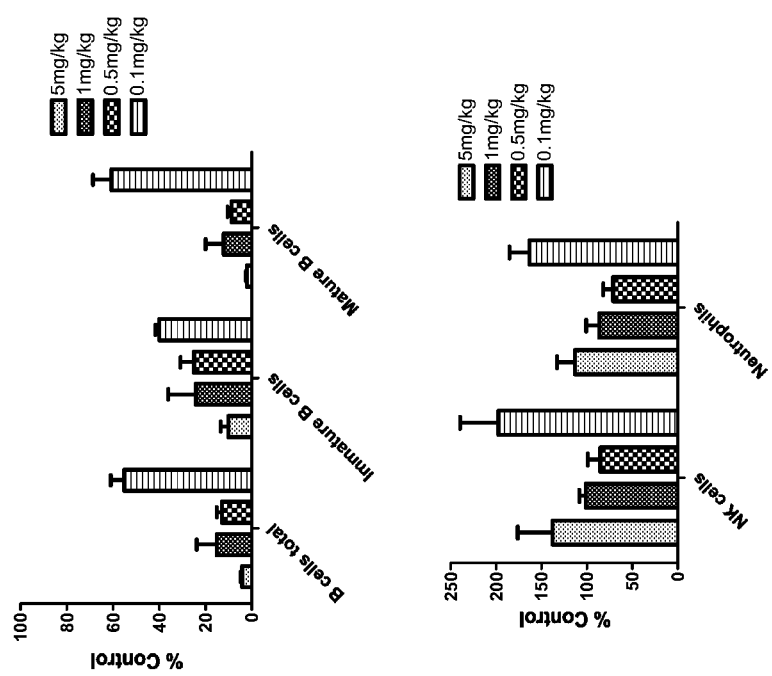
Figure 57A:
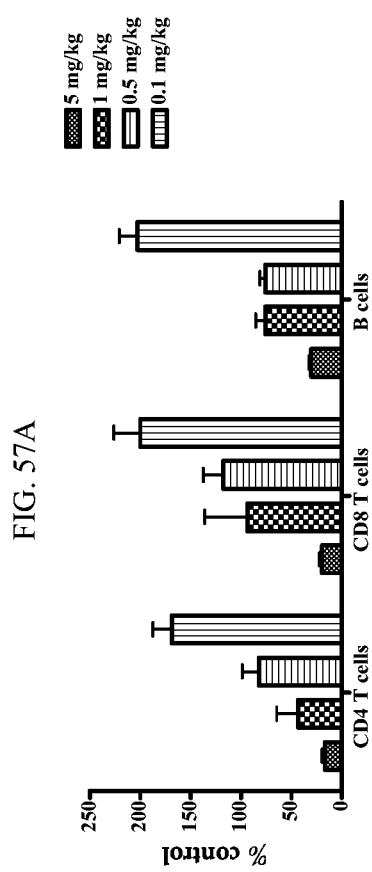
FIGS. 57A-57E show the level of CD4+ T cells, CD8+ T cells, B220+ B cells, NK cells, and neutrophils in the spleen 72 hours after dosing with 2C3-SFD1/K12 antibodies.
Figure 57B:
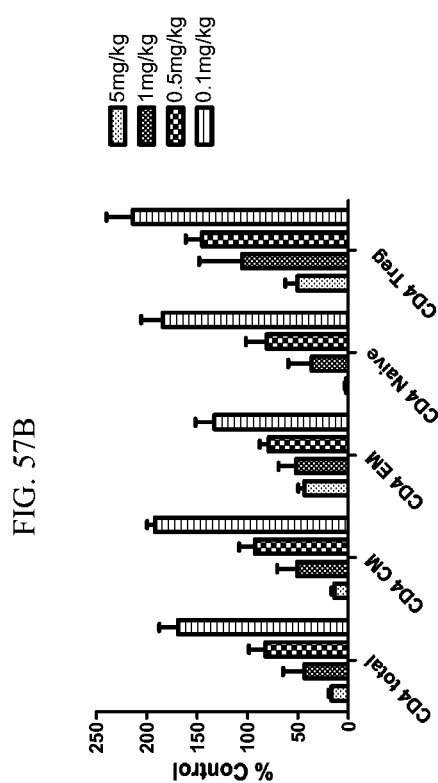
Figure 57C:
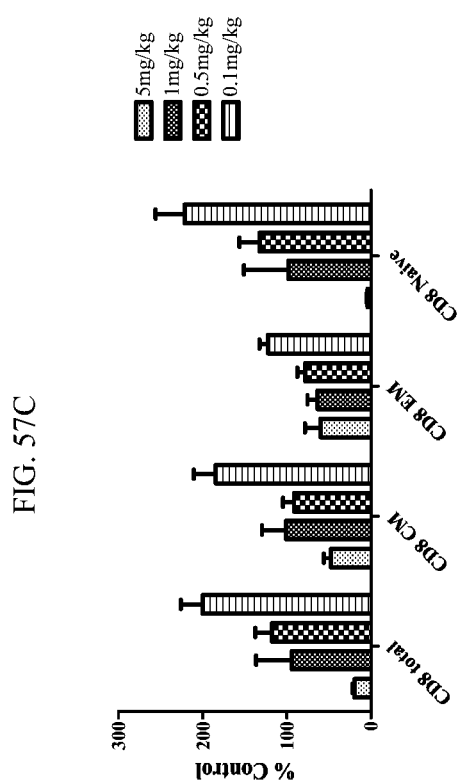
Figures 57D, 57E:
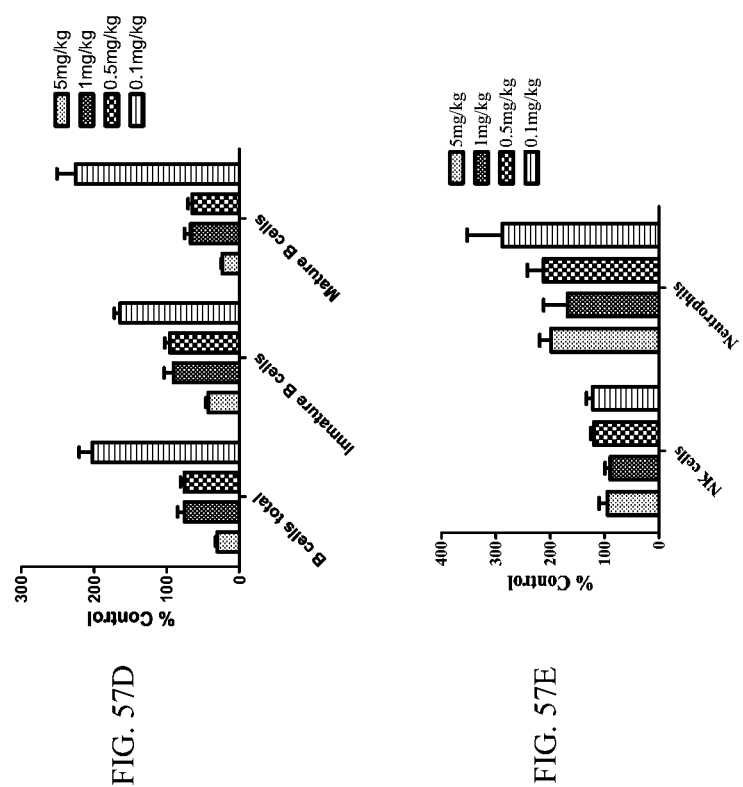
Figure 58:
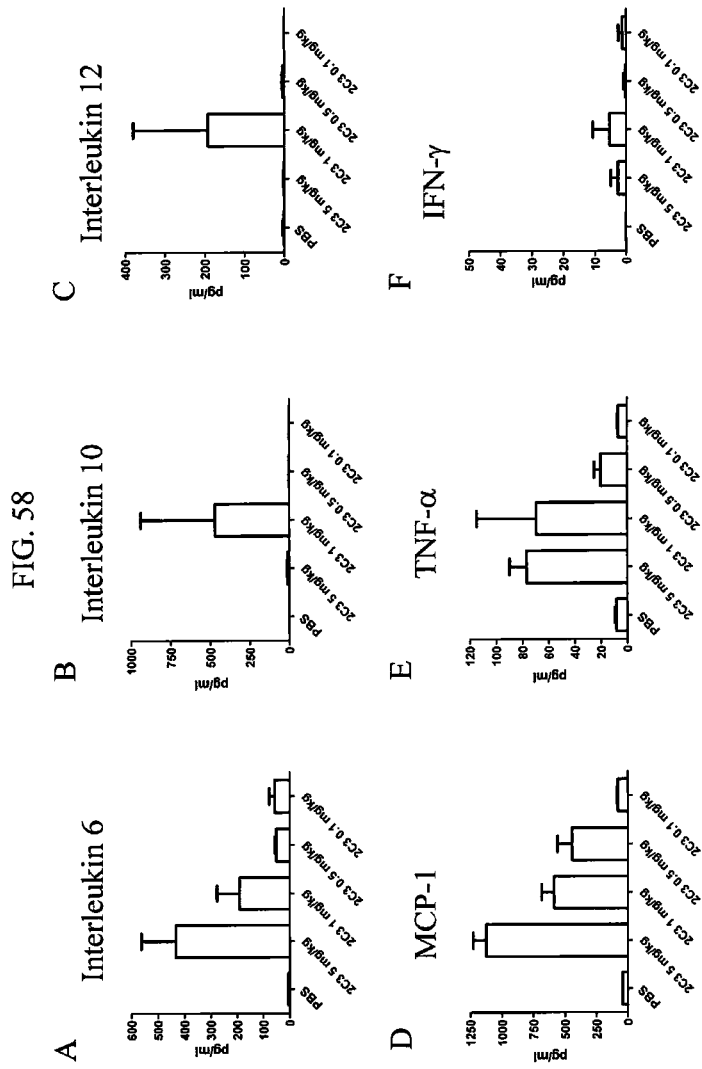
FIGS. 58A-58F show the levels of circulating cytokines 2 hours after dosing with 2C3-SFD1/K12 ("2C3") antibodies.

FIG. 55 shows the level of Campath-1H® ("Campath"), 7F11-chimeric antibody and humanized 7F11-SFD1/K2 and 7F11-SFD2/K2 antibodies in the blood over a timecourse after dosing.

Example 46

Analysis of Depletion and Repopulation of Anti-CD52 Antibodies in huCD52 Transgenic Mice (2C3-SFD1/K12)

The depleting activity of the 2C3-SFD1/K12 clone at different dose levels was examined in the huCD52 transgenic mouse. Mice were injected intravenously with 0.1, 0.5, 1.0 or 5.0 mg/kg of antibody. Two hours post dosing, serum was collected to potentially examine the level of circulating cytokines. Three days post dosing, mice were sacrificed, and blood and spleens were collected from each mouse (N=5) to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. A subset of mice (N=5) were kept alive to monitor the repopulation kinetics. Administration of 2C3-SFD1/K12 at the 5, 1, and 0.5 mg/kg doses resulted in depletion of a significant number of both T cells and B cells in the blood. A variable level of lymphocyte depletion was observed in the blood at the 0.1 mg/kg dose with CD4+ T cells and B cells being depleted to a greater extent than CD8+ T cells. These data also demonstrated that various T and B cell subsets are depleted to differing degrees depending on the dose of antibody used. Naïve T cells (both CD4 and CD8) demonstrated the most depletion compared to other cell populations (including memory and T reg cells), which were depleted to a lesser degree. In the B cell compartment, mature B cells were depleted more readily than immature B cells. In the spleen, dose dependent depletion was observed with significant depletion of lymphocytes being observed at the 5 and 1 mg/kg dose levels. Similar to Campath-1H®, naïve T cells were more readily depleted than memory cells. Depletion was observed for NK cells and neutrophils in the blood, but little to no depletion was observed in the spleen at any of the doses injected. Serum cytokine analysis demonstrated dose dependent increases for both TNFα and IL-6 with the 5 mg/kg dose inducing the highest level of each cytokine. Levels comparable to untreated mice were observed in the 0.5 and 0.1 mg/kg dose levels for TNFα and the 0.1 mg/kg dose level for IL-6. Dose dependent increases in the level of circulating MCP-1 were also noted.

By 30 days post dosing, lymphocyte levels for the 0.1 and 0.5 mg/kg groups had rebounded to the levels of untreated mice. In the 1.0 and 5.0 mg/kg groups, lymphocytes had returned to normal levels by 80 days post dosing. Total lymphocytes were monitored for repopulation in the blood.

Figure 59:
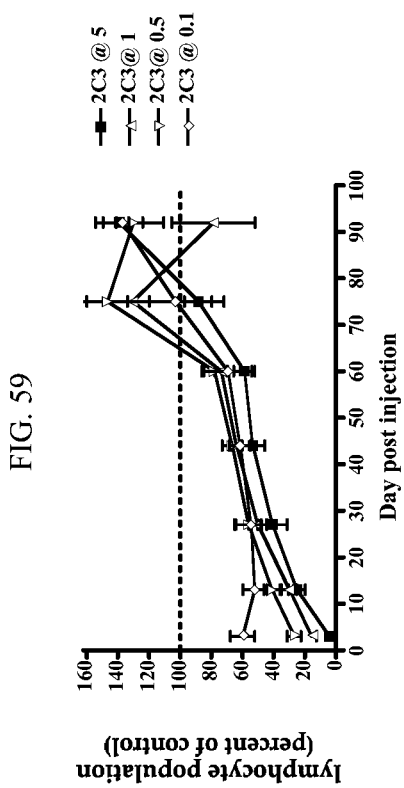
FIG. 59 shows the repopulation of circulating lymphocytes over a timecourse after dosing with 2C3-SFD1/K12 antibodies, (mg/kg).
Figure 60A:
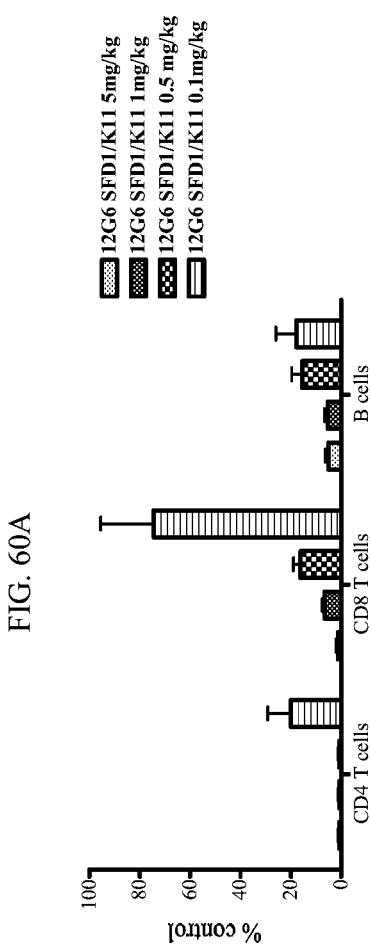
FIGS. 60A-60E show the level of CD4+ T cells, CD8+ T cells, B220+ B cells, NK cells, myeloid cells, macrophages, and neutrophils in the blood 72 hours after dosing with 12G6-SFD1/K11 antibodies.
Figure 60B:
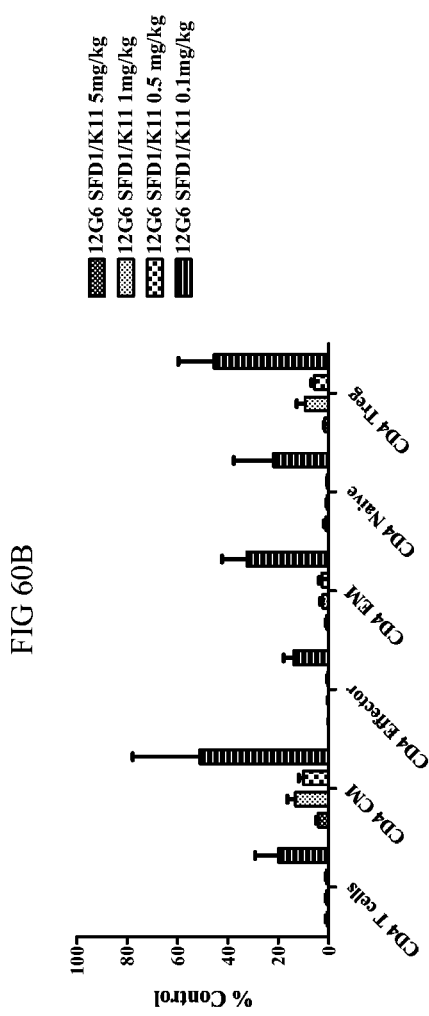
Figure 60C:
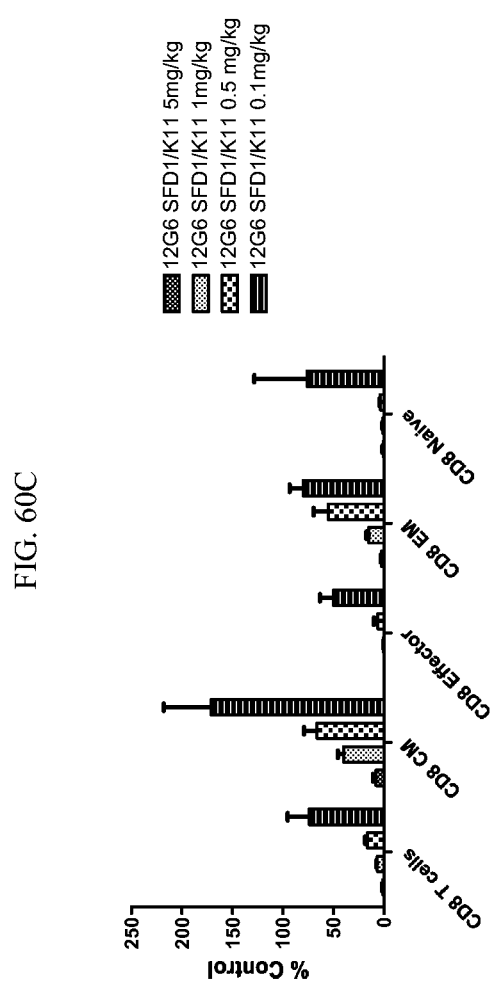
Figure 60D:
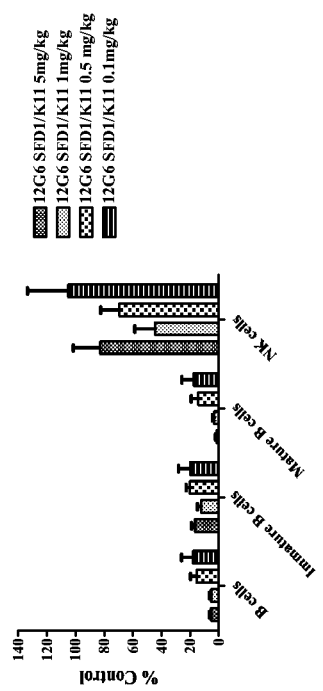
Figure 60E:
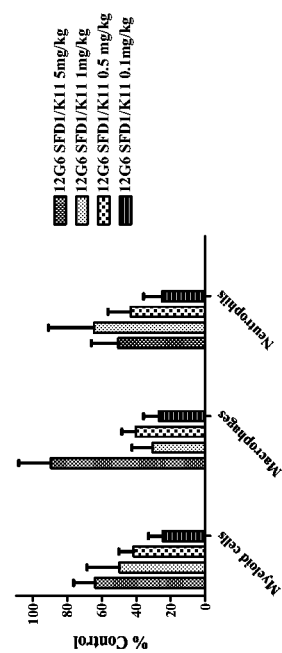
Figure 61A:
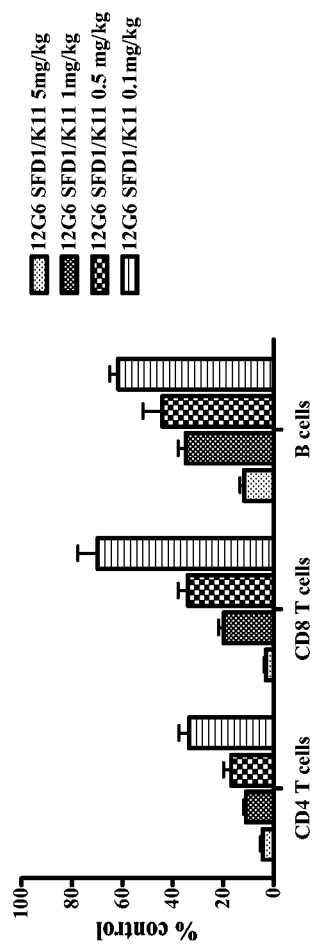
FIGS. 61A-61E show the level of CD4+ T cells, CD8+ T cells, B220+ B cells, NK cells, macrophages, neutrophils, and myeloid cells in the spleen 72 hours after dosing with 12G6-SFD1/K11 antibodies.
Figure 61B:
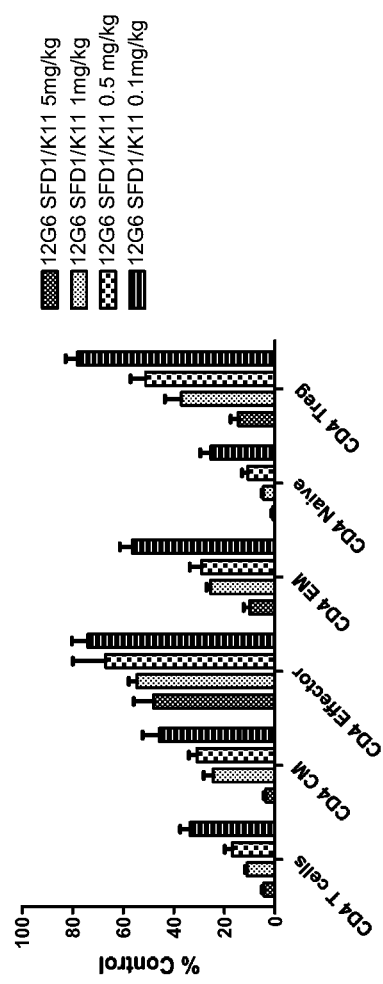
Figure 61C:
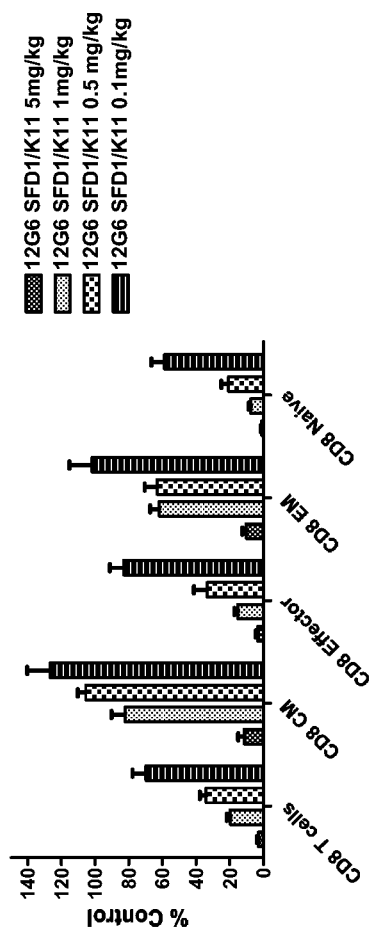
Figure 61D:
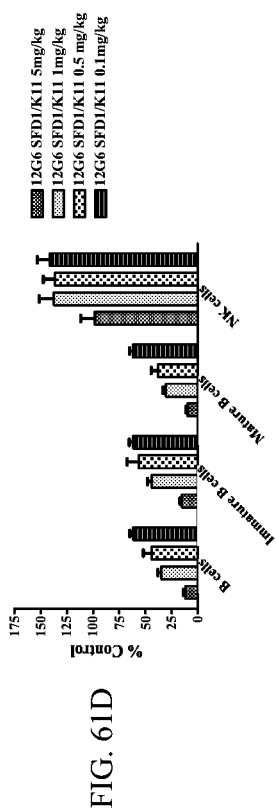
Figure 61E:
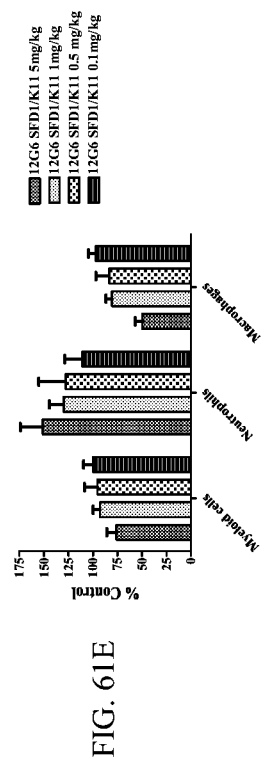
Figure 62:
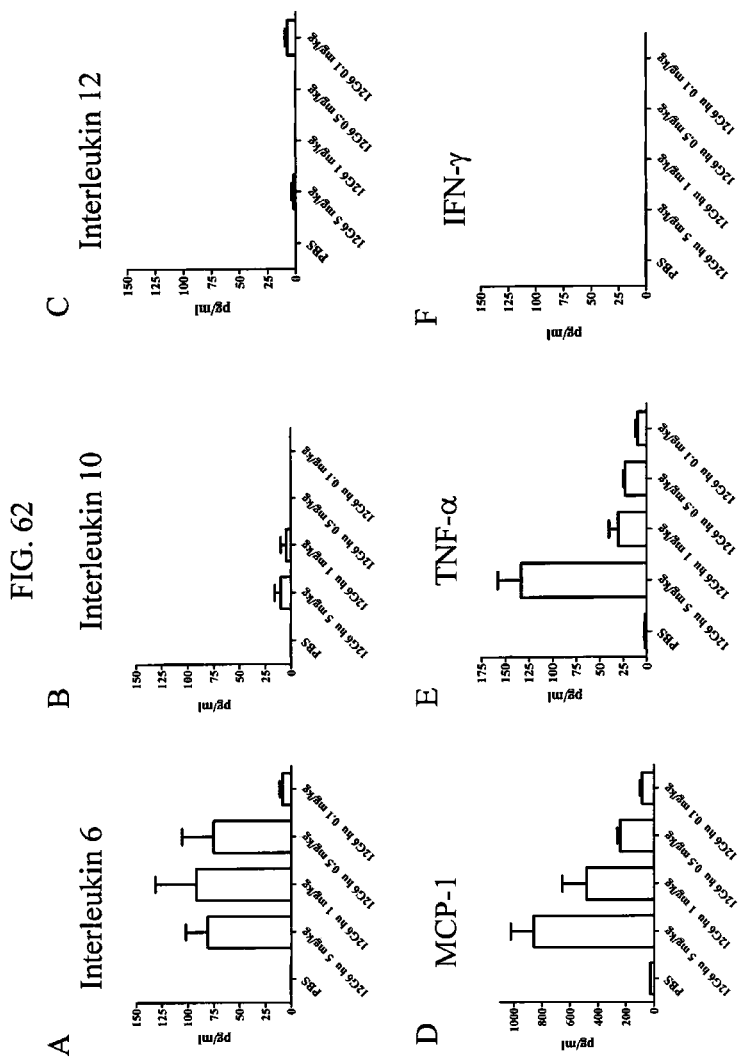
FIGS. 62A-62F show the levels of circulating cytokines 2 hours after dosing with 12G6-SFD1/K11 ("12G6 hu") antibodies.

FIGS. 56A-56E show the level of CD4+ T cells, CD8+ T cells and B220 B cells in the blood 72 hours after dosing with 2C3-SFD1/K12 antibodies. FIGS. 57A-57E show the level of CD4+ T cells, CD8+ T cells and B220+ B cells in the spleen 72 hours after dosing with 2C3-SFD1/K12 antibodies. FIGS. 58A-58F show the levels of circulating cytokines 2 hours after dosing with 2C3-SFD1/K12 antibodies. FIG. 59 shows the repopulation of circulating lymphocytes over a timecourse after dosing with 2C3-SFD1/K12 antibodies.

Example 47

Analysis of Depletion and Repopulation of Anti-CD52 Antibodies in huCD52 Transgenic Mice (12G6-SFD1/K11)

The depleting activity of the 12G6-SFD1/K11 clone at different dose levels was examined in the huCD52 transgenic mouse. Mice were injected intravenously with 0.1, 0.5, 1.0 or 5.0 mg/kg of antibody. Two hours post dosing, serum was collected to potentially examine the level of circulating cytokines. Three days post dosing, mice were sacrificed, and blood and spleens were collected from each mouse (N=5) to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. A subset of mice (N=5) were kept alive to monitor the repopulation kinetics. Administration of 12G6-SFD1/K11 at the 5, 1, and 0.5 mg/kg doses resulted in depletion of a significant number of both T cells and B cells in the blood. A variable level of lymphocyte depletion was observed in the blood at the 0.1 mg/kg dose with CD4+ T cells and B cells being depleted to a greater extent than CD8+ T cells. These data also demonstrated that various T and B cell subsets are depleted to differing degrees depending on the dose of antibody used. Naïve T cells (both CD4 and CD8) demonstrated the most depletion compared to other cell populations (including memory and T reg cells), which were depleted to a lesser degree. In the B cell compartment, mature B cells were depleted more readily than immature B cells. In the spleen, dose dependent depletion was observed with significant depletion of lymphocytes being observed at the 5 and 1 mg/kg dose levels. Similar to Campath-1H®, naïve T cells were more readily depleted than memory cells. Depletion was observed for NK cells and neutrophils in the blood but little to no depletion was observed in the spleen at any of the doses injected. Serum cytokine analysis demonstrated dose dependent increases for both TNFα and IL-6 with the 5 mg/kg dose inducing the highest level of each cytokine. Levels comparable to untreated mice were observed in the 0.5 and 0.1 mg/kg dose levels for TNFα and the 0.1 mg/kg dose level for IL-6. Dose dependent increases in the level of circulating MCP-1 were also noted.

By 30 days post dosing, lymphocyte levels had rebounded to the levels of untreated mice. In the 1.0 and 5.0 mg/kg groups, lymphocytes had returned to normal levels by 80 days post dosing. Total lymphocytes were monitored for repopulation in the blood.

Figure 63:
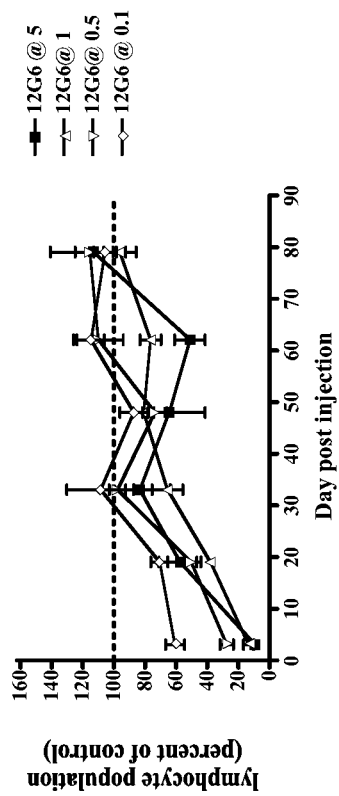
FIG. 63 shows the repopulation of circulating lymphocytes over a timecourse after dosing with 12G6-SFD1/K11 antibodies, (mg/kg).

FIGS. 60A-60E show the level of CD4+ T cells, CD8+ T cells and B220+ B cells in the blood 72 hours after dosing with 12G6-SFD1/K11 antibodies. FIGS. 61A-61E show the level of CD4+ T cells, CD8+ T cells and B220+ B cells in the spleen 72 hours after dosing with 12G6-SFD1/K11 antibodies. FIGS. 62A-62F show the levels of circulating cytokines 2 hours after dosing with 12G6-SFD1/K11 ("12G6 hu") antibodies. FIG. 63 shows the repopulation of circulating lymphocytes over a timecourse after dosing with 12G6-SFD1/K11 antibodies.

Example 48

Analysis of PK Profile of Anti-CD52 Antibodies in CD52 Transgenic Mice (2C3-SFD1/K12, 12G6-SFD1/K11 and 9D9-H10/K12)

The pharmacokinetic profiles of anti-CD52 antibodies were determined in huCD52 transgenic mice. This experiment compared the humanized and chimeric forms of the antibodies to ensure that the humanization process did not alter the clearance rate of the antibodies. Comparisons included chimeric 2C3, 12G6, and 9D9 antibodies and humanized 2C3-SFD1/K12, 12G6-SFD1/K11, and 9D9-H10/K12 antibodies. Mice were injected i.v. with antibodies at 5 mg/kg and blood was collected at various timepoints beginning two hours post dosing. The circulating levels of each antibody were evaluated using an anti-human IgG ELISA. For each of the chimeric/humanized antibody pairs analyzed, there was a slight difference in the Cmax noted at 2 hours post dosing. For the 2C3 and 12G6 antibodies, the Cmax of the humanized version (i.e., 2C3-SFD1/K12 and 12G6-SFD1/K11) was slightly higher while the chimeric version was slightly higher for the 9D9 pair. Clearance rates for the antibody pairs were similar over the course of the experiment indicating that the humanization process did not significantly alter the pharmacokinetic profile of the antibodies.

Figure 64:
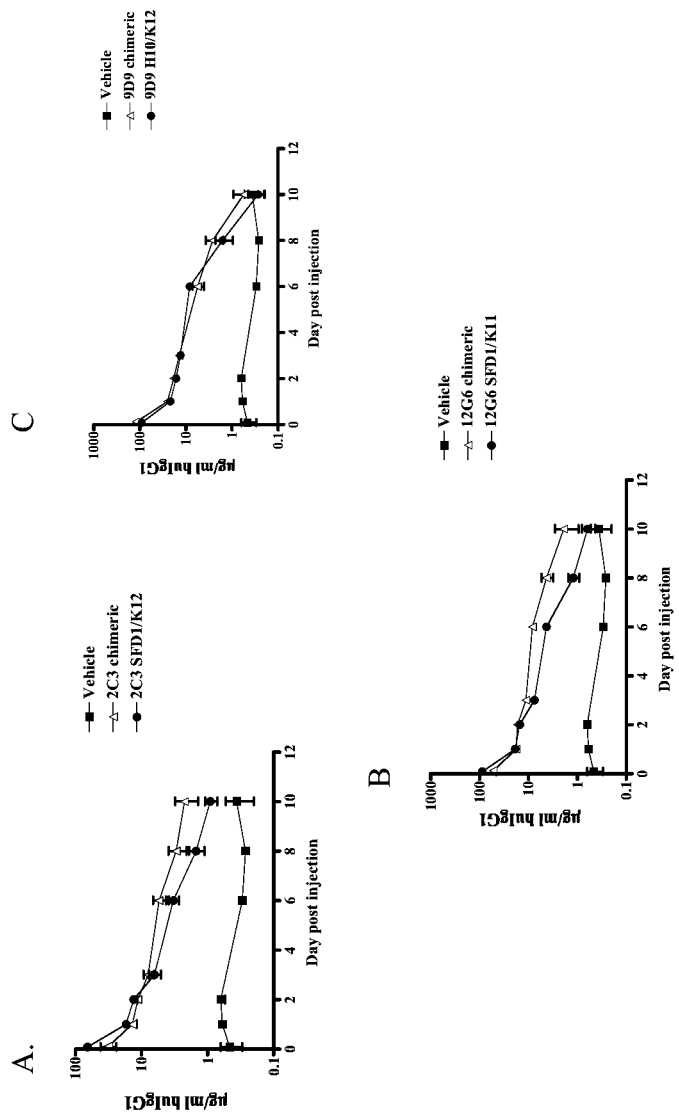
FIGS. 64A-64C show the level of 2C3-chimeric, 2C3-SFD1/K12, 12G6-chimeric, 12G6-SFD1/K11, 9D9-chimeric, and 9D9-H10/K12 antibodies in the blood over a timecourse after dosing.
Figure 65A:
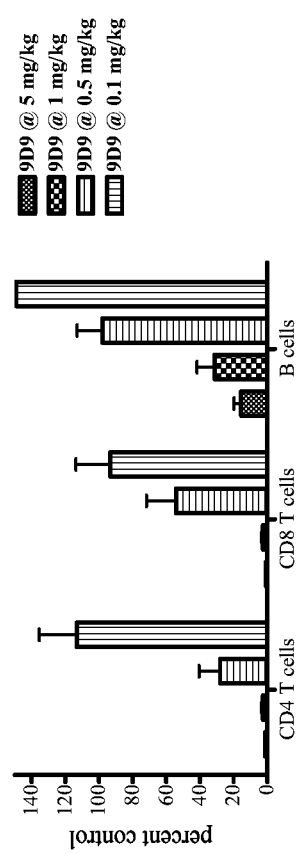
FIGS. 65A-65E show the level of CD4+ T cells, CD8+ T cells, B220+ B cells, NK cells, myeloid cells, macrophages, and neutrophils in the blood 72 hours after dosing with 9D9-H10/K12 ("9D9") antibodies.
Figure 65B:
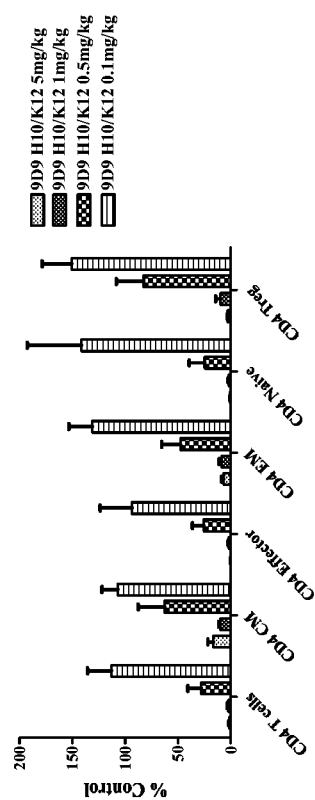
Figure 65C:
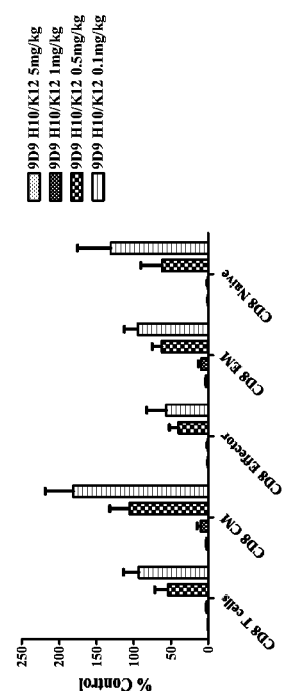
Figure 65D:
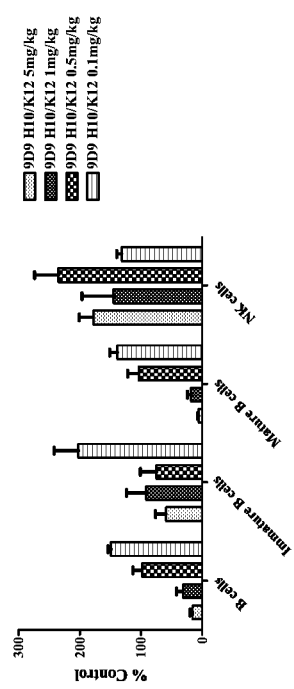
Figure 65E:
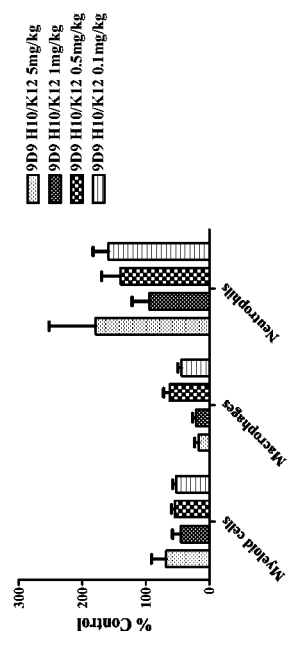
Figure 66A:
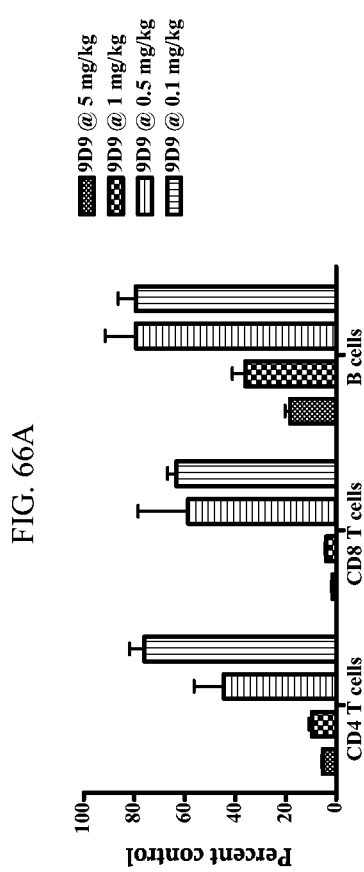
FIGS. 66A-66E show the level of CD4+ T cells, CD8+ T cells, B220+ B cells, NK cells, myeloid cells, neutrophils, and macrophages in the spleen 72 hours after dosing with 9D9-H10/K12 ("9D9") antibodies.
Figure 66B:
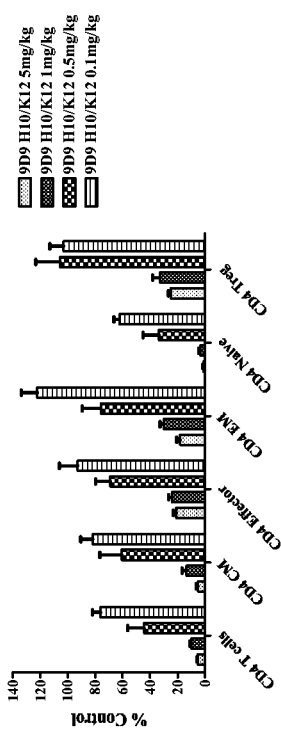
Figure 66C:
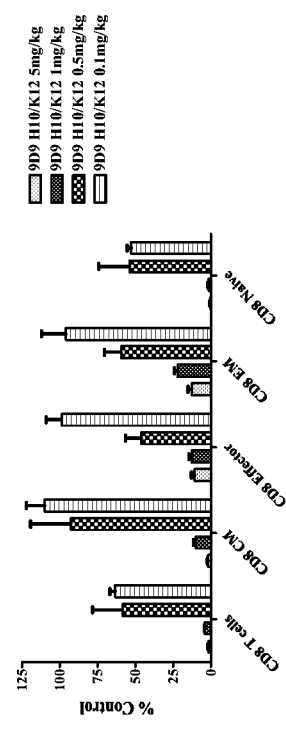
Figure 66D:
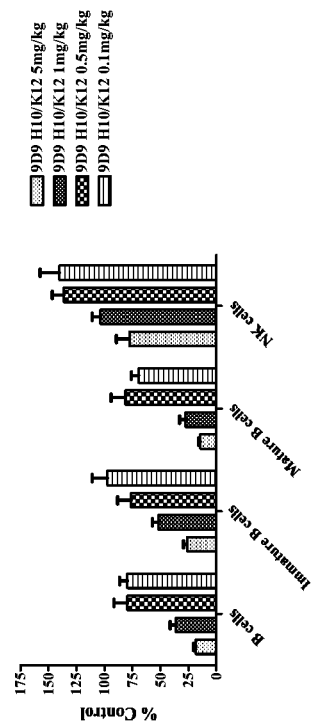
Figure 66E:
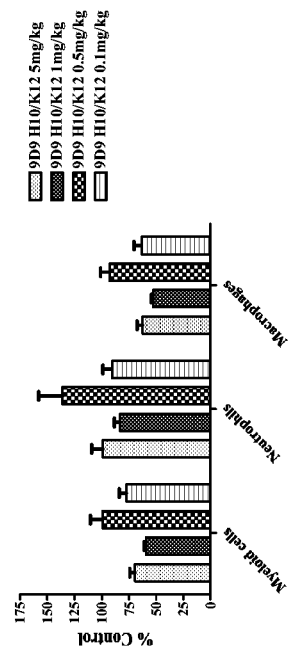
Figure 67:
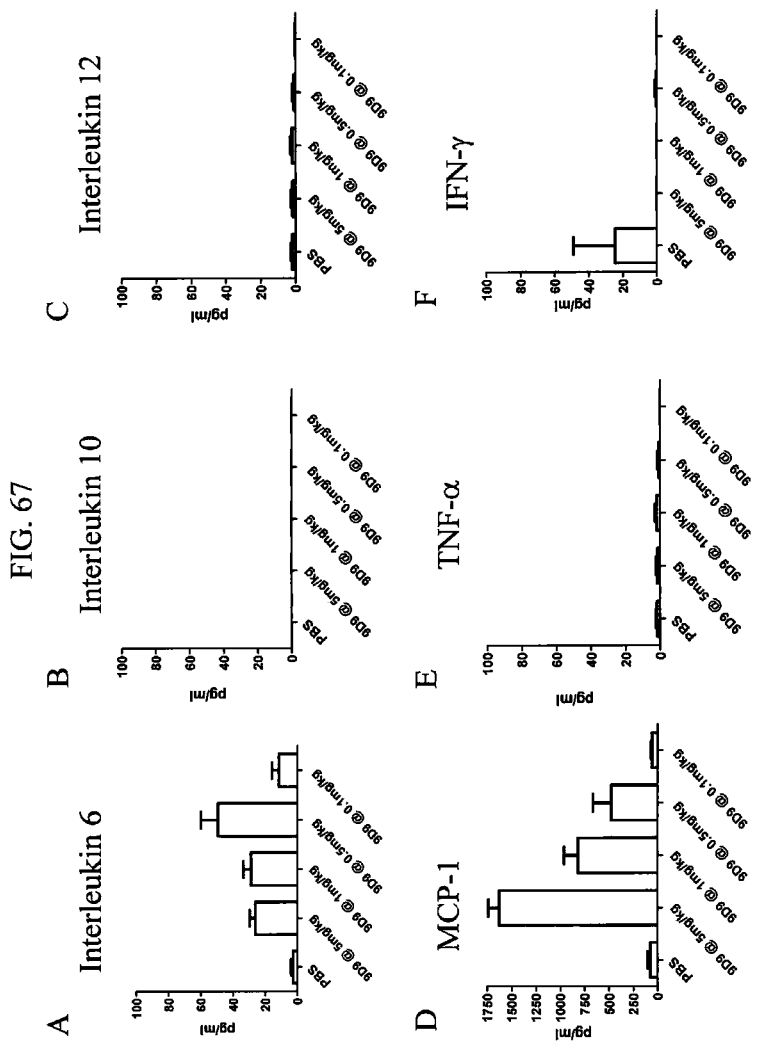
FIGS. 67A-67F show the levels of circulating cytokines 2 hours after dosing with 9D9-H10/K12 ("9D9") antibodies.

FIGS. 64A-64C show the level of 2C3-chimeric, 2C3-SFD1/K12, 12G6-chimeric, 12G6-SFD1/K11, 9D9-chimeric, and 9D9-H10/K12 antibodies in the blood over a timecourse after dosing.

Example 49

Analysis of Depletion and Repopulation of Anti-CD52 Antibodies in huCD52 Transgenic Mice (9D9-H10/K12)

The depleting activity of the 9D9-H10/K12 clone at different dose levels was examined in the huCD52 transgenic mouse. Mice were injected intravenously with 0.1, 0.5, 1.0 or 5.0 mg/kg of antibody. Two hours post dosing, serum was collected to potentially examine the level of circulating cytokines. Three days post dosing, mice were sacrificed, and blood and spleens were collected from each mouse (N=5) to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. A subset of mice (N=5) were kept alive to monitor the repopulation kinetics Administration of 9D9-H10/K12 at the 5, 1, and 0.5 mg/kg doses resulted in depletion of a significant number of both T cells and B cells in the blood. Only a modest level of lymphocyte depletion was observed in the blood at the 0.1 mg/kg dose. These data also demonstrated that various T and B cell subsets are depleted to differing degrees depending on the dose of antibody used. Naïve T cells (both CD4 and CD8) demonstrated the most depletion compared to other cell populations (including memory and T reg cells), which were depleted to a lesser degree. In the B cell compartment, mature B cells were depleted more readily than immature B cells. In the spleen, significant depletion of these cells was only observed at the 5 and 1 mg/kg dose levels. Similar to Campath-1H®, naïve T cells were more readily depleted than memory cells. Depletion was observed for NK cells and neutrophils in the blood but little to no depletion was observed in the spleen at any of the doses injected. Serum cytokine analysis demonstrated no significant increases for either TNFα or IL-6 at any of the dose levels analyzed. Dose dependent increases in the level of circulating MCP-1, however, were noted.

The repopulation portion of this experiment was terminated early when lymphocytes were 50-80% repopulated (depending on the dose). Lymphocyte repopulation was monitored based on total lymphocyte counts and not on a T and B cell basis.

Figure 68:
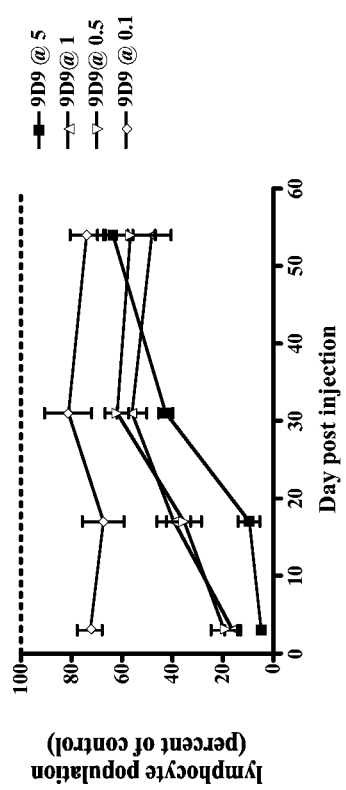
FIG. 68 shows the repopulation of circulating lymphocytes over a timecourse after dosing with 9D9-H10/K12 ("9D9") antibodies, (mg/kg).
Figure 69A:
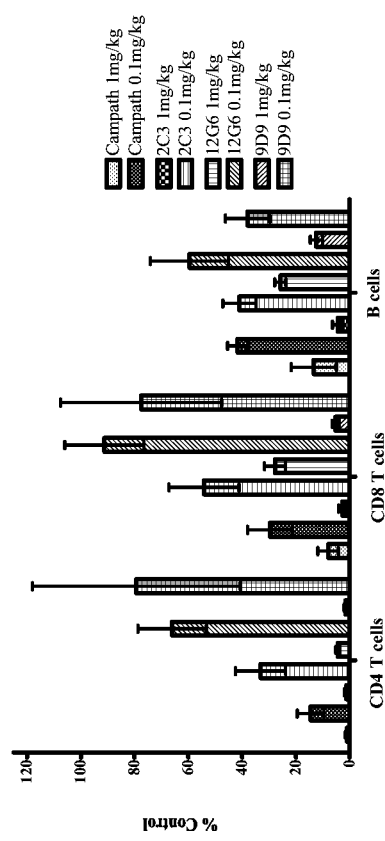
FIGS. 69A-69D show the level of bulk lymphocyte populations (CD4+ T cells, CD8+ T cells, and B cells) and CD4+ T cell, CD8+ T cell, B220+ B cell and NK cell subtypes in the blood 72 hours after dosing with Campath-1H® ("Campath"), 2C3-SFD1/K12 ("2C3"), 12G6-SFD1/K11 ("12G6"), and 9D9-H10/K12 ("9D9") antibodies.
Figures 69B, 69C:
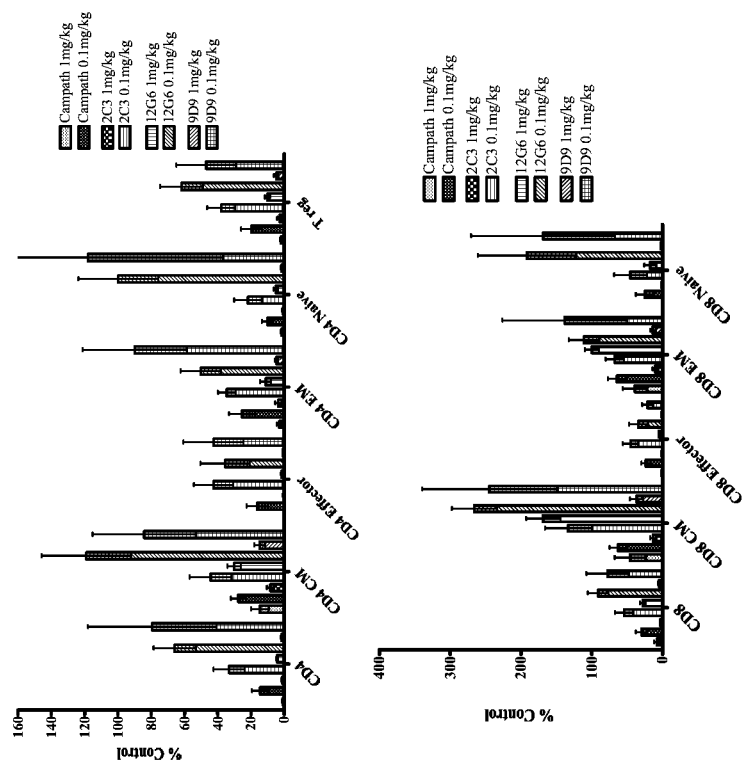
Figure 69D:
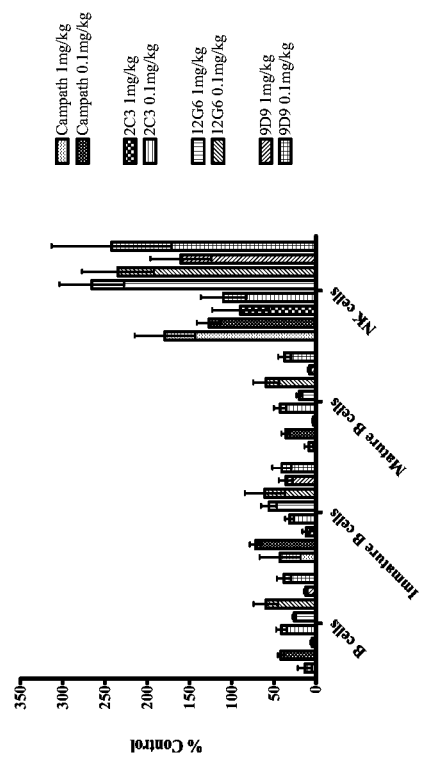
Figure 70A:
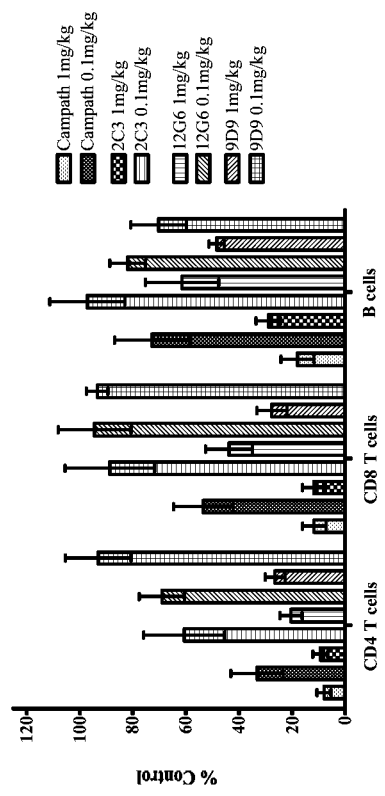
FIGS. 70A-70D show the level of bulk lymphocyte populations (CD4+ T cells, CD8+ T cells, and B cells) and CD4+ T cell, CD8+ T cell, B220+ B cell and NK cell subtypes in the spleen 72 hours after dosing with Campath-1H® ("Campath"), 2C3-SFD1/K12 ("2C3"), 12G6-SFD1/K11 ("12G6"), and 9D9-H10/K12 ("9D9") antibodies.
Figures 70B, 70C:
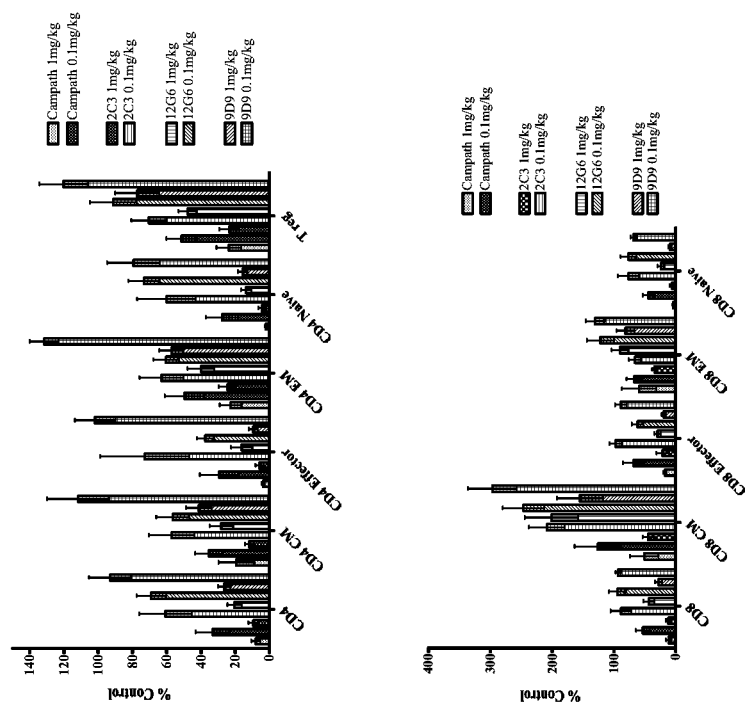
Figure 70D:
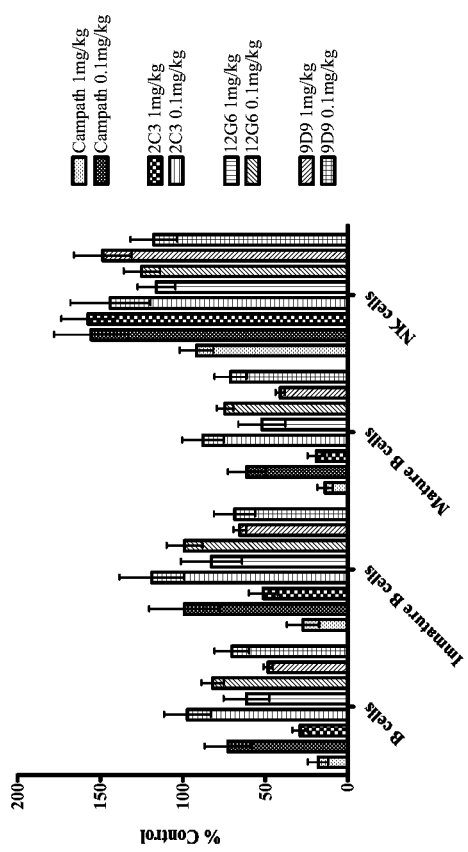
Figure 71:
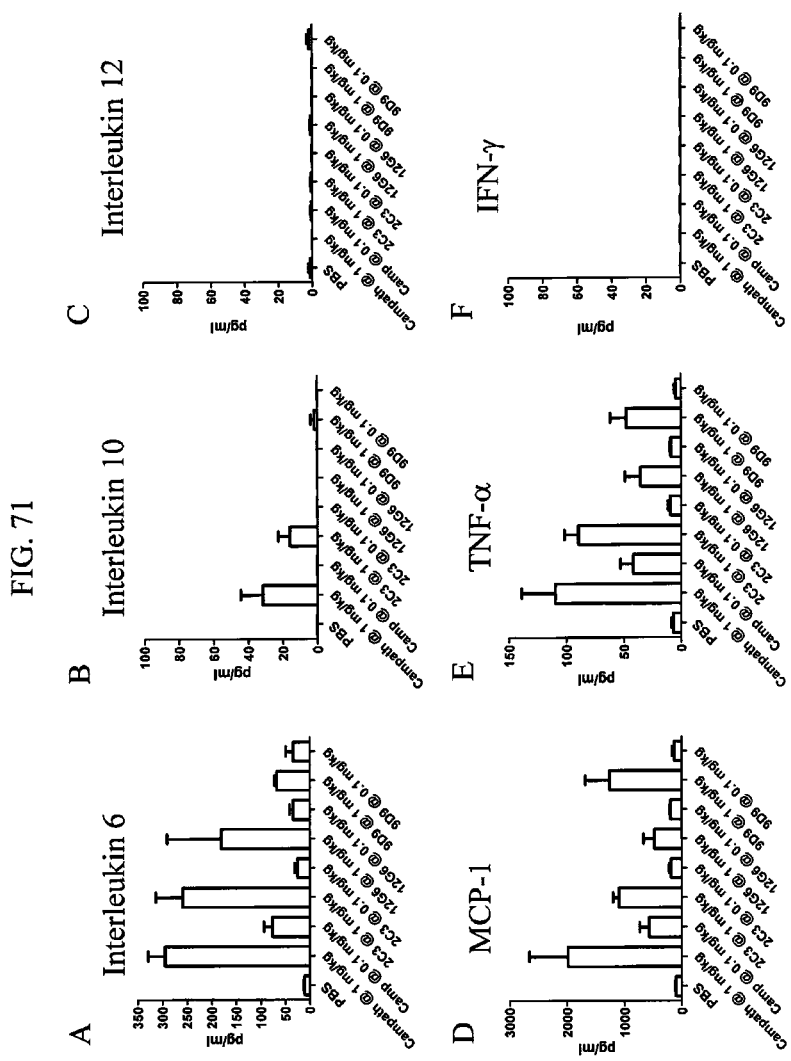
FIGS. 71A-71F show the levels of circulating cytokines 2 hours after dosing with Campath-1H®, 2C3-SFD1/K12, 12G6-SFD1/K11, and 9D9-H10/K12 antibodies.

FIGS. 65A-65E show the level of CD4+ T cells, CD8+ T cells and B220+ B cells in the blood 72 hours after dosing with 9D9-H10/K12 ("9D9") antibodies. FIGS. 66A-66E show the level of CD4+ T cells, CD8+ T cells and B220+ B cells in the spleen 72 hours after dosing with 9D9-H10/K12 ("9D9") antibodies. FIGS. 67A-67F show the levels of circulating cytokines 2 hours after dosing with 9D9-H10/K12 ("9D9") antibodies. FIG. 68 shows the repopulation of circulating lymphocytes over a timecourse after dosing with 9D9-H10/K12 ("9D9") antibodies.

Example 50

Analysis of Depletion and Repopulation of Anti-CD52 Antibodies in huCD52 Transgenic Mice (2C3-SFD1/K12, 12G6-SFD1/K11 and 9D9-H10/K12)

The depleting activity of Campath-1H® and the humanized 2C3-SFD1/K12, 12G6-SFD1/K11 and 9D9-H10/K12 clones at different dose levels was examined in the huCD52 transgenic mouse. Mice were injected intravenously with either 0.1 or 1.0 mg/kg of antibody. Two hours post dosing, serum was collected to potentially examine the level of circulating cytokines. Three days post dosing, mice were sacrificed, and blood and spleens were collected from each mouse to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. All of the humanized antibodies (2C3-SFD1/K12, 12G6-SFD1/K11 and 9D9-H10/K12) mediated depletion of lymphocytes within the spleen and blood when compared with PBS treated animals. Depletion was more robust in the blood than the spleen for all antibodies, and the depletion was dose-dependent in both tissues. Depletion was most dramatic for CD4 and CD8+ T cells with less depletion in the B cell compartment. Various T and B cell subsets were depleted to differing degrees. Naïve T cells (both CD4 and CD8) demonstrated the most depletion compared to other cell populations (including memory and T reg cells), which were depleted to a lesser degree. In the B cell compartment, mature B cells were depleted more readily than immature B cells. Serum cytokine analysis revealed significant increases in the level of IL-6, MCP-1 and TNFα 2 hours post dosing. Increases were noted for all antibodies, including Campath-1H®, and were dose dependent (i.e. higher cytokine levels were noted for the 1.0 mg/kg dose level than the 0.1 mg/kg dose). In comparison to Campath-1H®, 2C3-SFD1/K12 and 12G6-SFD1/K11 induced similar levels of IL-6 while 9D9-H10/K12 induced IL-6 to a significantly lower degree. For MCP-1, the 12G6-SFD1/K11 antibody induced lower levels, and both 12G6-SFD1/K11 and 9D9-H10/K12 decreased TNFα levels compared to Campath-1H®.

FIGS. 69A-69D show the level of bulk lymphocyte populations (CD4+ T cells, CD8+ T cells, and B cells) and CD4+ T cell, CD8+ T cell and B220+ B/NK cell subtypes in the blood 72 hours after dosing with Campath-1H® ("Campath"), 2C3-SFD1/K12 ("2C3"), 12G6-SFD1/K11 ("12G6"), and 9D9-H10/K12 ("9D9") antibodies. FIGS. 70A-70D show the level of bulk lymphocyte populations (CD4+ T cells, CD8+ T cells, and B cells) and CD4+ T cell, CD8+ T cell and B220+ B/NK cell subtypes in the spleen 72 hours after dosing with Campath-1H® ("Campath"), 2C3-SFD1/K12 ("2C3"), 12G6-SFD1/K11 ("12G6"), and 9D9-H10/K12 ("9D9") antibodies. FIGS. 71A-71F show the levels of circulating cytokines 2 hours after dosing with Campath-1H®, 2C3-SFD1/K12, 12G6-SFD1/K11, and 9D9-H10/K12 antibodies.

Example 51

Direct Comparison of Anti-huCD52 Humanized 9D9 Clones in huCD52 Transgenic Mice (9D9 H10/K12 and 9D9 H11/K12)

The depleting activity of two humanized anti-CD52 9D9 clones (9D9-H10/K12 and 9D9-H11/K12) was examined in huCD52 transgenic mice. Mice were injected intravenously with either 0.1 or 1.0 mg/kg of antibody. Three days post dosing, mice were sacrificed, and blood and spleens were collected from each mouse to determine the level of cell depletion using flow cytometry analysis. Samples were evaluated to determine the relative numbers of total T helper cell (CD4+), cytotoxic T cell (CD8+), B cell (B2200+) and NK cell subpopulations present in the circulating peripheral blood or spleen of huCD52 transgenic mice. Treatment with either antibody resulted in similar lymphocyte depletion within the blood and spleen, with lymphocyte depletion in the blood being more robust. Further, CD4 and CD8+ T cells were more strongly depleted than B cells and NK cells in both tissues. While the depletion with the 9D9-H10/K12 clone appears less robust than the depletion with the 9D9-H11/K12 clone, the difference is not statistically significant.

Figure 72:
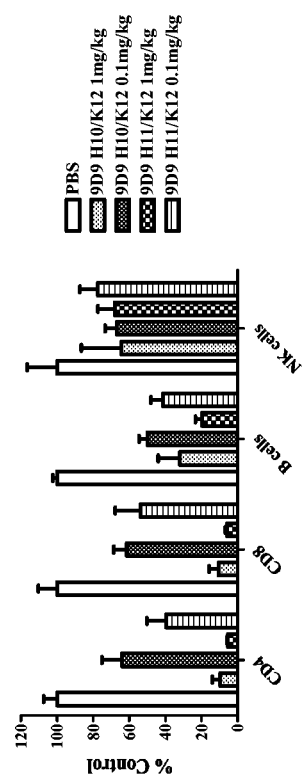
FIG. 72 shows the level of CD4+ T cells, CD8+ T cells, B220+ B cells, and NK cells in the blood 72 hours after dosing with 9D9-H10/K12 and 9D9-H11/K12 antibodies.
Figure 73:
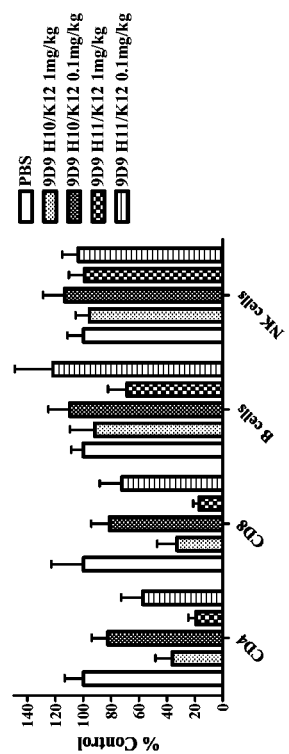
FIG. 73 shows the level of CD4+ T cells, CD8+ T cells, B220+ B cells, and NK cells in the spleen 72 hours after dosing with 9D9-H10/K12 and 9D9-H11/K12 antibodies.
Figures 74A, 74B:
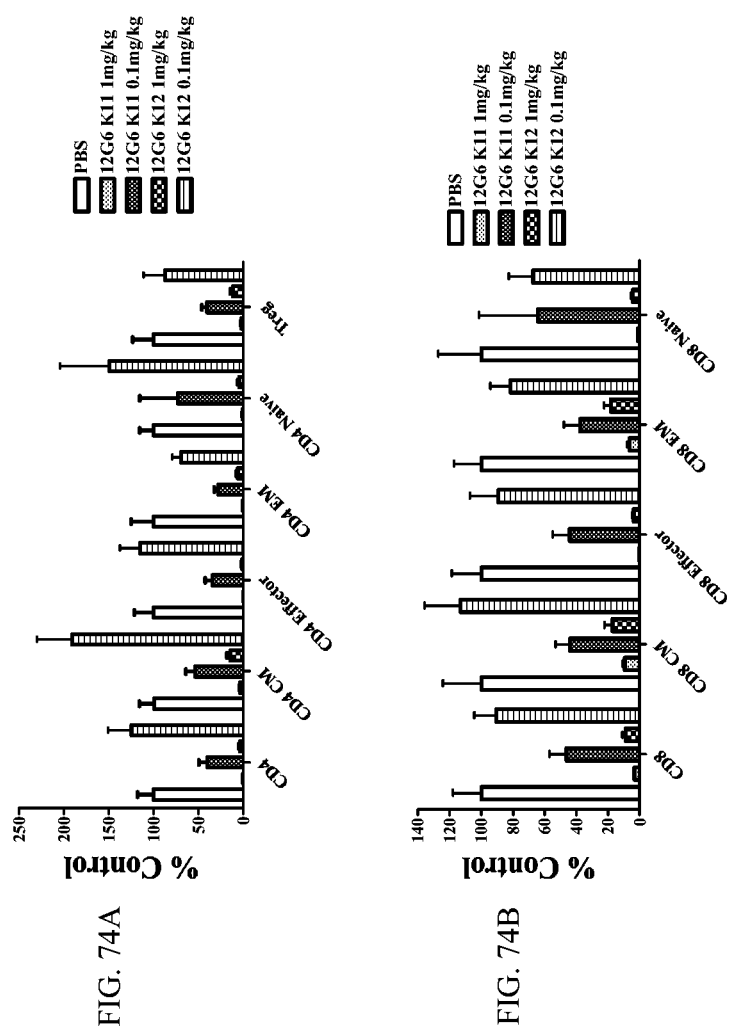
FIGS. 74A-74D show the level of CD4+ T cells, CD8+ T cells, B220+ B cells, NK cells, and myeloid cells in the blood 72 hours after dosing with 12G6-SFD1/K11 ("12G6 K11") and 12G6-SFD1/K12 ("12G6 K12") antibodies.
Figure 74C:
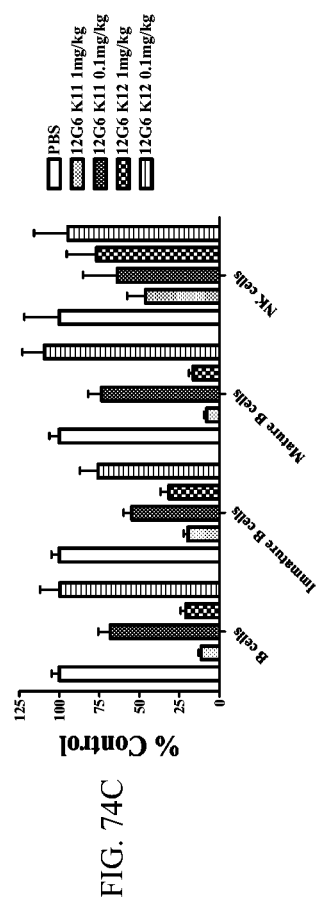
Figure 74D:
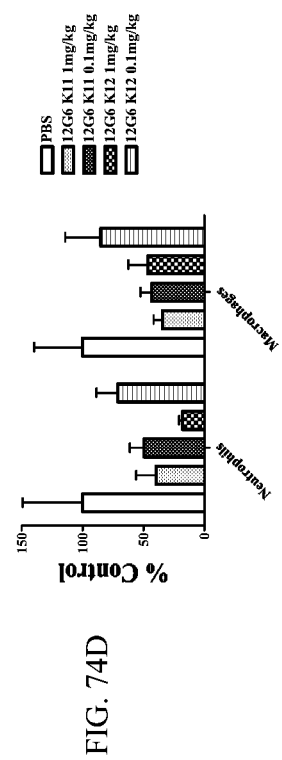
Figure 75A:
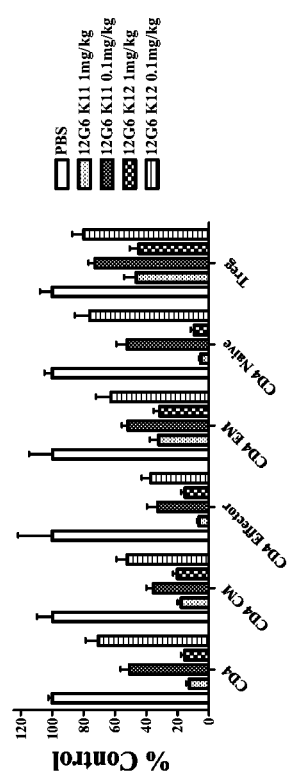
Figure 75B:
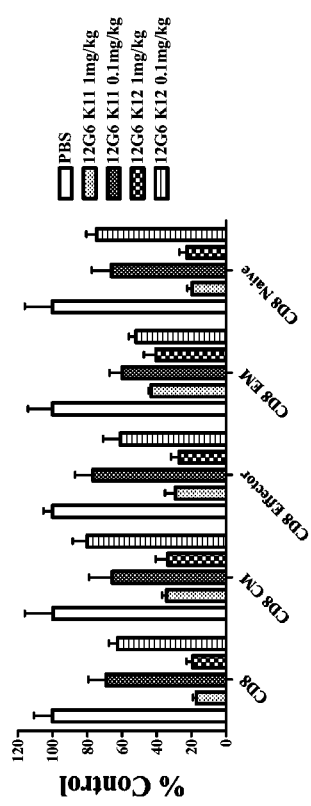

FIG. 72 shows the level of CD4+ T cells, CD8+ T cells, B220+ B cells, and NK cells in the blood 72 hours after dosing with 9D9-H10/K12 and 9D9-H11/K12 antibodies. FIG. 73 shows the level of CD4+ T cells, CD8+ T cells, B220+ B cells, and NK cells in the spleen 72 hours after dosing with 9D9-H10/K12 and 9D9-H11/K12 antibodies.

Example 52

Direct Comparison of Anti-huCD52 Humanized 12G6 Clones in huCD52 Transgenic Mice (12G6-SFD1/K11 and 12G6-SFD1-K12)

The depleting activity of two humanized anti-CD52 12G6 clones (12G6-SFD1/K11 and 12G6-SFD1/K12) was examined in the huCD52 transgenic mouse. Mice were injected intravenously with either 0.1 or 1.0 mg/kg of antibody. Two hours post dosing, serum was collected to potentially examine the level of circulating cytokines. Three days post dosing, mice were sacrificed, and blood and spleens were collected from each mouse to determine the level of cell depletion using flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. Administration of either the 12G6-SFD1/K11 antibody or the 12G6-SFD1/K12 antibody resulted in a significant level of lymphocyte depletion within the blood. There appeared to be little to no difference in the lymphocyte depleting activity of the two clones. The pattern of lymphocyte depletion was s such that naïve CD4 and CD8+ T cells were depleted to a higher degree than memory T cells or Treg cells. Myeloid cell populations were depleted to a lesser degree regardless of the clone (12G6-SFD1/K11 or 12G6-SFD1/K12) or dose. Serum cytokine analysis was not performed for this experiment.

FIGS. 74A-74D show the level of CD4+ T cells, CD8+ T cells, B220+ B/NK cells, and myeloid cells in the blood 72 hours after dosing with 12G6-SFD1/K11 ("12G6 K11") and 12G6-SFD1/K12 ("12G6 K12") antibodies. FIGS. 75A-75D show the level of CD4+ T cells, CD8+ T cells, B220+ B/NK cells, and myeloid cells in the spleen 72 hours after dosing with 12G6-SFD1/K11 ("12G6 K11") and 12G6-SFD1/K12 ("12G6 K12") antibodies.

Example 53

Direct Comparison of Anti-huCD52 Humanized 9D9 Clones in huCD52 Transgenic Mice (9D9 H11/K12, 9D9 H16/K13, and 9D9 H18/K13)

The depleting activity of three humanized 9D9 antibodies (9D9-H11/K12, 9D9-H16/K13, and 9D9-H18/K13) was compared in the huCD52 transgenic mouse. Human CD52 transgenic mice were treated with PBS as a vehicle control or injected with either 1 mg/kg or 0.1 mg/kg of each antibody. At two hours post dosing, serum was collected to determine the level of circulating cytokines. Three days later, mice were sacrificed, and peripheral blood and spleens were collected and processed for flow cytometry analysis. Samples were evaluated to determine the relative numbers of total T helper cell (CD4+), cytotoxic T cell (CD8+), B cell (B220+) and myeloid cell subpopulations present in the circulating peripheral blood or spleen of huCD52 transgenic mice. In addition, T and B cell subset analysis was performed to determine the overall depleting effect. All 9D9 (9D9-H11/K12, 9D9-H16/K13, and 9D9-H18/K13) antibodies mediated cellular depletion of lymphocyte and myeloid cell populations in the blood and spleen to a similar extent. More robust lymphocyte and myeloid cell depletion was observed in the blood than the spleen. Comparison of the depleting activity of the 9D9 clones (9D9-H11/K12, 9D9-H16/K13, and 9D9-H18/K13) demonstrated that 9D9-H16/K13 resulted in the most robust depletion, followed by 9D9-H18/K13 and 9D9-H11/K12. This was most apparent for lymphocytes in the spleen at the 1 mg/kg dose in which 9D9-H16/K13 treatment resulted in a higher degree of depletion than either of the other clones (9D9-H18/K13 and 9D9-H11/K12). Further, the pattern of depletion was such that naïve CD4 and CD8+ T cells were depleted to a higher degree than memory T cells or Treg cells, and B cell populations were depleted to a higher level with 9D9-H16/K13. Myeloid cell populations were less impacted by anti-CD52 treatment regardless of the clone of antibody (9D9-H11/K12, 9D9-H16/K13, or 9D9-H18/K13) or dose. Of the cytokines analyzed, increases were noted in IL-6, TNFα and MCP-1. Following injection, similar circulating level of IL6 and MCP-1 were observed for all of the 9D9 clones (9D9-H11/K12, 9D9-H16/K13, and 9D9-H18/K13) at both the 0.1 and 1.0 mg/kg dose levels. Slight differences were observed with circulating TNFα levels in which injection of the 9D9-H16/K13 clone resulted in a modest increase at the 1.0 mg/kg dose.

Figure 76:
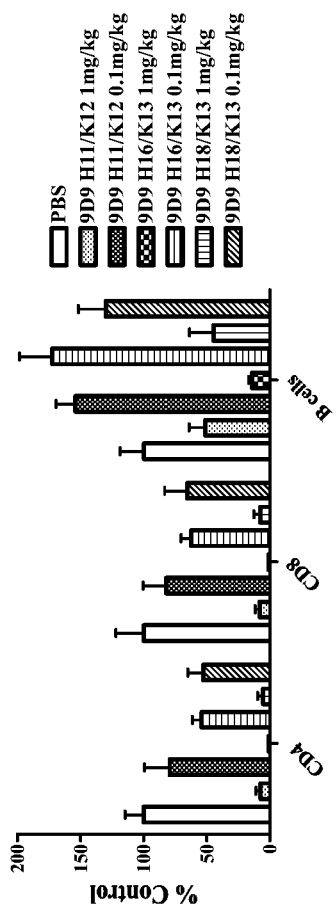
FIG. 76 shows the level of bulk lymphocyte populations (CD4+ T cells, CD8+ T cells, and B220+ B cells) in the blood 72 hours after dosing with 9D9-H11/K12, 9D9-H16/K13, and 9D9-H18/K13 antibodies.
Figures 77A, 77B:
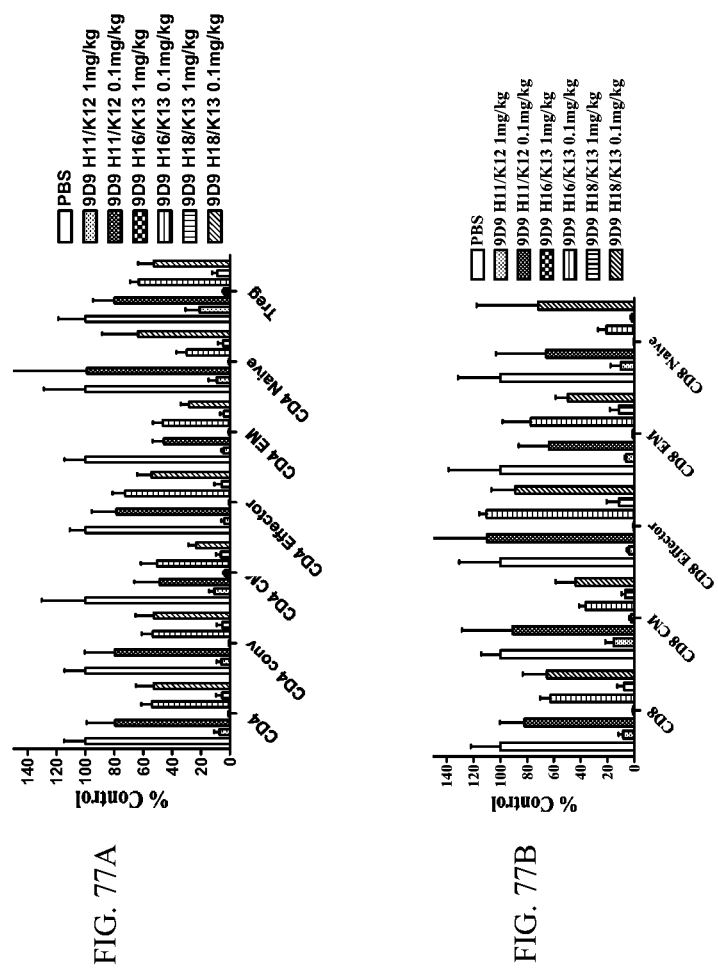
FIGS. 77A-77D show the level of CD4+ T cell, CD8+ T cell, B220+ B cell, NK cell, and myeloid cell subtypes in the blood 72 hours after dosing with 9D9-H11/K12, 9D9-H16/K13, and 9D9-H18/K13 antibodies.
Figure 77C:
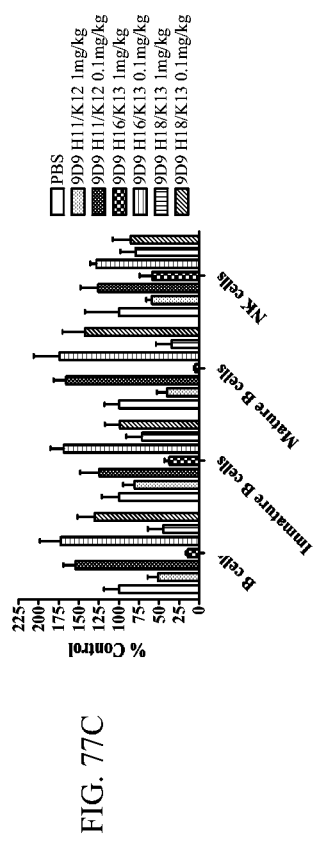
Figure 77D:
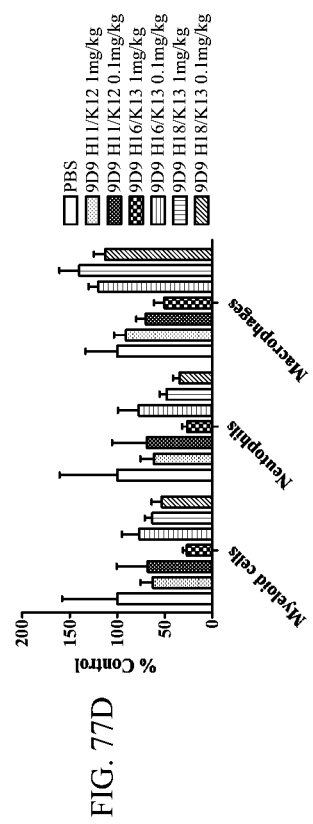
Figure 78:
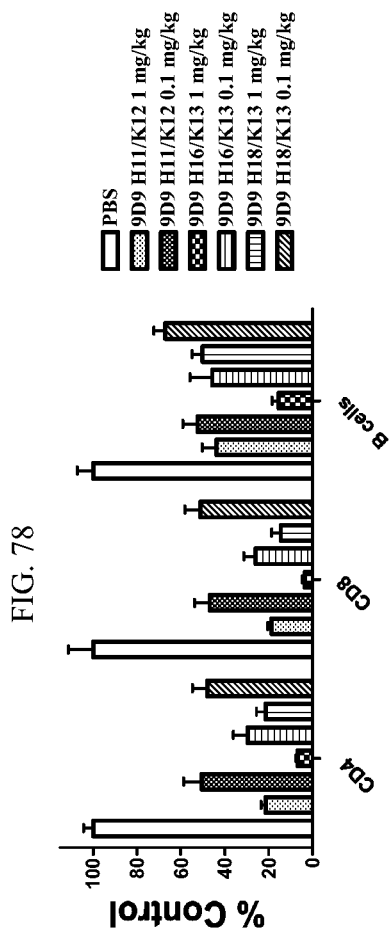
FIG. 78 shows the level of bulk lymphocyte populations (CD4+ T cells, CD8+ T cells, and B220+ B cells) in the spleen 72 hours after dosing with 9D9-H11/K12, 9D9-H16/K13, and 9D9-H18/K13 antibodies.
Figure 79A:
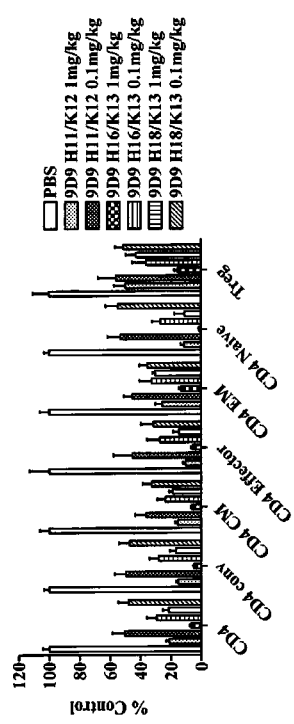
FIGS. 79A-79D show the level of CD4+ T cell, CD8+ T cell, B220+ B cell, NK cell, and myeloid cell subtypes in the spleen 72 hours after dosing with 9D9-H11/K12, 9D9-H16/K13, and 9D9-H18/K13 antibodies.
Figure 79B:
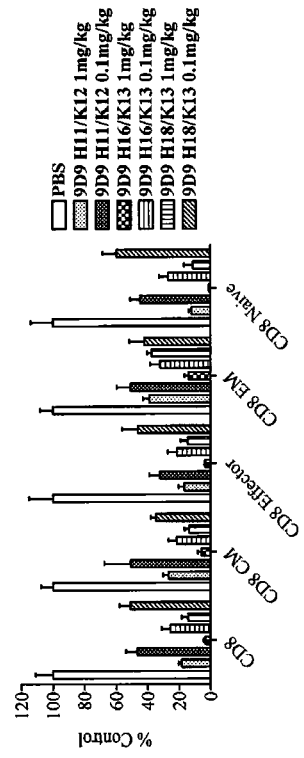
Figure 79C:
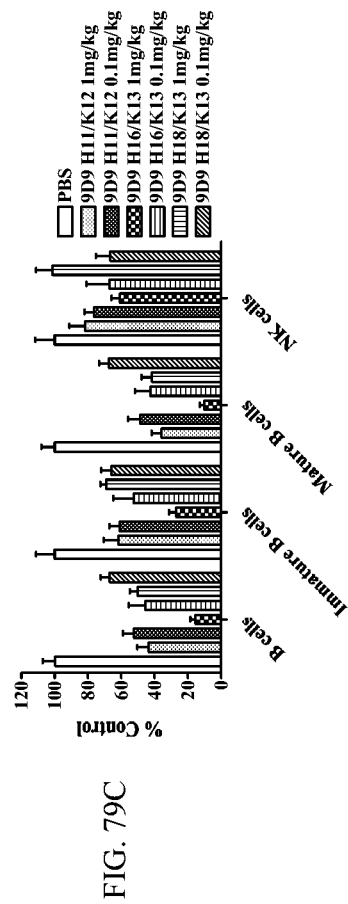
Figure 79D:
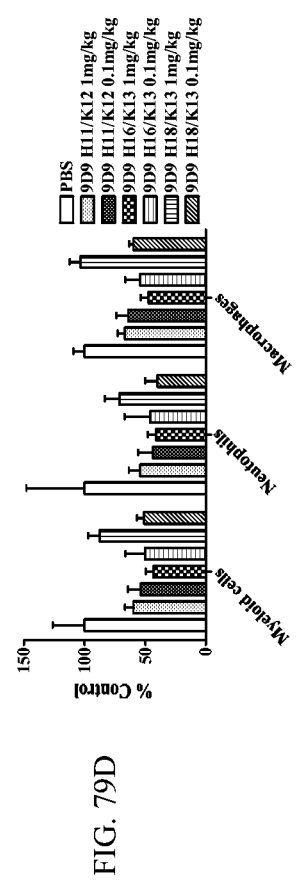
Figure 80:
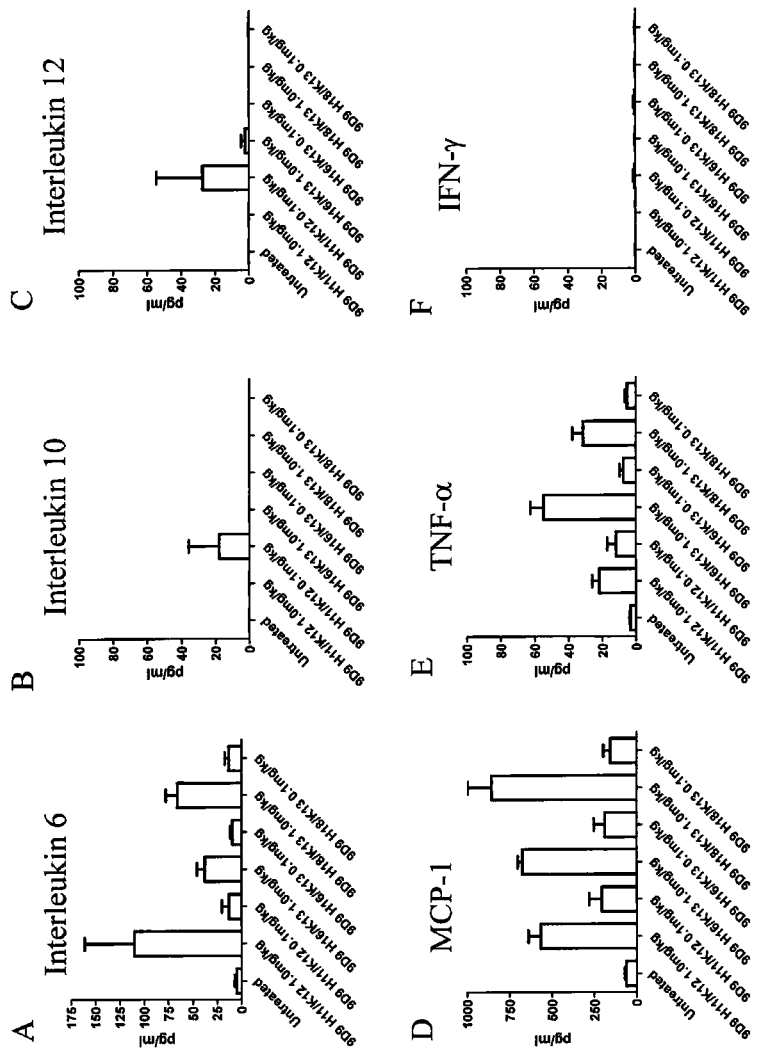
FIGS. 80A-80F show the levels of circulating cytokines 2 hours after dosing with 9D9-H11/K12, 9D9-H16/K13, and 9D9-H18/K13 antibodies.

FIG. 76 shows the level of bulk lymphocyte populations (CD4+ T cells, CD8+ T cells, and B220+ B cells) in the blood 72 hours after dosing with 9D9-H11/K12, 9D9-H16/K13, and 9D9-H18/K13 antibodies. FIGS. 77A-77D show the level of CD4+ T cell, CD8+ T cell, B220+ B/NK cell, and myeloid cell subtypes in the blood 72 hours after dosing with 9D9-H11/K12, 9D9-H16/K13, and 9D9-H18/K13 antibodies. FIG. 78 shows the level of bulk lymphocyte populations (CD4+ T cells, CD8+ T cells, and B220+ B cells) in the spleen 72 hours after dosing with 9D9-H11/K12, 9D9-H16/K13, and 9D9-H18/K13 antibodies. FIGS. 79A-79D show the level of CD4+ T cell, CD8+ T cell, B220+ B/NK cell, and myeloid cell subtypes in the spleen 72 hours after dosing with 9D9-H11/K12, 9D9-H16/K13, and 9D9-H18/K13 antibodies. FIGS. 80A-80F show the levels of circulating cytokines 2 hours after dosing with 9D9-H11/K12, 9D9-H16/K13, and 9D9-H18/K13 antibodies.

Example 54

Analysis of PK Profile of Anti-CD52 Antibodies from the 2C3, 12G6, and 9D9 Families in CD52 Transgenic Mice The pharmacokinetic profiles of humanized 2C3-SFD1/K12, 12G6-SFD1/K11, 12G6-SFD1/K12, 9D9-H16/K13 and 9D9-H18/K13 were determined in huCD52 transgenic mice. Mice were injected i.v. with antibodies at 1 mg/kg and blood was collected at various timepoints beginning two hours post dosing. The circulating levels of each antibody were evaluated using an anti-human Ig ELISA. The calculated half-lives were: 2C3-SFD1/K12 79.0±23.9 hours, 12G6-SFD1/K11 49.0±14.4 hours, 12G6-SFD1/K12 75.1±28.5, 9D9-H16/K13 59.8+26.6 hours and 9D9-H18/K13 42.2+15.7 hours.

Overall, there was significant inter-animal variability for exposure in these studies. The terminal elimination half-lives for 2C3-SFD1/K12 and 12G6-SFD1/K12 were similar while the half-life of 12G6-SFD1/K11 was shorter but not significantly different. Clearance was fastest with 2C3-SFD1/K12 followed by 12G6-SFD1/K11 and 12G6-SFD1/K12. The two 12G6 treatments mirrored each other for most of the time points measured, while 2C3-SFD1/K12 showed less exposure and faster clearance. 9D9-H16/K13 and 9D9-H18/K13 were quite similar for all PK parameters measured.

Figure 81:
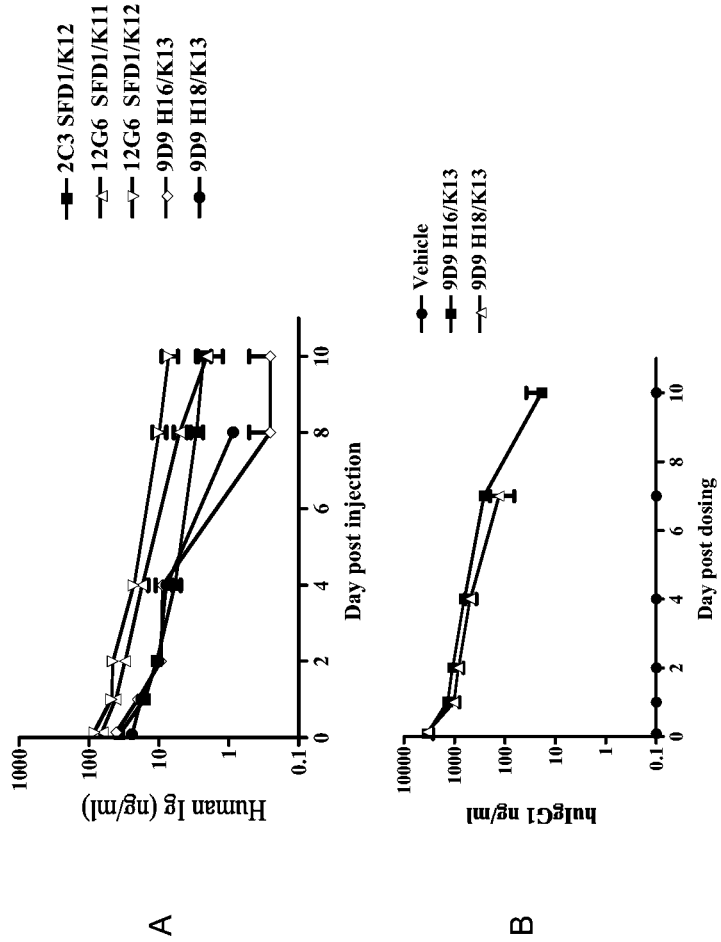
FIGS. 81A and 81B show the level of 2C3-SFD1/K12, 12G6-SFD1/K11, 12G6-SFD1/K12, 9D9-H16/K13 and 9D9-H18/K13 antibodies in the blood over a timecourse after dosing.
Figure 82A:
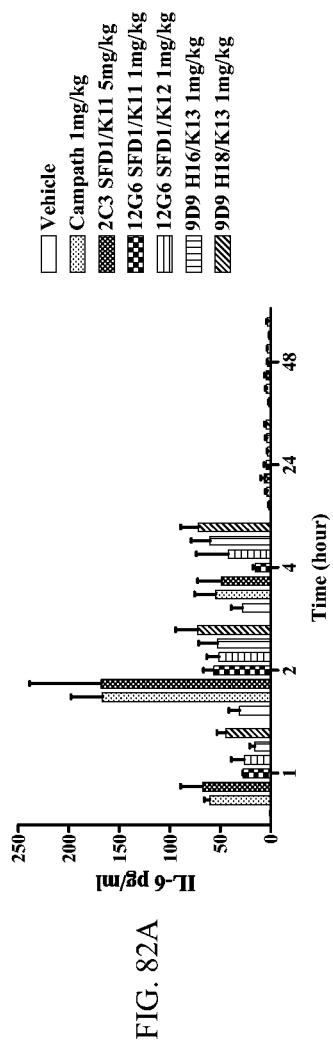
FIGS. 82A-82F show the level of cytokines in the blood over a 48-hour timecourse following dosing with Campath-1H® ("Campath"), 2C3-SFD1/K11, 12G6-SFD1/K11, 12G6-SFD1/K12, 9D9-H16/K13 or 9D9-H18/K13 antibodies.
Figure 82B:
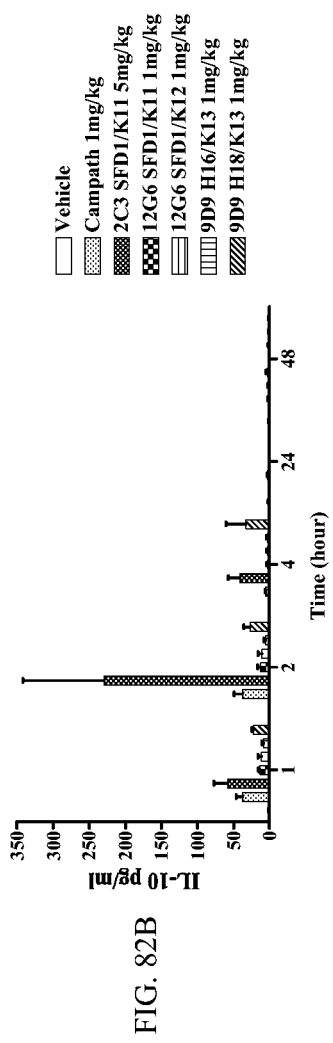
Figures 82C, 82D:
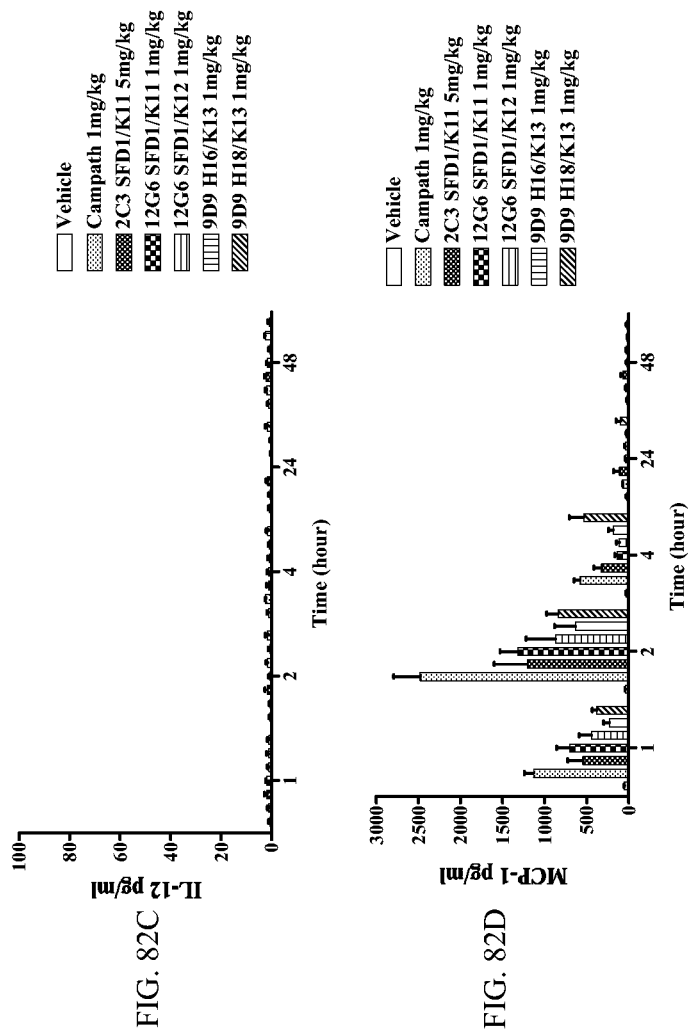
Figures 82E, 82F:
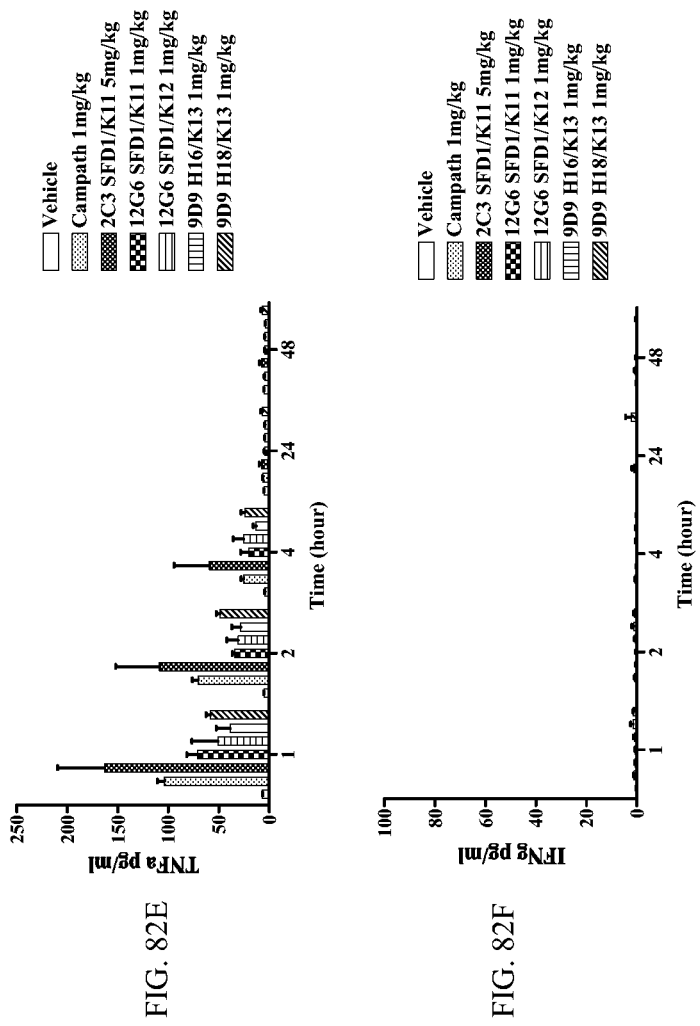
Figure 83A:
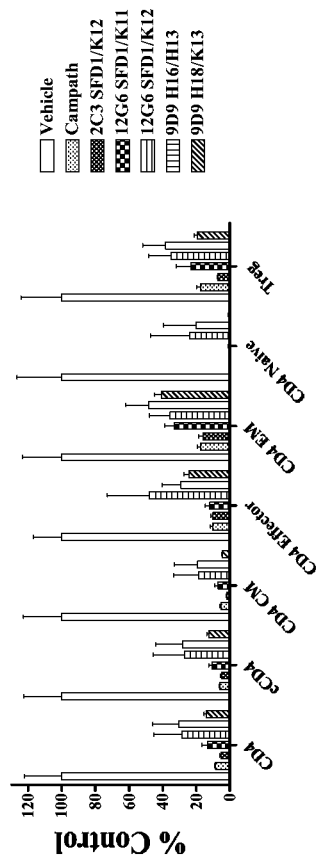
FIGS. 83A-83E show the level of bulk lymphocytes, CD4+ T cells, CD8+ T cells, B220+ B cells, NK cells, and myeloid cells in the spleen 72 hours after dosing with Campath-1H® ("Campath"), 2C3-SFD1/K11, 12G6-SFD1/K11, 12G6-SFD1/K12, 9D9-H16/K13 or 9D9-H18/K13 antibodies.
Figure 83B:
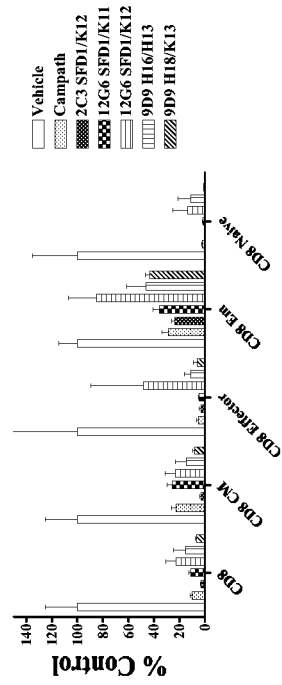
Figure 83C:
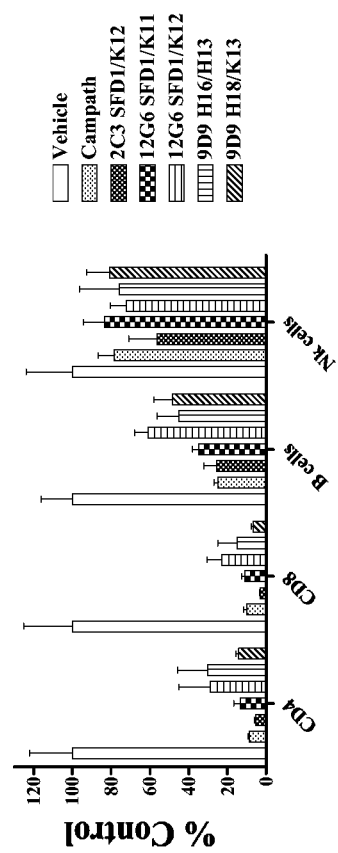
Figures 83D, 83E:
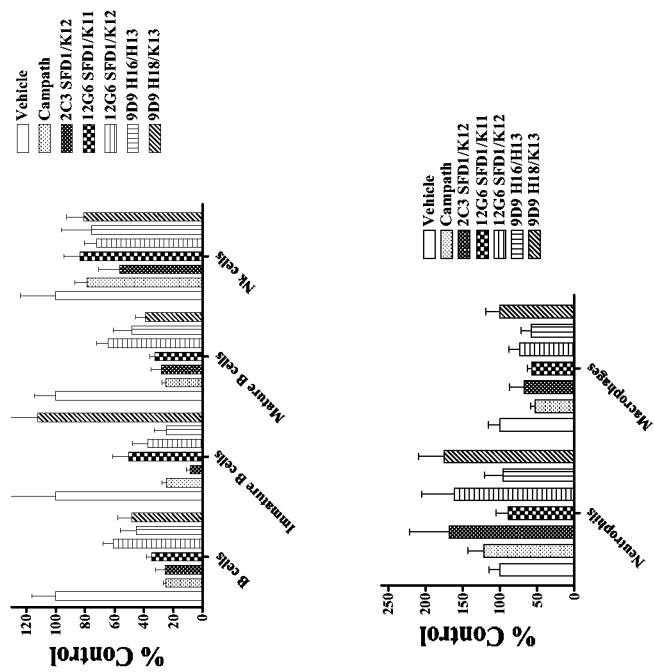
Figure 84A:
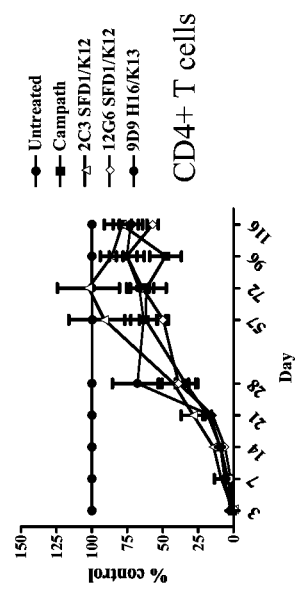
FIGS. 84A-84G show the repopulation of circulating CD4+ and CD8+ T cells, regulatory T cells, B cells, NK cells, neutrophils and macrophages over a timecourse after dosing with Campath-1H® ("Campath"), 2C3-SFD1/K12, 9D9-H16/K13 and 12G6-SFD1/K12 antibodies.
Figure 84B:
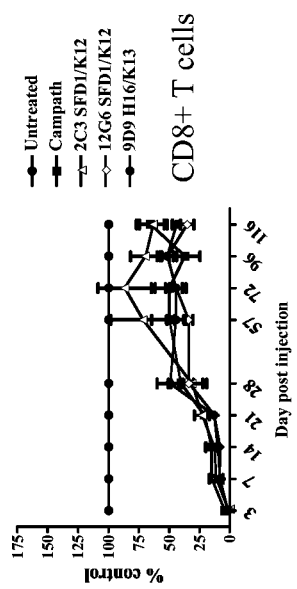
Figures 84C, 84D:
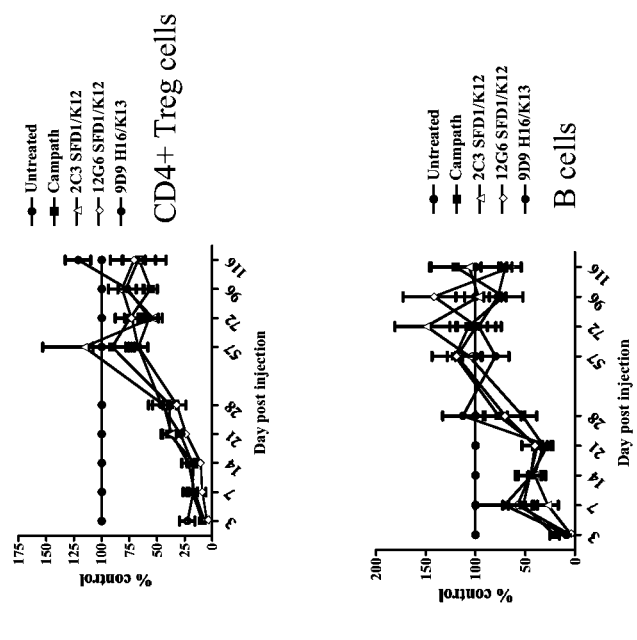
Figure 84E:
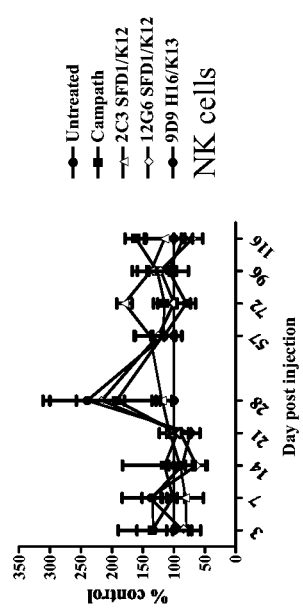
Figure 84F:
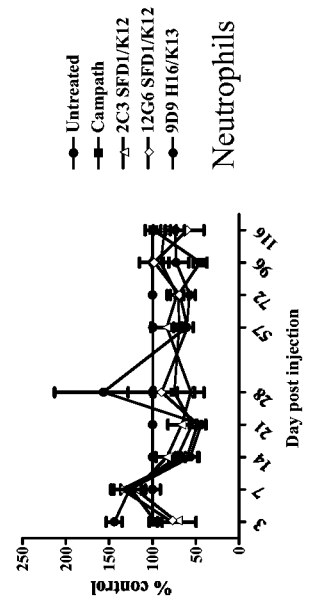
Figure 84G:
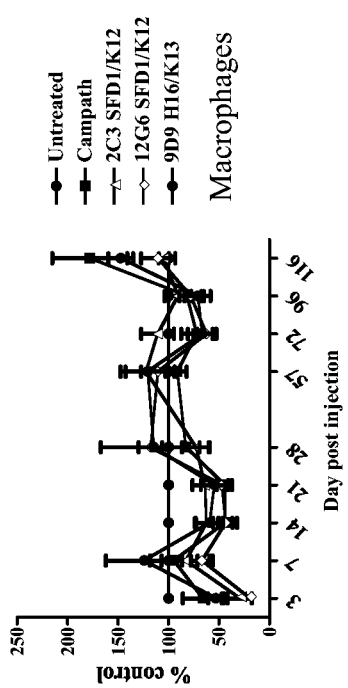

FIGS. 81A-81B show the level of 2C3-SFD1/K12, 12G6-SFD1/K11, 12G6-SFD1/K12, 9D9-H16/K13 and 9D9-H18/K13 antibodies in the blood over a timecourse after dosing.

TABLE 16

|  | PK Parameters | | | | |
| --- | --- | --- | --- | --- | --- |
|  | 2C3-SFD1/K12 | 12G6-SFD1/K11 | 12G6-SFD1/K12 | 9D9-H16/K13 | 9D9-H18/K13 |
| $t_{1/2}$ (hr) | 79.0 ± 23.9 | 49.0 ± 14.4 | 75.1 ± 28.5 | 59.8 ± 26.6 | 42.2 ± 15.7 |
| Cl (ml/hr/kg) | 20.3 ± 2.9 | 10.6 ± 1.69 | 7.08 ± 1.80 | 5.64 ± 1.73 | 6.65 ± 3.02 |
| Vz (ml/kg) | 2251 ± 539 | 770 ± 294 | 721 ± 224 | 445 ± 133 | 366 ± 100 |
| AUC (ug * hr/ml) | 251 ± 37.2 | 485 ± 104 | 747 ± 188 | 196 ± 70.2 | 174 ± 65.2 |
| Cmax (ug/ml) | 4.22 ± 0.54 | 7.12 ± 1.97 | 8.96 ± 2.33 | 3.58 ± 2.16 | 4.35 ± 1.54 |

Example 55

Evaluation of Cytokine Storm in Response to Treatment with Anti-CD52 Antibodies

The release of serum cytokine following treatment with anti-CD52 antibodies was evaluated in huCD52 transgenic mice. Animals were treated with 1 mg/kg of Campath-1H®, 12G6-SFD1/K11, 12G6-SFD1/K12, 9D9-H16/K13 or 9D9-H18/K13. One group of animals was treated with 5 mg/kg of 2C3-SFD1/K12 in view of previous results indicating that injection with 2C3-SFD1/K12 may result in lower levels of depletion compared to the other antibodies, thereby normalizing the groups based on the dose needed to achieve similar levels of depletion. All groups were bled 1 2, 4, 24, and 48 hours post treatment and CBA analysis for inflammatory cytokines was conducted. All groups were also sacrificed 3 days post treatment and the spleens were evaluated for depletion of lymphocytes in the spleen by flow cytometry. Treatment with each of the antibodies resulted in depletion of various targets similar to that observed for Campath-1H®. This was also true for 2C3-SFD1/K12, in which a 5 mg/kg dose was used to elicit similar depletion. Some variability in depletion was observed with 12G6-SFD1/K12 and 9D9-H16/K13, most likely due to the repeated bleeding of the animals to acquire serum for cytokine analysis. Cytokine expression, however, was reduced for antibodies from the 12G6 (12G6-SFD1/K11 and 12G6-SFD1/K12) and 9D9 (9D9-H16/K13 and 9D9-H18/K13) family members. This was most noticeable for release of IL-6, MCP-1 and TNFα at the early 1 and 2 hour time points.

FIGS. 82A-82F show the level of cytokines in the blood over a 48-hour timecourse following dosing with Campath- 1H® ("Campath"), 12G6-SFD1/K11, 12G6-SFD1/K12, 9D9-H16/K13 or 9D9-H18/K13 antibodies. FIGS. 83A-83E show the level of bulk lymphocytes, CD4+ T cells, CD8+ T cells, B220+ B/NK cells, and myeloid cells in the spleen 72 hours after dosing with Campath-1H® ("Campath"), 12G6-SFD1/K11, 12G6-SFD1/K12, 9D9-H16/K13 or 9D9-H18/K13 antibodies.

Example 56

Evaluation of the Repopulation Kinetics in the Blood of CD52 Transgenic Mice Following Treatment with Anti-CD52 Antibodies The repopulation kinetics of several cell types in the blood were assessed following administration of humanized anti-CD52 2C3-SFD1/K12, 9D9-H16/K13 and 12G6-SFD1/K12 antibodies. Mice were injected i.v. with each antibody at 2 mg/kg to ensure a robust level of depletion. At various timepoints post injection, blood was collected for flow cytometry analysis to determine the level of circulating lymphocytes in the blood, including CD4+ and CD8+ T cells, regulatory T cells, B cells, NK cells, neutrophils and macrophages. No differences were observed in the initial depleting activity for each antibody, which was confirmed on day 3 post injection. Mice were bled weekly for the first month and biweekly thereafter to monitor the kinetics of repopulation. The kinetics of lymphocyte repopulation were similar for any of the anti-CD52 (2C3-SFD1/K12, 9D9-H16/K13 and 12G6-SFD1/K12) antibodies compared to Campath-1H®. By day 57, the B cells returned to baseline in the blood while T cells approached baseline levels by day 84. By day 116, CD8+ T cells had not returned to control levels, but similar repopulation kinetics for all other cell types monitored were observed with each of the anti-CD52 (2C3-SFD1/K12, 9D9-H16/K13 and 12G6-SFD1/K12) antibodies and Campath-1H®.

FIGS. 84A-84G show the repopulation of circulating CD4+ and CD8+ T cells, regulatory T cells, B cells, NK cells, neutrophils and macrophages over a timecourse after dosing with Campath-1H® ("Campath"), 2C3-SFD1/K12, 9D9-H16/K13 and 12G6-SFD1/K12 antibodies.

Example 57

Evaluation of CD52 Expression in CD52 Transgenic Mice Using the Anti-CD52 Antibodies Expression of huCD52 was evaluated using the humanized anti-CD52 antibodies to determine whether similar staining patterns could be observed on mature and developing cell populations in huCD52 transgenic mice. 2C3-SFD1/K12, 12G6-SFD1/K11, 12G6-SFD1/K12, 9D9-H16/K13, and 9D9-H18/K13 antibodies were conjugated with FITC to use in flow cytometry staining. Tissues from huCD52 transgenic mice were collected and processed for staining. 2C3-SFD1/K12, 12G6-SFD1/K11, 12G6-SFD1/K12, 9D9-H16/K13, and 9D9-H18/K13 antibodies stained lymphocytes expressing huCD52 from the spleen of transgenic mice similar to Campath-1H®. The staining patterns were representative of the lymphocyte populations and subsets found in other lymphoid organs such as the thymus and bone marrow.

Figure 85:
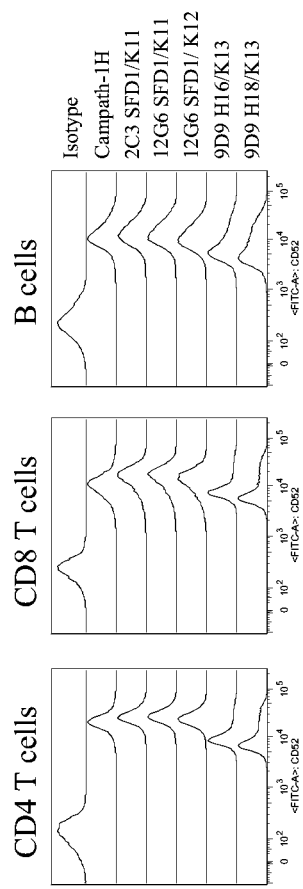
FIG. 85 shows the ability of FITC-labeled Campath-1H® ("Campath"), 2C3-SFD1/K12 ("2C3 K12"), 12G6-SFD1/K11 ("12G6 K11"), 12G6-SFD1/K12 ("12G6 K12"), 9D9-H16/K13 ("9D9 H16"), and 9D9-H18/K13 ("9D9 H18") antibodies to specifically bind huCD52 lymphocyte cell populations in the spleen.
Figure 86A:
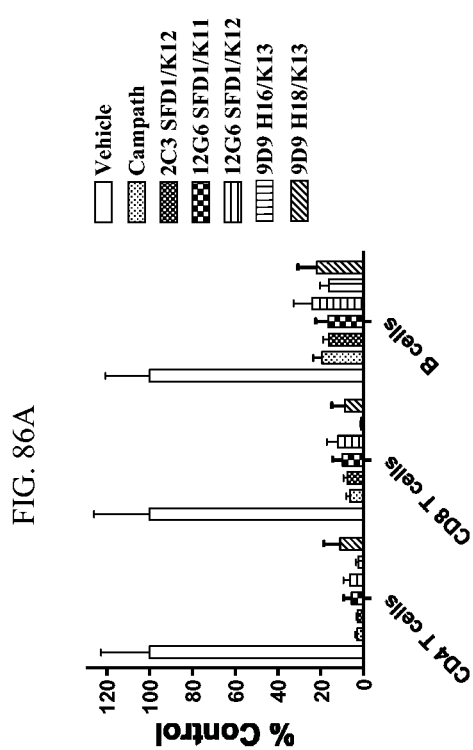
Figure 86B:
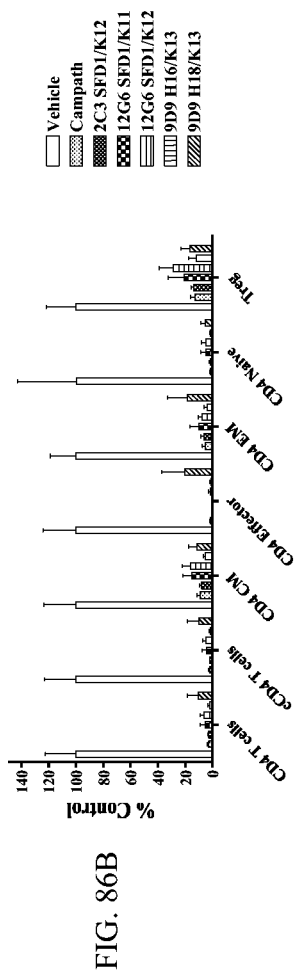
Figure 86C:
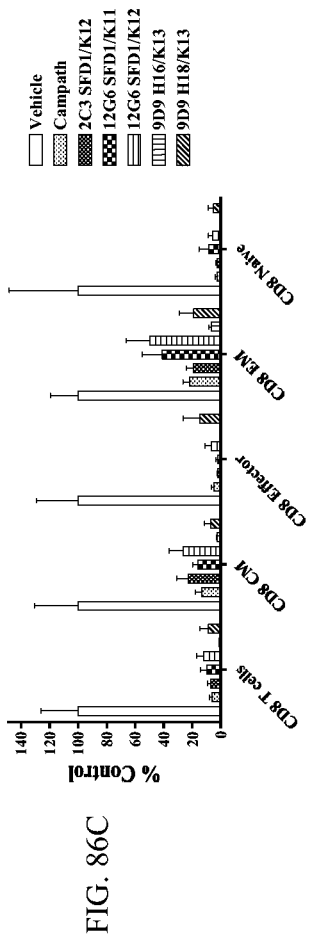
Figure 87A:
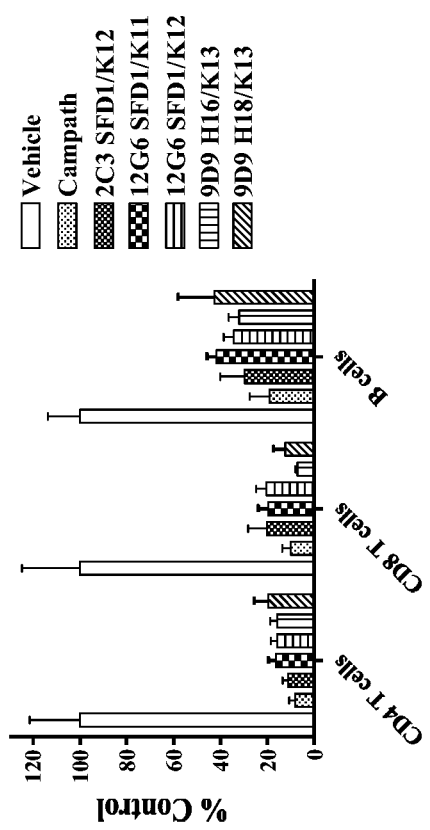
FIGS. 87A-87E show the level of bulk lymphocyte populations (CD4+ T cells, CD8+ T cells, and B220+ B cells) and CD4+ T cell, CD8+ T cell, B220+ B cell, NK cell, and myeloid cell subtypes in the spleen 72 hours after dosing with Campath-1H® ("Campath"), 2C3-SFD1/K12, 12G6-SFD1/K11, 12G6-SFD1/K12, 9D9-H16/K13, and 9D9-H18/K13 antibodies.
Figure 87B:
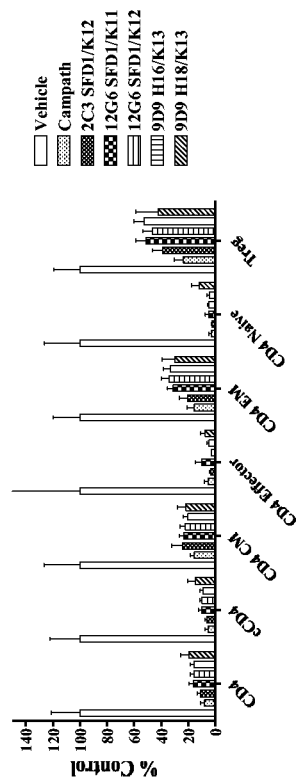
Figure 87C:
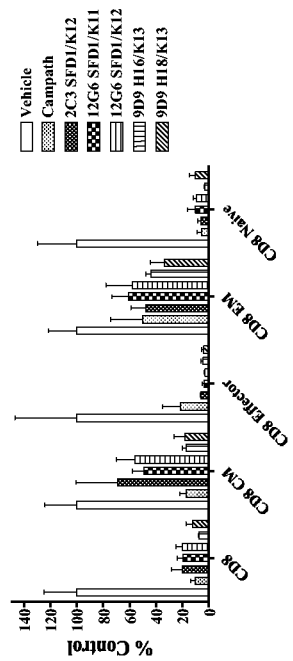
Figures 87D, 87E:
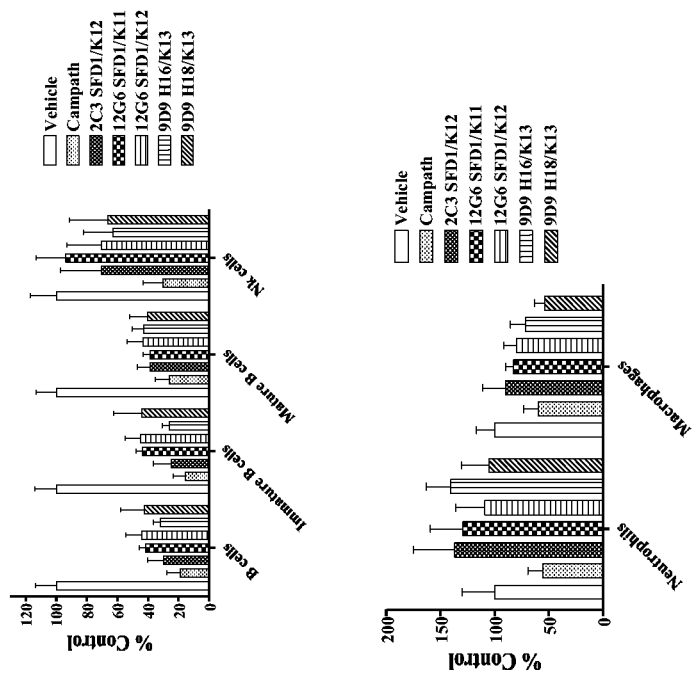

FIG. 85 shows the ability of FITC-labeled Campath-1H®, 2C3-SFD1/K12, 12G6-SFD1/K11, 12G6-SFD1/K12, 9D9-H16/K13, and 9D9-H18/K13 antibodies to specifically bind huCD52 lymphocyte cell populations in the spleen.

Example 58

Direct Comparison of Single Dose Treatment with Anti-huCD52 in huCD52 Transgenic Mice The depleting activity of several humanized anti-CD52 antibodies (2C3-SFD1/K12, 12G6-SFD1/K11, 12G6-SFD1/K12, 9D9-H16/K13, and 9D9-H18/K13) was compared in the huCD52 transgenic mouse. Mice were injected with antibodies i.v. at 1 mg/kg. At 2-hours post dosing, serum was collected for cytokine analysis. Three days later mice were sacrificed and blood and spleen collected to compare the level of lymphocyte depletion. Significant levels of B and T cell depletion were observed for all of the anti-CD52 antibodies (2C3-SFD1/K12, 12G6-SFD1/K11, 12G6-SFD1/K12, 9D9-H16/K13, and 9D9-H18/K13) and were comparable to those observed following Campath-1H® administration. Subset analysis also revealed no significant differences in the level of depletion for each antibody (2C3-SFD1/K12, 12G6-SFD1/K11, 12G6-SFD1/K12, 9D9-H16/K13, and 9D9-H18/K13) in either blood or spleen. Following injection of Campath-1H®, there was a marked increase in the circulating levels of both IL-6 and TNFα. Although injection of each of the anti-CD52 antibodies (2C3-SFD1/K12, 12G6-SFD1/K11, 12G6-SFD1/K12, 9D9-H16/K13, and 9D9-H18/K13) resulted in a significant decrease in the level of TNFα compared to Campath-1H®, the levels of IL-6 were similar.

Figure 88:
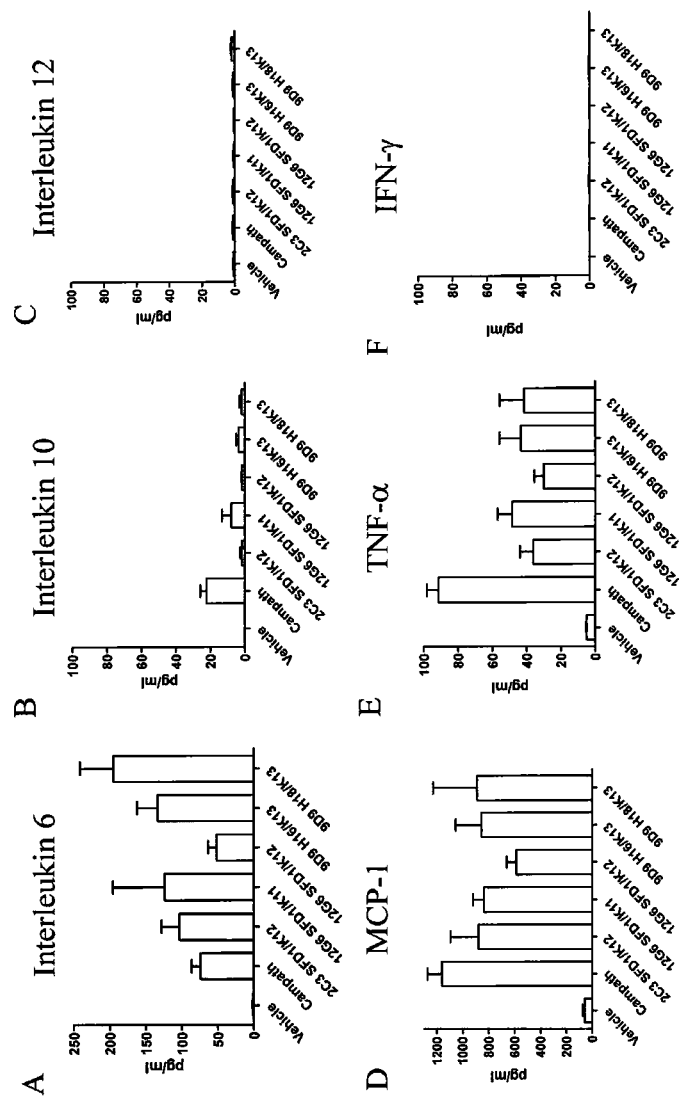
FIGS. 88A-88F show the levels of circulating cytokines 2 hours after dosing with Campath-1H® ("Campath"), 2C3-SFD1/K12, 12G6-SFD1/K11, 12G6-SFD1/K12, 9D9-H16/K13, and 9D9-H18/K13 antibodies.
Figure 89A:
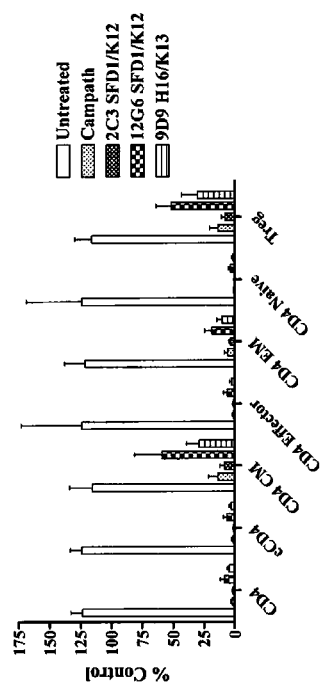
FIGS. 89A-89D show the level of CD4+ T cell, CD8+ T cell, B220+ B cell, and NK/myeloid cell subtypes in the blood 72 hours after dosing with Campath-1H® ("Campath"), 2C3-SFD1/K12, 9D9-H16/K13 and 12G6-SFD1/K12 antibodies.
Figure 89B:
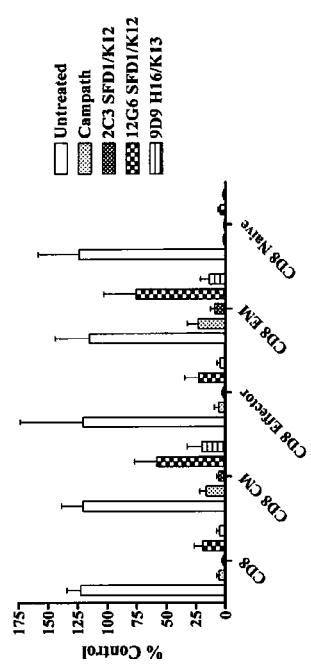
Figure 89C:
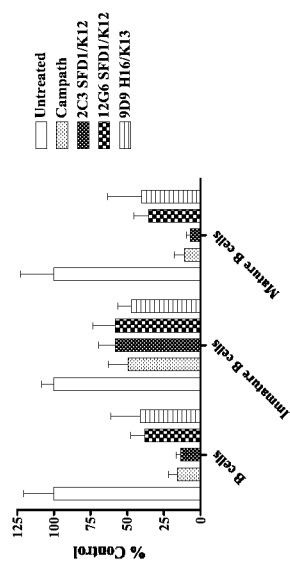
Figure 89D:
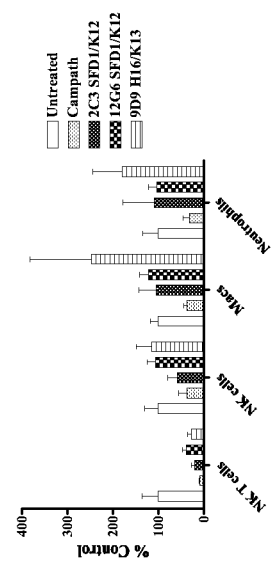
Figure 90A:
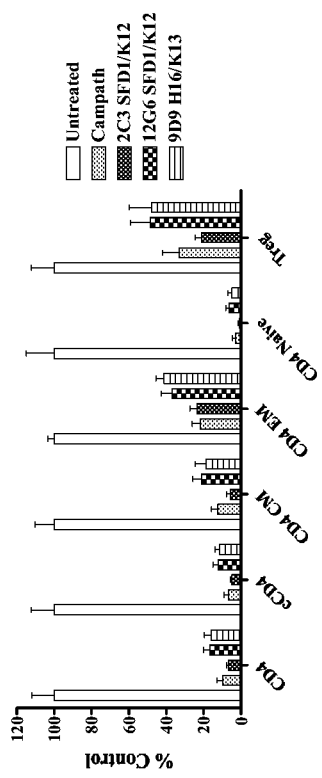
FIGS. 90A-90D show the level of CD4+ T cell, CD8+ T cell, B220+ B cell, and NK/myeloid cell subtypes in the spleen 72 hours after dosing with Campath-1H® ("Campath"), 2C3-SFD1/K12, 9D9-H16/K13 and 12G6-SFD1/K12 antibodies.
Figure 90B:
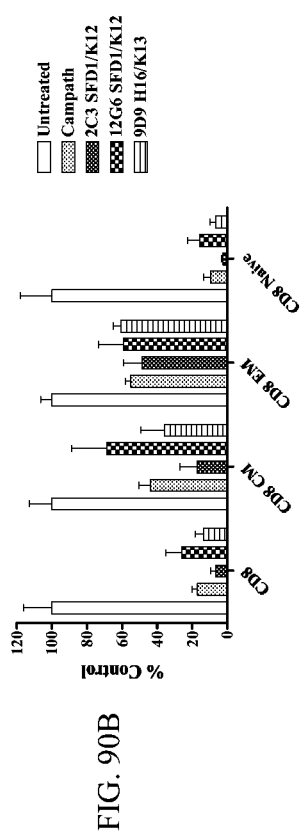
Figure 90C:
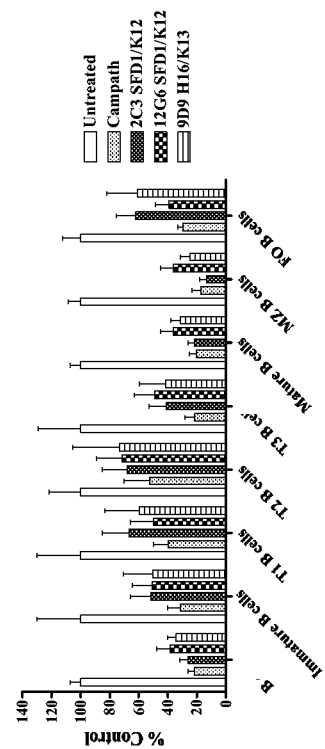
Figure 90D:
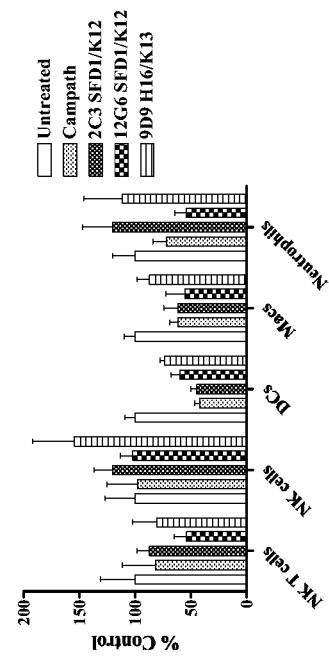
Figure 91A:
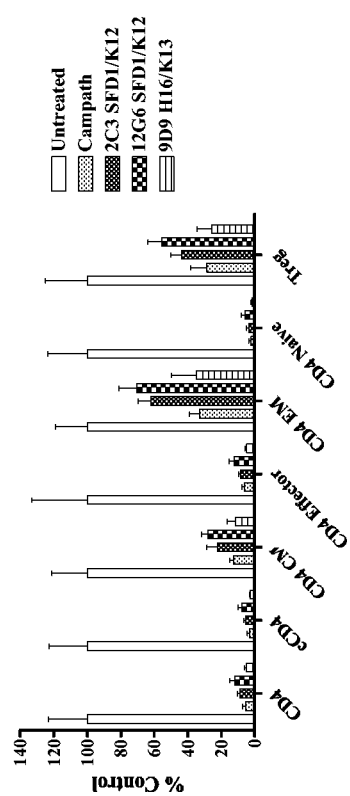
FIGS. 91A-91D show the level of CD4+ T cell, CD8+ T cell, B220+ B cell, and NK/myeloid cell subtypes in the lymph node 72 hours after dosing with Campath-1H® ("Campath"), 2C3-SFD1/K12, 9D9-H16/K13 and 12G6-SFD1/K12 antibodies.
Figure 91B:
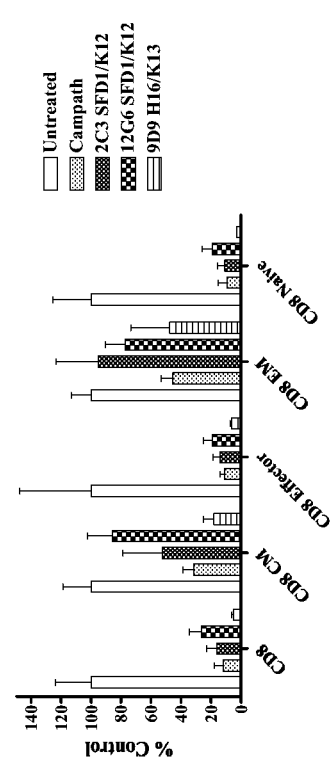
Figure 91C:
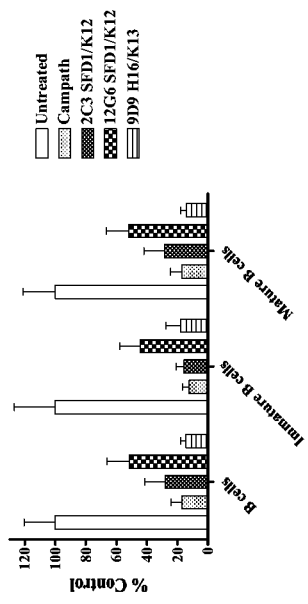
Figure 91D:
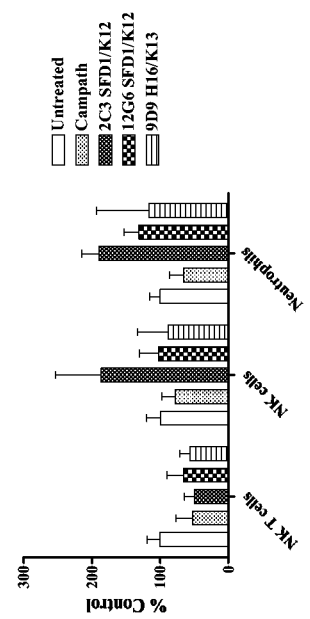

FIGS. 86A-86E show the level of bulk lymphocyte populations (CD4+ T cells, CD8+ T cells, and B220+ B cells) and CD4+ T cell, CD8+ T cell, B220+ B/NK cell, and myeloid cell subtypes in the blood 72 hours after dosing with Campath-1H® ("Campath"), 2C3-SFD1/K12, 12G6-SFD1/K11, 12G6-SFD1/K12, 9D9-H16/K13, and 9D9-H18/K13 antibodies. FIGS. 87A-87E show the level of bulk lymphocyte populations (CD4+ T cells, CD8+ T cells, and B220+ B cells) and CD4+ T cell, CD8+ T cell, B220+ B/NK cell, and myeloid cell subtypes in the spleen 72 hours after dosing with Campath-1H® ("Campath"), 2C3-SFD1/K12, 12G6-SFD1/K11, 12G6-SFD1/K12, 9D9-H16/K13, and 9D9-H18/K13 antibodies. FIGS. 88A-88C show the levels of circulating cytokines 2 hours after dosing with Campath-1H® ("Campath"), 2C3-SFD1/K12, 12G6-SFD1/K11, 12G6-SFD1/K12, 9D9-H16/K13, and 9D9-H18/K13 antibodies.

Example 59

In Depth Depletion of Lymphocytes in huCD52 Transgenic Mice Following Single Dose Treatment with Anti-huCD52 Antibodies Extensive depletion analysis was performed in the huCD52 transgenic mouse using anti-CD52 2C3-SFD1/K12, 9D9-H16/K13 and 12G6-SFD1/K12 antibodies. Mice (N=4) were injected i.v. with a single dose of each antibody at 1 mg/kg. Three days later, the mice were sacrificed, and blood, spleen, lymph nodes, and thymus were collected to compare the level of lymphocyte depletion using multi-color flow cytometry analysis. Significant levels of B and T cell depletion were observed for all of the anti-CD52 2C3-SFD1/K12, 9D9-H16/K13 and 12G6-SFD1/K12 antibodies and were comparable to those observed following Campath1H® administration in each tissue examined. Subset analysis also revealed no significant differences in the level of depletion for each antibody in either blood or spleen. Significant levels of lymphocyte depletion were also observed in the lymph nodes of mice. There did, however, appear to be some variability in the activity of the antibody, especially when looking at the central and effector memory T cell subset. Due to technical issues regarding the LSR-II and the CD8 stain, the thymus could not be evaluated.

FIGS. 89A-89D show the level of CD4+ T cell, CD8+ T cell, B220+ B cell, and NK/myeloid cell subtypes in the blood 72 hours after dosing with Campath-1H® ("Campath"), 2C3-SFD1/K12, 9D9-H16/K13 and 12G6-SFD1/K12 antibodies. FIGS. 90A-90D show the level of CD4+ T cell, CD8+ T cell, B220+ B cell, and NK/myeloid cell subtypes in the spleen 72 hours after dosing with Campath-1H® ("Campath"), 2C3-SFD1/K12, 9D9-H16/K13 and 12G6-SFD1/K12 antibodies. FIGS. 91A-91D show the level of CD4+ T cell, CD8+ T cell, B220+ B cell, and NK/myeloid cell subtypes in the lymph node 72 hours after dosing with Campath-1H® ("Campath"), 2C3-SFD1/K12, 9D9-H16/K13 and 12G6-SFD1/K12 antibodies.

Example 60

Creation and Evaluation of the huCD52 Knock-In/Knock-Out (KI/KO) Transgenic Mouse on the C57BL/6 Background A new human CD52 knock-in/knock-out mouse model was created on the C57Bl/6 background. To create this mouse, the mouse CD52 gene sequence was replaced by the human CD52 gene sequence. The targeting strategy allowed for the replacement of the mouse sequence with the human sequence while maintaining the exon-intron structure. A selection marker was used to identify progeny containing the new gene sequence. The final allele was created by removal of the selection marker leaving only the human CD52 gene sequence.

Basic characterization of the huCD52 KI/KO mouse model involved determining the level of human CD52 expression on lymphocytes. Blood from huCD52-KI/KO transgenic mice (N=4) and C57BL/6 mice (N=2) were stained for hCD52 expression and the number of CD52 molecules/cell was enumerated using the Bang's labs Simply Cellular anti-human antibody assay. Staining of peripheral blood cells from huCD52-KI/KO transgenic mice demonstrated that expression of huCD52 is very high on the majority of lymphocytes from these animals. Expression levels were similar to those observed in human CD4, CD8, and B cell populations. Expression levels on NK cells and macrophages were lower than those observed for T cells and B cells. An increased level of huCD52 expression was detected on neutrophils in these mice, contrary to the decreased expression level in human neutrophils or similar cells from the original transgenic mouse line on the CD-1 background. Similar levels of CD52 expression were observed on T and B cells from the original huCD52 CD1 transgenic mouse and the huCD52 KI/KI mouse.

Figure 92:
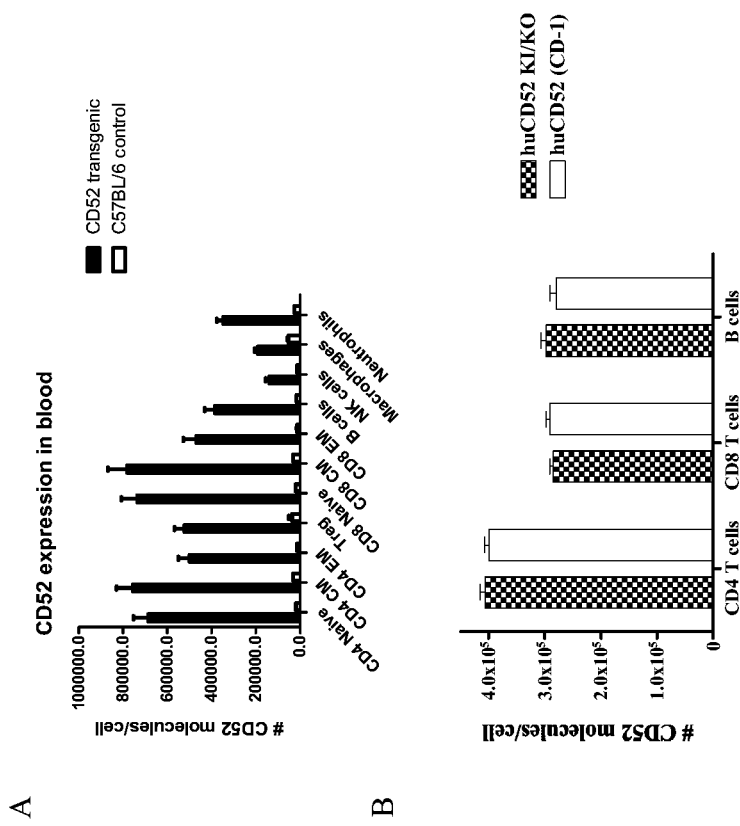
FIG. 92A shows the huCD52 expression level on CD4+ T cell, CD8+ T cell, B220+ B cell, and NK/myeloid cell subtypes in huCD52-KI/KO and non-transgenic control mice.
FIG. 92B shows the huCD52 expression level on CD4+ T cells, CD8+ T cells, and B cells in huCD52-KI/KO and huCD52 CD1 transgenic mice.

FIG. 92A shows the huCD52 expression level on CD4+ T cell, CD8+ T cell, B220+ B cell, and NK/myeloid cell subtypes in huCD52-KI/KO and non-transgenic control mice. FIG. 92B shows the huCD52 expression level on CD4+ T cells, CD8+ T cells, and B cells in huCD52-KI/KO and huCD52 CD1 transgenic mice.

Example 61

Direct Comparison of Depletion Characteristics Between Small and Large Scale Lots of 12G6 and 2C3 huCD52 KI/KO transgenic mice were dosed with 12G6-SFD1/K12 or 2C3-SFD1/K12 to determine the depleting activity. In addition, activity was examined using antibodies generated from two different sources (small scale and large scale lots) at Genzyme. Mice were injected i.v. with each antibody at 1 mg/kg. Three days post injection, mice were sacrificed, and blood was collected for flow cytometry analysis to determine the levels of circulating CD4+ and CD8+ T cells, B cells, NK cells, neutrophils and macrophages. No significant differences in depletion of CD4 T cells, CD8+ T cells, B cells, and NK cells were observed between the small scale and large scale lot derived antibodies.

The various lots of 12G6-SFD1/K12 and 2C3-SFD1/K12 antibodies were also evaluated by flow cytometry to compare the intensity of staining on splenocytes from huCD52-KI/KO transgenic mice. Both 12G6-SFD1/K12 and 2C3-SFD1/K12 antibodies appear to recognize human CD52 to the same extent as Campath-1H® on isolated splenocytes. In addition, there was no difference in the level of recognition between the two sources (small scale and large scale lots) of antibody.

Figure 93:
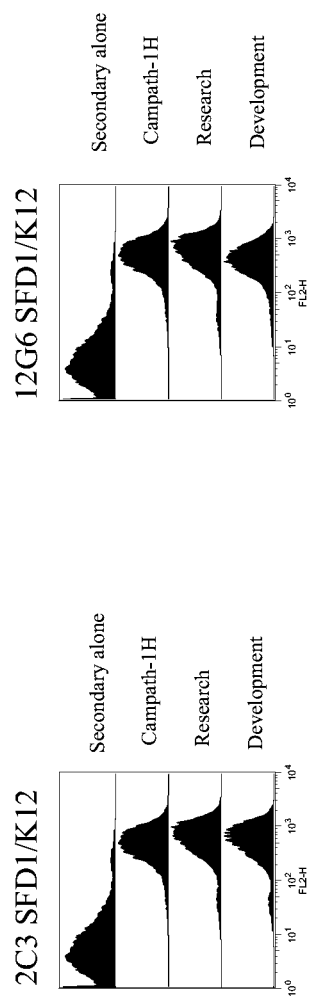
FIG. 93 shows the binding to huCD52 of 12G6-SFD1/K12 and 2C3-SFD1/K12 antibodies from various production sources ("small scale" and "large scale") as compared to a Campath-1H® control.
Figure 94:
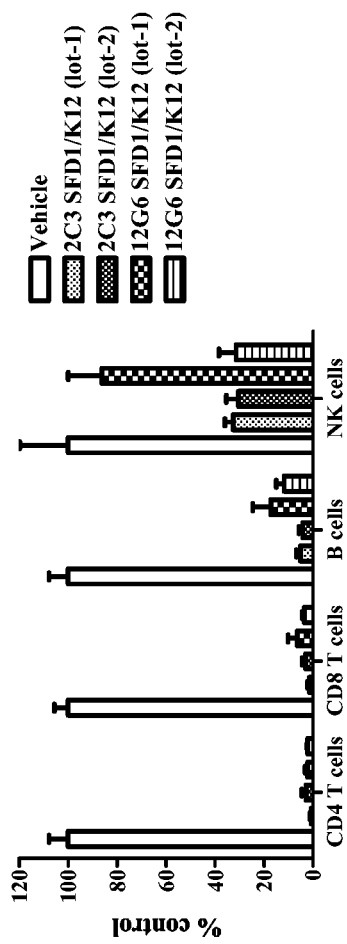
FIG. 94 shows the level of bulk lymphocyte populations (CD4+ T cells, CD8+ T cells, B220+ B cells and NK cells) in the blood 72 hours after dosing with 12G6-SFD1/K12 and 2C3-SFD1/K12 antibodies from various production sources ("small scale" and "large scale").

FIGS. 93A-93B show binding to huCD52 of 12G6-SFD1/K12 and 2C3-SFD1/K12 antibodies (from various production sources) as compared to a Campath-1H® control. FIG. 94 shows the level of bulk lymphocyte populations (CD4+ T cells, CD8+ T cells, and B220+ B cells) in the blood 72 hours after dosing with 12G6-SFD1/K12 and 2C3-SFD1/K12 antibodies from various production sources.

Example 62

Analysis of PK Profile for Anti-CD52 Antibodies in huCD52-KI/KO Transgenic Mice

The pharmacokinetic profiles of humanized 2C3-SFD1/K12, 9D9-H16/K13 and 12G6-SFD1/K12 antibodies were determined in huCD52 KI/KO transgenic mice. Mice were injected i.v. with antibodies at 1 mg/kg, and blood was collected at various timepoints beginning two hours post dosing. The circulating levels of each antibody were evaluated using an anti-human Ig ELISA. The overall clearance rate was similar for each of the humanized anti-CD52 2C3-SFD1/K12, 9D9-H16/K13 and 12G6-SFD1/K12 antibodies with 2C3-SFD1/K12 exhibiting potentially faster kinetics, while 12G6-SFD1/K12 was present in the serum for the longest period of time.

Figure 95:
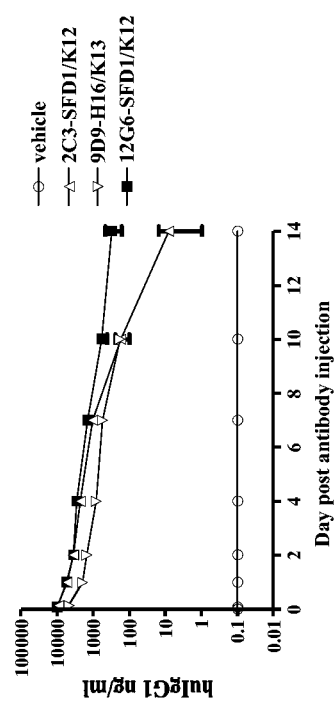
FIG. 95 shows the levels of 2C3-SFD1/K12, 9D9-H16/K13 and 12G6-SFD1/K12 antibodies in the blood over a timecourse after dosing.

FIGS. 95A-95B show the levels of 2C3-SFD1/K12, 9D9-H16/K13 and 12G6-SFD1/K12 antibodies in the blood over a timecourse after dosing.

Example 63

Evaluation of 12G6 and 2C3 Pretreatment on EAE in huCD52-KI/KO Transgenic Mice

The efficacy of anti-CD52 antibody treatment on reducing the overall disease incidence and severity of Experimental Autoimmune Encephalomyelitis (EAE) was evaluated in huCD52 KI/KO mice. huCD52-KI/KO mice were treated with a course of either 2C3-SFD1/K12 or 12G6-SFD1/K12 on days −5 thru −1. EAE (a model of multiple sclerosis) was induced by immunization with MOG35-55 peptide emulsified in CFA, and treatment with pertussis toxin, on days 0 and 2. Vehicle treated mice began to display signs of paralysis by day 10 post injection, which developed into severe progressive disease. In contrast, pretreatment of mice with either the 2C3-SFD1/K12 or 12G6-SFD1/K12 antibody delayed the onset of disease and decreased the overall disease severity.

Figure 96:
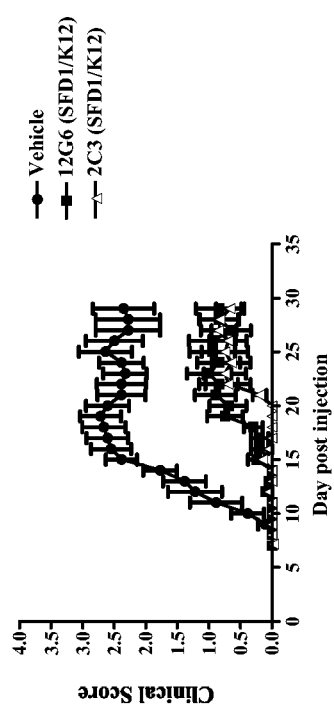
FIG. 96 demonstrates the EAE clinical score of 2C3-SFD1/K12 and 12G6-SFD1/K12 over a timecourse of disease progression.

FIG. 96 demonstrates the EAE clinical score of 2C3-SFD1/K12 and 12G6-SFD1/K12 over a timecourse of disease progression.

Example 64

Fc Modification of Antibodies to Alter the Pharmacokinetic Profile of Anti-CD52 Antibodies Alterations in the Fc region of antibodies 1) affect the biological activity of the antibody by altering interactions with Fc receptors and/or 2) alter the pharmacokinetic profile of the antibody by altering interactions with the FcRn neonatal receptor. The FcRn molecule is expressed on vascular endothelium and is believed to be the main site of IgG recycling. The FcRn binds to the antibody Fc portion which then becomes internalized within a cell. Antibodies that have high affinity interactions with the FcRn will be recycled back to the surface of the cell and will be released back into circulation. Antibodies that have lower affinity interactions dissociate within the cell and ultimately degrade. Site directed mutagenesis to increase the interaction with FcRn generates an antibody that can be maintained in circulation for longer periods of time compared to an unmodified antibody. Conversely, mutations within the Fc region of an antibody that decrease FcRn binding shorten the circulating half-life of the antibody. Mutations that have been described to decrease binding to FcRn resulting in shorter circulating half-lives include the His435Ala single mutation and the His310Ala/His435Gln double mutation (see, e.g., Kim et al., "Mapping the site on human IgG for binding of the MHC class I-related receptor, FcRn," *Eur. J. Immunol.*, 29:2819-2825 (1999) and Kenanova et al., "Tailoring the Pharmacokinetics and Positron Emission Tomography Imaging Properties of Anti-Carcinoembryonic Antigen Single-Chain Fv-Fc Antibody Fragments," *Cancer. Res.* 65(2):622-631 (2005)).

The 2C3-SFD1/K12 antibody was mutated to generate His435Ala 2C3-SFD1/K12 ("2C3-SFD1/K12-Modified 1") and His310Ala/His435Gln 2C3-SFD1/K12 ("2C3-SFD1/K12-Modified 2") antibodies that have altered PK profiles. Biacore analysis was conducted to confirm decreased binding to both mouse and human FcRn molecules. Both Campath-1H® and 2C3-SFD1/K12 antibodies bound to each of the mouse and human FcRn molecules with similar kinetics. In contrast, His435Ala 2C3-SFD1/K12 antibodies bound at low levels to the mouse FcRn but not to human FcRn. His310Ala/His435Gln 2C3-SFD1/K12 antibodies did not bind to either mouse or human FcRn molecule, indicating that the incorporation of either the single or double mutation into the 2C3-SFD1/K12 Fc region significantly affects binding to mouse and human FcRn.

Figure 97A:
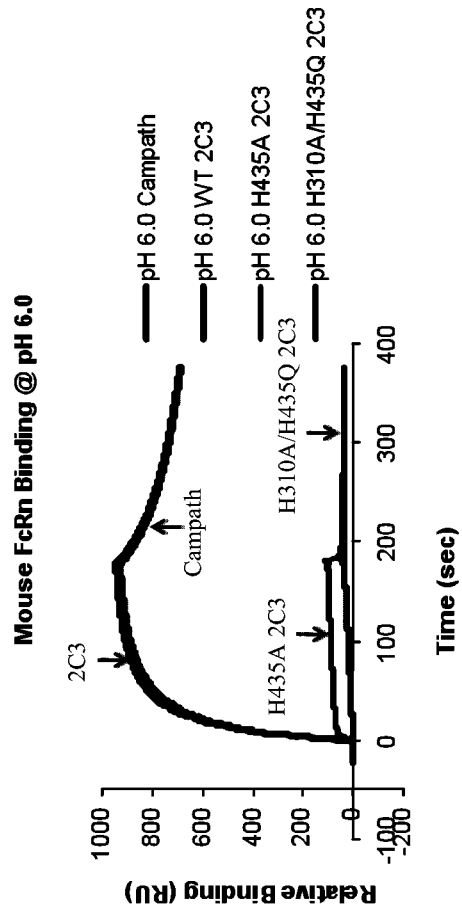
FIGS. 97A and 97B demonstrate the ability of Campath1H® ("Campath"), 2C3-SFD1/K12 ("2C3"), His435Ala 2C3-SFD1/K12 ("H435A 2C3") and His310Ala/His435Gln 2C3-SFD1/K12 ("H310A/H435Q 2C3") to bind to mouse and human FcRn molecules.
Figure 97B:
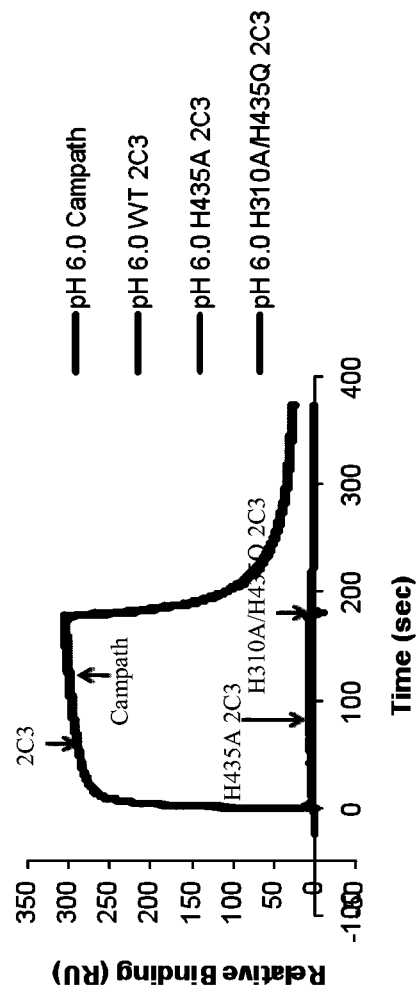

FIGS. 97A-97B demonstrate the ability of Campath1H® ("Campath"), 2C3-SFD1/K12 ("2C3"), His435Ala 2C3-SFD1/K12 ("H435A 2C3") and His310Ala/His435Gln 2C3-SFD1/K12 ("H310A/H435Q 2C3") to bind to mouse and human FcRn molecules.

Example 65

Evaluation of the Half-Life of Fc Modified Anti-CD52 Antibodies Following I.V. Administration in C57Bl/6 Mice Fc modifications were incorporated into the 2C3-SFD1/K12 backbone to generate 2C3-SFD1/K12-Modified 1 and 2C3-SFD1/K12-Modified 2 antibodies that exhibited decreased binding to the FcRn receptor responsible for maintaining antibodies in circulation. The pharmacokinetic profile was determined for the 2C3-SFD1/K12 antibody and the 2C3-SFD1/K12-Modified 1 and 2C3-SFD1/K12-Modified 2 antibodies with reduced FcRn binding. C57BL/6 mice were used to evaluate the PK profile in the absence of target antigen (2C3-SFD1/K12 binds to human CD52 but does not cross-react with mouse CD52). Mice were injected i.v. with antibodies at 1 mg/kg. At various timepoints, blood was collected to analyze the level of circulating human IgG1 in the mouse serum by ELISA. Both 2C3-SFD1/K12-Modified 1 and 2C3-SFD1/K12-Modified 2 antibodies were cleared from the blood faster than the 2C3-SFD1/K12 antibody. 2C3-SFD1/K12 had a half-life of 403 hrs, while 2C3-SFD1/K12-Modified 1 had a half-life of 51 hours and 2C3-SFD1/K12-Modified 2 had a half-life of 8 hours. PK profiles for 2C3-SFD1/K12 and 2C3-SFD1/K12-Modified-1 were consistent with a 1-compartment model with only a single phase of elimination. In contrast, profiles for 2C3-SFD1/K12-Modified-2 were consistent with a 2 compartment model, with 2 distinct phases of elimination (specified as alpha and beta in the table). The first phase lasted until 48 hr post dose (alpha) and the second phase (beta, also called the terminal elimination phase) started 48 hr post dose.

Figure 98:
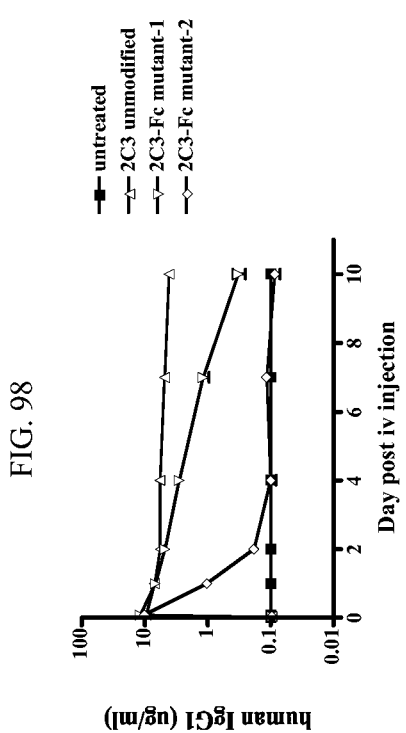
FIG. 98 shows the in vivo clearance of 2C3-SFD1/K12 ("2C3 unmodified"), 2C3-SFD1/K12-Modified 1 ("2C3-Fc mutant 1") and 2C3-SFD1/K12-Modified 2 ("2C3-Fc mutant 2") in nontransgenic mice.

FIG. 98 shows the in vivo clearance of 2C3-SFD1/K12 ("2C3 unmodified"), 2C3-SFD1/K12-Modified 1 ("2C3-Fc mutant 1") and 2C3-SFD1/K12-Modified 2 ("2C3-Fc mutant 2") in nontransgenic mice.

TABLE 17

Summary of Pharmacokinetic Data Across Groups

|  | 2C3-SFD1/K12 | 2C3-SFD1/K12-Modified 1 | 2C3-SFD1/K12-Modified 2 |
|---|---|---|---|
| $t_{1/2}$ (hr) | 403 ± 140 | 51.0 ± 12.3 | 8.05 ± 0.74 (Alpha) 282 ± 385 (Beta) |
| Cl (ml/hr/kg) | 0.29 ± 0.09 | 1.35 ± 0.36 | 5.90 ± 4.67 |
| Vz (ml/kg) | 156 ± 40.7 | 94.8 ± 14.3 | 1932 ± 1341 |
| AUC (ug * hr/ml) | 3748 ± 937 | 781 ± 171 | 230 ± 105 |
| Cmax (ug/ml) | 9.65 ± 1.72 | 11.9 ± 0.83 | 9.64 ± 3.70 |

TABLE 18

Individual Animal Data

| Group[#] | Animal | HL_Lambda_z (hr) | Cmax (ug/ml) | AUCINF_obs (hr * ug/ml) | Vz_obs (ml/kg) | Cl_obs (ml/hr/kg) |
|---|---|---|---|---|---|---|
| 2C3 | 2.1 | 197.26 | 11.56 | 2967.86 | 95.89 | 0.34 |
| 2C3 | 2.2 | 494.01 | 10.54 | 4635.96 | 153.73 | 0.22 |
| 2C3 | 2.3 | 324.61 | 10.06 | 3783.76 | 123.77 | 0.26 |
| 2C3 | 2.4 | 283.68 | 10.57 | 3130.92 | 130.72 | 0.32 |
| 2C3 | 2.5 | 330.89 | 6.15 | 2025.29 | 235.71 | 0.49 |

TABLE 18-continued

Individual Animal Data

| | | | | | | |
|---|---|---|---|---|---|---|
| 2C3 | 2.6 | 547.78 | 10.56 | 4469.73 | 176.81 | 0.22 |
| 2C3 | 2.7 | 597.92 | 10.57 | 4764.75 | 181.04 | 0.21 |
| 2C3 | 2.8 | 320.65 | 7.61 | 3415.82 | 135.43 | 0.29 |
| 2C3 | 2.9 | 527.01 | 9.27 | 4533.82 | 167.70 | 0.22 |
| | AVG | 402.65 | 9.65 | 3747.55 | 155.64 | 0.29 |
| | SD | 140.22 | 1.72 | 937.38 | 40.73 | 0.09 |
| 2C3-M1 | 3.1 | 35.20 | 12.84 | 513.50 | 98.89 | 1.95 |
| 2C3-M1 | 3.2 | 42.74 | 11.68 | 842.55 | 73.17 | 1.19 |
| 2C3-M1 | 3.3 | 50.55 | 11.39 | 902.62 | 80.80 | 1.11 |
| 2C3-M1 | 3.4 | 46.61 | 12.49 | 717.95 | 93.67 | 1.39 |
| 2C3-M1 | 3.5 | 56.38 | 12.94 | 911.32 | 89.26 | 1.10 |
| 2C3-M1 | 3.6 | 63.40 | 12.41 | 995.22 | 91.91 | 1.00 |
| 2C3-M1 | 3.7 | 33.86 | 12.02 | 513.17 | 95.19 | 1.95 |
| 2C3-M1 | 3.8 | 63.14 | 10.56 | 842.79 | 108.08 | 1.19 |
| 2C3-M1 | 3.9 | 66.75 | 11.02 | 788.59 | 122.12 | 1.27 |
| | AVG | 50.96 | 11.93 | 780.86 | 94.79 | 1.35 |
| | SD | 12.30 | 0.83 | 170.51 | 14.33 | 0.36 |

| Group# | Animal | Alpha HL_Lambda (hr) | Beta HL_Lambda (hr) | Cmax (ug/ml) | AUCINF_obs (hr * ug/ml) | Vz_obs (ml/kg) | Cl_obs (ml/hr/kg) |
|---|---|---|---|---|---|---|---|
| 2C3-M2 | 4.1* | 8.31 | Missing | 10.62 | 177.07 | 67.74 | 5.65 |
| 2C3-M2 | 4.2 | 7.42 | 994.71 | 11.35 | 390.03 | 3679.37 | 2.56 |
| 2C3-M2 | 4.3 | 7.37 | 703.09 | 10.48 | 315.82 | 3211.80 | 3.17 |
| 2C3-M2 | 4.4 | 7.72 | 227.03 | 11.78 | 247.96 | 1320.92 | 4.03 |
| 2C3-M2 | 4.5** | Missing | Missing | Missing | Missing | Missing | Missing |
| 2C3-M2 | 4.6** | Missing | Missing | Missing | Missing | Missing | Missing |
| 2C3-M2 | 4.7*** | 77.89 | 77.89 | 1.32 | 61.71 | 1820.87 | 16.20 |
| 2C3-M2 | 4.8 | 8.18 | 150.98 | 11.41 | 221.89 | 981.64 | 4.51 |
| 2C3-M2 | 4.9 | 9.33 | 77.61 | 10.49 | 194.31 | 576.21 | 5.15 |
| | AVG | 8.05 | 281.98 | 9.64 | 229.83 | 1931.80 | 5.90 |
| | SD | 0.74 | 384.82 | 3.70 | 104.69 | 1341.43 | 4.67 |

The tested groups were 2C3-SFD1/K12 ("2C3"), 2C3-SFD1/K12-Modified 1 ("2C3-M1") and 2C3-SFD1/K12-Modified 2 ("2C3-M2")
*Animal 4.1 no beta t½, Vz outlier.
**Animals 4.5 & 4.6, not enough data for PK analysis.
***Animal 4.7 incomplete injection

Example 66

Evaluation of the Half-Life of Fc Modified Anti-CD52 Antibodies Following I.V. Administration in Heterozygous huCD52 Transgenic Mice The pharmacokinetic profile was determined for the 2C3-SFD1/K12 antibody and the 2C3-SFD1/K12-Modified 1 and 2C3-SFD1/K12-Modified 2 antibodies with reduced FcRn binding in vitro. huCD52 transgenic mice were used to evaluate the PK profile in the presence of the 2C3-SFD1/K12 antibody target antigen. Mice were injected i.v. with antibodies at 1 mg/kg. At various timepoints, blood was collected to determine the level of circulating human IgG1 in the mouse serum by ELISA. Both 2C3-SFD1/K12-Modified 1 and 2C3-SFD1/K12-Modified 2 antibodies were cleared from the blood faster than the 2C3-SFD1/K12 antibody. 2C3-SFD1/K12 had a half-life of 64 hrs, while 2C3-SFD1/K12-Modified 1 had a half-life of 32 hours, and 2C3-SFD1/K12-Modified 2 had a half-life of 6.5 hours.

Figure 99:
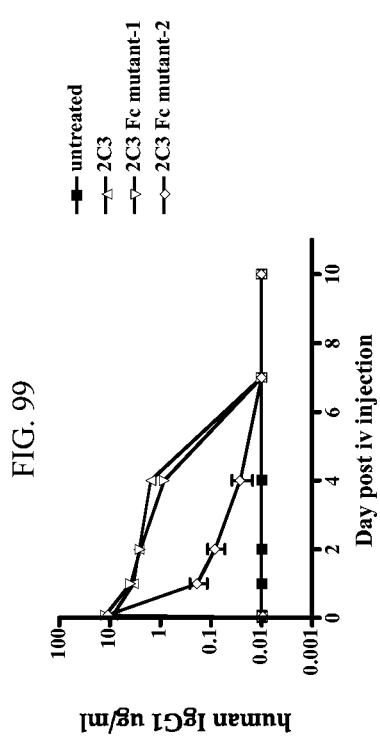
FIG. 99 shows the in vivo clearance of 2C3-SFD1/K12 ("2C3"), 2C3-SFD1/K12-Modified 1 ("2C3-Fc mutant 1") and 2C3-SFD1/K12-Modified 2 ("2C3-Fc mutant 2") in huCD52 transgenic mice.

FIG. 99 shows the in vivo clearance of 2C3-SFD1/K12 ("2C3"), 2C3-SFD1/K12 modified 1 ("2C3-Fc mutant 1") and 2C3-SFD1/K12 modified 2 ("2C3-Fc mutant 2") in huCD52 transgenic mice.

TABLE 19

Summary of Pharmacokinetic Data Across Groups

| | 2C3-SFD1/K12 | 2C3-SFD1/K12-Modified 1 | 2C3-SFD1/K12-Modified 2 |
|---|---|---|---|
| $t_{1/2}$ (hr) | 64.2 ± 12.1 | 32.3 ± 3.25 | 6.58 ± 2.03 |
| Cl (ml/hr/kg) | 2.15 ± 0.31 | 2.51 ± 0.28 | 5.41 ± 0.83 |
| Vz (ml/kg) | 198 ± 42.8 | 117 ± 21.1 | 49.7 ± 11.1 |
| AUC (ug * hr/ml) | 475 ± 73.4 | 403 ± 44.5 | 188 ± 27.2 |
| Cmax (ug/ml) | 8.88 ± 1.69 | 12.4 ± 1.67 | 12.9 ± 1.91 |

TABLE 20

Individual Animal Data

| Group# | Animal | HL_Lambda_z (hr) | Cmax (ug/ml) | AUCINF_obs (hr * ug/ml) | Vz_obs (ml/kg) | Cl_obs (ml/hr/kg) |
|---|---|---|---|---|---|---|
| 2C3 | 2.1 | 77.32 | 8.19 | 421.87 | 264.42 | 2.37 |
| 2C3 | 2.11 | 61.47 | 10.38 | 483.25 | 183.51 | 2.07 |

TABLE 20-continued

Individual Animal Data

| Group# | Animal | HL_Lambda_z (hr) | Cmax (ug/ml) | AUCINF_obs (hr * ug/ml) | Vz_obs (ml/kg) | Cl_obs (ml/hr/kg) |
| --- | --- | --- | --- | --- | --- | --- |
| 2C3 | 2.2 | 78.28 | 9.28 | 496.58 | 227.42 | 2.01 |
| 2C3 | 2.3 | 82.38 | 6.99 | 441.98 | 268.91 | 2.26 |
| 2C3 | 2.4 | 53.60 | 9.08 | 465.09 | 166.28 | 2.15 |
| 2C3 | 2.5 | 58.02 | 9.09 | 526.59 | 158.95 | 1.90 |
| 2C3 | 2.6 | 44.97 | 6.03 | 371.17 | 174.78 | 2.69 |
| 2C3 | 2.7 | 56.52 | 9.38 | 476.41 | 171.16 | 2.10 |
| 2C3 | 2.8 | 67.99 | 12.13 | 641.28 | 152.97 | 1.56 |
| 2C3 | 2.9 | 61.46 | 8.30 | 421.65 | 210.29 | 2.37 |
|  | Mean | 64.20 | 8.88 | 474.59 | 197.87 | 2.15 |
|  | SD | 12.06 | 1.69 | 73.40 | 42.80 | 0.31 |
| 2C3-M1 | 3.1 | 28.48 | 15.19 | 412.41 | 99.64 | 2.42 |
| 2C3-M1 | 3.11 | 34.64 | 12.60 | 468.36 | 106.69 | 2.14 |
| 2C3-M1 | 3.2 | 27.57 | 14.17 | 411.82 | 96.60 | 2.43 |
| 2C3-M1 | 3.3 | 34.27 | 11.96 | 401.38 | 123.20 | 2.49 |
| 2C3-M1 | 3.4 | 29.10 | 12.51 | 400.36 | 104.85 | 2.50 |
| 2C3-M1 | 3.5 | 29.63 | 11.11 | 470.98 | 90.77 | 2.12 |
| 2C3-M1 | 3.6 | 32.76 | 9.75 | 348.72 | 135.53 | 2.87 |
| 2C3-M1 | 3.7 | 35.68 | 10.41 | 328.71 | 156.61 | 3.04 |
| 2C3-M1 | 3.8 | 36.41 | 13.52 | 390.24 | 134.61 | 2.56 |
| 2C3-M1 | 3.9 | 34.06 | 12.39 | 392.53 | 125.19 | 2.55 |
|  | Mean | 32.26 | 12.36 | 402.55 | 117.37 | 2.51 |
|  | SD | 3.25 | 1.67 | 44.48 | 21.05 | 0.28 |
| 2C3-M2 | 4.1 | 7.64 | 13.45 | 197.24 | 55.85 | 5.07 |
| 2C3-M2 | 4.11 | Missing | 9.00 | Missing | Missing | Missing |
| 2C3-M2 | 4.2 | 7.79 | 14.92 | 217.80 | 51.61 | 4.59 |
| 2C3-M2 | 4.3 | 7.35 | 12.79 | 183.44 | 57.78 | 5.45 |
| 2C3-M2 | 4.4 | 3.54 | 10.34 | 152.92 | 33.44 | 6.54 |
| 2C3-M2 | 4.5 | Missing | Missing | Missing | Missing | Missing |
| 2C3-M2 | 4.6 | Missing | Missing | Missing | Missing | Missing |
| 2C3-M2 | 4.7 | Missing | Missing | Missing | Missing | Missing |
| 2C3-M2 | 4.8 | Missing | Missing | Missing | Missing | Missing |
| 2C3-M2 | 4.9 | Missing | Missing | Missing | Missing | Missing |
|  | Mean | 6.58 | 12.10 | 187.85 | 49.67 | 5.41 |
|  | SD | 2.03 | 2.40 | 27.23 | 11.12 | 0.83 |

PK parameters not available for 4.11, 4.5, 4.6, 4.7, 4.8, and 4.9 due to insufficient data.
The tested groups were 2C3-SFD1/K12 ("2C3"), 2C3-SFD1/K12-Modified 1 ("2C3-M1") and 2C3-SFD1/K12-Modified 2 ("2C3-M2")

Example 67

Figure 100:
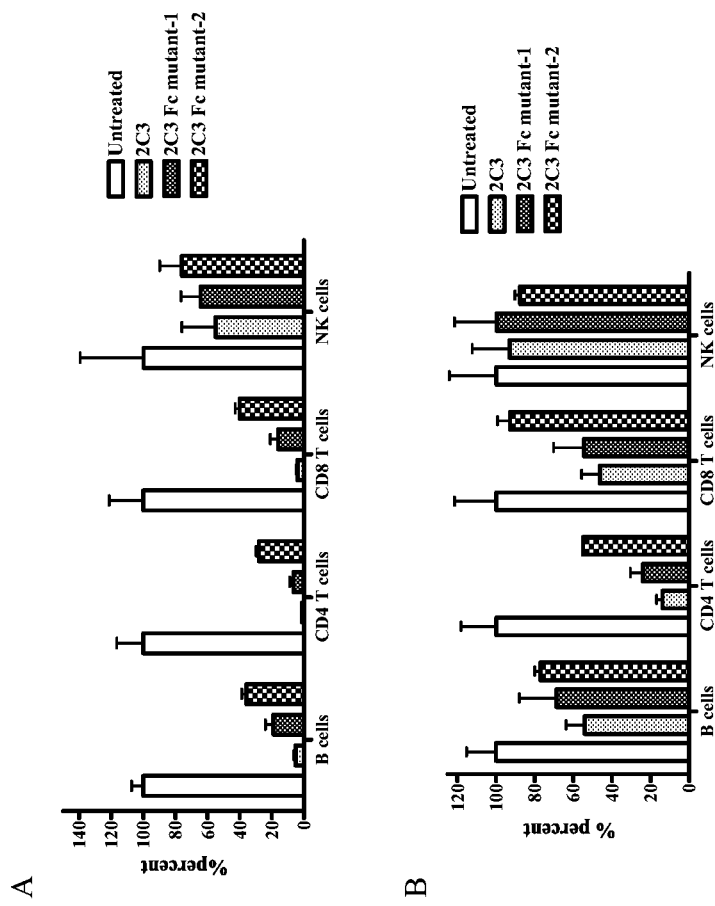
FIGS. 100A and 100B show the level of bulk lymphocyte populations (CD4+ T cells, CD8+ T cells, B220+ B cells, and NK cells) in the blood and spleen 72 hours after dosing with 2C3-SFD1/K12 ("2C3"), 2C3-SFD1/K12-Modified 1 ("2C3 Fc mutant-1"), and 2C3-SFD1/K12-Modified 2 ("2C3 Fc mutant-2") antibodies.

Evaluation of In Vivo Depletion Following I.V. Administration of Fc Modified Anti-CD52 Antibodies in Heterozygous huCD52 Transgenic Mice The depletion activity was determined for the 2C3-SFD1/K12, 2C3-SFD1/K12-Modified 1, and 2C3-SFD1/K12-Modified 2 antibodies in huCD52 transgenic mice. Mice were treated with 1 mg/kg of 2C3-SFD1/K12, 2C3-SFD1/K12-Modified 1, or 2C3-SFD1/K12-Modified 2 antibodies and evaluated for the presence of CD4 T cells, CD8+ T cells, B cells, and NK cells 72 hours later. Administration of 2C3-SFD1/K12-Modified 1 or 2C3-SFD1/K12-Modified 2 antibodies resulted in decreased levels of depletion in the blood and spleen compared administration of 2C3-SFD1/K12 antibodies. Further, 2C3-SFD1/K12-Modified 1 elicited greater depletion than 2C3-SFD1/K12-Modified 2 in both the blood and spleen FIGS. 100A-100B show the level of bulk lymphocyte populations (CD4+ T cells, CD8+ T cells, B220+ B cells, and NK cells) in the blood and spleen 72 hours after dosing with 2C3-SFD1/K12 ("2C3"), 2C3-SFD1/K12 modified 1 ("2C3 Fc mutant-1"), and 2C3-SFD1/K12 modified 2 ("2C3 Fc mutant-2") antibodies.

Example 68

Detailed Epitope Specificities of Humanized Anti-CD52 Antibodies

Detailed epitope specificities of the humanized 12G6-SFD1/K12, 2C3-SFD1/K12, and 9D9-H16/K13 antibodies were determined using a Biacore T100 instrument. As a control, the epitope specificity of clone 097 (purified anti-human CD52 antibody, Biolegend) was evaluated using the same methodologies. The epitope specificity of clone 097 had previously been characterized using a peptide ELISA method (Hale G, "Synthetic peptide mimotype of the CAMPATH-1 (CD52) antigen, a small glycosylphosphatidylinositol-anchored glycoprotein," Immunotechnology, 1:175-187 (1995)). In this Biacore T100 assay, the antibodies were directly immobilized on Biacore CM5 Series S carboxymethyl dextran sensor chips (GE #BR-1006-68) using amine coupling. The carboxymethyl dextran surface was activated using a 1:1 mixture of 0.1M N-hydroxysuccinimide (NHS) and 0.4M N-ethyl-N'-(3-dimethylaminopropyl)carbodiimide hydrochloride (EDC), allowing the surface to bind reactive amine groups on the antibodies. Because IgM antibodies tend to have a higher level of non-specific binding compared to IgGs, the binding of a mouse IgMκ (mIgMκ) isotype control (Biolegend clone #MM-30) was also investigated. Following antibody immobilization, the reactive sensor chip surface was quenched using 1M ethanolamine hydrochloride/NaOH pH 8.5. One flow cell on each chip was a blank reference surface, and subsequent flow cells were immobilized with 10,000 RU of antibody.

Figure 101A:
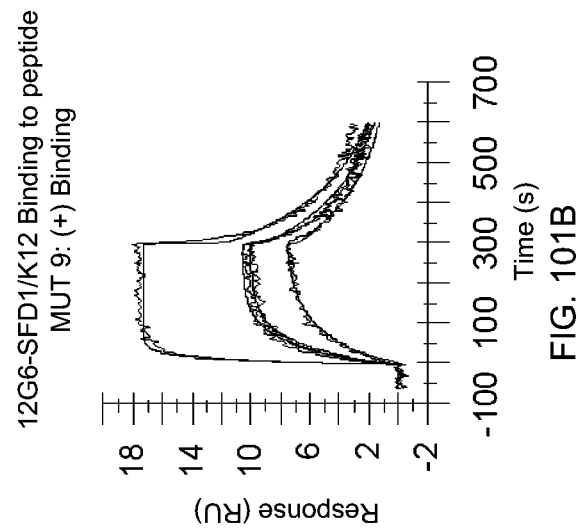
FIGS. 101A and 101B are representative sensorgrams of Biacore T100 assays to determine the epitope specificity of the humanized 12G6-SFD1/K12 antibody and mutant peptides generated by alanine scanning.
Figure 101B:
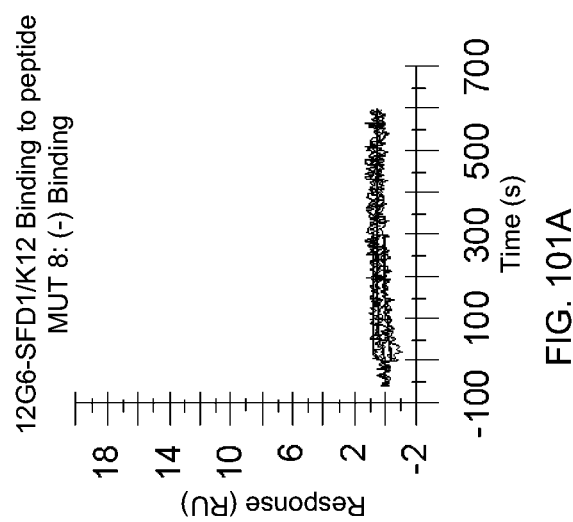

A series of alanine-scanning mutant peptides comprising the human CD52 sequence (MUT 1-MUT 12 (SEQ ID NOS: 169-180, respectively), Table 21) (see, e.g., Hale G, "Synthetic peptide mimotype of the CAMPATH-1 (CD52) antigen, a small glycosylphosphatidylinositol-anchored glycoprotein," Immunotechnology, 1:175-187 (1995)) were synthesized. Antibody binding to these mutant CD52 peptides and to wildtype human CD52 peptides was tested at concentrations of 500 nM, 100 nM, 50 nM, and 0 nM. Peptides were diluted into the assay running buffer, HBS-EP+ (10 mM HEPES, 150 mM NaCl, 0.05% P20 surfactant, 3 mM EDTA, pH 7.4). Duplicates of 100 nM samples were included. The light (kappa) chain specific rat anti-mouse IgM antibody (Southern Biotech Clone #1B4B1) was also included as an IgM control. The T100 instrument sample chamber and assay temperatures were set to 4° C. and 25° C., respectively. The human CD52 peptide samples were injected for five minutes at a 50 µl/min flow rate to measure association, and washed in HBS-EP+ for five minutes at a 50 µl/min flow rate to measure dissociation. The antibody surface was stripped of any remaining bound peptide using a sixty second injection of 10 mM glycine-HCl pH 2.0 at a 50 µl/min flow rate. Analysis was performed using Biacore T100 Kinetics Evaluation software v2.0 (GE Healthcare). Data was fit to a 1:1 model with reference flow cell and 0 nM concentration subtraction (double-reference subtraction). Representative sensorgrams of 12G6-SFD1/K12 antibody negative ((−), MUT 8) and positive ((+), MUT 9) peptide epitope recognition are shown in FIG. 101A and FIG. 101B, respectively. The compiled peptide binding data is summarized in Table 21.

The previously characterized binding specificity of clone 097 (Hale G, "Synthetic peptide mimotype of the CAMPATH-1 (CD52) antigen, a small glycosylphosphatidylinositol-anchored glycoprotein," Immunotechnology, 1:175-187 (1995)) was determined by coating ELISA plates with peptides containing the six residues of the C-terminal portion of human CD52 and then measuring the binding of the antibody to the fixed peptide. Each of the residues was substituted by all 20 amino acids. Because the peptides were attached to a solid surface in this ELISA, the assay may have been more influenced by avidity effects than the Biacore T100 assay described herein, which uses an antibody fixed to the surface over which the peptides are flowed. In the ELISA study, alanine substitutions at positions 11 and 12 (wildtype residues proline and serine, respectively) of the mature form of human CD52 were found to reduce strong binding of clone 097 to the peptide. In the present Biacore T100 study, alanine substitutions at positions 11 and 12 (as well as positions 7, 8, 9, and 10) were found to abrogate binding of clone 097. The hypothesized avidity effects of the ELISA assay are likely the reason why the mapped epitope of clone 097 is smaller as determined by the ELISA method than as determined by the described Biacore T100 assay.

The binding of both the 2C3-SFD1/K12 and 12G6-SFD1/K12 humanized antibodies to the human CD52 peptide sequence is sensitive to alanine substitutions at positions 7, 8, and 11 and the binding of humanized 9D9-H16/K13 is sensitive to alanine substitutions at positions 4 and 11. These defined epitope specificities overlap with the results observed in Example 4 (summarized in Table 8). Slight variations between the results are not unexpected given that the Biacore T100 method used to measure binding in the present case was significantly different from the method used in Example 4. In contrast to the present case, in Example 4, engineered CHO cells were used to express wildtype or alanine-substituted mutants of human CD52. Human CD52 expressed in such mammalian cells can be glycosylated, affecting binding. This is not the case for the human CD52 used in the Biacore T100 assay.

TABLE 21

Binding to alanine-scanning mutant hCD52 peptides

| Peptide | SEQ ID NO: | Peptide Sequence | 2C3-SFD1/K12 Binding | 9D9-H16/K13 Binding | 12G6-SFD1/K12 Binding | 097 Binding | Control mIgM Binding |
|---|---|---|---|---|---|---|---|
| MUT 1 | 169 | AQNDTSQTSSPSADC | + | + | + | + | − |
| MUT 2 | 170 | GANDTSQTSSPSADC | + | + | + | + | − |
| MUT 3 | 171 | GQADTSQTSSPSADC | + | + | + | + | − |
| MUT 4 | 172 | GQNATSQTSSPSADC | + | − | + | + | − |
| MUT 5 | 173 | GQNDASQTSSPSADC | + | + | + | + | − |
| MUT 6 | 174 | GQNDTAQTSSPSADC | + | + | + | + | − |
| MUT 7 | 175 | GQNDTSATSSPSADC | − | + | − | − | − |
| MUT 8 | 176 | GQNDTSQASSPSADC | − | + | − | − | − |
| MUT 9 | 177 | GQNDTSQTASPSADC | + | + | + | − | − |
| MUT 10 | 178 | GQNDTSQTSAPSADC | + | + | + | − | − |
| MUT 11 | 179 | GQNDTSQTSSASADC | − | − | − | − | − |
| MUT 12 | 180 | GQNDTSQTSSPAADC | + | + | + | − | − |

TABLE 21-continued

Binding to alanine-scanning mutant hCD52 peptides

| Peptide | SEQ ID NO | Peptide Sequence | 2C3-SFD1/K12 Binding | 9D9-H16/K13 Binding | 12G6-SFD1/K12 Binding | 097 Binding | Control mIgM Binding |
|---|---|---|---|---|---|---|---|
| Controls | | | | | | | |
| WT 1 | 181 | GQNDTSQTSSPSADK-Biotin | + | + | + | + | − |
| WT 2 | 182 | Biotin-GQNDTSQTSSPSAD | + | − | + | + | − |
| Rat anti-mIgM | N/A | N/A | N/A | N/A | N/A | + | + |

(+) Binding detected: Maximum response ($R_{max}$) > 2RUs for 500 nM peptide injection
(−) No binding detected: Maximum response ($R_{max}$) < 2RUs for 500 nM peptide injection Example 69

Assessment of CD4+ T Cell Responses Induced by Campath-1H® or 12G6-SFD1/K12

The CD4+ T cell proliferative response was evaluated after repeated in vitro stimulation with autologous dendritic cells (DC) preloaded with a set of overlapping 15-mer peptides comprising sequences from the variable regions of either Campath-1H® or the humanized 12G6-SFD1/K12 antibody. These experiments utilized normal human donor T cells and DCs. Results were measured by quantifying tritiated thymidine incorporation of the proliferating human CD4+ T cells in response to autologous peptide pulsed antigen presenting cells (APC).

Cell preparation: PBMCs were isolated from a normal human donor apheresis product acquired from BioMed Supplies (Carlsbad, Calif.). HLA haplotype screening of the donor blood was performed by Key Biologics, LLC (Memphis, Tenn.) (Table 22). PBMCs were isolated using the Ficoll-Paque PLUS density gradient (GE Healthcare) and a series of washes with phosphate buffered saline (PBS, Invitrogen, Carlsbad, Calif.). CD4+ T cells were isolated from PBMC using the Dynal CD4+ bead-based positive isolation kit (Invitrogen), following the manufacturer's recommended protocol. Isolated CD4+ T cells were frozen in Recovery Cell Culture Freezing Media (Invitrogen) and stored in liquid nitrogen. Dendritic Cells (DC) were induced from PBMCs by plating adherent cells with GM-CSF (Leukine, Bayer, Leverkusin, Germany) and IL-4 (Peprotech, Rocky Hill, N.J.) for six days. Media supplemented with GM-CSF and IL-4 was replaced on day 4. DCs were subsequently isolated from the flasks and frozen in the Freezing Media then transferred to liquid nitrogen storage tanks.

TABLE 22

HLA haplotype of blood donors

| Donor | HLA DR haploytpe | | peptide set |
|---|---|---|---|
| BMS170 | DRB1_0701 | DRB1_1503 | Campath |
| BMS154 | DRB1_0301 | DRB1_0302 | Campath |
| BMS150 | DRB1_1101 | DRB1_1302 | Campath |
| BMS167 | DRB1_0701 | DRB1_1503 | Campath |
| BMS200 | DRB1_0804 | DRB1_1202 | Campath |
| BMS301 | DRB1_1401 | DRB1_1503 | Campath |
| BMS352 | DRB1_0301 | DRB1_1101 | Campath |
| BMS362 | DRB1_0302 | DRB1_0302 | Campath |
| BMS484 | DRB1_0103 | DRB1_1201 | Campath/GLD52 |
| BMS486 | DRB1_1302 | DRB1_1303 | Campath/GLD52 |
| BMS640 | DRB1_0301 | DRB1_1302 | GLD52 |
| BMS656 | DRB1_301 | DRB1_1101 | GLD52 |
| BMS902 | DRB1_0302 | DRB1_0804 | GLD52 |
| BMS928 | DRB1_1001 | DRB1_1503 | GLD52 |
| BMS927 | DRB1_1001 | DRB1_1503 | GLD52 |
| BMS963 | DRB1_0302 | DRB1_1401 | GLD52 |
| BMS361 | DRB1_1102 | DRB1_1401 | GLD52 |
| BMS165 | DRB1_1102 | DRB1_1501 | GLD52 |

Peptide: Peptides encompassing the heavy and light chain variable regions of Campath-1H® and 12G6-SFD1/K12 were synthesized using a Rainin Symphony automated peptide synthesizer using standard Fmoc-chemistry on CLEAR resin (Peptides International, Louisville, Ky.) Amino acids (EMD Biosciences, San Diego, Calif. or Anaspec, San Jose, Calif.) were orthogonally protected with tert-Butoxycarbonyl (BOC), tert-Butyl (tBu), 2,2,4,6,7-Pentamethyldihydro-benzofuran-5-sulfonyl (Pbf), or Trityl (Trt) groups. Couplings were performed using an amino acid/HCTU/HOBt/DIEA/resin with a molar ratio of 6:6:3:12:1. A solution of 20% Piperidine and 2.5% 1,8-diazabicyclo[5.4.0]undec-7-ene (DBU) in DMF was used to remove Fmoc from the amino terminus during each cycle. Deprotection/cleavage from resin was performed using a cocktail of 15 mls/0.1 mM resin of 2.5% water/2.5% TIS/5% Anisole/90% TFA v/v ratio for 3 hours. Supernatant was precipitated in diethyl-ether (−80° C.) and pelleted at 3000 rpm for 10 minutes. Ether was decanted and the pellet was washed again. Crude peptide was then lyophilized. Analytical HPLC (XBridge C18 4.5×100 mm, Waters Corp., Milford, Mass.) and MALDI-TOF mass spectrometry (Synapt, Waters Corp., Milford, Mass.) were used to verify the sequences and assess purity. All reagents were HPLC grade (EMD Biosciences, San Diego, Calif. or Sigma Aldrich, St. Louis, Mo.). Lyophilized peptides were resuspended in 100% DMSO (Sigma). Forty three Campath-1H® peptides were combined into 11 linear groups, each containing 3 or 4 peptides per group (Table 23: from top to bottom, light chain peptides are denoted by SEQ ID NOs: 187-206 and heavy chain peptides are denoted by SEQ ID NOs: 207-229). The 42 12G6-SFD1/K12 peptides were combined into 8 linear groups, each containing five or six peptides per group (Table 24: from top to bottom, light chain peptides are denoted by SEQ ID NOs: 230-250 and heavy chain peptides are denoted by SEQ ID NOs: 251-271).

TABLE 23

Campath-1H ® 15-mer light chain and heavy chain peptides, overlapping by 10 amino acids each
Campath-1H ® Peptides

| light chain | | heavy chain | |
|---|---|---|---|
| Peptide | ID# | Peptide | ID# |
| DIQMTQSPSSLSASV | 978 | QVQLQESGPGLVRPS | 998 |
| QSPSSLSASVGDRVT | 979 | ESGPGLVRPSQTLSL | 999 |
| LSASVGDRVTITCKA | 980 | LVRPSQTLSLTCTVS | 1000 |
| GDRVTITCKASQNID | 981 | QTLSLTCTVSGFTFT | 1001 |
| ITCKASQNIDKYLNW | 982 | TCTVSGFTFTDFYMN | 1002 |
| SQNIDKYLNWYQQKP | 983 | GFTFTDFYMNWVRQP | 1003 |
| KYLNWYQQKPGKAPK | 984 | DFYMNWVRQPPGRGL | 1004 |
| YQQKPGKAPKLLIYN | 985 | WVRQPPGRGLEWIGF | 1005 |
| GKAPKLLIYNTNNLQ | 986 | PGRGLEWIGFIRDKA | 1006 |
| LLIYNTNNLQTGVPS | 987 | EWIGFIRDKAKGYTT | 1007 |
| TNNLQTGVPSRFSGS | 988 | IRDKAKGYTTEYNPS | 1008 |
| TGVPSRFSGSGSGTD | 989 | KGYTTEYNPSVKGRV | 1009 |
| RFSGSGSGTDFTFTI | 990 | EYNPSVKGRVTMLVD | 1010 |
| GSGTDFTFTISSLQP | 991 | VKGRVTMLVDTSKNQ | 1011 |
| FTFTISSLQPEDIAT | 992 | TMLVDTSKNQFSLRL | 1012 |
| SSLQPEDIATYYCLQ | 993 | TSKNQFSLRLSSVTA | 1013 |
| EDIATYYCLQHISRP | 994 | FSLRLSSVTAADTAV | 1014 |
| YYCLQHISRPRTFGQ | 995 | SSVTAADTAVYYCAR | 1015 |
| HISRPRTFGQGTKVE | 996 | ADTAVYYCAREGHTA | 1016 |
| RTFGQGTKVEIKRTV | 997 | YYCAREGHTAAPFDY | 1017 |
| | | EGHTAAPFDYWGQGS | 1018 |
| | | APFDYWGQGSLVTVS | 1019 |
| | | WGQGSLVTVSSASTK | 1020 |

TABLE 24

42 12G6-SFD1/K12 15-mer light chain and heavy chain peptides, overlapping by 10 amino acids each
12G6-SFD1/K12 Peptides

| light chain | | heavy chain | |
|---|---|---|---|
| Peptide | ID# | Peptide | ID# |
| DIVMTQTPLSLSVTP | 1027 | EVQLVESGGGLVQPG | 1048 |
| QTPLSLVTPGQPAS | 1028 | ESGGGLVQPGGSLRL | 1049 |
| LSVTPGQPASISCKS | 1029 | LVQPGGSLRLSCAAS | 1050 |
| GQPASISCKSSQSLL | 1030 | GSLRLSCAASGFPFS | 1079 |
| ISCKSSQSLLYSNGK | 1031 | SCAASGFPFSNYWMN | 1080 |
| SQSLLYSNGKTYLNW | 1032 | GFPFSNYWMNWVRQA | 1081 |
| YSNGKTYLNWVLQKP | 1072 | NYWMNWVRQAPGKGL | 1082 |
| TYLNWVLQKPGQSPQ | 1073 | WVRQAPGKGLEWVGQ | 1055 |
| VLQKPGQSPQRLIYL | 1074 | PGKGLEWVGQIRLKS | 1056 |
| GQSPQRLIYLVSKLD | 1036 | EWVGQIRLKSNNYAT | 1060 |
| RLIYLVSKLDSGVPD | 1037 | IRLKSNNYATHYAES | 1061 |
| VSKLDSGVPDRFSGS | 1038 | NNYATHYAESVKGRF | 1062 |
| SGVPDRFSGSGSGTD | 1039 | HYAESVKGRFTISRD | 1063 |
| RFSGSGSGTDFTLKI | 1040 | VKGRFTISRDDSKNS | 1064 |
| GSGTDFTLKISRVEA | 1041 | TISRDDSKNSLYLQM | 1065 |
| FTLKISRVEAEDVGV | 1042 | DSKNSLYLQMNSLKT | 1066 |
| SRVEAEDVGVYYCVQ | 1043 | LYLQMNSLKTEDTAV | 1067 |
| EDVGVYYCVQGSHFH | 1075 | NSLKTEDTAVYYCTP | 1068 |
| YYCVQGSHFHTFGQG | 1076 | EDTAVYYCTPIDYWG | 1083 |
| GSHFHTFGQGTKLEI | 1077 | YYCTPIDYWGQGTTV | 1084 |
| TFGQGTKLEIKRTVA | 1078 | IDYWGQGTTVTVSSA | 1085 |

In Vitro Stimulation

DC antigen pulsing and maturation: Before treatment with the peptides, DCs were thawed, washed and plated in RPMI (Invitrogen, Carlsbad, Calif.) supplemented with 5% Human Serum (HS, Sigma, St. Louis, Mo.), 1% Penicillin-Streptomycin (Invitrogen, Carlsbad, Calif.), 100 ng/ml GM-CSF, and 20 ng/ml IL-4. DCs were plated at $2 \times 10^5$ cells/ml in 4 ml media in 6-well tissue culture plates and allowed to adhere for 1 hour at 37° C. Following cell adherence, 10 µg/ml (40 µg total) of each peptide were added to wells containing DCs, correlating to either 120 µg or 160 µg of total peptides added to each well (Campath-1H® 3-peptide or 4-peptide groups), or 200 µg or 240 µg of total peptide added to each well (12G6-SFD1/K12 5-peptide or 6-peptide groups). 40 µg of the pan-DR binding epitope (PADRE) were added to one well of DCs and served as a positive control, as it can bind to most HLA-DR molecules (Alexander J, et al., "Development of high potency universal DR-restricted helper epitopes by modification of high affinity DR-blocking peptides," *Immunity*, 1:751-761 (1994)). Likewise, 40 µg of each of three HLA-DR binding Tetanus toxoid peptides (DTIMMEPPYCKGLDIYYKA (SEQ ID NO: 183), SAMLTNLIIFGPGPVLNKNEV (SEQ ID NO: 184), and NNFTVSFWLRVPKVSASHLE (SEQ ID NO: 185)) were added to one well of DCs. Similarly, a heat inactivated adenovirus was employed as a positive antigen source and was added to one well of DCs at 1 µg/ml. Lastly, one group of DCs remained unpulsed with antigen and served as a 'null' educated group. The DCs pulsed with the various antigens were incubated for at least three hours at 37° C. DCs were then treated with a 'maturating cytokine cocktail' containing 50 ng/ml TNF-α, 10 ng/ml IL-6, 25 ng/ml IL-1beta (Peprotech, Rocky Hill, N.J.) and 500 ng/ml PGE-2 (Sigma Aldrich, St. Louis, Mo.). The antigen pulsed DCs were then allowed to mature overnight at 37° C.

Establishment of co-culture: Following peptide loading and maturation, DCs were washed twice with PBS and replenished with 4 ml RPMI supplemented with 10% HS. Autologous CD4+ T cells were thawed and resuspended at $2\times10^6$ cells/ml in RPMI supplemented with 10% HS, Penicillin, and Streptomycin. The DCs were then cultured with naïve CD4+ T cells at a 10:1 T cell:DC ratio ($8\times10^6$ T cells: $8\times10^5$ DCs) in 8 mls media. The co-culture was then incubated at 37° C. for 7 days. Approximately 72 hours after initiation of co-culture, the cells were supplemented with 25 IU recombinant IL-2 (Peprotech, Rocky Hill, N.J.), and further supplemented with 25 IU recombinant IL-2 in fresh media every 3-4 days thereafter.

Restimulation of co-culture: At day 7 (Stim #2) and day 14 (Stim #3), the co-cultures were restimulated following the above procedure.

Proliferation assay: DCs were plated, antigen pulsed and matured as stated above at $5\times10^5$ cells/ml in 1 ml media on 24-well low binding plates to ease the subsequent transfer of cells to U-bottom assay plates. An irrelevant HLA_DR binding peptide, CS 378-398 (peptide sequence DIEKKIAK-MEKASSVFNVVNS (SEQ ID NO: 186)), was used as a negative control (Alexander J, et al., "Development of high potency universal DR-restricted helper epitopes by modification of high affinity DR-blocking peptides," *Immunity*, 1:751-761 (1994)). Following 24 hour DC maturation, the cells were detached from plates using ice cold PBS washes. DCs were plated in U-bottom 96 well plates with the antigen stimulated T cells at a 1:1 T cell:DC ratio ($2.5\times10^4$ DC/well). Each T cell group was assayed in triplicate with DC pulsed with the educating peptide(s) (specific response) and DC pulsed with irrelevant peptide (nonspecific response), as well as T cell only and DC only controls. The assay proceeded for 72 hours prior to the addition of 1 uCi tritiated thymidine per well (Perkin Elmer, Waltham, Mass.). Cells were harvested on a 96 well plate harvester (Perkin Elmer) and the amount of tritiated thymidine incorporated quantified by measuring CPM on a Wallac Microbeta Trilux counter (Perkin Elmer). The stimulation index was calculated by dividing the specific CPM by the nonspecific CPM.

T Cell Receptor (TCR) V beta usage: Any CD4+ T cells remaining after establishment of the proliferation assay were frozen for eventual determination of T cell receptor V beta chain expression. Cells were thawed and stained with antibodies recognizing 24 conjugated Vbeta family members for 30 minutes following manufacturer's directions in the IOTest Beta Mark Kit (Beckman Coulter, France). After washing with PBS and resuspending in 1% formaldehyde, cells were analyzed on FACScalibur (Becton Dickinson, Franklin Lakes, N.J.). The percentage of cells expressing each of the detected V-beta chains was calculated, as summarized in FIG. 102 and FIG. 103.

Campath-1H® Immunogenicity Assessment

Figure 102:
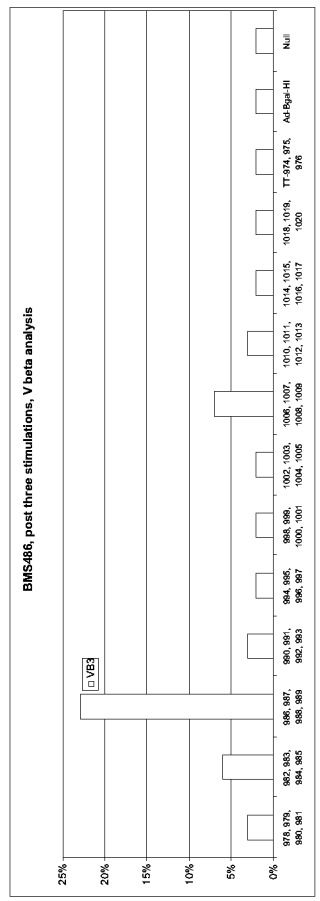
FIG. 102 shows the TCR V beta analysis for donor BMS486. CD4+ T cells educated with Campath-1H® peptide group 986-989 exhibited preferential expansion of a single V beta (Vβ3).

Immunogenicity assessment of Campath-1H® peptides was performed as described above using PBMCs from ten normal donors, from BioMedSupply (BMS). The summary of the responses as indicated by the stimulation index are depicted in Table 25A. Each donor is listed on one column, and each row lists the group of peptides used to stimulate CD4+ T cells. The Stimulation index (SI) is determined by dividing the specific immune response to the educating peptide group by an irrelevant response. SI values <2.0 are not listed. The proliferation data for each of the ten donors summarized in Table 25A is reported in FIG. 104A-J. Six donors exhibited a stimulation index greater than 2.0, and as a result were termed 'Campath-1H® responders'. Educated CD4+ T cells from one of the responders, BMS352, exhibited specific immune responses when assayed with two different peptide groups. A seventh donor, BMS486, was also classified as 'responder'. In this donor, a stimulation index 1.7 times background was recorded with the light chain peptide group 986-989. When assessing the V beta upregulation in the educated T cell cultures within this donor, it was shown that the 986-989 educated T cells exhibited high upregulation of a single V beta, Vβ3 (FIG. 102). The upregulation of a single V beta and specific proliferative response indicated that BMS486 was a Campath-1H® responder. The three non-responding donors, BMS200, BMS154, and BMS167, did not show proliferative data or V beta upregulation, indicating that a peptide specific immune response did not occur. The Campath-1H® data was quantified as a 70% (7/10) responder rate. The total number of peptide groups eliciting an immune response was eight. Three of those eight immunogenic peptide groups elicited strong responses in the respective donors with stimulation indices of 3.0 or above (Table 26).

Table 25: Summary of Stimulation Index Data

TABLE 25A

Campath-1H ® Stimulation Index
Campath-1H ® Stimulation Index

| | BMS200 | BMS301 | BMS154 | BMS484 | BMS362 | BMS486 | BMS150 | BMS167 | BMS170 | BMS352 |
|---|---|---|---|---|---|---|---|---|---|---|
| 982, 983, 984 & 987 | | | | | | nd | | | | |
| 988, 989 & 990 | | | | | | | | | | |
| 985, 986, 991 & 992 | | 2.6 | | | | | | | | |
| 993, 994, 995 & 996 | | | | | | | | | | |
| 997, 998 & 999 | | | | | | | | | | |
| 978, 979, 980, 981 | | | | | | | | | | |
| 982, 983, 984, 985 | | | | | | | | | | 2.0 | 
| 986, 987, 988, 989 | | | 2.1 | | | 1.7 | | | | |
| 990, 991, 992, 993 | | | | | | | | | | |
| 994, 995, 996, 997 | | | | | | | | | | 2.1 |

TABLE 25A-continued

Campath-1H ® Stimulation Index
Campath-1H ® Stimulation Index

| | BMS200 | BMS301 | BMS154 | BMS484 | BMS362 | BMS486 | BMS150 | BMS167 | BMS170 | BMS352 |
|---|---|---|---|---|---|---|---|---|---|---|
| 998, 999, 1000, 1001 | | | | | | | | | | |
| 1002, 1003, 1004, 1005 | | | | | | | | | | |
| 1006, 1007, 1008, 1009 | | | | | | | 4.2 | | | 5.4 |
| 1010, 1011, 1012, 1013 | | | | | 3.0 | | | | | |
| 1014, 1015, 1016, 1017 | | | | | | | | | | |
| 1018, 1019, 1020 | | | | | | | | | | |
| PADRE | 2.0 | | | 2.0 | | 2.5 | 2.5 | 2.8 | 10.5 | 2.6 |
| Tetanus | 11.2 | | | | | 2.3 | 4.5 | | 2.3 | 25.9 |
| Ad-Bgal-HI Null | 27.6 | 4.5 | 2.6 | 3.1 | 13.0 | 3.8 | 24.2 | 44.5 | 46.6 | 3.2 |

TABLE 25B

12G6-SFD1/K12 Stimulation Index
12G6-SFD1/K12 Stimulation Index

| | BMS484 | BMS486 | BMS656 | BMS640 | BMS361 | BMS165 | BMS902 | BMS928 | BMS927 | BMS963 |
|---|---|---|---|---|---|---|---|---|---|---|
| 1027, 1028, 1029, 1030, 1031 | | | | | | | | | | |
| 1032, 1072, 1073, 1074, 1036 | 2.1 | | | | | | | | 2.5 | |
| 1037, 1038, 1039, 1040, 1041 | | | | | | | | | | |
| 1042, 1043, 1075, 1076, 1077, 1078 | | | | | | | | | | |
| 1048, 1049, 1050, 1079, 1080 | | | | | | | | | | |
| 1081, 1082, 1055, 1056, 1060 | 2.1 | | | | | | | | | |
| 1061, 1062, 1063, 1064, 1065 | 2.0 | | | | | | | | nd | |
| 1066, 1067, 1068, 1083, 1084, 1085 | | | | | | | | 2.0 | | |
| PADRE | 3.0 | 3.6 | 2.2 | 9.8 | 2.4 | | 2.3 | | 4.7 | |
| TT-974, 975, 976 | 2.9 | 5.2 | | 3.2 | 5.7 | 12.9 | 3.7 | 4.3 | 22.4 | |
| Ad-Bgal Null | 17.6 | 11.0 | 10.9 | 31.7 | 29.1 | | 29.3 | 10.3 | 8.4 | 6.3 |

Example 70

Assessment of CD4+ T Cell Responses Induced by 12G6-SFD1/K12

Figure 103:
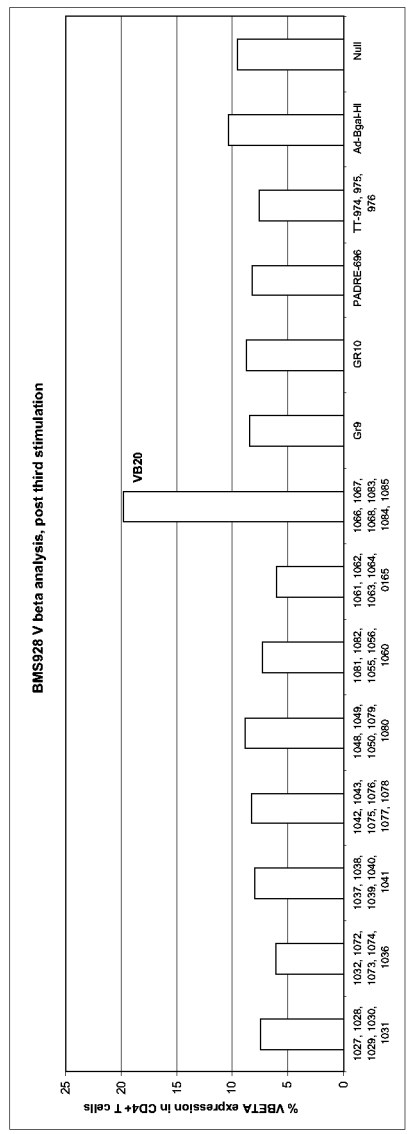
FIG. 103 shows the TCR V beta analysis for donor BMS928. CD4+ T cells educated with 12G6-SFD1/K12 peptide groups 1066-67-68 and 1083-84-85 exhibited preferential expansion of a single V beta (Vβ20).
Figure 104A:
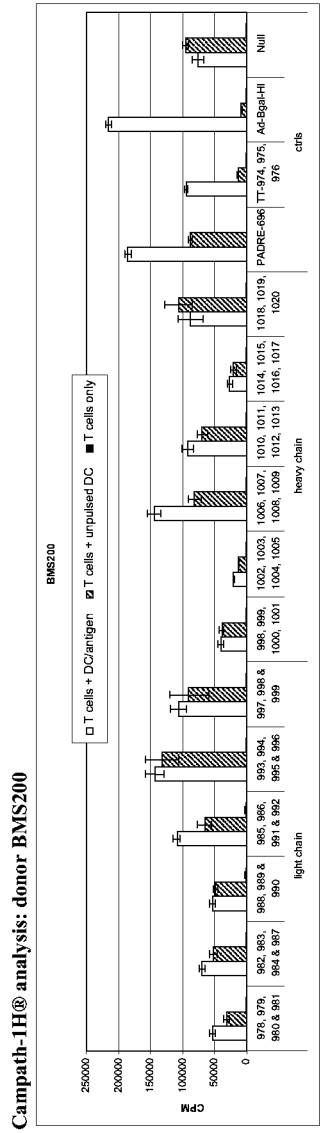
FIGS. 104A-104J show the Campath-1H® immunogenicity assessment. Proliferative responses are shown in CPM for individual donors A-J. The X axis depicts the groups of peptides used to stimulate autologous CD4+ T cells three times. Each group of T cells was assayed in triplicate with autologous DCs pulsed with the educating antigen/peptide group (specific response, left bar, white), irrelevant DR binding peptide (middle bar, striped), or media (right bar, black).
Figure 104B:
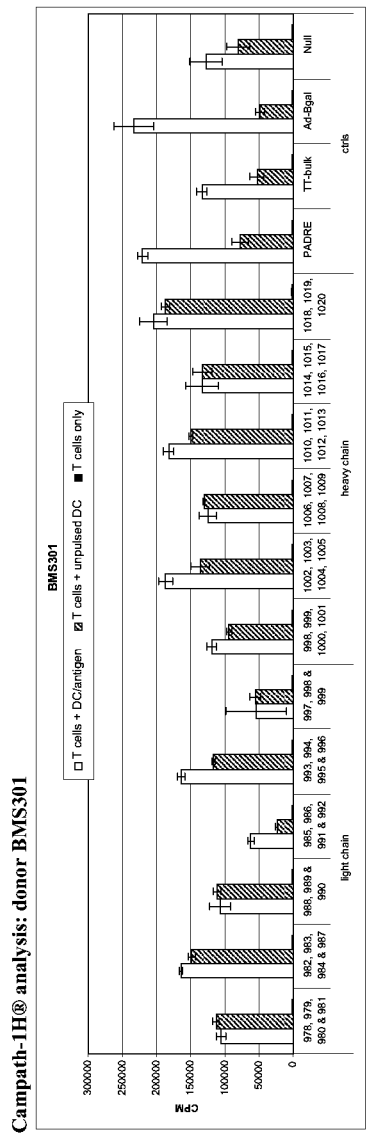
Figure 104C:
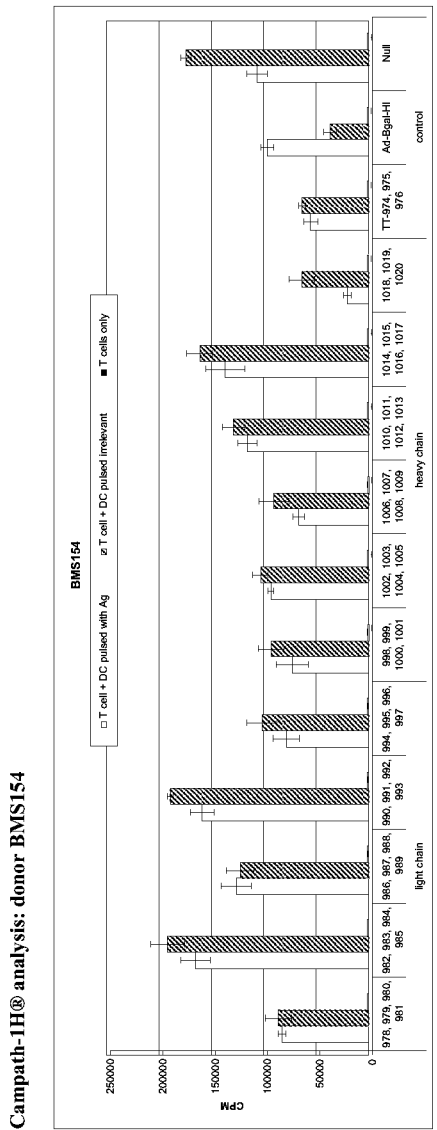
Figure 104D:
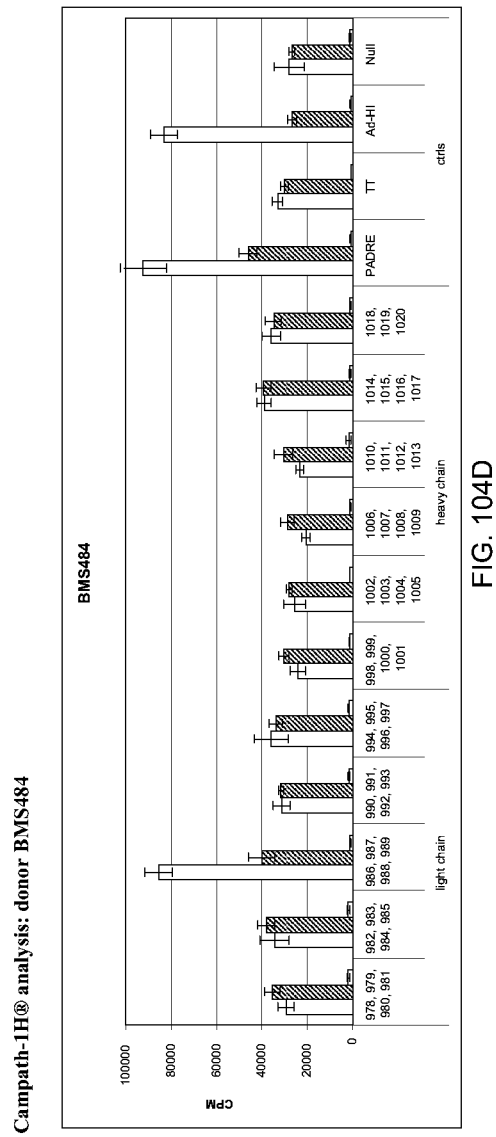
Figure 104E:
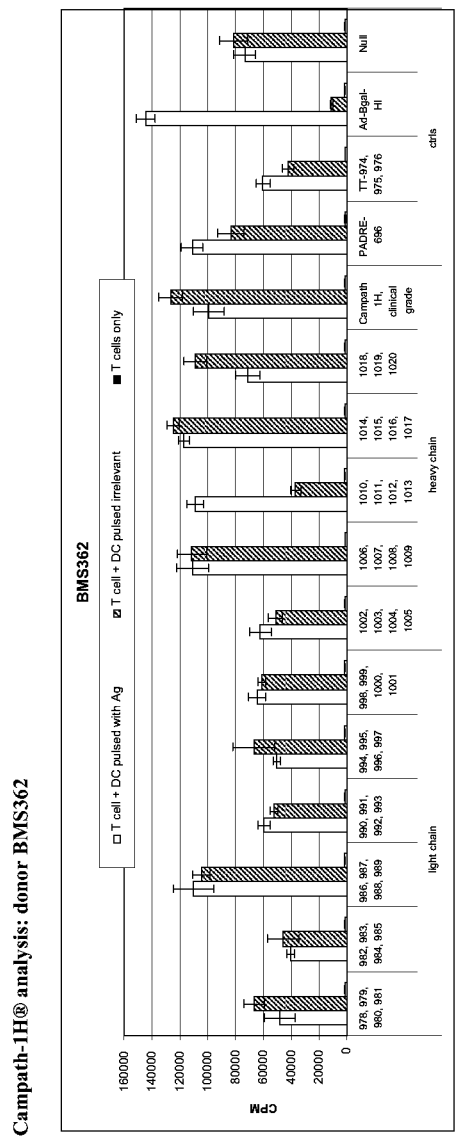
Figure 104F:
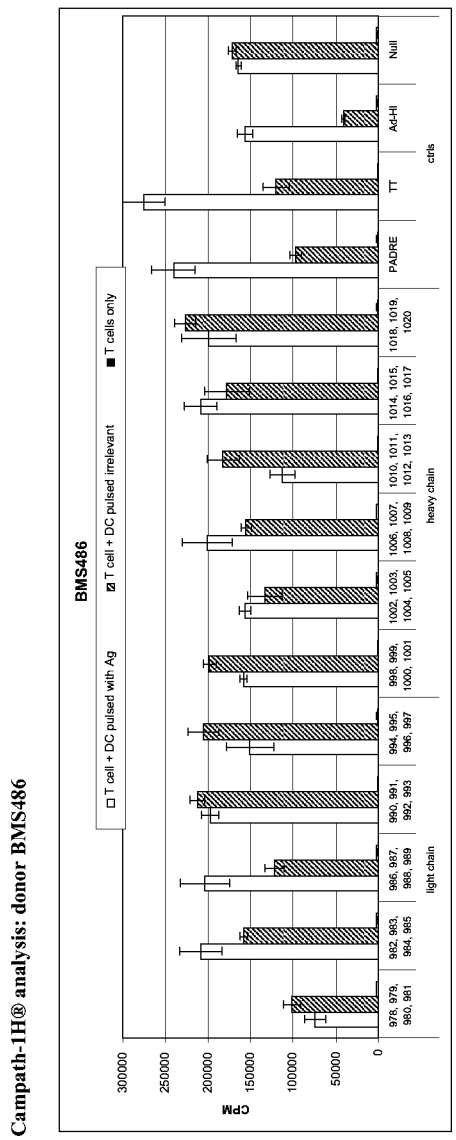
Figure 104G:
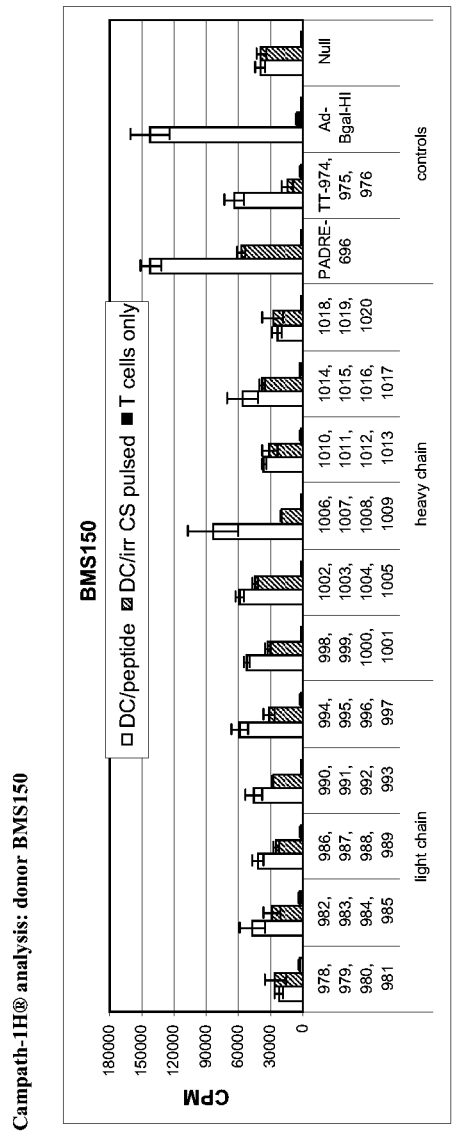
Figure 104H:
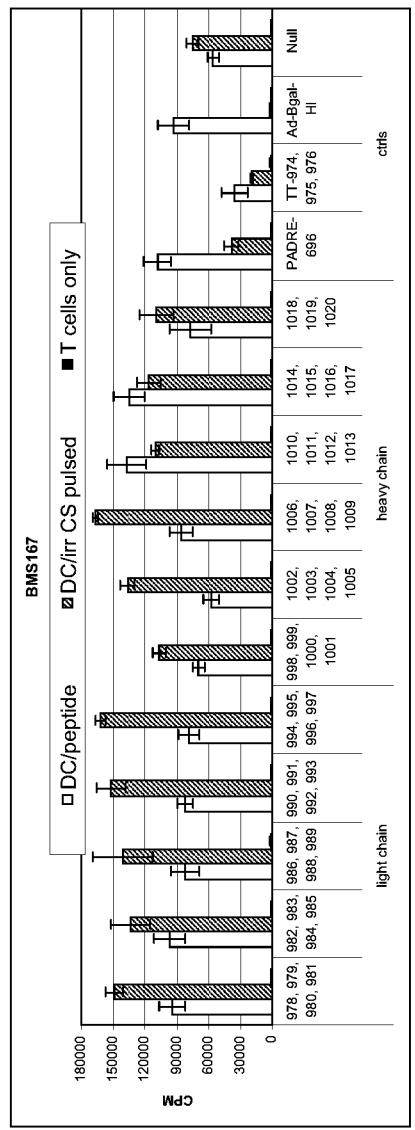
Figure 104I:
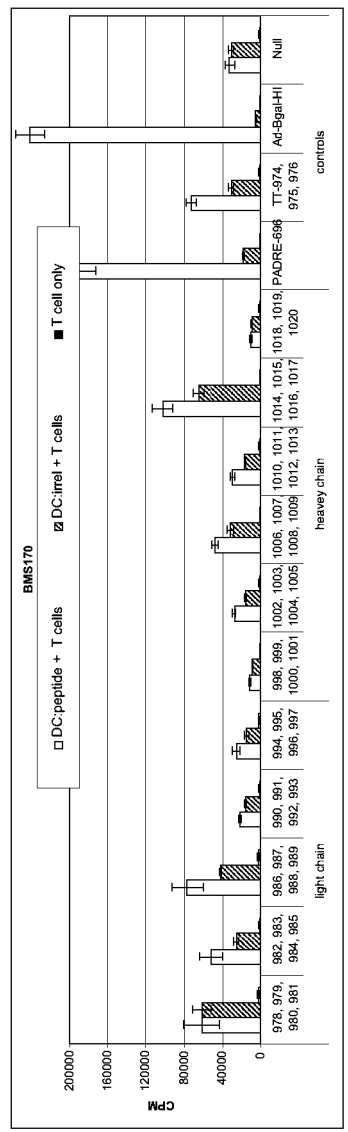
Figure 104J:
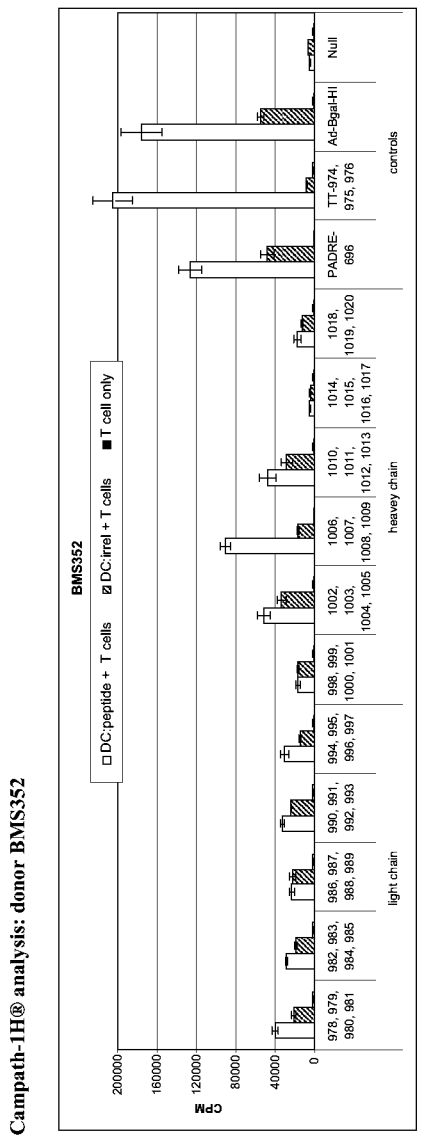
Figure 105A:
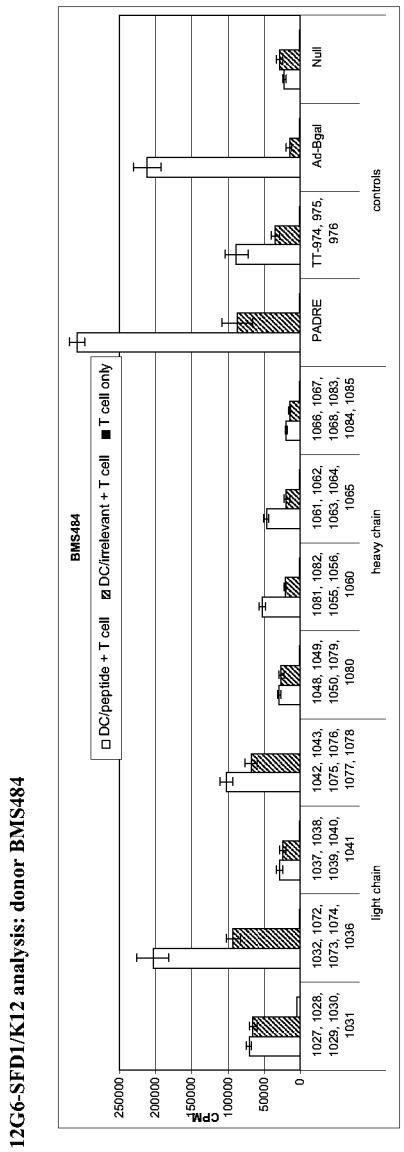
FIGS. 105A-105J show the 12G6-SFD1/K12 immunogenicity assessment. Proliferative responses are shown in CPM for individual donors A-J. The X axis depicts the groups of peptides used to stimulate autologous CD4+ T cells three times. Each group of T cells was assayed in triplicate with autologous DCs pulsed with the educating peptide group (specific response, left bar, white), irrelevant DR binding peptide (middle bar, striped), or media (right bar, black). In groups assayed without the media control, the left bar (white) represents DCs pulsed with the educating peptide, and the right bar (striped) represents DCs pulsed with the irrelevant peptide.
Figure 105B:
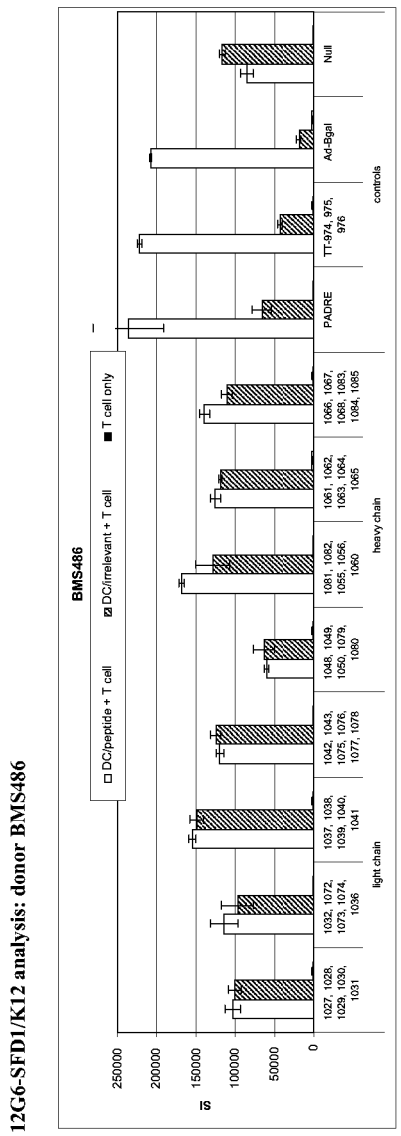
Figure 105C:
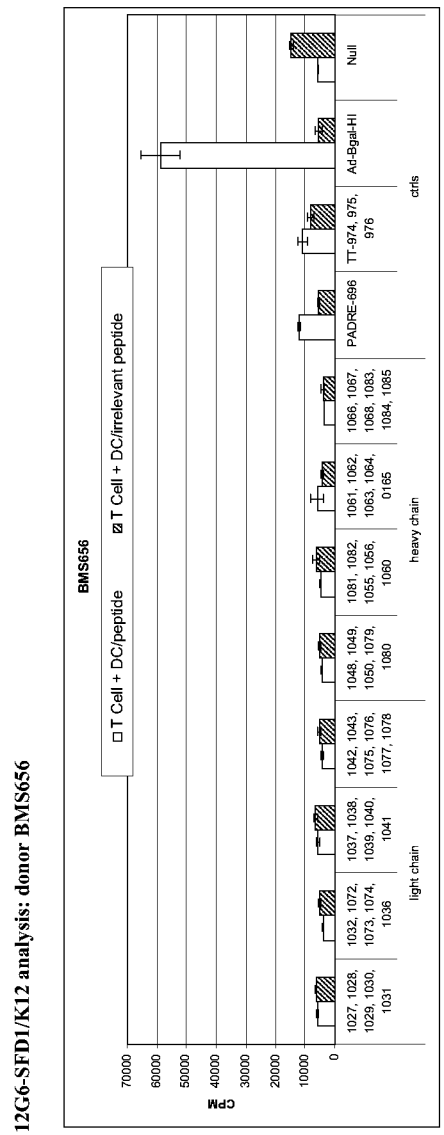
Figure 105D:
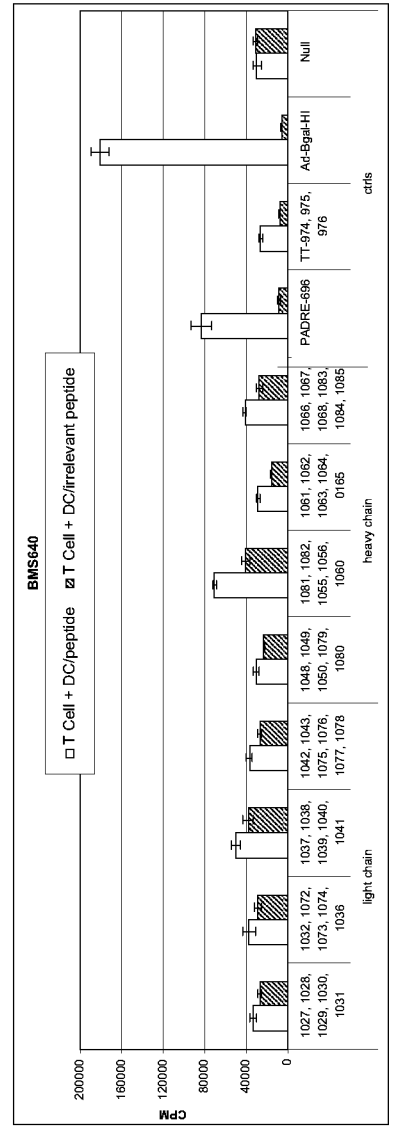
Figure 105E:
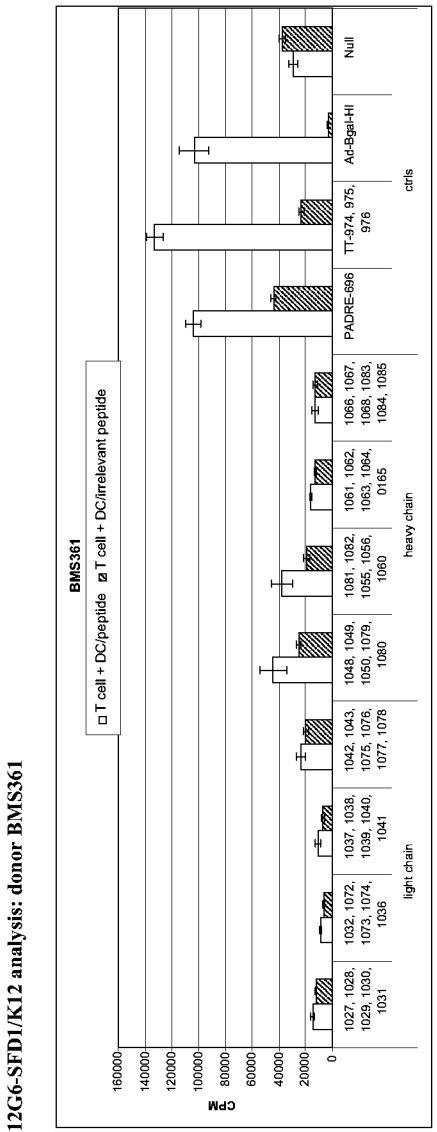
Figure 105F:
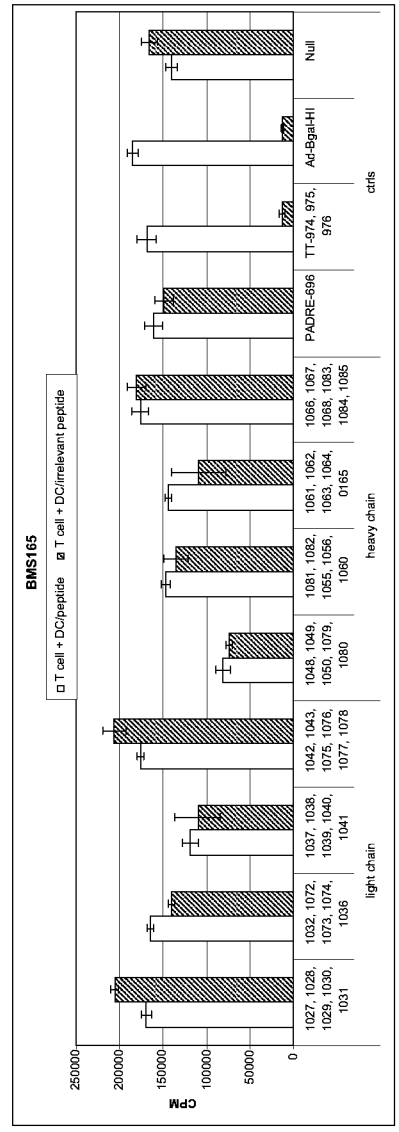
Figure 105G:
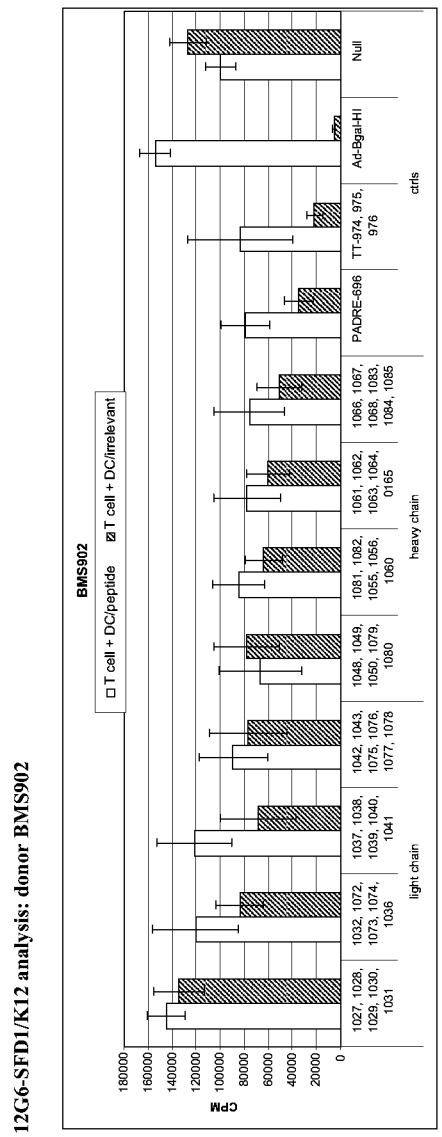
Figure 105H:
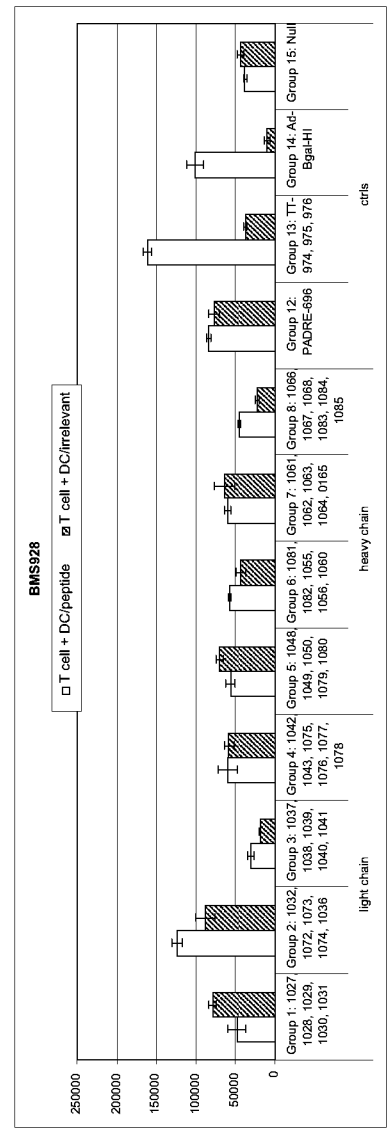
Figure 105I:
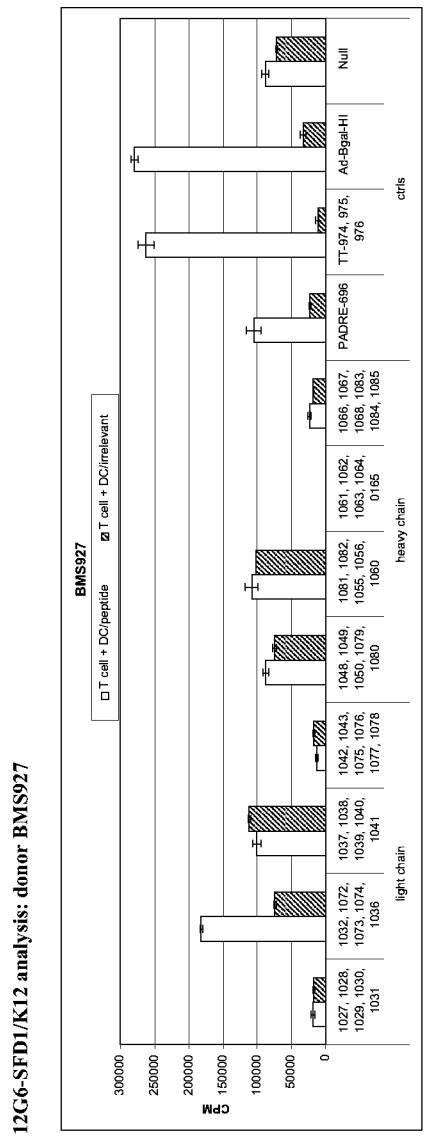
Figure 105J:
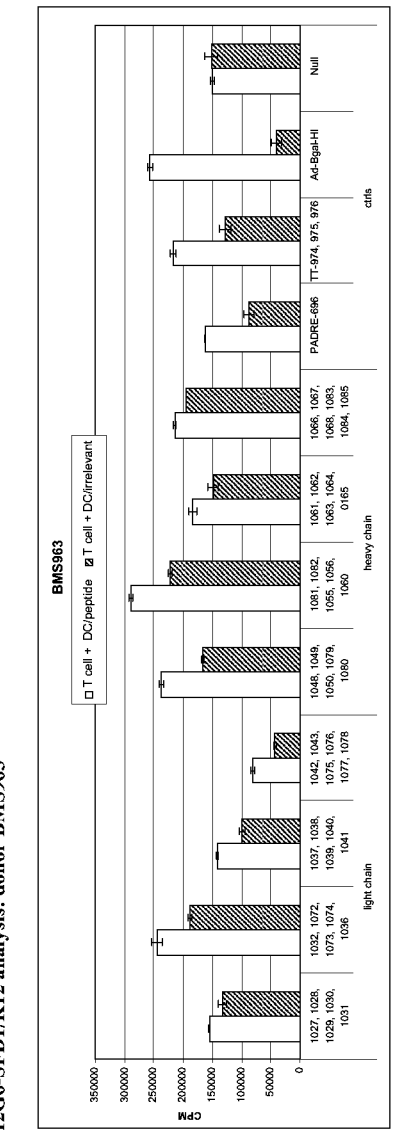

Immunogenicity assessment and V beta analysis of the variable region of 12G6-SFD1/K12 were performed as described in Example 69 for Campath-1H®, employing cells from ten normal donors. The proliferation data for each of the ten donors summarized in Table 25B is reported in FIG. 105A-J. Two of these ten donors were also used in the Campath-1H® assessment described above (BMS486 and BMS484), while the remaining eight donors were tested only with the 12G6-SFD1/K12 peptides. One donor, BMS484, responded to three peptide groups and was classified as a '12G6-SFD1/K12 responder' (Table 25B). Two donors, BMS927 and BMS928, each responded to one group of peptides and were therefore also classified as responders. Donor BMS928 showed a weak stimulation index of 2.0 to the group containing heavy chain peptides 1066, 1067, 1068, 1083, 1084, and 1085. This response was confirmed by analyzing the proliferative T cells for V beta usage. The responding BMS928 T cells exhibited an upregulation of a single V beta, V$\beta$20 (FIG. 103). Donor BMS927 showed a stimulation index of 2.5 in T cells educated with one group of light chain peptides. V beta analysis of the responding BMS927 T cells did not indicate a single V beta upregulation over background. However, this donor remains in the 'responder' category, as the V beta kit represents only 70% of all possible V beta usages. The 12G6-SFD1/K12 rate of immunogenicity in these 10 donors was 30% (3/10), less than half the rate of Campath-1H® responders (70%). A total of five peptide groups elicited a response, while none of those five groups resulted in a stimulation index greater than 3.0 (Table 26).

TABLE 26

Summary of Campath-1H ® and 12G6-SFD1/K12 immune responses

|  | Campath-1H ® | 12G6-SFD1/K12 |
|---|---|---|
| Percentage of responders | 70% (7/10) | 30% (3/10) |
| Number of peptide groups eliciting response | 8 | 5 |
| Responding peptide groups with Stimulation Index ≥ 3.0 | 3/8 (38%) | 0/3 (0%) |

SUMMARY

Peptides correlating to the heavy and light chain variable regions of humanized anti-CD52 monoclonal antibody 12G6-SFD1/K12 induced fewer immune responses from ten donors (30%) than peptides from the heavy and light chain variable regions of Campath-1H® (70%). The CD4+ T cell based immune responses that were generated with 12G6-SFD1/K12 were also of less magnitude than the Campath-1H® induced responses.

The following table lists the sequence identification numbers used herein.

TABLE 26

List of SEQ ID NOs

| SEQ ID NO | TYPE | DESCRIPTION |
|---|---|---|
| 1 | light chain variable region (VL) | Campath-1G ® |
| 2 | | CF1D12 |
| 3 | | 8G3 (mouse) |
| 4 | | 4G7 (mouse) |
| 5 | | 9D9 (mouse) |
| 6 | | 11C11 (mouse) |
| 7 | | 3G7 (mouse) |
| 8 | | 5F7 (mouse) |
| 9 | | 12G6 (mouse) |
| 10 | | 23E6 (mouse) |
| 11 | | 2C3 (mouse) |
| 12 | | 7F11 (mouse) |
| 13 | | 4B10 (mouse) |
| 14 | heavy chain variable region (VH) | Campath-1G ® |
| 15 | | CF1D12 |
| 16 | | 8G3 (mouse) |
| 17 | | 4G7 (mouse) |
| 18 | | 9D9 (mouse) |
| 19 | | 11C11 (mouse) |
| 20 | | 3G7 (mouse) |
| 21 | | 5F7 (mouse) |
| 22 | | 12G6 (mouse) |
| 23 | | 23E6 (mouse) |
| 24 | | 2C3 (mouse) |
| 25 | | 7F11 (mouse) |
| 26 | | 4B10 (mouse) |
| 27 | light chain CDR-1 | Campath-1H ® |
| 28 | | CF1D12 (mouse) |
| 29 | | 8G3, 4G7, 9D9, 11C11, 3G7 (mouse) |
| 30 | | 5F7 (mouse) |
| 31 | | 12G6, 23E6, 2C3 (mouse) |
| 32 | | 7F11 (mouse) |
| 33 | | 4B10 (mouse) |
| 34 | light chain CDR-2 | Campath-1H ® |
| 35 | | CF1D12 (mouse) |
| 36 | | 8G3, 11C11, 12G6, 23E6, 2C3 (mouse) |
| 37 | | 4G7 (mouse) |
| 38 | | 9D9 (mouse) |
| 39 | | 3G7 (mouse) |
| 40 | | 5F7 (mouse) |
| 41 | | 7F11, 4B10 (mouse) |
| 42 | light chain CDR-3 | Campath-1H ® |
| 43 | | CF1D12, 8G3, 4G7, 9D9, 11C11, 3G7, 5F7 (mouse) |
| 44 | | 12G6 (mouse) |
| 45 | | 23E6 (mouse) |
| 46 | | 2C3 (mouse) |
| 47 | | 7F11 (mouse) |
| 48 | | 4B10 (mouse) |
| 49 | heavy chain CDR-1 | Campath-1H ® |
| 50 | | CF1D12, 4G7, 9D9, 11C11, 3G7 (mouse) |
| 51 | | 8G3 (mouse) |
| 52 | | 5F7 (mouse) |
| 53 | | 12G6 (mouse) |
| 54 | | 23E6 (mouse) |

TABLE 26-continued

List of SEQ ID NOs

| SEQ ID NO | TYPE | DESCRIPTION |
|---|---|---|
| 55 | | 2C3 (mouse) |
| 56 | | 7F11, 4B10 (mouse) |
| 57 | heavy chain CDR-2 | Campath-1H ® |
| 58 | | CF1D12 (mouse) |
| 59 | | 8G3 (mouse) |
| 60 | | 4G7 (mouse) |
| 61 | | 9D9, 11C11, 5F7 (mouse) |
| 62 | | 3G7 (mouse) |
| 63 | | 12G6, 2C3 (mouse) |
| 64 | | 23E6 (mouse) |
| 65 | | 7F11 (mouse) |
| 66 | | 4B10 (mouse) |
| 67 | heavy chain CDR-3 | Campath-1H ® |
| 68 | | CF1D12, 9D9 (mouse) |
| 69 | | 8G3, 4G7, 11C11, 3G7 (mouse) |
| 70 | | 5F7 (mouse) |
| 71 | | 12G6, 23E6 (mouse) |
| 72 | | 2C3 (mouse) |
| 73 | | 7F11 (mouse) |
| 74 | | 4B10 (mouse) |
| 75 | light chain primers | Lead-ML kappa (forward primer in leader sequence) |
| 76 | | FR1-ML kappa (forward primer in the framework 1) |
| 77 | | ML kappa const (reverse primer in constant region) |
| 78 | | VK-MK (forward primer in the framework 1) |
| 79 | | MKC-Const (reverse primer in constant region) |
| 80 | heavy chain primers | MH-SP-ALT1 (forward primer in leader sequence) |
| 81 | | MH-SP-ALT2 (forward primer in leader sequence) |
| 82 | | MH-FR1 (forward primer in the framework 1) |
| 83 | | MH-FR1-1 (forward primer in the framework 1) |
| 84 | | MH-J2 (reverse primer in J region) |
| 85 | | MH-gamma-const (reverse primer in constant region) |
| 86 | | VH MH1 (forward primer in the framework 1) |
| 87 | | VH MH2 (forward primer in the framework 1) |
| 88 | | VH MH3 (forward primer in the framework 1) |
| 89 | | VH MH4 (forward primer in the framework 1) |
| 90 | | VH MH5 (forward primer in the framework 1) |
| 91 | | VH MH6 (forward primer in the framework 1) |
| 92 | | VH MH7 (forward primer in the framework 1) |
| 93 | | IgG1 (reverse primer in mouse IgG1 CH1 constant region) |
| 94 | | IgG2A (reverse primer in mouse IgG2A CH1 constant region) |
| 95 | | IgG2B (reverse primer in mouse IgG2B CH1 constant region) |
| 96 | VH (partial) | 4B10 (mouse): alignment |
| 97 | human germline (VH) | VH3-72: alignment |
| 98 | VH (partial) | 4B10 (humanized): alignment |
| 99 | mouse VL (partial) | 4B10 (mouse): alignment |
| 100 | human germline (VL) | VK2-A18b: alignment |
| 101 | VL (partial) | 4B10 (humanized): alignment |
| 102 | VL | 4B10-VK1 (humanized) |
| 103 | VH | 4B10-VH1 (humanized) |
| 104 | CD52 alanine-scanning mutant peptides | WT |
| 105 | | MUT 1 |
| 106 | | MUT 2 |
| 107 | | MUT 3 |
| 108 | | MUT 4 |
| 109 | | MUT 5 |
| 110 | | MUT 6 |
| 111 | | MUT 7 |
| 112 | | MUT 8 |
| 113 | | MUT 9 |
| 114 | | MUT 10 |
| 115 | LC CDR-1 | K/RSSQSLL/V/IXS/TN/DGXS/TYLX |
| 116 | | K/RSSQSLL/V/IHS/TNGXS/TYLH |
| 117 | | RSSQSLVHTNGNS/TYLH |
| 118 | LC CDR-2 | XVSXXXS |
| 119 | | XVSXRXS |

TABLE 26-continued

List of SEQ ID NOs

| SEQ ID NO | TYPE | DESCRIPTION | |
|---|---|---|---|
| 120 | | MVSXRFS | |
| 121 | LC CDR-3 | XQXXH/R/KF/LN/IXX | |
| 122 | | SQSXH/R/KF/LN/IPX | |
| 123 | | SQSXHVPF/P | |
| 124 | HC CDR-1 | GFXFXXYW/YMX | |
| 125 | | GFTFXXYW/YMX | |
| 126 | | GFTFTDYW/YMS | |
| 127 | HC CDR-2 | XIRXKXBXYXTXYXXSVKG | |
| 128 | | XIRXKXNXYTTEYXXSVKG | |
| 129 | | FIRNKANGYTTEYXXSVKG | |
| 130 | HC CDR-3 | TXXXY/F/W | |
| 131 | | TRYXY/F/WFDY | |
| 132 | | TRYIF/WFDY | |
| 133 | JH6 | WGQGTTVTVSS | |
| 134 | JK2 | FGQGTKLEIK | |
| 135 | JK5 | FGQGTRLEIK | |
| 136 | VH | SFD1 | 7F11 |
| 137 | | SFD2 | |
| 138 | VL | VK2 | |
| 139 | VH | SFD1 | 2C3 |
| 140 | | 12 | |
| 141 | | 15 | |
| 142 | | 16 | |
| 143 | | 17 | |
| 144 | | 19 | |
| 145 | VL | VK1 | |
| 146 | | VK11 | |
| 147 | | VK12 | |
| 148 | | VK13 | |
| 149 | VH | SFD1 | 12G6 |
| 150 | | VH10 | |
| 151 | | VH11 | |
| 152 | | VH12 | |
| 153 | VL | VK1 | |
| 154 | | VK10 | |
| 155 | | VK11 | |
| 156 | | VK12 | |
| 157 | | VK13 | |
| 158 | VH | VH10 | 9D9 |
| 159 | | VH11 | |
| 160 | | VH15 | |
| 161 | | VH16 | |
| 162 | | VH17 | |
| 163 | | VH18 | |
| 164 | VL | VK2 | |
| 165 | | VK12 | |
| 166 | | VK13 | |
| 167 | | VK14 | |
| 168 | | VK15 | |
| 169 | CD52 alanine-scanning | MUT 1 | |
| 170 | peptides | MUT 2 | |
| 171 | | MUT 3 | |
| 172 | | MUT 4 | |
| 173 | | MUT 5 | |
| 174 | | MUT 6 | |
| 175 | | MUT 7 | |
| 176 | | MUT 8 | |
| 177 | | MUT 9 | |
| 178 | | MUT 10 | |
| 179 | | MUT 11 | |
| 180 | | MUT 12 | |
| 181 | | WT1 | |
| 182 | | WT2 | |

TABLE 26-continued

List of SEQ ID NOs

| SEQ ID NO | TYPE | DESCRIPTION |
|---|---|---|
| 183 | Tetanus toxoid HLA-DR-binding peptides | DTIMMEPPYCKGLDIYYKA |
| 184 | | SAMLTNLIIFGPGPVLNKNEV |
| 185 | | NNFTVSFWLRVPKVSASHLE |
| 186 | "irrelevant" HLA-DR-binding peptide | CS 378-398 |
| 187 | Campath-1H ® | 978 |
| 188 | LC overlapping 15-mer | 979 |
| 189 | peptides for | 980 |
| 190 | immunogenicity study | 981 |
| 191 | | 982 |
| 192 | | 983 |
| 193 | | 984 |
| 194 | | 985 |
| 195 | | 986 |
| 196 | | 987 |
| 197 | | 988 |
| 198 | | 999 |
| 199 | | 990 |
| 200 | | 991 |
| 201 | | 992 |
| 202 | | 993 |
| 203 | | 994 |
| 204 | | 995 |
| 205 | | 996 |
| 206 | | 997 |
| 207 | Campath-1H ® | 998 |
| 208 | HC overlapping 15- | 999 |
| 209 | mer peptides for | 1000 |
| 210 | immunogenicity study | 1001 |
| 211 | | 1002 |
| 212 | | 1003 |
| 213 | | 1004 |
| 214 | | 1005 |
| 215 | | 1006 |
| 216 | | 1007 |
| 217 | | 1008 |
| 218 | | 1009 |
| 219 | | 1010 |
| 220 | | 1011 |
| 221 | | 1012 |
| 222 | | 1013 |
| 223 | | 1014 |
| 224 | | 1015 |
| 225 | | 1016 |
| 226 | | 1017 |
| 227 | | 1018 |
| 228 | | 1019 |
| 229 | | 1020 |
| 230 | 12G6-SFD1/K12 | 1027 |
| 231 | LC | 1028 |
| 232 | overlapping 15-mer | 1029 |
| 233 | peptides for | 1030 |
| 234 | immunogenicity study | 1031 |
| 235 | | 1032 |
| 236 | | 1072 |
| 237 | | 1073 |
| 238 | | 1074 |
| 239 | | 1036 |
| 240 | | 1037 |
| 241 | | 1038 |
| 242 | | 1039 |
| 243 | | 1040 |
| 244 | | 1041 |
| 245 | | 1042 |
| 246 | | 1043 |
| 247 | | 1075 |
| 248 | | 1076 |
| 249 | | 1077 |
| 250 | | 1078 |
| 251 | 12G6-SFD1/K12 | 1048 |

TABLE 26-continued

List of SEQ ID NOs

| SEQ ID NO | TYPE | DESCRIPTION | |
|---|---|---|---|
| 252 | HC | 1049 | |
| 253 | overlapping 15-mer | 1050 | |
| 254 | peptides for | 1079 | |
| 255 | immunogenicity study | 1080 | |
| 256 | | 1081 | |
| 257 | | 1082 | |
| 258 | | 1055 | |
| 259 | | 1056 | |
| 260 | | 1060 | |
| 261 | | 1061 | |
| 262 | | 1062 | |
| 263 | | 1063 | |
| 264 | | 1064 | |
| 265 | | 1065 | |
| 266 | | 1066 | |
| 267 | | 1067 | |
| 268 | | 1068 | |
| 269 | | 1083 | |
| 270 | | 1084 | |
| 271 | | 1085 | |
| 272 | HC | 2C3-SFD1 | 2C3 |
| 273 | LC | 2C3-K12 | |
| 274 | HC | 7F11-SFD1 | 7F11 |
| 275 | LC | 7F11-K2 | |
| 276 | HC | 9D9-H16 | 9D9 |
| 277 | | 9D9-H18 | |
| 278 | LC | 9D9-K13 | |
| 279 | HC | 12G6-SFD1 | 12G6 |
| 280 | LC | 12G6-K12 | |
| 281 | HC | 4B10-H1 | 4B10 |
| 282 | LC | 4B10-K1 | |
| 283 | HC (nucleic acid) | 2C3-SFD1 | 2C3 |
| 284 | LC (nucleic acid) | 2C3-K12 | |
| 285 | HC (nucleic acid) | 7F11-SFD1 | 7F11 |
| 286 | LC (nucleic acid) | 7F11-K2 | |
| 287 | HC (nucleic acid) | 9D9-H16 | 9D9 |
| 288 | | 9D9-H18 | |
| 289 | LC (nucleic acid) | 9D9-K13 | |
| 290 | HC (nucleic acid) | 12G6-SFD1 | 12G6 |
| 291 | LC (nucleic acid) | 12G6-K12 | |
| 292 | HC (nucleic acid) | 4B10-H1 | 4B10 |
| 293 | LC (nucleic acid) | 4B10-K1 | |
| 294 | HC CDR-3 | 7F11-SFD2 (ARYIFFDY) | 7F11 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A monoclonal anti-human CD52 antibody or an antigen-binding portion that binds to human CD52, wherein the light chain and heavy chain of said antibody comprise the three complementarity determining regions (CDRs) found in
   a) SEQ ID NOs: 3 and 16, respectively;
   b) SEQ ID NOs: 4 and 17, respectively;
   c) SEQ ID NOs: 5 and 18, respectively;
   d) SEQ ID NOs: 6 and 19, respectively;
   e) SEQ ID NOs: 7 and 20, respectively;
   f) SEQ ID NOs: 8 and 21, respectively;
   g) SEQ ID NOs: 9 and 22, respectively;
   h) SEQ ID NOs: 10 and 23, respectively;
   i) SEQ ID NOs: 11 and 24, respectively;
   j) SEQ ID NOs: 12 and 25, respectively;
   k) SEQ ID NOs: 12 and 137, respectively; or
   l) SEQ ID NOs: 13 and 26, respectively.

2. A monoclonal anti-human CD52 antibody or an antigen-binding portion that binds to human CD52, wherein the heavy chain and the light chain of said antibody comprise the amino acid sequences of SEQ ID NOs: 279 and 280, respectively, without the signal sequences.

3. A monoclonal anti-human CD52 antibody or an antigen-binding portion that binds to human CD52, wherein the light chain of said antibody comprises an amino acid sequence selected from the group consisting of SEQ ID NOs: 102, 138, 145-148, 153-157, and 164-168.

4. A monoclonal anti-human CD52 antibody or an antigen-binding portion that binds to human CD52, wherein the light chain of said antibody comprises an amino acid sequence selected from the group consisting of SEQ ID NOs: 273, 275, 278, 280, and 282, without the signal sequences.

5. An antibody light chain comprising an amino acid sequence selected from the group consisting of SEQ ID NOs: 102, 138, 145-148, 153-157, 164-168, 273, 275, 278, 280, and 282, without the signal sequences if present.

6. A monoclonal anti-human CD52 antibody or an antigen-binding portion that binds to human CD52, wherein the heavy chain of said antibody comprises an amino acid sequence selected from the group consisting of SEQ ID NOs: 103, 136, 137, 139-144, 149-152, and 158-163.

7. A monoclonal anti-human CD52 antibody or an antigen-binding portion that binds to human CD52, wherein the heavy chain of said antibody comprises an amino acid sequence selected from the group consisting of SEQ ID NOs: 272, 274, 276, 277, 279, and 281, without the signal sequences.

8. An antibody heavy chain comprising an amino acid sequence selected from the group consisting of SEQ ID NOs: 103, 136, 137, 139-144, 149-152, 158-163, 272, 274, 276, 277, 279, and 281, without the signal sequences if present.

9. The monoclonal antibody or antigen-binding portion of claim 1, wherein the antibody is a humanized antibody, a mouse antibody, or a chimeric antibody.

10. The monoclonal antibody or antigen-binding portion of claim 1, wherein the framework regions of the heavy chain utilize a VH3-72 or VH3-23 human germline sequence, and wherein the framework regions of the light chain utilize a VK2 A18b human germline sequence.

11. The monoclonal antibody or antigen-binding portion of claim 1, wherein the antibody comprises heavy chain (H)-CDR1, H-CDR2, H-CDR3, and light chain (L)-CDR1, L-CDR2, and L-CDR3 whose amino acid sequences are:
   a) SEQ ID NOs: 51, 59, 69, 29, 36, and 43, respectively;
   b) SEQ ID NOs: 50, 60, 69, 29, 37, and 43, respectively;
   c) SEQ ID NOs: 50, 61, 68, 29, 38, and 43, respectively;
   d) SEQ ID NOs: 50, 61, 69, 29, 36, and 43, respectively;
   e) SEQ ID NOs: 50, 62, 69, 29, 39, and 43, respectively;
   f) SEQ ID NOs: 52, 61, 70, 30, 40, and 43, respectively;
   g) SEQ ID NOs: 53, 63, 71, 31, 36, and 44, respectively;
   h) SEQ ID NOs: 54, 64, 71, 31, 36, and 45, respectively;
   i) SEQ ID NOs: 55, 63, 72, 31, 36, and 46, respectively;
   j) SEQ ID NOs: 56, 65, 73, 32, 41, and 47, respectively;
   k) SEQ ID NOs: 56, 65, 294, 32, 41, and 47, respectively; or
   l) SEQ ID NOs: 56, 66, 74, 33, 41, and 48, respectively.

12. The monoclonal antibody or antigen-binding portion of claim 1, wherein the light chain and heavy chain of said antibody comprise the amino acid sequences of:
   a) SEQ ID NOs: 3 and 16, respectively;
   b) SEQ ID NOs: 4 and 17, respectively;
   c) SEQ ID NOs: 5 and 18, respectively;
   d) SEQ ID NOs: 6 and 19, respectively;
   e) SEQ ID NOs: 7 and 20, respectively;
   f) SEQ ID NOs: 8 and 21, respectively;
   g) SEQ ID NOs: 9 and 22, respectively;
   h) SEQ ID NOs: 10 and 23, respectively;
   i) SEQ ID NOs: 11 and 24, respectively;
   j) SEQ ID NOs: 12 and 25, respectively; or
   k) SEQ ID NOs: 13 and 26, respectively.

13. The monoclonal antibody or antigen-binding portion of claim 1, wherein said heavy chain and light chain comprise the amino acid sequences of
   a) SEQ ID NOs: 103 and 102, respectively;
   b) SEQ ID NOs: 136 and 138, respectively;
   c) SEQ ID NOs: 137 and 138, respectively;
   d) SEQ ID NOs: 139 and 147, respectively;
   e) SEQ ID NOs: 149 and 155, respectively;
   f) SEQ ID NOs: 149 and 156, respectively;
   g) SEQ ID NOs: 158 and 165, respectively;
   h) SEQ ID NOs: 158 and 166, respectively;
   i) SEQ ID NOs: 159 and 165, respectively;
   j) SEQ ID NOs: 159 and 166, respectively;
   k) SEQ ID NOs: 161 and 166, respectively; or
   l) SEQ ID NOs: 163 and 166, respectively.

14. A monoclonal anti-human CD52 antibody or an antigen-binding portion that binds to human CD52, wherein the heavy chain and the light chain of said antibody comprise the amino acid sequences of SEQ ID NOs: 272 and 273, respectively, without the signal sequences.

15. A monoclonal anti-human CD52 antibody or an antigen-binding portion that binds to human CD52, wherein the heavy chain and the light chain of said antibody comprise the amino acid sequences of SEQ ID NOs: 274 and 275, respectively, without the signal sequences.

16. A monoclonal anti-human CD52 antibody or an antigen-binding portion that binds to human CD52, wherein the heavy chain and the light chain of said antibody comprise the amino acid sequences of SEQ ID NOs: 276 and 278, respectively, without the signal sequences.

17. A monoclonal anti-human CD52 antibody or an antigen-binding portion that binds to human CD52, wherein the heavy chain and the light chain of said antibody comprise the amino acid sequences of SEQ ID NOs: 277 and 278, respectively, without the signal sequences.

18. A monoclonal anti-human CD52 antibody or an antigen-binding portion that binds to human CD52, wherein the heavy chain and the light chain of said antibody comprise the amino acid sequences of SEQ ID NOs: 281 and 282, respectively, without the signal sequences.

19. The monoclonal antibody of any one of claims 1, 3, 6, and 11-13, wherein said antibody is an IgG1, IgG2, IgG3, or IgG4 molecule.

20. The antigen-binding portion of any one of claims 1, 3, and 6, wherein said portion is a single chain antibody, Fv, Fab, Fab', F(ab')$_2$, Fd, single chain Fv molecule (scFv), bispecific single chain Fv dimer, diabody, domain-deleted antibody or single domain antibody (dAb).

21. The monoclonal antibody or antigen-binding portion of claim 1, wherein said antibody or portion binds to an amino acid sequence comprising SEQ ID NO: 104, and optionally, the binding of said antibody or portion to SEQ ID NO: 104 is reduced by an alanine substitution at one or more of residues 4, 7, 8, and 11 of SEQ ID NO: 104.

22. The monoclonal antibody or antigen-binding portion of any one of claims 1, 3, and 6, wherein said antibody or antigen-binding portion has one or more properties selected from the group consisting of:
  a) depletes T or B lymphocytes, or both;
  b) preferentially depletes T lymphocytes as compared to B lymphocytes;
  c) increases circulating serum levels of TNF-alpha, IL-6, or MCP-1;
  d) mediates antibody-dependent cell mediated cytotoxicity (ADCC) of CD52-expressing cells;
  e) mediates complement-dependent cytotoxicity (CDC) of CD52-expressing cells;
  f) binds to human CD52 in the presence of neutralizing antibodies to alemtuzumab; and
  g) promotes intracellular signaling in human T or B lymphocytes, or both.

23. A composition comprising the monoclonal antibody or antigen-binding portion of any one of claims 1, 2, 3, 4, 6, 7 and 11-18, and a pharmaceutically acceptable vehicle or carrier.

24. An isolated nucleic acid encoding the heavy chain, or the light chain, or both, of an antibody or antigen-binding portion of any one of claims 1, 2, 3, 4, 5, 7, and 11-18.

25. The isolated nucleic acid of claim 24, wherein said isolated nucleic acid comprises:
  a) a heavy chain nucleotide sequence selected from the group consisting of SEQ ID NOs: 283, 285, 287, 288, 290, and 292, or said nucleotide sequence without the sequence encoding a signal peptide;
  b) a light chain nucleotide sequence selected from the group consisting of SEQ ID NOs: 284, 286, 289, 291, and 293, or said nucleotide sequence without the sequence encoding a signal peptide; or
  c) the nucleotide sequences of both a) and b).

26. The isolated nucleic acid of claim 25, wherein said isolated nucleic acid comprises a heavy chain nucleotide sequence and a light chain nucleotide sequence selected from the group consisting of:

a) SEQ ID NO: 283 and SEQ ID NO: 284, respectively, both without sequences encoding signal peptides;
  b) SEQ ID NO: 285 and SEQ ID NO: 286, respectively, both without sequences encoding signal peptides;
  c) SEQ ID NO: 287 and SEQ ID NO: 289, respectively, both without sequences encoding signal peptides;
  d) SEQ ID NO: 288 and SEQ ID NO: 289, respectively, both without sequences encoding signal peptides;
  e) SEQ ID NO: 290 and SEQ ID NO: 291, respectively, both without sequences encoding signal peptides; and
  f) SEQ ID NO: 292 and SEQ ID NO: 293, respectively, both without sequences encoding signal peptides.

27. A host cell comprising a first nucleic acid sequence encoding the heavy chain of a monoclonal antibody or antigen-binding portion of any one of claims 1, 2, 3, 4, 6, 7, and 11-18, said first nucleic acid sequence operably linked to an expression control element, and a second nucleic acid sequence encoding the light chain of said monoclonal antibody or antigen-binding portion, said second nucleic acid sequence operably linked to an expression control element.

28. A method of expressing an anti-human CD52 antibody or an antigen-binding portion that binds to human CD52, comprising maintaining the host cell of claim 27 under conditions appropriate for expression of the antibody or portion, and expressing said antibody or portion.

29. A method for inducing immunosuppression in a patient, comprising administering to the patient an effective amount of the antibody or antigen-binding portion of any one of claims 1, 2, 3, 4, 6, 7, and 11-18.

30. The method of claim 29, wherein the patient has an autoimmune disease.

31. A method for targeting CD52$^+$cells in a cancer patient, comprising administering to the patient an effective amount of the monoclonal antibody or antigen-binding portion of any one of claims 1, 2, 3, 4, 6, 7, and 11-18.

32. A method of inhibiting angiogenesis in a patient in need thereof, comprising administering an effective amount of the monoclonal antibody or portion of any one of claims 1, 2, 3, 4, 6, 7, and 11-18, to the patient.

33. The method of claim 29, wherein the patient is receiving transplantation.

34. The method of claim 30, wherein said autoimmune disease is multiple sclerosis, rheumatoid arthritis, systemic lupus erythematosus, or vasculitis.

35. The method of claim 31, wherein the cancer patient has leukemia.

36. The method of claim 31, wherein the cancer patient has lymphoma.

37. The method of claim 31, wherein the cancer patient has T cell malignancy, and the antibody or portion preferentially depletes T cells as compared to B cells.

38. The method of claim 31, wherein the cancer patient has a solid tumor.

39. The method of claim 29, further comprising administering to the patient a neutrophil or NK cell stimulatory agent.

40. The method of claim 31, further comprising administering to the patient a neutrophil or NK cell stimulatory agent.

41. The method of claim 29, further comprising administering to the patient a T regulatory cell stimulatory agent.

42. The method of claim 31, further comprising administering to the patient a T regulatory cell stimulatory agent.

43. The method of claim 32, wherein the patient has a solid tumor.

44. The method of claim 32, wherein the patient has neovascularization.

* * * * *

SEQUENCE LISTING

<160> NUMBER OF SEQ ID NOS: 294

<210> SEQ ID NO 1
<211> LENGTH: 107
<212> TYPE: PRT
<213> ORGANISM: Rattus sp.

<400> SEQUENCE: 1

Asp Ile Lys Met Thr Gln Ser Pro Ser Phe Leu Ser Ala Ser Val Gly
1               5                   10                  15

Asp Arg Val Thr Leu Asn Cys Lys Ala Ser Gln Asn Ile Asp Lys Tyr
            20                  25                  30

Leu Asn Trp Tyr Gln Gln Lys Leu Gly Glu Ser Pro Lys Leu Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Ile Ser Arg Pro Arg
                85                  90                  95

Thr Phe Gly Thr Gly Thr Lys Leu Glu Leu Lys
            100                 105

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Val Met Thr Gln Thr Pro Leu Ala Leu Ser Val Thr Ile Gly
1               5                   10                  15

His Pro Ala Ser Ile Ser Cys Lys Ser Ser Gln Ser Leu Leu Glu Ser
            20                  25                  30

Asp Gly Arg Thr Tyr Leu Asn Trp Leu Phe Gln Arg Pro Gly Gln Ser
        35                  40                  45

Pro Lys Arg Leu Ile Tyr Leu Val Ser Asn Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Leu Lys
            100                 105                 110

<210> SEQ ID NO 3
<211> LENGTH: 112
<212> TYPE: PRT
<213> ORGANISM: Mus sp.

<400> SEQUENCE: 3

Asp Ile Val Leu Thr Gln Ser Thr Leu Ser Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Met Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

```
Thr His Phe Pro Trp Thr Phe Gly Gly Gly Thr Lys Leu Glu Ile Lys
        100                 105                 110
```

<210> SEQ ID NO 4
<211> LENGTH: 112
<212> TYPE: PRT
<213> ORGANISM: Mus sp.

<400> SEQUENCE: 4

```
Asp Ile Val Ile Thr Gln Ser Thr Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Met Tyr Leu Val Ser Asn Leu Gly Ser Gly Val Pro
    50                  55                  60

Asp Arg Phe Thr Gly Ser Gly Ser Gly Thr Asp Phe Thr Leu Lys Val
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Ile
        100                 105                 110
```

<210> SEQ ID NO 5
<211> LENGTH: 112
<212> TYPE: PRT
<213> ORGANISM: Mus sp.

<400> SEQUENCE: 5

```
Asp Ile Val Met Thr Gln Thr Pro Leu Thr Leu Ser Val Thr Ile Gly
1               5                   10                  15

Gln Pro Ala Ser Ile Phe Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Ala Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Trp Thr Phe Gly Gly Gly Thr Lys Leu Glu Ile Lys
        100                 105                 110
```

<210> SEQ ID NO 6
<211> LENGTH: 112
<212> TYPE: PRT
<213> ORGANISM: Mus sp.

<400> SEQUENCE: 6

```
Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Ser Gln Arg Pro Gly Gln Ser
        35                  40                  45

Pro Lys Arg Leu Ile Tyr Leu Val Ser Lys Leu Asp Ser Gly Val Pro
```

-continued

```
                50                  55                  60
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Trp Thr Phe Gly Gly Gly Thr Lys Leu Glu Ile Lys
            100                 105                 110

<210> SEQ ID NO 7
<211> LENGTH: 112
<212> TYPE: PRT
<213> ORGANISM: Mus sp.

<400> SEQUENCE: 7

Asp Ile Val Met Thr Gln Ser Pro Leu Thr Leu Ser Val Thr Ile Gly
  1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Asn Leu Asn Ser Gly Leu Pro
     50                  55                  60

Asp Arg Phe Ile Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Trp Thr Phe Gly Gly Gly Thr Lys Leu Glu Ile Lys
            100                 105                 110

<210> SEQ ID NO 8
<211> LENGTH: 112
<212> TYPE: PRT
<213> ORGANISM: Mus sp.

<400> SEQUENCE: 8

Asp Ile Val Leu Thr Gln Thr Thr Leu Thr Leu Ser Val Thr Ile Gly
  1               5                  10                  15

Gln Pro Ala Ser Ile Ser Cys Lys Ser Ser Gln Ser Leu Leu Asp Ser
             20                  25                  30

Asp Gly Arg Thr Tyr Leu Asn Trp Leu Phe Gln Arg Pro Gly Gln Ser
         35                  40                  45

Pro Lys Arg Leu Ile Phe Leu Val Ser His Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Trp Gln Gly
                 85                  90                  95

Thr His Phe Pro Trp Thr Phe Gly Gly Gly Thr Lys Leu Glu Ile Lys
            100                 105                 110

<210> SEQ ID NO 9
<211> LENGTH: 111
<212> TYPE: PRT
<213> ORGANISM: Mus sp.

<400> SEQUENCE: 9

Asp Ile Val Met Thr Gln Thr Pro Leu Thr Leu Ser Val Thr Ile Gly
  1               5                  10                  15
```

```
Gln Pro Ala Ser Ile Ser Cys Lys Ser Ser Gln Ser Leu Leu Tyr Ser
            20                  25                  30

Asn Gly Lys Thr Tyr Leu Asn Trp Val Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Ser His Phe His Thr Phe Gly Ala Gly Thr Lys Leu Glu Leu Lys
            100                 105                 110

<210> SEQ ID NO 10
<211> LENGTH: 111
<212> TYPE: PRT
<213> ORGANISM: Mus sp.

<400> SEQUENCE: 10

Asp Ile Val Leu Thr Gln Thr Pro Arg Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ala Gly Ser Gly Ser Gly Thr Asp Phe Thr Leu Lys Ile
65                  70                  75                  80

Ser Arg Val Glu Ala Glu Asp Leu Gly Ile Tyr Tyr Cys Val Gln Gly
                85                  90                  95

Thr Arg Phe His Thr Phe Gly Ala Gly Thr Lys Leu Glu Leu Lys
            100                 105                 110

<210> SEQ ID NO 11
<211> LENGTH: 111
<212> TYPE: PRT
<213> ORGANISM: Mus sp.

<400> SEQUENCE: 11

Asp Ile Val Ile Thr Gln Thr Pro Leu Thr Leu Ser Val Thr Ile Gly
1               5                   10                  15

Gln Pro Val Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Leu His Thr Phe Gly Ala Gly Thr Lys Leu Glu Leu Lys
            100                 105                 110

<210> SEQ ID NO 12
<211> LENGTH: 112
<212> TYPE: PRT
```

<213> ORGANISM: Mus sp.

<400> SEQUENCE: 12

Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Thr
            20                  25                  30

Asn Gly Asn Ser Tyr Leu His Trp Tyr Leu Gln Lys Pro Gly Gln Ser
        35                  40                  45

Pro Lys Leu Leu Ile Tyr Met Val Ser Asn Arg Phe Ser Gly Val Pro
    50                  55                  60

Asp Arg Phe Ser Gly Ile Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 13
<211> LENGTH: 113
<212> TYPE: PRT
<213> ORGANISM: Mus sp.

<400> SEQUENCE: 13

Asp Ile Val Met Thr Gln Ser Pro Leu Ser Leu Thr Val Ser Leu Gly
1               5                   10                  15

Asp Gln Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Met Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ala His Val Pro Pro Leu Thr Phe Gly Ala Gly Thr Lys Leu Glu Leu
            100                 105                 110

Lys

<210> SEQ ID NO 14
<211> LENGTH: 121
<212> TYPE: PRT
<213> ORGANISM: Rattus sp.

<400> SEQUENCE: 14

Glu Val Lys Leu Leu Glu Ser Gly Gly Gly Leu Val Gln Pro Gly Gly
1               5                   10                  15

Ser Met Arg Leu Ser Cys Ala Gly Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr

```
                      85                  90                  95

Tyr Cys Ala Arg Glu Gly His Thr Ala Ala Pro Phe Asp Tyr Trp Gly
                100                 105                 110

Gln Gly Val Met Val Thr Val Ser Ser
        115                 120

<210> SEQ ID NO 15
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Asn Lys Ala Lys Asn His Val Ala Tyr Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Thr Leu Asp Ser Trp Gly Gln Gly Thr Ala Leu Thr Val
                100                 105                 110

Ser Ser

<210> SEQ ID NO 16
<211> LENGTH: 114
<212> TYPE: PRT
<213> ORGANISM: Mus sp.

<400> SEQUENCE: 16

Glu Val Lys Leu Glu Glu Ser Gly Gly Gly Leu Val Gln Pro Gly Gly
1               5                   10                  15

Ser Met Lys Leu Ser Cys Ala Val Ser Arg Phe Thr Phe Ser Asp Ala
                20                  25                  30

Trp Met Asp Trp Val Arg Gln Ser Pro Glu Lys Gly Leu Glu Trp Ile
            35                  40                  45

Ala Glu Ile Arg Asn Lys Ala Asn Asn His Ala Thr Tyr Tyr Ala Glu
        50                  55                  60

Ser Val Lys Gly Arg Phe Thr Ile Ser Arg Asp Asp Ser Lys Ser Arg
65                  70                  75                  80

Val Phe Leu Gln Met Asn Asn Leu Arg Pro Glu Asp Thr Gly Ile Tyr
                85                  90                  95

Tyr Cys Thr Ser Leu Asp Tyr Trp Gly Gln Gly Thr Thr Leu Thr Val
                100                 105                 110

Ser Ser

<210> SEQ ID NO 17
<211> LENGTH: 114
<212> TYPE: PRT
<213> ORGANISM: Mus sp.

<400> SEQUENCE: 17
```

```
Glu Val Lys Leu Glu Glu Ser Gly Gly Gly Leu Val Gln Pro Gly Gly
1               5                   10                  15

Ser Met Lys Leu Ser Cys Ala Val Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Lys Asn His Val Lys Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Thr Glu Asp Thr Gly Ile Tyr
                85                  90                  95

Tyr Cys Thr Ser Leu Asp Tyr Trp Gly Gln Gly Thr Ala Leu Thr Val
            100                 105                 110

Ser Ser
```

<210> SEQ ID NO 18
<211> LENGTH: 114
<212> TYPE: PRT
<213> ORGANISM: Mus sp.

<400> SEQUENCE: 18

```
Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Leu Thr
        35                  40                  45

Ala Glu Ile Arg Asn Lys Ala Lys Asn His Ala Thr Tyr Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Ser Leu Arg Thr Glu Asp Thr Gly Ile Tyr
                85                  90                  95

Tyr Cys Thr Thr Leu Asp Ser Trp Gly Gln Gly Thr Ser Val Thr Val
            100                 105                 110

Ser Ser
```

<210> SEQ ID NO 19
<211> LENGTH: 114
<212> TYPE: PRT
<213> ORGANISM: Mus sp.

<400> SEQUENCE: 19

```
Glu Val Lys Leu Glu Glu Ser Gly Gly Gly Leu Val Gln Pro Gly Gly
1               5                   10                  15

Ser Met Lys Leu Ser Cys Ala Val Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Lys Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Arg Leu Arg Ala Glu Asp Thr Gly Ile Tyr
                85                  90                  95
```

Tyr Cys Thr Ser Leu Asp Tyr Trp Gly Gln Gly Ser Thr Leu Thr Val
            100                 105                 110

Ser Ser

<210> SEQ ID NO 20
<211> LENGTH: 114
<212> TYPE: PRT
<213> ORGANISM: Mus sp.

<400> SEQUENCE: 20

Glu Val Lys Leu Glu Glu Ser Gly Gly Gly Leu Val Gln Pro Gly Gly
1               5                   10                  15

Ser Met Lys Leu Ser Cys Thr Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Lys Lys Val Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Ser Leu Asp Tyr Trp Gly Gln Gly Thr Thr Leu Ser Val
            100                 105                 110

Ser Ser

<210> SEQ ID NO 21
<211> LENGTH: 114
<212> TYPE: PRT
<213> ORGANISM: Mus sp.

<400> SEQUENCE: 21

Glu Val Lys Leu Glu Glu Ser Gly Gly Gly Leu Val Gln Pro Gly Gly
1               5                   10                  15

Ser Met Lys Leu Ser Cys Ala Val Ser Gly Leu Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Asn Lys Ala Lys Asn His Ala Thr Tyr Tyr Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Tyr Cys Thr Gly Leu Asp Tyr Trp Gly His Gly Thr Ser Val Thr Val
            100                 105                 110

Ser Ser

<210> SEQ ID NO 22
<211> LENGTH: 114
<212> TYPE: PRT
<213> ORGANISM: Mus sp.

<400> SEQUENCE: 22

Glu Val Gln Leu Glu Glu Ser Gly Gly Gly Leu Val Gln Pro Gly Gly
1               5                   10                  15

Ser Met Lys Leu Ser Cys Val Ala Ser Gly Phe Pro Phe Ser Asn Tyr

```
                     20                  25                  30

Trp Met Asn Trp Val Arg Gln Ser Pro Glu Lys Gly Leu Glu Trp Val
            35                  40                  45

Ala Gln Ile Arg Leu Lys Ser Asn Asn Tyr Ala Thr His Tyr Ala Glu
        50                  55                  60

Ser Val Lys Gly Arg Phe Thr Ile Ala Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Pro Ile Asp Tyr Trp Gly Gln Gly Thr Thr Leu Thr Val
            100                 105                 110

Ser Ser

<210> SEQ ID NO 23
<211> LENGTH: 114
<212> TYPE: PRT
<213> ORGANISM: Mus sp.

<400> SEQUENCE: 23

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn Lys Tyr
            20                  25                  30

Trp Met Asn Trp Val Arg Gln Ser Pro Asp Lys Gly Leu Glu Cys Ile
            35                  40                  45

Ala Gln Ile Arg Leu Lys Ser Asp Asn Tyr Ala Thr His Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Pro Ile Asp Tyr Trp Gly Gln Gly Thr Thr Leu Thr Val
            100                 105                 110

Ser Ser

<210> SEQ ID NO 24
<211> LENGTH: 114
<212> TYPE: PRT
<213> ORGANISM: Mus sp.

<400> SEQUENCE: 24

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn Thr Tyr
            20                  25                  30

Trp Met Asn Trp Val Arg Gln Ser Pro Glu Lys Gly Leu Glu Trp Val
            35                  40                  45

Ala Gln Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Asn Ser
65                  70                  75                  80

Val Tyr Leu Gln Met Asn Asn Leu Arg Ala Glu Asp Thr Gly Ile Tyr
                85                  90                  95

Tyr Cys Thr Pro Val Asp Phe Trp Gly Gln Gly Thr Thr Leu Thr Val
            100                 105                 110

Ser Ser
```

<210> SEQ ID NO 25
<211> LENGTH: 117
<212> TYPE: PRT
<213> ORGANISM: Mus sp.

<400> SEQUENCE: 25

Glu Val Lys Leu Glu Glu Ser Gly Gly Gly Leu Val Gln Pro Gly Gly
1               5                   10                  15

Ser Leu Ser Leu Ser Cys Val Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Asn Ala
    50                  55                  60

Ser Val Lys Gly Arg Phe Thr Ile Ser Arg Asp Tyr Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Thr Arg Tyr Ile Phe Phe Asp Tyr Trp Gly Gln Gly Thr Thr
            100                 105                 110

Leu Thr Val Ser Ser
        115

<210> SEQ ID NO 26
<211> LENGTH: 117
<212> TYPE: PRT
<213> ORGANISM: Mus sp.

<400> SEQUENCE: 26

Glu Val Gln Leu Glu Glu Ser Gly Gly Gly Leu Val Gln Pro Gly Gly
1               5                   10                  15

Ala Leu Ser Leu Ser Cys Ala Gly Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asp Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Thr Arg Tyr Ile Trp Phe Asp Tyr Trp Gly Gln Gly Thr Thr
            100                 105                 110

Leu Thr Val Ser Ser
        115

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ala Ser Gln Asn Ile Asp Lys Tyr Leu Asn
1               5                   10

```
<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Ser Ser Gln Ser Leu Leu Glu Ser Asp Gly Arg Thr Tyr Leu Asn
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ser Ser Gln Ser Leu Leu Asp Ser Asp Gly Lys Thr Tyr Leu Asn
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Ser Ser Gln Ser Leu Leu Asp Ser Asp Gly Arg Thr Tyr Leu Asn
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ser Ser Gln Ser Leu Leu Tyr Ser Asn Gly Lys Thr Tyr Leu Asn
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Ser Gln Ser Leu Val His Thr Asn Gly Asn Ser Tyr Leu His
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

-continued

Arg Ser Ser Gln Ser Leu Val His Thr Asn Gly Asn Thr Tyr Leu His
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Thr Asn Asn Leu Gln Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Val Ser Asn Leu Asp Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Val Ser Lys Leu Asp Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Val Ser Asn Leu Gly Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Val Ser Ala Leu Asp Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Leu Val Ser Asn Leu Asn Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Val Ser His Leu Asp Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Val Ser Asn Arg Phe Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Gln His Ile Ser Arg Pro Arg Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Gln Gly Thr His Phe Pro Trp Thr
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Gln Gly Ser His Phe His Thr
1               5

<210> SEQ ID NO 45
<211> LENGTH: 8

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Gln Gly Thr Arg Phe His Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Gln Gly Thr His Leu His Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gln Ser Thr His Val Pro Phe Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gln Ser Ala His Val Pro Pro Leu Thr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Thr Asp Phe Tyr Met Asn
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Thr Phe Ser Asp Ala Trp Met Asp
1               5                   10
```

```
<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Phe Thr Phe Ser Asp Ala Trp Met Asp
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Leu Thr Phe Ser Asp Ala Trp Met Asp
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Pro Phe Ser Asn Tyr Trp Met Asn
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Thr Phe Asn Lys Tyr Trp Met Asn
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Thr Phe Asn Thr Tyr Trp Met Asn
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Gly Phe Thr Phe Thr Asp Tyr Tyr Met Ser
1               5                   10

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Ile Arg Asp Lys Ala Lys Gly Tyr Thr Thr Glu Tyr Asn Pro Ser
1               5                   10                  15

Val Lys Gly

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Ile Arg Asn Lys Ala Lys Asn His Val Ala Tyr Tyr Ala Glu Ser
1               5                   10                  15

Val Lys Gly

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Ile Arg Asn Lys Ala Asn Asn His Ala Thr Tyr Tyr Ala Glu Ser
1               5                   10                  15

Val Lys Gly

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Ile Arg Asn Lys Ala Lys Asn His Val Lys Tyr Tyr Ala Glu Ser
1               5                   10                  15

Val Lys Gly

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Glu Ile Arg Asn Lys Ala Lys Asn His Ala Thr Tyr Tyr Ala Glu Ser
1               5                   10                  15

Val Lys Gly

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Ile Arg Lys Lys Val Asn Asn His Ala Thr Tyr Tyr Ala Glu Ser
1               5                   10                  15

Val Lys Gly

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ile Arg Leu Lys Ser Asn Asn Tyr Ala Thr His Tyr Ala Glu Ser
1               5                   10                  15

Val Lys Gly

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ile Arg Leu Lys Ser Asp Asn Tyr Ala Thr His Tyr Ala Glu Ser
1               5                   10                  15

Val Lys Gly

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Ile Arg Asn Lys Ala Asn Gly Tyr Thr Thr Glu Tyr Asn Ala Ser
1               5                   10                  15

Val Lys Gly

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66
```

```
Phe Ile Arg Asn Lys Ala Asn Gly Tyr Thr Thr Glu Tyr Ser Ala Ser
1               5                   10                  15

Val Lys Gly

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Arg Glu Gly His Thr Ala Ala Pro Phe Asp Tyr
1               5                   10

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Thr Leu Asp Ser
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Ser Leu Asp Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Gly Leu Asp Tyr
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Pro Ile Asp Tyr
1               5

<210> SEQ ID NO 72
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 72

Thr Pro Val Asp Phe
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Arg Tyr Ile Phe Phe Asp Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Arg Tyr Ile Trp Phe Asp Tyr
1               5

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atgggcwtca aratgrarwc wcat                                          24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gayattgtgm tracmcarkm tcaa                                          24

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
actggatggt gggaagatgg a                                             21

<210> SEQ ID NO 78
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 78
gayattgtgm tsacmcarwc tmca                                          24

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggatacagtt ggtgcagcat c                                             21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
atgrasttsk ggytmarctk grtt                                          24

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atgraatgsa sctgggtywt yctct                                         25

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
saggtsmarc tgcagsagtc t                                             21

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
saggtgmagc tcswrsaryc sggg                                          24

<210> SEQ ID NO 84
<211> LENGTH: 24
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 84
tgaggagact gtgagagtgg tgcc                                          24

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ayctccacac acaggrrcca gtggatagac                                    30

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other

<400> SEQUENCE: 86
sargtnmagc tgsagsagtc                                               20

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other

<400> SEQUENCE: 87
sargtnmagc tgsagsagtc wgg                                           23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
caggttactc tgaaagwgts tg                                            22

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaggtccarc tgcaacartc                                               20
```

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
caggtccaac tvcagcarcc                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91 gaggtgaasstggtggaatc                                               20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gatgtgaact tggaagtgtc                                              20

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
atagacagat ggggtgtcg ttttggc                                       27

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cttgaccagg catcctagag tca                                          23

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aggggccagt ggatagagtg atgg                                         24

<210> SEQ ID NO 96

```
<211> LENGTH: 100
<212> TYPE: PRT
<213> ORGANISM: Mus sp.

<400> SEQUENCE: 96

Glu Val Gln Leu Glu Glu Ser Gly Gly Gly Leu Val Gln Pro Gly Gly
1               5                   10                  15

Ala Leu Ser Leu Ser Cys Ala Gly Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asp Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Thr Arg
            100

<210> SEQ ID NO 97
<211> LENGTH: 100
<212> TYPE: PRT
<213> ORGANISM: Homo sapiens

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 98
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asp Ser Lys Asn Ser
```

```
                    65                  70                  75                  80
Leu Tyr Leu Gln Met Asn Ser Leu Lys Thr Glu Asp Thr Ala Val Tyr
                85                  90                  95

Tyr Cys Ala Arg
            100
```

<210> SEQ ID NO 99
<211> LENGTH: 100
<212> TYPE: PRT
<213> ORGANISM: Mus sp.

<400> SEQUENCE: 99

```
Asp Ile Val Met Thr Gln Ser Pro Leu Ser Leu Thr Val Ser Leu Gly
1               5                   10                  15

Asp Gln Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Met Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ala His Val Pro
            100
```

<210> SEQ ID NO 100
<211> LENGTH: 100
<212> TYPE: PRT
<213> ORGANISM: Homo sapiens

<400> SEQUENCE: 100

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100
```

<210> SEQ ID NO 101
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Asp Ile Val Met Thr Gln Thr Pro Leu Ser Leu Ser Val Thr Pro Gly
1               5                   10                  15
```

Gln Pro Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Met Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ala His Val Pro
            100

<210> SEQ ID NO 102
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Met Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ala His Val Pro Pro Leu Thr Phe Gly Gln Gly Thr Arg Leu Glu Ile
            100                 105                 110

Lys

<210> SEQ ID NO 103
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

```
Tyr Cys Ala Arg Tyr Ile Trp Phe Asp Tyr Trp Gly Gln Gly Thr Thr
            100                 105                 110

Val Thr Val Ser Ser
        115

<210> SEQ ID NO 104
<211> LENGTH: 12
<212> TYPE: PRT
<213> ORGANISM: Homo sapiens

<400> SEQUENCE: 104

Gly Gln Asn Asp Thr Ser Gln Thr Ser Ser Pro Ser
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Gln Asn Asp Thr Ser Gln Thr Ser Ser Pro Ser
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ala Asn Asp Thr Ser Gln Thr Ser Ser Pro Ser
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gln Ala Asp Thr Ser Gln Thr Ser Ser Pro Ser
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gln Asn Ala Thr Ser Gln Thr Ser Ser Pro Ser
1               5                   10

<210> SEQ ID NO 109
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 109

Gly Gln Asn Asp Ala Ser Gln Thr Ser Ser Pro Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Gln Asn Asp Thr Ala Gln Thr Ser Ser Pro Ser
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gln Asn Asp Thr Ser Ala Thr Ser Ser Pro Ser
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gln Asn Asp Thr Ser Gln Ala Ser Ser Pro Ser
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gln Asn Asp Thr Ser Gln Thr Ala Ser Pro Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Gln Asn Asp Thr Ser Gln Thr Ser Ala Pro Ser
1               5                   10

<210> SEQ ID NO 115

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (7)..(7)
<223> OTHER INFORMATION: Leu, Val or Ile
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Ser or Thr
<220> FEATURE:
<221> NAME/KEY: MOD_RES
<222> LOCATION: (10)..(10)
<223> OTHER INFORMATION: Asn or Asp
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Ser or Thr
<220> FEATURE:
<221> NAME/KEY: MOD_RES
<222> LOCATION: (16)..(16)
<223> OTHER INFORMATION: Any amino acid

<400> SEQUENCE: 115

Xaa Ser Ser Gln Ser Leu Xaa Xaa Xaa Xaa Gly Xaa Xaa Tyr Leu Xaa
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (7)..(7)
<223> OTHER INFORMATION: Leu, Val or Ile
<220> FEATURE:
<221> NAME/KEY: MOD_RES
<222> LOCATION: (9)..(9)
<223> OTHER INFORMATION: Ser or Thr
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Ser or Thr

<400> SEQUENCE: 116

Xaa Ser Ser Gln Ser Leu Xaa His Xaa Asn Gly Xaa Xaa Tyr Leu His
1               5                   10                  15

<210> SEQ ID NO 117
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ser or Thr

<400> SEQUENCE: 117

Arg Ser Ser Gln Ser Leu Val His Thr Asn Gly Asn Xaa Tyr Leu His
1               5                   10                  15

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(6)
<223> OTHER INFORMATION: Any amino acid

<400> SEQUENCE: 118

Xaa Val Ser Xaa Xaa Xaa Ser
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 119

Xaa Val Ser Xaa Arg Xaa Ser
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 120

Met Val Ser Xaa Arg Phe Ser
```

```
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: His, Arg or Lys
<220> FEATURE:
<221> NAME/KEY: MOD_RES
<222> LOCATION: (6)..(6)
<223> OTHER INFORMATION: Phe, Leu, Val or Ile
<220> FEATURE:
<221> NAME/KEY: MOD_RES
<222> LOCATION: (7)..(8)
<223> OTHER INFORMATION: Any amino acid

<400> SEQUENCE: 121

Xaa Gln Xaa Xaa Xaa Xaa Xaa Xaa
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: His, Arg or Lys
<220> FEATURE:
<221> NAME/KEY: MOD_RES
<222> LOCATION: (6)..(6)
<223> OTHER INFORMATION: Phe, Leu, Val or Ile
<220> FEATURE:
<221> NAME/KEY: MOD_RES
<222> LOCATION: (8)..(8)
<223> OTHER INFORMATION: Any amino acid

<400> SEQUENCE: 122

Ser Gln Ser Xaa Xaa Xaa Pro Xaa
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Phe or Pro

<400> SEQUENCE: 123

Ser Gln Ser Xaa His Val Pro Xaa
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Trp or Tyr
<220> FEATURE:
<221> NAME/KEY: MOD_RES
<222> LOCATION: (10)..(10)
<223> OTHER INFORMATION: Any amino acid

<400> SEQUENCE: 124

Gly Phe Xaa Phe Xaa Xaa Tyr Xaa Met Xaa
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Trp or Tyr
<220> FEATURE:
<221> NAME/KEY: MOD_RES
<222> LOCATION: (10)..(10)
<223> OTHER INFORMATION: Any amino acid

<400> SEQUENCE: 125

Gly Phe Thr Phe Xaa Xaa Tyr Xaa Met Xaa
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Trp or Tyr
```

```
<400> SEQUENCE: 126

Gly Phe Thr Phe Thr Asp Tyr Xaa Met Ser
1               5                   10

<210> SEQ ID NO 127
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 127

Xaa Ile Arg Xaa Lys Xaa Asx Xaa Tyr Xaa Thr Xaa Tyr Xaa Xaa Ser
1               5                   10                  15

Val Lys Gly

<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 128
```

Xaa Ile Arg Xaa Lys Xaa Asn Xaa Tyr Thr Thr Glu Tyr Xaa Xaa Ser
1               5                   10                  15

Val Lys Gly

<210> SEQ ID NO 129
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(15)
<223> OTHER INFORMATION: Any amino acid

<400> SEQUENCE: 129

Phe Ile Arg Asn Lys Ala Asn Gly Tyr Thr Thr Glu Tyr Xaa Xaa Ser
1               5                   10                  15

Val Lys Gly

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (5)..(5)
<223> OTHER INFORMATION: Tyr, Phe or Trp

<400> SEQUENCE: 130

Thr Xaa Xaa Xaa Xaa
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Tyr, Phe or Trp

<400> SEQUENCE: 131

Thr Arg Tyr Xaa Xaa Phe Asp Tyr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (5)..(5)
<223> OTHER INFORMATION: Phe or Trp

<400> SEQUENCE: 132

Thr Arg Tyr Ile Xaa Phe Asp Tyr
1               5

<210> SEQ ID NO 133
<211> LENGTH: 11
<212> TYPE: PRT
<213> ORGANISM: Homo sapiens

<400> SEQUENCE: 133

Trp Gly Gln Gly Thr Thr Val Thr Val Ser Ser
1               5                   10

<210> SEQ ID NO 134
<211> LENGTH: 10
<212> TYPE: PRT
<213> ORGANISM: Homo sapiens

<400> SEQUENCE: 134

Phe Gly Gln Gly Thr Lys Leu Glu Ile Lys
1               5                   10

<210> SEQ ID NO 135
<211> LENGTH: 10
<212> TYPE: PRT
<213> ORGANISM: Homo sapiens

<400> SEQUENCE: 135

Phe Gly Gln Gly Thr Arg Leu Glu Ile Lys
1               5                   10

<210> SEQ ID NO 136
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Asn Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg Tyr Ile Phe Phe Asp Tyr Trp Gly Gln Gly Thr Thr
            100                 105                 110

Val Thr Val Ser Ser
        115

<210> SEQ ID NO 137
<211> LENGTH: 117
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Asn Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Ile Phe Phe Asp Tyr Trp Gly Gln Gly Thr Thr
            100                 105                 110

Val Thr Val Ser Ser
            115

<210> SEQ ID NO 138
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Asn Gly Asn Ser Tyr Leu His Trp Tyr Leu Gln Lys Pro Gly Gln Ser
        35                  40                  45

Pro Gln Leu Leu Ile Tyr Met Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gln Gly Thr Lys Leu Glu Ile Lys
            100                 105                 110

<210> SEQ ID NO 139
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

```
Trp Met Asn Trp Val Arg Gln Ala Pro Gly Lys Gly Leu Glu Trp Val
            35                  40                  45

Gly Gln Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
                100                 105                 110

Ser Ser
```

<210> SEQ ID NO 140
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
            35                  40                  45

Gly Gln Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
                100                 105                 110

Ser Ser
```

<210> SEQ ID NO 141
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
            35                  40                  45

Ala Gln Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95
```

Tyr Cys Thr Pro Val Asp Phe Trp Gly Gln Gly Thr Thr Val Thr Val
            100                 105                 110

Ser Ser

<210> SEQ ID NO 142
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

Ser Ser

<210> SEQ ID NO 143
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

Ser Ser

<210> SEQ ID NO 144
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Asn Thr Tyr
            20                  25                  30

Trp Met Asn Trp Val Arg Gln Ala Pro Glu Lys Gly Leu Glu Trp Val
        35                  40                  45

Ala Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

Ser Ser

<210> SEQ ID NO 145
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Leu His Thr Phe Gly Gly Gly Thr Arg Leu Glu Ile Lys
            100                 105                 110

<210> SEQ ID NO 146
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Tyr Leu Gln Lys Pro Gly Gln Ser
        35                  40                  45

Pro Gln Arg Leu Ile Tyr Leu Val Ser Lys Leu Asp Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Leu His Thr Phe Gly Gln Gly Thr Arg Leu Glu Ile Lys
            100                 105                 110

<210> SEQ ID NO 147
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
             20                  25                  30

Asn Gly Lys Thr Tyr Leu Asn Trp Leu Leu Gln Lys Pro Gly Gln Ser
         35                  40                  45

Pro Gln Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Leu His Thr Phe Gly Gln Gly Thr Arg Leu Glu Ile Lys
            100                 105                 110

<210> SEQ ID NO 148
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Ile Val Ile Thr Gln Thr Pro Leu Ser Leu Ser Val Thr Pro Gly
 1               5                  10                  15

Gln Pro Val Ser Ile Ser Cys Lys Ser Ser Gln Ser Leu Leu Tyr Ser
             20                  25                  30

Asn Gly Lys Thr Tyr Leu Asn Trp Leu Leu Gln Lys Pro Gly Gln Ser
         35                  40                  45

Pro Lys Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Leu His Thr Phe Gly Gln Gly Thr Arg Leu Glu Ile Lys
            100                 105                 110

<210> SEQ ID NO 149
<211> LENGTH: 114
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Ile Asp Tyr Trp Gly Gln Gly Thr Thr Val Thr Val
            100                 105                 110

Ser Ser

<210> SEQ ID NO 150
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Pro Ile Asp Tyr Trp Gly Gln Gly Thr Thr Val Thr Val
            100                 105                 110

Ser Ser

<210> SEQ ID NO 151
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Asn Tyr
            20                  25                  30

-continued

Trp Met Asn Trp Val Arg Gln Ala Pro Gly Lys Gly Leu Glu Trp Val
            35                  40                  45

Ala Gln Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Thr Pro Ile Asp Tyr Trp Gly Gln Gly Thr Thr Val Thr Val
            100                 105                 110

Ser Ser

<210> SEQ ID NO 152
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Pro Phe Ser Asn Tyr
             20                  25                  30

Trp Met Asn Trp Val Arg Gln Ala Pro Gly Lys Gly Leu Glu Trp Val
            35                  40                  45

Ala Gln Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Ala Val Tyr
                 85                  90                  95

Tyr Cys Thr Pro Ile Asp Tyr Trp Gly Gln Gly Thr Thr Val Thr Val
            100                 105                 110

Ser Ser

<210> SEQ ID NO 153
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
             20                  25                  30

Asn Gly Lys Thr Tyr Leu Asn Trp Tyr Leu Gln Lys Pro Gly Gln Ser
            35                  40                  45

Pro Gln Leu Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys
                100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Val Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
                100                 105                 110

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Val Leu Gln Lys Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
                100                 105                 110

<210> SEQ ID NO 156
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Val Met Thr Gln Thr Pro Leu Ser Leu Ser Val Thr Pro Gly
1               5                   10                  15

-continued

```
Gln Pro Ala Ser Ile Ser Cys Lys Ser Ser Gln Ser Leu Leu Tyr Ser
                20                  25                  30

Asn Gly Lys Thr Tyr Leu Asn Trp Val Leu Gln Lys Pro Gly Gln Ser
            35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys
                100                 105                 110
```

<210> SEQ ID NO 157
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

```
Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Tyr Leu Gln Lys Pro Gly Gln Ser
            35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys
                100                 105                 110
```

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Ala
                20                  25                  30

Trp Met Asp Trp Val Arg Gln Ala Pro Gly Lys Gly Leu Glu Trp Val
            35                  40                  45

Ser Glu Ile Arg Asn Lys Ala Lys Asn His Ala Thr Tyr Tyr Ala Glu
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95
```

Tyr Cys Thr Thr Leu Asp Ser Trp Gly Gln Thr Thr Val Thr Val Ser
                100                 105                 110
Ser

<210> SEQ ID NO 159
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Leu Thr
        35                  40                  45

Ala Glu Ile Arg Asn Lys Ala Lys Asn His Ala Thr Tyr Tyr Ala Glu
    50                  55                  60

Ser Val Lys Gly Arg Phe Thr Ile Ser Arg Asp Asn Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Thr Leu Asp Ser Trp Gly Gln Gly Thr Thr Val Thr Val
                100                 105                 110

Ser Ser

<210> SEQ ID NO 160
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Leu Thr
        35                  40                  45

Ala Glu Ile Arg Asn Lys Ala Lys Asn His Ala Thr Tyr Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Thr Leu Asp Ser Trp Gly Gln Gly Thr Thr Val Thr Val
                100                 105                 110

Ser Ser

<210> SEQ ID NO 161
<211> LENGTH: 114
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Leu Val
        35                  40                  45

Ser Glu Ile Arg Asn Lys Ala Lys Asn His Ala Thr Tyr Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Thr Leu Asp Ser Trp Gly Gln Gly Thr Thr Val Thr Val
            100                 105                 110

Ser Ser

<210> SEQ ID NO 162
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Leu Thr
        35                  40                  45

Ser Glu Ile Arg Asn Lys Ala Lys Asn His Ala Thr Tyr Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Thr Leu Asp Ser Trp Gly Gln Gly Thr Thr Val Thr Val
            100                 105                 110

Ser Ser

<210> SEQ ID NO 163
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Leu Val
        35                  40                  45

Ala Glu Ile Arg Asn Lys Ala Lys Asn His Ala Thr Tyr Tyr Ala Glu
            50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Thr Leu Asp Ser Trp Gly Gln Gly Thr Val Thr Val
            100                 105                 110

Ser Ser

<210> SEQ ID NO 164
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ala Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Leu Glu Ile Lys
            100                 105                 110

<210> SEQ ID NO 165
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Lys Arg Leu Ile Tyr Leu Val Ser Ala Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Leu Glu Ile Lys
            100                 105                 110

<210> SEQ ID NO 166
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Ala Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Leu Glu Ile Lys
            100                 105                 110

<210> SEQ ID NO 167
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Gln Arg Leu Ile Tyr Leu Val Ser Ala Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Leu Glu Ile Lys
            100                 105                 110

<210> SEQ ID NO 168
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

```
Asp Gly Lys Thr Tyr Leu Asn Trp Tyr Leu Gln Lys Pro Gly Gln Ser
             35                  40                  45

Pro Lys Arg Leu Ile Tyr Leu Val Ser Ala Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Trp Thr Phe Gly Gln Gly Thr Lys Leu Glu Ile Lys
            100                 105                 110

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Gln Asn Asp Thr Ser Gln Thr Ser Ser Pro Ser Ala Asp Cys
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ala Asn Asp Thr Ser Gln Thr Ser Ser Pro Ser Ala Asp Cys
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Gln Ala Asp Thr Ser Gln Thr Ser Ser Pro Ser Ala Asp Cys
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gln Asn Ala Thr Ser Gln Thr Ser Ser Pro Ser Ala Asp Cys
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 173

Gly Gln Asn Asp Ala Ser Gln Thr Ser Ser Pro Ser Ala Asp Cys
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Gln Asn Asp Thr Ala Gln Thr Ser Ser Pro Ser Ala Asp Cys
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Gln Asn Asp Thr Ser Ala Thr Ser Ser Pro Ser Ala Asp Cys
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gln Asn Asp Thr Ser Gln Ala Ser Ser Pro Ser Ala Asp Cys
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Gln Asn Asp Thr Ser Gln Thr Ala Ser Pro Ser Ala Asp Cys
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Gln Asn Asp Thr Ser Gln Thr Ser Ala Pro Ser Ala Asp Cys
1               5                   10                  15

<210> SEQ ID NO 179
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 179

Gly Gln Asn Asp Thr Ser Gln Thr Ser Ser Ala Ser Ala Asp Cys
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Gln Asn Asp Thr Ser Gln Thr Ser Ser Pro Ala Ala Asp Cys
1               5                   10                  15

<210> SEQ ID NO 181
<211> LENGTH: 15
<212> TYPE: PRT
<213> ORGANISM: Homo sapiens

<400> SEQUENCE: 181

Gly Gln Asn Asp Thr Ser Gln Thr Ser Ser Ala Ser Ala Asp Cys
1               5                   10                  15

<210> SEQ ID NO 182
<211> LENGTH: 15
<212> TYPE: PRT
<213> ORGANISM: Homo sapiens

<400> SEQUENCE: 182

Gly Gln Asn Asp Thr Ser Gln Thr Ser Ser Pro Ala Ala Asp Cys
1               5                   10                  15

<210> SEQ ID NO 183
<211> LENGTH: 19
<212> TYPE: PRT
<213> ORGANISM: Unknown
<220> FEATURE:
<223> OTHER INFORMATION: Description of Unknown: Tetanus toxoid peptide

<400> SEQUENCE: 183

Asp Thr Ile Met Met Glu Pro Pro Tyr Cys Lys Gly Leu Asp Ile Tyr
1               5                   10                  15

Tyr Lys Ala

<210> SEQ ID NO 184
<211> LENGTH: 21
<212> TYPE: PRT
<213> ORGANISM: Unknown
<220> FEATURE:
<223> OTHER INFORMATION: Description of Unknown: Tetanus toxoid peptide

<400> SEQUENCE: 184

Ser Ala Met Leu Thr Asn Leu Ile Ile Phe Gly Pro Gly Pro Val Leu
1               5                   10                  15

Asn Lys Asn Glu Val
                20

<210> SEQ ID NO 185
<211> LENGTH: 20
<212> TYPE: PRT
```

<213> ORGANISM: Unknown
<220> FEATURE:
<223> OTHER INFORMATION: Description of Unknown: Tetanus toxoid peptide

<400> SEQUENCE: 185

Asn Asn Phe Thr Val Ser Phe Trp Leu Arg Val Pro Lys Val Ser Ala
1 5 10 15

Ser His Leu Glu
20

<210> SEQ ID NO 186
<211> LENGTH: 21
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

Asp Ile Glu Lys Lys Ile Ala Lys Met Glu Lys Ala Ser Ser Val Phe
1 5 10 15

Asn Val Val Asn Ser
20

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Asp Ile Gln Met Thr Gln Ser Pro Ser Ser Leu Ser Ala Ser Val
1 5 10 15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Gln Ser Pro Ser Ser Leu Ser Ala Ser Val Gly Asp Arg Val Thr
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Leu Ser Ala Ser Val Gly Asp Arg Val Thr Ile Thr Cys Lys Ala
1 5 10 15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 190

Gly Asp Arg Val Thr Ile Thr Cys Lys Ala Ser Gln Asn Ile Asp
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ile Thr Cys Lys Ala Ser Gln Asn Ile Asp Lys Tyr Leu Asn Trp
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Gln Asn Ile Asp Lys Tyr Leu Asn Trp Tyr Gln Gln Lys Pro
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Lys Tyr Leu Asn Trp Tyr Gln Gln Lys Pro Gly Lys Ala Pro Lys
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Tyr Gln Gln Lys Pro Gly Lys Ala Pro Lys Leu Leu Ile Tyr Asn
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Lys Ala Pro Lys Leu Leu Ile Tyr Asn Thr Asn Asn Leu Gln
1               5                   10                  15

<210> SEQ ID NO 196
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 196

Leu Leu Ile Tyr Asn Thr Asn Asn Leu Gln Thr Gly Val Pro Ser
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Thr Asn Asn Leu Gln Thr Gly Val Pro Ser Arg Phe Ser Gly Ser
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Thr Gly Val Pro Ser Arg Phe Ser Gly Ser Gly Ser Gly Thr Asp
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Phe Ser Gly Ser Gly Ser Gly Thr Asp Phe Thr Phe Thr Ile
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Ser Gly Thr Asp Phe Thr Phe Thr Ile Ser Ser Leu Gln Pro
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Phe Thr Phe Thr Ile Ser Ser Leu Gln Pro Glu Asp Ile Ala Thr
1               5                   10                  15
```

```
<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Ser Leu Gln Pro Glu Asp Ile Ala Thr Tyr Tyr Cys Leu Gln
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Glu Asp Ile Ala Thr Tyr Tyr Cys Leu Gln His Ile Ser Arg Pro
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Tyr Tyr Cys Leu Gln His Ile Ser Arg Pro Arg Thr Phe Gly Gln
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

His Ile Ser Arg Pro Arg Thr Phe Gly Gln Gly Thr Lys Val Glu
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Thr Phe Gly Gln Gly Thr Lys Val Glu Ile Lys Arg Thr Val
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207
```

Gln Val Gln Leu Gln Glu Ser Gly Pro Gly Leu Val Arg Pro Ser
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Glu Ser Gly Pro Gly Leu Val Arg Pro Ser Gln Thr Leu Ser Leu
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Leu Val Arg Pro Ser Gln Thr Leu Ser Leu Thr Cys Thr Val Ser
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Thr Leu Ser Leu Thr Cys Thr Val Ser Gly Phe Thr Phe Thr
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Cys Thr Val Ser Gly Phe Thr Phe Thr Asp Phe Tyr Met Asn
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Phe Thr Phe Thr Asp Phe Tyr Met Asn Trp Val Arg Gln Pro
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic

```
                                       peptide

<400> SEQUENCE: 213

Asp Phe Tyr Met Asn Trp Val Arg Gln Pro Pro Gly Arg Gly Leu
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Trp Val Arg Gln Pro Pro Gly Arg Gly Leu Glu Trp Ile Gly Phe
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Pro Gly Arg Gly Leu Glu Trp Ile Gly Phe Ile Arg Asp Lys Ala
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Glu Trp Ile Gly Phe Ile Arg Asp Lys Ala Lys Gly Tyr Thr Thr
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile Arg Asp Lys Ala Lys Gly Tyr Thr Thr Glu Tyr Asn Pro Ser
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Lys Gly Tyr Thr Thr Glu Tyr Asn Pro Ser Val Lys Gly Arg Val
1               5                   10                  15

<210> SEQ ID NO 219
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Glu Tyr Asn Pro Ser Val Lys Gly Arg Val Thr Met Leu Val Asp
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Val Lys Gly Arg Val Thr Met Leu Val Asp Thr Ser Lys Asn Gln
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Met Leu Val Asp Thr Ser Lys Asn Gln Phe Ser Leu Arg Leu
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Thr Ser Lys Asn Gln Phe Ser Leu Arg Leu Ser Ser Val Thr Ala
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Phe Ser Leu Arg Leu Ser Ser Val Thr Ala Ala Asp Thr Ala Val
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Ser Val Thr Ala Ala Asp Thr Ala Val Tyr Tyr Cys Ala Arg
1               5                   10                  15
```

```
<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Asp Thr Ala Val Tyr Tyr Cys Ala Arg Glu Gly His Thr Ala
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Tyr Cys Ala Arg Glu Gly His Thr Ala Ala Pro Phe Asp Tyr
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Glu Gly His Thr Ala Ala Pro Phe Asp Tyr Trp Gly Gln Gly Ser
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Pro Phe Asp Tyr Trp Gly Gln Gly Ser Leu Val Thr Val Ser
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Trp Gly Gln Gly Ser Leu Val Thr Val Ser Ser Ala Ser Thr Lys
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 230

Asp Ile Val Met Thr Gln Thr Pro Leu Ser Leu Ser Val Thr Pro
1               5                   10                  15

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gln Thr Pro Leu Ser Leu Val Thr Pro Gly Gln Pro Ala Ser
1               5                   10

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Leu Ser Val Thr Pro Gly Gln Pro Ala Ser Ile Ser Cys Lys Ser
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Gln Pro Ala Ser Ile Ser Cys Lys Ser Ser Gln Ser Leu Leu
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Ser Cys Lys Ser Ser Gln Ser Leu Leu Tyr Ser Asn Gly Lys
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Gln Ser Leu Leu Tyr Ser Asn Gly Lys Thr Tyr Leu Asn Trp
1               5                   10                  15

<210> SEQ ID NO 236
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 236

Tyr Ser Asn Gly Lys Thr Tyr Leu Asn Trp Val Leu Gln Lys Pro
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Thr Tyr Leu Asn Trp Val Leu Gln Lys Pro Gly Gln Ser Pro Gln
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Val Leu Gln Lys Pro Gly Gln Ser Pro Gln Arg Leu Ile Tyr Leu
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Gln Ser Pro Gln Arg Leu Ile Tyr Leu Val Ser Lys Leu Asp
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Arg Leu Ile Tyr Leu Val Ser Lys Leu Asp Ser Gly Val Pro Asp
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Val Ser Lys Leu Asp Ser Gly Val Pro Asp Arg Phe Ser Gly Ser
1               5                   10                  15
```

```
<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Gly Val Pro Asp Arg Phe Ser Gly Ser Gly Ser Gly Thr Asp
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Arg Phe Ser Gly Ser Gly Ser Gly Thr Asp Phe Thr Leu Lys Ile
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Ser Gly Thr Asp Phe Thr Leu Lys Ile Ser Arg Val Glu Ala
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Phe Thr Leu Lys Ile Ser Arg Val Glu Ala Glu Asp Val Gly Val
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Arg Val Glu Ala Glu Asp Val Gly Val Tyr Tyr Cys Val Gln
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247
```

```
Glu Asp Val Gly Val Tyr Tyr Cys Val Gln Gly Ser His Phe His
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Tyr Tyr Cys Val Gln Gly Ser His Phe His Thr Phe Gly Gln Gly
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Ser His Phe His Thr Phe Gly Gln Gly Thr Lys Leu Glu Ile
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Thr Phe Gly Gln Gly Thr Lys Leu Glu Ile Lys Arg Thr Val Ala
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Val Gln Leu Val Glu Ser Gly Gly Gly Leu Val Gln Pro Gly
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Glu Ser Gly Gly Gly Leu Val Gln Pro Gly Gly Ser Leu Arg Leu
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 253

Leu Val Gln Pro Gly Gly Ser Leu Arg Leu Ser Cys Ala Ala Ser
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Ser Leu Arg Leu Ser Cys Ala Ala Ser Gly Phe Pro Phe Ser
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Cys Ala Ala Ser Gly Phe Pro Phe Ser Asn Tyr Trp Met Asn
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Phe Pro Phe Ser Asn Tyr Trp Met Asn Trp Val Arg Gln Ala
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asn Tyr Trp Met Asn Trp Val Arg Gln Ala Pro Gly Lys Gly Leu
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Trp Val Arg Gln Ala Pro Gly Lys Gly Leu Glu Trp Val Gly Gln
1               5                   10                  15

<210> SEQ ID NO 259
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Pro Gly Lys Gly Leu Glu Trp Val Gly Gln Ile Arg Leu Lys Ser
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Glu Trp Val Gly Gln Ile Arg Leu Lys Ser Asn Asn Tyr Ala Thr
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ile Arg Leu Lys Ser Asn Asn Tyr Ala Thr His Tyr Ala Glu Ser
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Asn Asn Tyr Ala Thr His Tyr Ala Glu Ser Val Lys Gly Arg Phe
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

His Tyr Ala Glu Ser Val Lys Gly Arg Phe Thr Ile Ser Arg Asp
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Val Lys Gly Arg Phe Thr Ile Ser Arg Asp Asp Ser Lys Asn Ser
1               5                   10                  15
```

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Thr Ile Ser Arg Asp Asp Ser Lys Asn Ser Leu Tyr Leu Gln Met
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Asp Ser Lys Asn Ser Leu Tyr Leu Gln Met Asn Ser Leu Lys Thr
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Leu Tyr Leu Gln Met Asn Ser Leu Lys Thr Glu Asp Thr Ala Val
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asn Ser Leu Lys Thr Glu Asp Thr Ala Val Tyr Tyr Cys Thr Pro
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Asp Thr Ala Val Tyr Tyr Cys Thr Pro Ile Asp Tyr Trp Gly
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 270

Tyr Tyr Cys Thr Pro Ile Asp Tyr Trp Gly Gln Gly Thr Thr Val
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ile Asp Tyr Trp Gly Gln Gly Thr Thr Val Thr Val Ser Ser Ala
1               5                   10                  15

<210> SEQ ID NO 272
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Asn Thr Tyr Trp Met Asn Trp Val Arg Gln Ala Pro Gly Lys Gly
        50                  55                  60

Leu Glu Trp Val Gly Gln Ile Arg Leu Lys Ser Asn Asn Tyr Ala Thr
65                  70                  75                  80

His Tyr Ala Glu Ser Val Lys Gly Arg Phe Thr Ile Ser Arg Asp Asp
                85                  90                  95

Ser Lys Asn Ser Leu Tyr Leu Gln Met Asn Ser Leu Lys Thr Glu Asp
            100                 105                 110

Thr Ala Val Tyr Tyr Cys Thr Pro Val Asp Phe Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270
```

-continued

```
Thr Pro Glu Val Thr Cys Val Val Asp Val Ser His Glu Asp Pro
            275                 280                 285
Glu Val Lys Phe Asn Trp Tyr Val Asp Gly Val Glu Val His Asn Ala
        290                 295                 300
Lys Thr Lys Pro Arg Glu Gln Tyr Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
        355                 360                 365
Pro Pro Ser Arg Asp Glu Leu Thr Lys Asn Gln Val Ser Leu Thr Cys
    370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
        435                 440                 445
Leu His Asn His Tyr Thr Gln Lys Ser Leu Ser Leu Ser Pro Gly Lys
    450                 455                 460

<210> SEQ ID NO 273
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Met Glu Ala Pro Ala Gln Leu Leu Phe Leu Leu Leu Leu Trp Leu Pro
1               5                   10                  15
Asp Thr Thr Gly Asp Ile Val Met Thr Gln Thr Pro Leu Ser Leu Ser
            20                  25                  30
Val Thr Pro Gly Gln Pro Ala Ser Ile Ser Cys Lys Ser Ser Gln Ser
        35                  40                  45
Leu Leu Tyr Ser Asn Gly Lys Thr Tyr Leu Asn Trp Leu Leu Gln Lys
    50                  55                  60
Pro Gly Gln Ser Pro Gln Arg Leu Ile Tyr Leu Val Ser Lys Leu Asp
65                  70                  75                  80
Ser Gly Val Pro Asp Arg Phe Ser Gly Ser Gly Ser Gly Thr Asp Phe
                85                  90                  95
Thr Leu Lys Ile Ser Arg Val Glu Ala Glu Asp Val Gly Val Tyr Tyr
            100                 105                 110
Cys Val Gln Gly Thr His Leu His Thr Phe Gly Gln Gly Thr Arg Leu
        115                 120                 125
Glu Ile Lys Arg Thr Val Ala Ala Pro Ser Val Phe Ile Phe Pro Pro
    130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
```

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 274
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Thr Asp Tyr Tyr Met Ser Trp Val Arg Gln Ala Pro Gly Lys Gly
    50                  55                  60

Leu Glu Trp Val Gly Phe Ile Arg Asn Lys Ala Asn Gly Tyr Thr Thr
65                  70                  75                  80

Glu Tyr Asn Ala Ser Val Lys Gly Arg Phe Thr Ile Ser Arg Asp Asp
                85                  90                  95

Ser Lys Asn Ser Leu Tyr Leu Gln Met Asn Ser Leu Lys Thr Glu Asp
            100                 105                 110

Thr Ala Val Tyr Tyr Cys Thr Arg Tyr Ile Phe Phe Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 275
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Met Glu Ala Pro Ala Gln Leu Leu Phe Leu Leu Leu Leu Trp Leu Pro
1               5                   10                  15

Asp Thr Thr Gly Asp Ile Val Met Thr Gln Thr Pro Leu Ser Leu Ser
            20                  25                  30

Val Thr Pro Gly Gln Pro Ala Ser Ile Ser Cys Arg Ser Ser Gln Ser
        35                  40                  45

Leu Val His Thr Asn Gly Asn Ser Tyr Leu His Trp Tyr Leu Gln Lys
    50                  55                  60

Pro Gly Gln Ser Pro Gln Leu Leu Ile Tyr Met Val Ser Asn Arg Phe
65                  70                  75                  80

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Val Tyr Tyr
        100                 105                 110

Cys Ser Gln Ser Thr His Val Pro Phe Thr Phe Gly Gln Gly Thr Lys
    115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
        180                 185                 190

```
Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235

<210> SEQ ID NO 276
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Met Glu Ala Pro Ala Gln Leu Leu Phe Leu Leu Leu Leu Trp Leu Pro
1               5                   10                  15

Asp Thr Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asp Ala Trp Met Asp Trp Val Arg Gln Ala Pro Gly Lys Gly
    50                  55                  60

Leu Glu Leu Val Ser Glu Ile Arg Asn Lys Ala Lys Asn His Ala Thr
65                  70                  75                  80

Tyr Tyr Ala Glu Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Thr Thr Leu Asp Ser Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320
```

```
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
                355                 360                 365
Pro Pro Ser Arg Asp Glu Leu Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
                420                 425                 430
Arg Trp Gln Gln Gly Asn Val Phe Ser Cys Ser Val Met His Glu Ala
            435                 440                 445
Leu His Asn His Tyr Thr Gln Lys Ser Leu Ser Leu Ser Pro Gly Lys
    450                 455                 460

<210> SEQ ID NO 277
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Met Glu Ala Pro Ala Gln Leu Leu Phe Leu Leu Leu Leu Trp Leu Pro
1               5                   10                  15
Asp Thr Thr Gly Glu Val Gln Leu Leu Glu Ser Gly Gly Gly Leu Val
                20                  25                  30
Gln Pro Gly Gly Ser Leu Arg Leu Ser Cys Ala Ala Ser Gly Phe Thr
            35                  40                  45
Phe Ser Asp Ala Trp Met Asp Trp Val Arg Gln Ala Pro Gly Lys Gly
    50                  55                  60
Leu Glu Leu Val Ala Glu Ile Arg Asn Lys Ala Lys Asn His Ala Thr
65                  70                  75                  80
Tyr Tyr Ala Glu Ser Val Lys Gly Arg Phe Thr Ile Ser Arg Asp Asn
                85                  90                  95
Ser Lys Asn Thr Leu Tyr Leu Gln Met Asn Ser Leu Arg Ala Glu Asp
                100                 105                 110
Thr Ala Val Tyr Tyr Cys Thr Thr Leu Asp Ser Trp Gly Gln Gly Thr
            115                 120                 125
Thr Val Thr Val Ser Ser Ala Ser Thr Lys Gly Pro Ser Val Phe Pro
    130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
                180                 185                 190
Ser Ser Gly Leu Tyr Ser Leu Ser Ser Val Val Thr Val Pro Ser Ser
            195                 200                 205
Ser Leu Gly Thr Gln Thr Tyr Ile Cys Asn Val Asn His Lys Pro Ser
    210                 215                 220
```

```
Asn Thr Lys Val Asp Lys Val Glu Pro Lys Ser Cys Asp Lys Thr
225                 230                 235                 240

His Thr Cys Pro Pro Cys Pro Ala Pro Glu Leu Leu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
            450                 455                 460

<210> SEQ ID NO 278
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Met Glu Ala Pro Ala Gln Leu Leu Phe Leu Leu Leu Leu Trp Leu Pro
1               5                   10                  15

Asp Thr Thr Gly Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Lys
    50                  55                  60

Pro Gly Gln Ser Pro Gln Arg Leu Ile Tyr Leu Val Ser Ala Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Trp Thr Phe Gly Gln Gly Thr Lys
            115                 120                 125
```

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 279
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Pro
        35                  40                  45

Phe Ser Asn Tyr Trp Met Asn Trp Val Arg Gln Ala Pro Gly Lys Gly
    50                  55                  60

Leu Glu Trp Val Gly Gln Ile Arg Leu Lys Ser Asn Asn Tyr Ala Thr
65                  70                  75                  80

His Tyr Ala Glu Ser Val Lys Gly Arg Phe Thr Ile Ser Arg Asp Asp
                85                  90                  95

Ser Lys Asn Ser Leu Tyr Leu Gln Met Asn Ser Leu Lys Thr Glu Asp
            100                 105                 110

Thr Ala Val Tyr Tyr Cys Thr Pro Ile Asp Tyr Trp Gly Gln Gly Thr
        115                 120                 125

Thr Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Lys Pro Lys Asp Thr Leu Met Ile Ser Arg
            260                 265                 270

Thr Pro Glu Val Thr Cys Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
    435                 440                 445

Leu His Asn His Tyr Thr Gln Lys Ser Leu Ser Leu Ser Pro Gly Lys
    450                 455                 460

<210> SEQ ID NO 280
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Met Glu Ala Pro Ala Gln Leu Leu Phe Leu Leu Leu Leu Trp Leu Pro
1               5                   10                  15

Asp Thr Thr Gly Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu Tyr Ser Asn Gly Lys Thr Tyr Leu Asn Trp Val Leu Gln Lys
    50                  55                  60

Pro Gly Gln Ser Pro Gln Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Val Tyr Tyr
        100                 105                 110

Cys Val Gln Gly Ser His Phe His Thr Phe Gly Gln Gly Thr Lys Leu
    115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
        180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 281
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asp Tyr Tyr Met Ser Trp Val Arg Gln Ala Pro Gly Lys Gly
50                  55                  60

Leu Glu Trp Val Gly Phe Ile Arg Asn Lys Ala Asn Gly Tyr Thr Thr
65                  70                  75                  80

Glu Tyr Ser Ala Ser Val Lys Gly Arg Phe Thr Ile Ser Arg Asp Asp
                85                  90                  95

Ser Lys Asn Ser Leu Tyr Leu Gln Met Asn Ser Leu Lys Thr Glu Asp
            100                 105                 110

Thr Ala Val Tyr Tyr Cys Ala Arg Tyr Ile Trp Phe Asp Tyr Trp Gly
        115                 120                 125

Gln Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 282
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Met Glu Ala Pro Ala Gln Leu Leu Phe Leu Leu Leu Leu Trp Leu Pro
1               5                   10                  15

Asp Thr Thr Gly Asp Ile Val Met Thr Gln Thr Pro Leu Ser Leu Ser
            20                  25                  30

Val Thr Pro Gly Gln Pro Ala Ser Ile Ser Cys Arg Ser Ser Gln Ser
        35                  40                  45

Leu Val His Thr Asn Gly Asn Thr Tyr Leu His Trp Tyr Leu Gln Lys
    50                  55                  60

Pro Gly Gln Ser Pro Gln Leu Leu Ile Tyr Met Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Ala His Val Pro Pro Leu Thr Phe Gly Gln Gly Thr
        115                 120                 125

Arg Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175
```

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 283
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283
atggaagccc cagcgcagct tctcttcctc ctgctactct ggctccctga taccaccgga      60
gaggtacagc tggtggagtc gggaggaggc ttggtacagc ctgggggttc tctgagactc     120
tcctgtgcag cttctggatt cactttcaat acctactgga tgaactgggt ccgccaggct     180
ccagggaagg gacttgagtg ggtgggtcaa attagattga aatctaataa ttatgcaaca     240
cattatgcgg agtctgtgaa agggcggttc accatctcca gagatgattc aaaaacagc     300 ctctatcttc aaatgaattc cctgaaaact gaagacactg ccgttttatta ctgtacccca     360 gttgactttt ggggccaagg caccactgtc acagtctcct cagcctccac caagggccca     420
tcggtcttcc ccctggcacc ctcctccaag agcacctctg ggggtacagc ggccctgggc     480
tgcctggtca aggactactt ccccgaaccg gtgacggtgt cgtggaactc aggcgccctg     540
accagcggcg tgcacacctt cccggctgtc ctacagtcct caggactcta ctccctcagc     600
agcgtggtga ccgtgccctc agcagcttg gcacccaga cctacatctg caacgtgaat     660
cacaagccca gcaacaccaa ggtggacaag aaagttgagc ccaaatcttg tgacaaaact     720
cacacatgcc caccgtgccc agcacctgaa ctcctggggg gaccgtcagt cttcctcttc     780 ccccccaaaac ccaaggacac cctcatgatc tcccggaccc ctgaggtcac atgcgtggtg     840
gtggacgtga gccacgaaga ccctgaggtc aagttcaact ggtacgtgga cggcgtggag     900
gtgcataatg ccaagacaaa gccgcgggag gagcagtaca acagcacgta ccgtgtggtc     960
agcgtcctca ccgtcctgca ccaggactgg ctgaatggca aggagtacaa gtgcaaggtc    1020
tccaacaaag ccctcccagc ccccatcgag aaaaccatct ccaaagccaa agggcagccc    1080
cgagaaccac aggtgtacac cctgcccca tcccgggatg agctgaccaa gaaccaggtc    1140
agcctgacat gcctggtcaa aggcttctat cccagcgaca tcgccgtgga gtgggagagc    1200
aatgggcagc cggagaacaa ctacaagacc acgcctcccg tgctggactc cgacggctcc    1260
ttcttcctct acagcaagct caccgtggac aagtccaggt ggcagcaggg gaacgtcttc    1320
tcatgctccg tgatgcatga ggctctgcac aaccactaca cgcagaagag cctctccctg    1380
tctccgggta aatga                                                     1395

<210> SEQ ID NO 284
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 284

```
atggaagccc cagcgcagct tctcttcctc ctgctactct ggctccctga taccaccgga    60
gacattgtga tgacccagac tccactcagt ttgtcagtta ccctggaca accagcctca   120
atctcttgca agtcaagtca gagcctctta tatagtaatg gaaaaaccta tttgaactgg   180
ttattacaga agccaggcca gtctccacag cgcctaatct atctggtgtc taaattggac   240
tctggagtcc ctgacaggtt cagtggcagt ggatcaggaa cagattttac actgaaaatc   300
agcagagtgg aggctgagga tgtgggagtt tattactgcg tgcaaggtac acatctgcac   360
acgttcggtc aagggaccag gctggagata aaacgaactg tggcagcacc aagcgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca aagtctacgc ctgcgaagtc   660
acccatcagg gcctgagctc gcccgtcaca aagagcttca acaggggaga gtgttag      717
```

<210> SEQ ID NO 285
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 285

```
atggaagccc cagcgcagct tctcttcctc ctgctactct ggctccctga taccaccgga    60
gaggtacagc tggtggagtc gggaggaggc ttggtacagc ctgggggttc tctgagactc   120
tcctgtgcag cttctggctt cacattcacc gactattaca tgagctgggt ccgccaggct   180
ccagggaagg gacttgagtg ggtgggtttc ataaggaaca aggctaacgg ttatacaacc   240
gagtacaacg cttccgttaa aggccggttc accatctcca gagatgattc caaaaacagc   300
ctctatcttc aaatgaattc cctgaaaact gaagacactg ccgttattac tgtaccagg   360
tatatctttt tcgattactg gggccaaggc accactgtca cagtctcctc agcctccacc   420
aagggcccat cggtcttccc cctggcaccc tcctccaaga gcacctctgg gggtacagcg   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacccagac ctacatctgc   660
aacgtgaatc acaagcccag caacaccaag gtggacaaga agttgagcc caaatcttgt   720
gacaaaactc acacatgccc accgtgccca gcacctgaac tcctggggg accgtcagtc   780
ttcctcttcc cccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggatga gctgaccaag  1140
aaccaggtca gcctgacatg cctggtcaaa ggcttctatc ccagcgacat cgccgtggag  1200
tgggagagca atgggcagcc ggagaacaac tacaagacca cgcctcccgt gctggactcc  1260
```

```
gacggctcct tcttcctcta cagcaagctc accgtggaca agtccaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 286
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286

```
atggaagccc cagcgcagct tctcttcctc ctgctactct ggctccctga taccaccgga     60
gatattgtaa tgacccaaac acccctctct ctttcagtca cacctggaca gccagcgtcc    120
atctcctgca ggtcctcaca gagtctcgtg cacaccaatg gcaattccta cctgcattgg    180
tacctgcaga agcccgggca gagcccccag ttgctgatct atatggtgtc taatcggttc    240
tccggagtcc ccgacagatt ttctggttca gggtctggaa ctgattttac actgaagatt    300
agtcgggtcg aggccgagga tgtaggcgtg tattactgct cacaaagcac acatgtgccg    360
ttcactttcg gccaaggaac aaagctcgaa atcaagcgaa ctgtggcagc accaagcgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct caacagggg agagtgttag    720
```

<210> SEQ ID NO 287
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1398)..(1398)
<223> OTHER INFORMATION: a, c, t, g, unknown or other

<400> SEQUENCE: 287

```
atggaagccc cagcgcagct tctcttcctc ctgctactct ggctccctga taccaccgga     60
gaggtacagc ttcttgaaag tggaggtggc cttgtccaac ccggagggtc attgcggttg    120
agctgtgcgg caagtggctt caccttctct gacgcttgga tggactgggt gagacaagcc    180
cccggtaagg gactggagtt ggtttctgaa atcaggaaca aggccaagaa ccatgcaaca    240
tattatgccg aaagtgtgaa gggaaggttc acaatcagta gagataacag caagaacaca    300
ctgtacctcc agatgaacag cctcagagct gaggacaccg ccgtctatta ttgtaccact    360
ctcgattcat gggggcaggg taccaccgtt acagtcagca gcgcctccac caagggccca    420
tcggtcttcc ccctggcacc ctcctccaag agcacctctg ggggtacagc ggccctgggc    480
tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc cagcagcttg ggcacccaga cctacatctg caacgtgaat    660
cacaagccca gcaacaccaa ggtggacaag aaagttgagc ccaaatcttg tgacaaaact    720
```

```
cacacatgcc caccgtgccc agcacctgaa ctcctggggg gaccgtcagt cttcctcttc    780 ccccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
agcctgacat gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct acagcaagct caccgtggac aagtccaggt ggcagcaggg gaacgtcttc   1320
tcatgctccg tgatgcatga ggctctgcac aaccactaca cgcagaagag cctctccctg   1380
tctccgggta aatga                                                    1395
```

<210> SEQ ID NO 288
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1398)..(1398)
<223> OTHER INFORMATION: a, c, t, g, unknown or other

<400> SEQUENCE: 288

```
atggaagccc cagcgcagct tctcttcctc ctgctactct ggctccctga taccaccgga     60
gaggtacagc ttcttgaaag tggaggtggc cttgtccaac ccggagggtc attgcggttg    120
agctgtgcgg caagtggctt caccttctct gacgcttgga tggactgggt gagacaagcc    180
cccggtaagg gactggagtt ggttgctgaa atcaggaaca aggccaagaa ccatgcaaca    240
tattatgccg aaagtgtgaa gggaaggttc acaatcagta gagataacag caagaacaca    300
ctgtacctcc agatgaacag cctcagagct gaggacaccg ccgtctatta ttgtaccact    360
ctcgattcat gggggcaggg taccaccgtt acagtcagca gcgccaccac caagggccca    420
tcggtcttcc ccctggcacc ctcctccaag agcacctctg ggggtacagc ggccctgggc    480
tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc cagcagcttg ggcacccaga cctacatctg caacgtgaat    660
cacaagccca gcaacaccaa ggtggacaag aaagttgagc ccaaatcttg tgacaaaact    720
cacacatgcc caccgtgccc agcacctgaa ctcctggggg gaccgtcagt cttcctcttc    780 ccccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
agcctgacat gcctggtcaa aggcttctat cccagcgaca tcgccgtgga gtgggagagc   1200
aatgggcagc cggagaacaa ctacaagacc acgcctcccg tgctggactc cgacggctcc   1260
```

| | |
|---|---|
| ttcttcctct acagcaagct caccgtggac aagtccaggt ggcagcaggg gaacgtcttc | 1320 |
| tcatgctccg tgatgcatga ggctctgcac aaccactaca cgcagaagag cctctccctg | 1380 |
| tctccgggta aatga | 1395 |

<210> SEQ ID NO 289
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 289

| | |
|---|---|
| atggaagccc cagcgcagct tctcttcctc ctgctactct ggctccctga taccaccgga | 60 |
| gatatcgtga tgacacaaac tccctgtct ctgtctgtaa ctccaggtca gccgcgagt | 120 |
| atttcatgta agagcagcca atccctgctg gacagcgacg ggaagaccta cctgaactgg | 180 |
| ttactccaaa agccaggaca aagtccccaa cgccttattt acctggtgtc agccctggac | 240 |
| tctggcgtgc ccgatcgatt tagcggcagc gggagtggca cagatttcac cctgaaaata | 300 |
| tcccgcgtcg aggccgaaga tgtgggcgtg tactactgct ggcagggcac acatttcccc | 360 |
| tggacatttg gtcaggggac aaagctggaa attaaacgaa ctgtggcagc accaagcgtc | 420 |
| ttcatcttcc cgccatctga tgagcagttg aaatctggaa ctgcctctgt tgtgtgcctg | 480 |
| ctgaataact tctatcccag agaggccaaa gtacagtgga aggtggataa cgccctccaa | 540 |
| tcgggtaact cccaggagag tgtcacagag caggacagca aggacagcac ctacagcctc | 600 |
| agcagcaccc tgacgctgag caaagcagac tacgagaaac acaaagtcta cgcctgcgaa | 660 |
| gtcacccatc agggcctgag ctcgcccgtc acaaagagct tcaacagggg agagtgttag | 720 |

<210> SEQ ID NO 290
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290

| | |
|---|---|
| atggaagccc cagcgcagct tctcttcctc ctgctactct ggctccctga taccaccgga | 60 |
| gaggtacagc tggtggagtc gggaggaggc ttggtacagc ctgggggttc tctgagactc | 120 |
| tcctgtgcag cttctggatt cccattcagt aactactgga tgaactgggt ccgccaggct | 180 |
| ccagggaagg gacttgagtg ggtgggtcaa attagattga aatctaataa ttatgcaaca | 240 |
| cattatgcgg agtctgtgaa agggcggttc accatctcca gagatgattc aaaaacagc | 300 |
| ctctatcttc aaatgaattc cctgaaaact gaagacactg ccgttttatta ctgtaccca | 360 |
| attgactatt ggggccaagg caccactgtc acagtctcct cagcctccac caagggccca | 420 |
| tcggtcttcc ccctggcacc ctcctccaag agcacctctg ggggtacagc ggccctgggc | 480 |
| tgcctggtca aggactactt ccccgaaccg gtgacggtgt cgtggaactc aggcgccctg | 540 |
| accagcggcg tgcacacctt cccggctgtc ctacagtcct caggactcta ctccctcagc | 600 |
| agcgtggtga ccgtgccctc cagcagcttg ggcacccaga cctacatctg caacgtgaat | 660 |
| cacaagccca gcaacaccaa ggtggacaag aaagttgagc ccaaatcttg tgacaaaact | 720 |
| cacacatgcc caccgtgccc agcacctgaa ctcctggggg gaccgtcagt cttcctcttc | 780 |
| cccccaaaac ccaaggacac cctcatgatc tcccggaccc ctgaggtcac atgcgtggtg | 840 |

```
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
agcctgacat gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct acagcaagct caccgtggac aagtccaggt ggcagcaggg gaacgtcttc   1320
tcatgctccg tgatgcatga ggctctgcac aaccactaca cgcagaagag cctctccctg   1380
tctccgggta aatga                                                   1395
```

<210> SEQ ID NO 291
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291

```
atggaagccc cagcgcagct tctcttcctc ctgctactct ggctccctga taccaccgga     60
gacattgtga tgacccagac tccactcagt ttgtcagtta cccctgggca accagcctct    120
atctcttgca agtcaagtca gagcctctta tatagtaatg gaaaaaccta tttgaactgg    180
gttttacaga agccaggcca gtctccacag cgcctaatct atctggtgtc taaactggac    240
tctggagtcc ctgacaggtt ctctggcagt ggatcaggaa cagattttac actgaaaatc    300
agcagagtgg aggctgagga tgtgggagtt tattactgcg tgcaaggttc acattttcac    360
acgttcggtc aagggaccaa gctggagatt aaacgaactg tggcagcacc aagcgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctacgc ctgcgaagtc    660
acccatcagg gcctgagctc gcccgtcaca aagagcttca caggggaga gtgttag       717
```

<210> SEQ ID NO 292
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292

```
atggaagccc cagcgcagct tctcttcctc ctgctactct ggctccctga taccaccgga     60
gaggtacagc tggtggagtc gggaggaggc ttggtacagc ctgggggttc tctgagactc    120
tcctgtgcag cttctggatt cacctttttct gattactaca tgagctgggt ccgccaggct    180
ccagggaagg gacttgagtg gtgggttttt attagaaaca agctaatgg ttacacaaca    240 gagtacagtg catctgtgaa gggtcggttc accatctcca gagatgattc aaaaacagc    300 ctctatcttc aaatgaattc cctgaaaact gaagacactg ccgtttatta ctgtgcaaga    360
tatatctggt ttgactactg gggccaaggc accactgtca cagtctcctc agcctccacc    420
```

-continued

```
aagggcccat cggtcttccc cctggcaccc tcctccaaga gcacctctgg gggtacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaac tcctggggg accgtcagtc    780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacatg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agtccaggtg gcagcagggg   1320
aacgtcttct catgctccgt gatgcatgag gctctgcaca accactacac gcagaagagc   1380
ctctccctgt ctccgggtaa atga                                          1404

<210> SEQ ID NO 293
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293
atggaagccc cagcgcagct tctcttcctc ctgctactct ggctccctga taccaccgga     60
gacattgtga tgacccaaac tccactctcc ctgtctgtca ctcctggaca accagcctcc    120
atctcttgca gatctagtca gagccttgta cacactaatg gaaacaccta tttacattgg    180
tacctgcaga agccaggcca gtctccacag ctcctgattt atatggtttc aaccgattt    240 tctggggtcc cagacaggtt cagtggcagt ggatcaggga cagatttcac actcaagatc    300
agcagagtgg aggctgagga tgtgggagtt tattactgct ctcaaagtgc acatgttcct    360
ccgctcacgt tcggtcaagg gaccaggctg gagattaaac gaactgtggc agcaccaagc    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga acacaaaagt ctacgcctgc    660
gaagtcaccc atcagggcct gagctcgccc gtcacaaaga gcttcaacag gggagagtgt    720
tag                                                                  723

<210> SEQ ID NO 294
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 294

Ala Arg Tyr Ile Phe Phe Asp Tyr
1               5